(12) United States Patent
Chao

(10) Patent No.: US 11,753,410 B2
(45) Date of Patent: Sep. 12, 2023

(54) HORMONE RECEPTOR MODULATORS FOR TREATING METABOLIC MUTAGENIC AND FIBROTIC CONDITIONS AND DISORDERS

(71) Applicant: Ardelyx, Inc., Fremont, CA (US)

(72) Inventor: Jianhua Chao, Fremont, CA (US)

(73) Assignee: Ardelyx, Inc., Fremont, CA (US)

( * ) Notice: Subject to any disclaimer, the term of this patent is extended or adjusted under 35 U.S.C. 154(b) by 233 days.

(21) Appl. No.: 16/647,385

(22) PCT Filed: Sep. 18, 2018

(86) PCT No.: PCT/US2018/051122
§ 371 (c)(1),
(2) Date: Mar. 13, 2020

(87) PCT Pub. No.: WO2019/055808
PCT Pub. Date: Mar. 21, 2019

(65) Prior Publication Data
US 2021/0380585 A1 Dec. 9, 2021

Related U.S. Application Data

(60) Provisional application No. 62/558,858, filed on Sep. 14, 2017.

(51) Int. Cl.
| | | |
|---|---|---|
| C07D 403/12 | (2006.01) | |
| C07D 401/14 | (2006.01) | |
| C07D 405/14 | (2006.01) | |
| C07D 413/14 | (2006.01) | |
| C07D 403/04 | (2006.01) | |
| C07D 403/14 | (2006.01) | |
| A61K 31/439 | (2006.01) | |
| A61P 35/00 | (2006.01) | |
| C07D 471/08 | (2006.01) | |

(52) U.S. Cl.
CPC .................. C07D 471/08 (2013.01)

(58) Field of Classification Search
CPC .. C07D 403/12; C07D 401/14; C07D 405/14; C07D 413/14; C07D 403/04; C07D 403/14; A61K 31/439; A61P 35/00
See application file for complete search history.

(56) References Cited

U.S. PATENT DOCUMENTS

| | | | |
|---|---|---|---|
| 4,988,691 | A | 1/1991 | Benelli et al. |
| 10,793,568 | B2 | 10/2020 | Chao et al. |
| 11,091,482 | B2 | 8/2021 | Chao et al. |
| 2013/0331349 | A1 | 12/2013 | Tully et al. |
| 2019/0308973 | A1 | 10/2019 | Chao et al. |
| 2021/0017177 | A1 | 1/2021 | Chao et al. |
| 2021/0024522 | A1 | 1/2021 | Fang et al. |
| 2021/0300927 | A1 | 9/2021 | Chao et al. |

FOREIGN PATENT DOCUMENTS

| | | |
|---|---|---|
| WO | 2009012125 A1 | 1/2009 |
| WO | 2011020615 A1 | 2/2011 |
| WO | 2012087519 A1 | 6/2012 |
| WO | 2012087520 A1 | 6/2012 |
| WO | 2012087521 A1 | 6/2012 |
| WO | 2013072693 A1 | 5/2013 |
| WO | 2016096115 A1 | 6/2016 |
| WO | 2016097933 A1 | 6/2016 |
| WO | 2016127924 A1 | 8/2016 |
| WO | 2018039386 A1 | 3/2018 |
| WO | 2019007418 A1 | 1/2019 |

OTHER PUBLICATIONS

U.S. Appl. No. 16/237,790, U.S. Pat. No. 11,091,482.
U.S. Appl. No. 17/224,518, 2021-0300927.
U.S. Appl. No. 16/327,791, U.S. Pat. No. 10,793,568.
U.S. Appl. No. 16/990,827, 2021-0017177.
U.S. Appl. No. 17/858,917.
Cannon, J, "Analog Design", Chapter Nineteen in Burger's Medicinal Chemistry and Drug Discovery, Fifth Ed. vol. I: Principles and Practice, 783-802 (1995).
Ettmayer, P, et al., "Lessons Learned from Marketed and Investigational Prodrugs", Journal of Medicinal Chemistry 47(10), 2393-2404 (2004).
Han, H, "Targeted Prodrug Design to Optimize Drug Delivery", AAPS Pharmsci 2(1), Article 6, 11 pages (2000).
Huang, W, et al., "FXR a metabolie regulator and cell protector", Cell Res 18, 1087-1095 (2008).
Matsubara, T, et al., "FXR signaling in the enterohepatic system", Mol Cell Endocrinol 368, 17-29 (2013).
Modica, S, et al., "Deciphering the nuclear bile acid receptor FXR paradigm", Nucl Recept Signal 8, e005, 28 pages (2010).
Moschetta, A, "Deciphering the nuclear bile acid receptor FXR paradigm", Nucl Recept Signal 8, e005, 28 pages (2010).
Patent Cooperation Treaty, International Search Report and Written Opinion for PCT/US2018/051122, 13 pages dated Nov. 13, 2018.
Shaik, F, et al., "Role of farnesoid X receptor in inflammation and resolution", Inflamm Res 64, 9-20 (2015).

(Continued)

*Primary Examiner* — Bruck Kifle
(74) *Attorney, Agent, or Firm* — Viksnins Harris Padys Malen LLP

(57) ABSTRACT

The invention relates to activators of FXR useful in the treatment of autoimmune disorders, liver disease, intestinal disease, kidney disease, cancer, and other diseases in which FXR plays a role, having the Formula (I): wherein $L_1$, A, $X_1$, $X_2$, $Y_1$, $Y_2$, $Y_3$, $Y_4$, $R^1$, $R^2$, and $R^3$ are described herein.

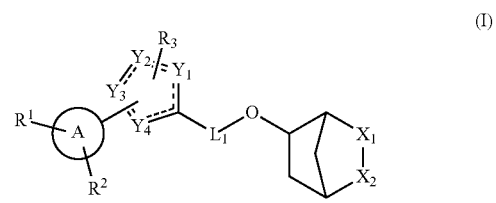

(I)

19 Claims, No Drawings

(56) References Cited

OTHER PUBLICATIONS

Testa, B , "Prodrug research: futile or fertile?", Biochemical Pharmacology 68, 2097-2106 (2004).
Tian, F , et al., "Factors affecting crystallization of hydrates", Journal of Pharmacy and Pharmacology 62, 1534-1546 (2010).
Vavassori, P , "The bile acid receptor FXR is a modulator of intestinal innate immunity", J Immunol 183, 6251-6261 (2009).
Venkatesh, S , et al., "Role of the Development Scientist in Compound Lead Selection and Optimization", Journal of Pharmaceutical Sciences 89 (2), 145-154 (2000).
Verbeke, L , "The FXR agonist obeticholic acid prevents gut barrier dysfunction and bacterial translocation in cholestatic rats", Am J Pathol 185, 409-419 (2015).
West, A , "Solid Solutions", Chapter 10, Solid State Chemistry and Its Applications, pp. 358 and 365 (1984).
Wolff , "Burger's Medicinal Chemistry and Drug Discovery", Fifth Edition, vol. 1: Principles and Practice, 975-977 (1995).

HORMONE RECEPTOR MODULATORS FOR TREATING METABOLIC MUTAGENIC AND FIBROTIC CONDITIONS AND DISORDERS

CROSS REFERENCE TO RELATED APPLICATIONS

This application claims priority to U.S. Provisional Application No. 62/558,858 that was filed on Sep. 14, 2017. The entire contents of the application referenced above is hereby incorporated by reference herein.

FIELD OF INVENTION

The present invention is directed to modulators of a nuclear hormone receptor, farnesoid X receptor (FXR), useful in the treatment of diseases or disorders associated with FXR proteins and its target genes. Specifically, the invention is related to compounds and compositions which modulate FXR, methods of treating diseases or disorders associated with FXR, and methods of synthesis of these compounds.

BACKGROUND OF THE INVENTION

FXR is a ligand-activated transcription factor. Upon binding of a ligand, FXR either binds to DNA at the FXR response elements (FXREs) as a monomer, or forms a heterodimer with retinoid X receptor (RXR) and then binds to FXREs, regulating the transcription of a variety of target genes. To date, more than 40 FXR target genes have been identified that are involved in a wide range of physiological functions including bile acid homeostasis (i.e., BACS, BAAT, BSEP, FGF15/19, etc.), cholesterol and lipoprotein metabolism (i.e., Apolipoprotein C-I, II, IV, Apolipoprotein E, MDR3, Human complement C3, ApoA-1, hepatic lipase, SREPB-1c), glucose metabolism (i.e., PEPCK, GSK3, AKR1B7, GLUT4, G6Pase), and xenobiotics metabolism (i.e., GSTα3, GSTα4, GSTµ1, GSTµ3, SULT1A1, SULT1A2). In addition to the regulation of metabolic related genes, recent results have identified FXR as a regulator of cellular inflammatory and immune responses. Activation of FXR can provide anti-inflammatory effects by negative regulation of nuclear factor κB (NFκB) pathway, reducing the expression of NFκB and the many pro-inflammatory cytokines associated with this pathway (Matsubara, T. et al., "FXR signaling in the enterohepatic system," *Mol. Cell Endocrinol.* 2013, 368, 17-29; Moschetta, A., "Deciphering the nuclear bile acid receptor FXR paradigm," *Nucl. Recept. Signal.,* 2010, 8, e005; Huang, W., et al., "FXR: a metabolic regulator and cell protector," *Cell Res.,* 2008, 1087-1095).

FXR plays a key role in the synthesis, transport and metabolism of bile acids (BAs) and the many physiological and pathophysiological conditions that involve BAs. In the liver, activation of FXR has been shown to lead to the increased expression of short heterodimer partner (SHP), which in turn inactivates liver receptor homolog-1 (LRH-1) and inhibits the cholesterol 7-alpha-hydroxylase (CYP7A1), the rate-limiting enzyme in the first step of biosynthesis of primary bile acids from cholesterol, thereby reduces the production of bile acids. Activation of FXR in the liver has also been shown to downregulate transporters like Na-taurocholate co-transporting polypeptide (NTCP) and organic anion-transporting peptides (OATPs) preventing the uptake of bile acids to liver. The accumulation of BAs in the liver plays a pivotal role in cholestasis-associated liver damage, pharmacological activation of FXR by synthetic ligands can provide therapeutic intervention.

FXR has also been shown to play an important role in the inflammation control of various liver and intestinal diseases (Shaik, F. B., et al., "Role of farnesoid X receptor in inflammation and resolution," *Inflamm. Res.* 2015, 64, 9-20). Activation of FXR has been shown to repress the NFκB pathway, a prototypical proinflammatory signaling pathway, and inhibit the expression of key cytokines such as TNFα, IL-1β, and IL-6. In the colon of FXR knockout mice, increased expression of both proinflammatory cytokines (e.g., TNFα, IL-1β, IFNγ) and profibrotic genes (i.e., Collagen α1, TIMP-1, and αSMA) has been observed, indicative of dysregulation in intestinal immunity and tissue remodeling. Activation of FXR with FXR activators in the TNBS induced murine inflammatory bowel disease model has been shown to inhibit the above cytokines and provide protection against inflammation and fibrosis, subsequently against the development of colitis (Vavassori, P., "The bile acid receptor FXR is a modulator of intestinal innate immunity," *J. Immunol.* 2009, 183, 6251-6261). Moreover, treatment with an FXR agonist in a rat model of cholestatic liver injury (bile-duct ligation) reduced NK cells and INFγ expression, leading to reduction in intestinal inflammation, reduction in bacterial translocation, and overall improvement in gut barrier function (Verbeke, L., "The FXR agonist obeticholic acid prevents gut barrier dysfunction and bacterial translocation in cholestatic rats," *Am. J. Pathol.* 2015, 185, 409-419).

Activation of FXR with small molecule activators has the potential to be a treatment for a range of diseases including bile acid related disorders, metabolic syndrome, type-2-diabetes, hyperlipidemia, hypertriglyceridemia, primary biliary cirrhosis (PBC), fatty liver disease, nonalcoholic steatohepatitis (NASH), inflammatory autoimmune diseases, Crohn's disease, multiple sclerosis, atherosclerosis, hepatic and colon cancers, and other disorders. However, known FXR activators have demonstrated toxicities, treatment limiting adverse effects, and other issues. For these reasons, there remains a need for novel and potent small molecule FXR activators.

SUMMARY OF THE INVENTION

In an aspect of the invention, there is provided a compound of Formula I:

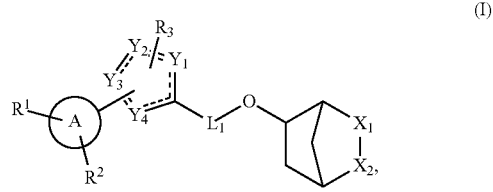

(I)

or a salt thereof, wherein:

one of $X_1$ or $X_2$ is $NR_x$ or $N^+(O^-)R_x$ and the other is $CHR_y$ or $C(O)$;

$Y_1$, $Y_2$, $Y_3$ and $Y_4$ are independently C, CH or N, wherein one of $Y_1$ and $Y_4$ is substituted with R3 and the other is substituted with ring A;

$R_x$ is

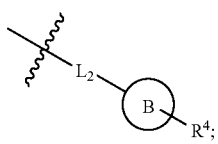

$R_y$ is H, alkyl, cycloalkyl or cycloalkylalkyl wherein said alkyl, cycloalkyl and cycloalkylalkyl are optionally substituted with halogen or alkoxy;

$L_1$ is —($CH_2$)$_m$(C=O)— or —($CH_2$)$_p$—;

$L_2$ is a bond or —S(O)$_2$—;

A is cycloalkyl, aryl, heterocycloalkyl or heteroaryl, wherein the cycloalkyl, aryl, heterocycloalkyl, or heteroaryl is optionally substituted with one or more $R^7$;

B is aryl or heteroaryl, wherein the aryl or heteroaryl is optionally substituted with one or more $R^5$;

$R^1$ and $R^2$ are each independently H, alkyl, alkoxy, haloalkyl, haloalkoxy, halogen, cycloalkyl, or CN, wherein the cycloalkyl is optionally substituted with one or more $R^9$; or when A is cycloalkyl or heterocycloalkyl, $R^1$ and $R^2$ together when attached to the same carbon atom form a spirocycloalkyl ring optionally substituted with one or more $R^8$; or when A is cycloalkyl or heterocycloalkyl, $R^1$ and $R^2$ together when attached to the same atom form a spiroheterocycloalkyl ring optionally substituted with one or more $R^8$; or $R^1$ and $R^2$ when on adjacent atoms together with the atoms to which they are attached form a cycloalkyl ring optionally substituted with one or more $R^8$; or $R^1$ and $R^2$ when on adjacent atoms together with the atoms to which they are attached form a heterocycloalkyl ring optionally substituted with one or more $R^8$; or $R^1$ and $R^2$ when on adjacent atoms together with the atoms to which they are attached form an aryl ring optionally substituted with one or more $R^8$; or $R^1$ and $R^2$ when on adjacent atoms together with the atoms to which they are attached form a heteroaryl ring optionally substituted with one or more $R^8$; or when A is cycloalkyl or heterocycloalkyl, $R^1$ and $R^2$ when on non-adjacent atoms, together with the atoms to which they are attached form a cycloalkyl ring optionally substituted with one or more $R^8$; or when cycloalkyl or heterocycloalkyl, $R^1$ and $R^2$ when on non-adjacent atoms, together with the atoms to which they are attached form a heterocycloalkyl ring optionally substituted with one or more $R^8$;

$R^3$ is alkyl, alkoxy, haloalkyl, haloalkoxy, hydroxyalkyl, or cycloalkyl optionally substituted with one or more substituents each independently selected from the group consisting of halogen, alkyl, alkoxy, haloalkyl, haloalkoxy, and —OH;

$R^4$ is COOR$^{6a}$, —(CH$_2$)$_n$—COOR$^{6a}$, CONR$^{6b}$OH, CONR$^{6b}$R$^{6c}$, CONH(CH$_2$)$_n$COOR$^{6a}$, CONH(CH$_2$)$_n$R$^{6a}$, —(CH$_2$)$_n$CONH(CH$_2$)$_n$R$^{6a}$, CONR$^{6b}$SO$_2$R$^{6d}$, CONR$^{6b}$SO$_2$(CH$_2$)$_n$R$^{6d}$, —(CH$_2$)$_n$—CONR$^{6b}$SO$_2$R$^{6d}$, CONR$^{6b}$SO$_2$(CH$_2$)$_n$N(CO)R$^{6d}$ CONH(CH$_2$)$_n$SO$_2$R$^{6e}$, COR$^{6f}$, (CH$_2$)$_n$PO(OR$^{6g}$)$_2$, CONR$^{6b}$(CH$_2$)$_n$PO(OR$^{6g}$)$_2$, CONR$^{6b}$SO$_2$(CH$_2$)$_n$N$^+$(R$^{6f}$)$_3$, COO(CH$_2$)$_n$PO(OR$^{6g}$)$_2$, SO$_2$NR$^{6b}$(CH$_2$)$_n$COOR$^{6a}$, SO$_2$R$^{6e}$, CN, —(CH$_2$)$_n$—NR$^{6b}$C(O)R$^{6c}$, —(CH$_2$)$_n$—N(OH)—C(O)R$^{6c}$, oxo, alkyl, cycloalkyl, —(CH$_2$)$_n$-cycloalkyl, heterocycloalkyl, —(CH$_2$)$_n$-heterocycloalkyl, heteroaryl or —(CH$_2$)$_n$-heteroaryl; wherein said alkyl, cycloalkyl, —(CH$_2$)$_n$-cycloalkyl, heterocycloalkyl, —(CH$_2$)$_n$-heterocycloalkyl, heteroaryl and —(CH$_2$)$_n$-heteroaryl are optionally substituted with COOR$^{6a}$, —(CH$_2$)$_n$—COOR$^{6a}$, CONR$^{6b}$OH, CONR$^{6b}$R$^{6c}$, CONH(CH$_2$)$_n$COOR$^{6a}$, CONH(CH$_2$)$_n$R$^{6a}$, —(CH$_2$)$_n$CONH(CH$_2$)$_n$R$^{6a}$, CONR$^{6b}$SO$_2$R$^{6d}$, CONR$^{6b}$SO$_2$(CH$_2$)$_n$R$^{6d}$, —(CH$_2$)$_n$—CONR$^{6b}$SO$_2$R$^{6d}$, CONR$^{6b}$SO$_2$(CH$_2$)$_n$N(CO)R$^{6d}$ CONH(CH$_2$)$_n$SO$_2$R$^{6e}$, COR$^{6f}$, (CH$_2$)$_n$PO(OR$^{6g}$)$_2$, COO(CH$_2$)$_n$PO(OR$^{6g}$)$_2$, SO$_2$NR$^{6b}$(CH$_2$)$_n$COOR$^{6a}$, SO$_2$R$^{6e}$, CN, —(CH$_2$)$_n$—NR$^{6b}$C(O)R$^{6c}$, or —(CH$_2$)$_n$—N(OH)—C(O)R$^{6c}$;

each $R^5$ is independently at each occurrence halogen, alkyl, haloalkyl, alkoxy, haloalkoxy, CN, cycloalkyl, spiroheterocycloalkyl, —O-cycloalkyl, —O-heterocycloalkyl, aryl, heterocycloalkyl, or heteroaryl wherein the cycloalkyl, aryl, heterocycloalkyl or heteroaryl are optionally substituted with one or more substituents each independently selected from the group consisting of halogen, alkyl, haloalkyl, alkoxy, and haloalkoxy;

$R^{6a}$ is H, alkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, NR$^{6b}$R$^{6c}$, SO$_2$NR$^{6b}$R$^{6c}$, and —OH;

$R^{6b}$ and $R^{6c}$ are each independently H, alkyl, haloalkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

$R^{6d}$ is alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, COOH, alkyl, haloalkyl, alkoxy, haloalkoxy, alkoxyalkoxy, —O—CO-alkyl, —O—COcycloalkyl, —O—CO-alkyl-COOH, NR$^{6b}$R$^{6c}$, NR$^{6f}$CO-alkyl, NR$^{6f}$CO-alkoxy, cycloalkyl, heterocycloalkyl and —OH;

$R^{6e}$ is —OH, alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

$R^{6f}$ is alkyl or haloalkyl;

$R^{6g}$ is H or alkyl optionally substituted with —O—CO-alkyl;

each $R^7$ is independently at each occurrence OH, alkyl, alkoxy, haloalkyl, haloalkoxy, halogen, or CN;

each $R^8$ is independently at each occurrence alkyl, alkoxy, haloalkyl, haloalkoxy, halogen, or —OH;

each $R^9$ is independently at each occurrence alkyl, alkoxy, haloalkyl, haloalkoxy, halogen, or —OH;

m is 0, 1, or 2;

n is 1, 2, 3, 4, 5, 6, 7, 8, 9, 10, 11, or 12; and p is 1 or 2.

Another aspect of the invention relates to a method of treating a disease or disorder in which FXR plays a role. The method comprises administering to a patient in need of a treatment for diseases or disorders in which FXR plays a role an effective amount of a compound of Formula (I), or a pharmaceutically acceptable salt, hydrate, solvate, prodrug, stereoisomer, or tautomer thereof.

Another aspect of the invention is directed to a method of modulating FXR. The method involves administering to a patient in need thereof an effective amount of a compound of Formula (I), or a pharmaceutically acceptable salt, hydrate, solvate, prodrug, stereoisomer, or tautomer thereof.

Another aspect of the invention is directed to a method of activating FXR. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a liver disease. The method comprises administering to a patient in need of a treatment for a liver disease an effective amount of a compound of Formula (I), or a pharmaceutically acceptable salt, hydrate, solvate, prodrug, stereoisomer, or tautomer thereof.

Another aspect of the invention relates to a method of treating an intestinal disease. The method comprises administering to a patient in need of a treatment for an intestinal disease an effective amount of a compound of Formula (I), or a pharmaceutically acceptable salt, hydrate, solvate, prodrug, stereoisomer, or tautomer thereof.

Another aspect of the invention relates to a method of treating a kidney disease. The method comprises administering to a patient in need of a treatment for a kidney disease an effective amount of a compound of Formula (I), or a pharmaceutically acceptable salt, hydrate, solvate, prodrug, stereoisomer, or tautomer thereof.

Another aspect of the invention relates to a method of treating an autoimmune disorder. The method comprises administering to a patient in need of a treatment for an autoimmune disorder an effective amount of a compound of Formula (I), or a pharmaceutically acceptable salt, hydrate, solvate, prodrug, stereoisomer, or tautomer thereof.

Another aspect of the invention relates to a method of treating cancer. The method comprises administering to a patient in need of a treatment for cancer an effective amount of a compound of Formula (I), or a pharmaceutically acceptable salt, hydrate, solvate, prodrug, stereoisomer, or tautomer thereof.

Another aspect of the invention is directed to pharmaceutical compositions comprising a compound of Formula (I), or a pharmaceutically acceptable salt, hydrate, solvate, prodrug, stereoisomer, or tautomer thereof, and a pharmaceutically acceptable carrier. The pharmaceutical acceptable carrier may further include an excipient, diluent, or surfactant.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with activating FXR.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease in which FXR plays a role.

Another aspect of the present invention relates to a compound of Formula (I), or a pharmaceutically acceptable salt, hydrate, solvate, prodrug, stereoisomer, or tautomer thereof, for use in the manufacture of a medicament for treating a liver disease.

Another aspect of the present invention relates to a compound of Formula (I), or a pharmaceutically acceptable salt, hydrate, solvate, prodrug, stereoisomer, or tautomer thereof, for use in the manufacture of a medicament for treating an intestinal disease.

Another aspect of the present invention relates to a compound of Formula (I), or a pharmaceutically acceptable salt, hydrate, solvate, prodrug, stereoisomer, or tautomer thereof, for use in the manufacture of a medicament for treating a kidney disease.

Another aspect of the present invention relates to a compound of Formula (I), or a pharmaceutically acceptable salt, hydrate, solvate, prodrug, stereoisomer, or tautomer thereof, for use in the manufacture of a medicament for treating an autoimmune disorder.

Another aspect of the present invention relates to a compound of Formula (I), or a pharmaceutically acceptable salt, hydrate, solvate, prodrug, stereoisomer, or tautomer thereof, for use in the manufacture of a medicament for treating cancer.

Another aspect of the present invention relates to a compound of Formula (I), or a pharmaceutically acceptable salt, hydrate, solvate, prodrug, stereoisomer, or tautomer thereof, for use in the treatment of a disease associated with activating FXR.

Another aspect of the present invention relates to a compound of Formula (I), or a pharmaceutically acceptable salt, hydrate, solvate, prodrug, stereoisomer, or tautomer thereof, for use in the treatment of a disease in which FXR plays a role.

Another aspect of the present invention relates to a compound of Formula (I), or a pharmaceutically acceptable salt, hydrate, solvate, prodrug, stereoisomer, or tautomer thereof, for use in the treatment of a liver disease.

Another aspect of the present invention relates to a compound of Formula (I), or a pharmaceutically acceptable salt, hydrate, solvate, prodrug, stereoisomer, or tautomer thereof, for use in the treatment of an intestinal disease.

Another aspect of the present invention relates to a compound of Formula (I), or a pharmaceutically acceptable salt, hydrate, solvate, prodrug, stereoisomer, or tautomer thereof, for use in the treatment of a kidney disease.

Another aspect of the present invention relates to a compound of Formula (I), or a pharmaceutically acceptable salt, hydrate, solvate, prodrug, stereoisomer, or tautomer thereof, for use in the treatment of an autoimmune disorder.

Another aspect of the present invention relates to a compound of Formula (I), or a pharmaceutically acceptable salt, hydrate, solvate, prodrug, stereoisomer, or tautomer thereof, for use in the treatment of cancer.

The present invention further provides methods of treating a disease or disorder associated with modulation of FXR including, but not limited to, liver diseases, intestinal diseases, kidney disease, autoimmune disorders, or cancer, comprising administering to a patient suffering from at least one of said diseases or disorder a compound of Formula (I), or a pharmaceutically acceptable salt, hydrate, solvate, prodrug, stereoisomer, or tautomer thereof.

The present invention provides activators of FXR that are therapeutic agents in the treatment of diseases, such as liver diseases, intestinal diseases, kidney disease, autoimmune disorders, and cancer. Ultimately the present invention provides the medical community with a novel pharmacological strategy for the treatment of diseases and disorders associated with the modulation of FXR.

DETAILED DESCRIPTION OF THE INVENTION

The present invention relates to compounds and compositions that are capable of modulating the activity of FXR. The invention features methods of treating, preventing or ameliorating a disease or disorder in which FXR plays a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of FXR dependent diseases and disorders by increasing the activity of nuclear receptor FXR. Activation or modulation of FXR provides a novel approach to the treatment, prevention, or amelioration of diseases including, but not limited to, liver diseases, intestinal diseases, kidney diseases, autoimmune disorders, and cancer.

In a first aspect of the invention, the compounds of Formula (I) are described:

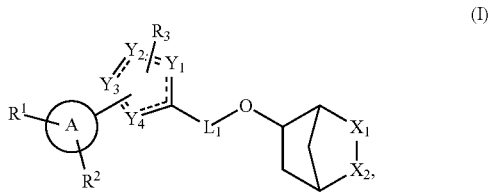

(I)

and pharmaceutically acceptable salts, hydrates, solvates, prodrugs, stereoisomers, and tautomers thereof, wherein $L_1$, A, $X_1$, $X_2$, $Y_1$, $Y_2$, $Y_3$, $Y_4$, $R^1$, $R^2$, and $R^3$ are as described herein.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used herein to refer to one or more than one (e.g., to at least one) of the grammatical object of the article. By way of example, "an element" means one element or more than one element.

The term "and/or" is used herein to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, ($C_1$-$C_6$) alkenyl, ($C_1$-$C_6$) alkynyl, ($C_1$-$C_6$) hydroxyalkyl, ($C_1$-$C_6$) alkoxy, ($C_1$-$C_6$) haloalkyl, ($C_1$-$C_6$) haloalkoxy, ($C_3$-$C_7$) cycloalkyl, aryl, heterocycloalkyl, heteroaryl, —O—($C_2$-$C_6$) alkenyl, —O—($C_2$-$C_6$) alkynyl, ($C_2$-$C_6$) alkenyl, ($C_2$-$C_6$) alkynyl, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)$_2$NH($C_1$-$C_6$) alkyl, and S(O)$_2$N(($C_1$-$C_6$) alkyl)$_2$. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, NH(($C_1$-$C_6$) alkyl), N(($C_1$-$C_6$) alkyl)$_2$, —S(O)$_2$—($C_1$-$C_6$) alkyl, —S(O)$_2$NH($C_1$-$C_6$) alkyl, and —S(O)$_2$N(($C_1$-$C_6$) alkyl)$_2$. Furthermore when containing two fused rings an aryl group herein defined may be fused to an unsaturated or partially saturated ring, or fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from the group consisting of N, O, and S, the remaining ring atoms being C. Heteroaryl as herein defined also means a bicyclic heteroaromatic group wherein the heteroatom is selected from the group consisting of N, O, and S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1λ$^2$-pyrrolo[2,1-b]

pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may be fused to an unsaturated or partially saturated ring containing a heteroatom selected from N, O and S;

or fused with a fully saturated ring containing a heteroatom selected from N, O and S. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

"Alkyl", either alone or in combination with other groups (e.g. alkoxy, haloalkyl and the like) refers to a straight or branched chain saturated, unsaturated (fully or partially) hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl. In an embodiment, "alkyl" is fully saturated.

"Alkoxy" refers to a straight or branched chain saturated or unsaturated (fully or partially) hydrocarbon containing 1-12 carbon atoms containing a terminal "O" in the chain, e.g., —O(alkyl). Examples of alkoxy groups include without limitation, methoxy, ethoxy, propoxy, butoxy, t-butoxy, or pentoxy groups. In an embodiment, "alkoxy" is fully saturated.

"Alkoxyalkoxy" refers to an alkoxy group as defined herein which is substituted with an alkoxy group e.g., —O(alkyl)-O-(alkyl). Examples of alkoxyalkoxy groups include without limitation, methoxymethoxy, ethoxyethoxy, propoxymethoxy, or ethoxymethoxy.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkynyl groups include ethynyl, propanyl, n-butynyl, iso-butynyl, pentynyl, or hexynyl. An alkynyl group can be unsubstituted or substituted.

"Cycloalkyl" or "carbocyclyl" means monocyclic or polycyclic saturated or unsaturated (fully or partially) non-aromatic carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl and derivatives thereof. A $C_3$-$C_8$ cycloalkyl is a cycloalkyl group containing between 3 and 8 carbon atoms. A cycloalkyl group can be fused (e.g., decalin) or bridged (e.g., norbornane). In an embodiment, "cycloalkyl" is fully saturated.

"Heterocyclyl" or "heterocycloalkyl" monocyclic or polycyclic rings containing carbon and heteroatoms taken from oxygen, nitrogen, or sulfur and wherein there is not delocalized π electrons (aromaticity) shared among the ring carbon or heteroatoms. In an embodiment, heterocycloalkyl comprises one or two 4- to 7-membered rings and 1-4 heteroatoms selected from the group consisting of N, O and S, or heteroaryl. The heterocycloalkyl ring structure may be substituted by one or more substituents. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl. In an embodiment, "heterocycle" or "heterocycloalkyl" is fully saturated.

The term "hydroxyalkyl" means an alkyl group as defined above, where the alkyl group is substituted with one or more —OH groups. Examples of hydroxyalkyl groups include HO—$CH_2$—, HO—$CH_2$—$CH_2$— and $CH_3$—CH(OH)—. In an embodiment, "hydroxyalkyl" is fully saturated.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc. In an embodiment, "haloalkyl" is fully saturated.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc. In an embodiment, "haloalkoxy" is fully saturated.

The term "cyano" as used herein means a substituent having a carbon atom joined to a nitrogen atom by a triple bond, e.g., C≡N.

The term "oxo" as used herein refers to an "=O" group.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A ($C_3$-$C_{12}$) spirocycloalkyl is a spirocycle containing between 3 and 12 carbon atoms. One or more of the carbon atoms can be substituted with a heteroatom. In an embodiment, "spirocycloalkyl" or "spirocyclyl" is fully saturated.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl). In an embodiment, "spiroheterocycloalkyl" or "spiroheterocyclyl" is fully saturated.

As defined herein, "GW4064" is an FXR agonist compound having the following structure.

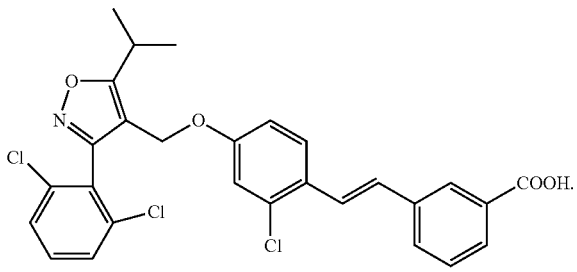

GW4064

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The invention also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used herein, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used herein to mean, and is used interchangeably with, the terms disease, condition, or illness, unless otherwise indicated.

The term "administer", "administering", or "administration" as used herein refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used herein, means a compound which is convertible in vivo by metabolic means (e.g., by hydrolysis) to a disclosed compound.

The term "autoimmune disease" includes, but is not limited to, the following autoimmune diseases: Amyotrophic Lateral Sclerosis (ALS), Autoimmune Atherosclerosis, Autoimmune Diabetes Insipidus, Autoimmune Gastritis, Autoimmune Hepatitis, Autoimmune Interstitial Cystitis, Autoimmune Uveitis, Autoimmune Vasculitis, Behcet's Disease, Celiac Disease, Chronic Fatigue Syndrome, Crohn's Disease, chronic active hepatitis, Diabetes Mellitus, Multiple Sclerosis, PBC, Primary Biliary Cirrhosis, Primary Glomerulonephritis, Primary Sclerosing Cholangitis, Psoriasis, Psoriatic Arthritis, Scleroderma, Sjogren's Syndrome, Systemic Lupus Erythematosus, Ulcerative Colitis, and Vasculitis.

The term "kidney disease" includes, but is not limited to the following kidney diseases: fibrotic renal disease and diabetic nephrophathy.

The term "liver disease" includes, but is not limited to, the following liver diseases: primary biliary cirrhosis (PBC), primary sclerosing cholangitis (PSC), non-alcoholic fatty liver disease (NAFLD), non-alcoholic steatohepatitis (NASH), alcoholic liver disease, intra- and extra-cholestasis, portal vein hypertension (PAH), obesity and Type 2 Diabetes.

The term "intestinal disease" includes, but is not limited to the following intestinal diseases: inflammatory bowel disease, Crohn's disease, ulcerative colitis, proctitis, pouchitis, Celiac's disease and bile acid diarrhea.

The term "cancer" includes, but is not limited to, the following cancers: hepatocellular carcinoma, hepatocellular adenoma, cholangiocarcinoma, colorectal cancer, colorectal adenoma, ileal adenoma, renal cancer, oesophageal cancer, gastric cancer, gastric carcinoma, colon carcinoma, gastrointestinal stromal carcinoma, bile duct carcinoma, renal carcinoma, breast cancer, and Barett's esophagus, and combinations thereof.

The present invention relates to compounds or pharmaceutically acceptable salts, hydrates, solvates, prodrugs, stereoisomers, or tautomers thereof, capable of activating FXR, which are useful for the treatment of diseases and disorders associated with modulation of a FXR protein or receptor. The invention further relates to compounds, or pharmaceutically acceptable salts, hydrates, solvates, prodrugs, stereoisomers, or tautomers thereof, which are useful for activating FXR.

The present invention relates to compounds or pharmaceutically acceptable salts, hydrates, solvates, prodrugs, stereoisomers, or tautomers thereof, capable of activating FXR, which are useful for the treatment of diseases and disorders associated with modulation of a FXR protein. The invention further relates to compounds, or pharmaceutically acceptable salts, hydrates, solvates, prodrugs, stereoisomers, or tautomers thereof, which are useful for activating FXR.

In one embodiment, compounds of the invention have the structure of Formula (I):

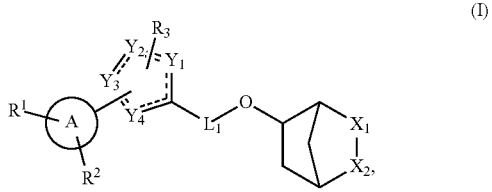

(I)

or a salt thereof, wherein:
one of $X_1$ or $X_2$ is $NR_x$ or $N^+(O^-)R_x$ and the other is $CHR_y$ or $C(O)$;
$Y_1$, $Y_2$, $Y_3$ and $Y_4$ are independently C, CH or N, wherein one of $Y_1$ and $Y_4$ is substituted with R3 and the other is substituted with ring A;
$R_x$ is

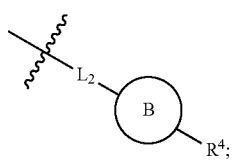

$R_y$ is H, alkyl, cycloalkyl or cycloalkylalkyl wherein said alkyl, cycloalkyl and cycloalkylalkyl are optionally substituted with halogen or alkoxy;
$L_1$ is $—(CH_2)_m(C=O)—$ or $—(CH_2)_p—$;
$L_2$ is a bond or $—S(O)_2—$;
A is cycloalkyl, aryl, heterocycloalkyl or heteroaryl, wherein the cycloalkyl, aryl, heterocycloalkyl, or heteroaryl is optionally substituted with one or more $R^7$;
B is aryl or heteroaryl, wherein the aryl or heteroaryl is optionally substituted with one or more $R^5$;
$R^1$ and $R^2$ are each independently H, alkyl, alkoxy, haloalkyl, haloalkoxy, halogen, cycloalkyl, or CN, wherein the cycloalkyl is optionally substituted with one or more $R^9$;
or when A is cycloalkyl or heterocycloalkyl, $R^1$ and $R^2$ together when attached to the same carbon atom form a spirocycloalkyl ring optionally substituted with one or more $R^8$; or when A is cycloalkyl or heterocycloalkyl, $R^1$ and $R^2$ together when attached to the same atom form a spiroheterocycloalkyl ring optionally substituted with one or more $R^8$; or $R^1$ and $R^2$ when on adjacent atoms together with the atoms to which they are attached form a cycloalkyl ring optionally substituted with one or more $R^8$; or $R^1$ and $R^2$ when on adjacent atoms together with the atoms to which they are attached form a heterocycloalkyl ring optionally substituted with one or more $R^8$; or $R^1$ and $R^2$ when on adjacent atoms together with the atoms to which they are attached form an aryl ring optionally substituted with one or more $R^8$; or $R^1$ and $R^2$ when on adjacent atoms together with the atoms to which they are attached form a heteroaryl ring optionally substituted with one or more $R^8$; or when A is cycloalkyl or heterocycloalkyl, $R^1$ and $R^2$ when on non-adjacent atoms, together with the atoms to which they are attached form a cycloalkyl ring optionally substituted with one or more $R^8$; or when cycloalkyl or heterocycloalkyl, $R^1$ and $R^2$ when on non-adjacent atoms, together with the atoms to which they are attached form a heterocycloalkyl ring optionally substituted with one or more $R^8$; cycloalkyl ring optionally substituted with one or more $R^8$; or when cycloalkyl or heterocycloalkyl, $R^1$ and $R^2$ together with the atoms to which they are attached form a heterocycloalkyl ring optionally substituted with one or more $R^8$;

$R^3$ is alkyl, alkoxy, haloalkyl, haloalkoxy, hydroxyalkyl, or cycloalkyl optionally substituted with one or more substituents each independently selected from the group consisting of halogen, alkyl, alkoxy, haloalkyl, haloalkoxy, and —OH;

$R^4$ is $COOR^{6a}$, $—(CH_2)_n—COOR^{6a}$, $CONR^{6b}OH$, $CONR^{6b}R^{6c}$, $CONH(CH_2)_nCOOR^{6a}$, $CONH(CH_2)_nR^{6a}$, $—(CH_2)_nCONH(CH_2)_nR^{6a}$, $CONR^{6b}SO_2R^{6d}$, $CONR^{6b}SO_2(CH_2)_nR^{6d}$, $—(CH_2)_n—CONR^{6b}SO_2R^{6d}$, $CONR^{6b}SO_2(CH_2)_nN(CO)R^{6d}CONH(CH_2)_nSO_2R^{6e}$, $COR^{6f}$, $(CH_2)_nP(OR^{6g})_2$, $COO(CH_2)_nPO(OR^{6g})_2$, $SO_2NR^{6b}(CH_2)_nCOOR^{6a}$, $SO_2R^{6e}$, CN, $—(CH_2)_n—NR^{6b}C(O)R^{6c}$, $—(CH_2)_n—N(OH)—C(O)R^{6c}$, oxo, alkyl, cycloalkyl, $—(CH_2)_n$-cycloalkyl, heterocycloalkyl, $—(CH_2)_n$-heterocycloalkyl, heteroaryl and $—(CH_2)_n$-heteroaryl; wherein said alkyl, cycloalkyl, $—(CH_2)_n$-cycloalkyl, heterocycloalkyl, $—(CH_2)_n$-heterocycloalkyl, heteroaryl and $—(CH_2)_n$-heteroaryl are optionally substituted with $COOR^{6a}$, $—(CH_2)_n—COOR^{6a}$, $CONR^{6b}OH$, $CONR^{6b}R^{6c}$, $CONH(CH_2)_nCOOR^{6a}$, $CONH(CH_2)_nR^{6a}$, $—(CH_2)_nCONH(CH_2)_nR^{6a}$, $CONR^{6b}SO_2R^{6d}$, $CONR^{6b}SO_2(CH_2)_nR^{6d}$, $—(CH_2)_n—CONR^{6b}SO_2R^{6d}$, $CONR^{6b}SO_2(CH_2)_nN(CO)R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$, CN, $—(CH_2)_n—NR^{6b}C(O)R^{6c}$, $—(CH_2)_n—N(OH)—C(O)R^{6c}$;

each $R^5$ is independently at each occurrence halogen, alkyl, haloalkyl, alkoxy, haloalkoxy, CN, cycloalkyl, aryl, heterocycloalkyl, or heteroaryl wherein the cycloalkyl, aryl, heterocycloalkyl or heteroaryl are optionally substituted with one or more substituents each independently selected from the group consisting of halogen, alkyl, haloalkyl, alkoxy, and haloalkoxy;

$R^{6a}$ is H, alkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, $NR^{6b}R^{6c}$ and —OH;

$R^{6b}$ and $R^{6c}$ are each independently H, alkyl, haloalkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

$R^{6d}$ is alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, COOH, alkyl, haloalkyl, alkoxy, haloalkoxy, alkoxyalkoxy, —O—CO-alkyl, —O—COcycloalkyl, —O—CO-alkyl-COOH, $NR^{6b}R^{6c}$, $NR^{6f}CO$-alkyl, $NR^{6f}CO$-alkoxy, cycloalkyl, heterocycloalkyl and —OH;

$R^{6e}$ is —OH, alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

$R^{6f}$ is alkyl or haloalkyl;

$R^{6g}$ is H or alkyl optionally substituted with —O—CO-alkyl;

each $R^7$ is independently at each occurrence alkyl, alkoxy, haloalkyl, haloalkoxy, halogen, or CN;

each $R^8$ is independently at each occurrence alkyl, alkoxy, haloalkyl, haloalkoxy, halogen, or —OH;

each $R^9$ is independently at each occurrence alkyl, alkoxy, haloalkyl, haloalkoxy, halogen, or —OH;

m is 0, 1, or 2;

n is 1, 2, 3, or 4; and p is 1 or 2.

In another embodiment, compounds of the invention have the Formula (I)

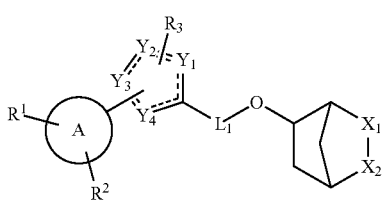
(I)

wherein:

one of $X_1$ or $X_2$ is $NR_x$ and the other is $CH_2$;

$Y_1$, $Y_2$, $Y_3$ and $Y_4$ are independently C, CH or N, wherein one of $Y_1$ and $Y_4$ is substituted with R3 and the other is substituted with ring A;

$R_x$ is

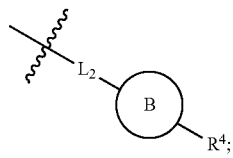

$L_1$ is —$(CH_2)_m(C=O)$— or —$(CH_2)_p$—;

$L_2$ is a bond or —$S(O)_2$—;

A is $(C_3-C_8)$ cycloalkyl, $(C_6-C_{10})$ aryl, heterocycloalkyl, wherein the heterocycloalkyl comprises one or two 5- to 7-membered rings and 1-4 heteroatoms selected from the group consisting of N, O and S, or heteroaryl, wherein the heteroaryl comprises one or two 5- or 6-membered rings and 1-4 heteroatoms selected from the group consisting of N, O and S, and wherein the cycloalkyl, aryl, heterocycloalkyl, or heteroaryl is optionally substituted with one or more $R^7$;

B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$;

$R^1$ and $R^2$ are each independently H, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, $(C_3-C_7)$ cycloalkyl, or CN, wherein the cycloalkyl is optionally substituted with one or more $R^9$;

or $R^1$ and $R^2$ together when attached to the same carbon atom form a $(C_3-C_8)$ spirocycloalkyl ring optionally substituted with one or more $R^8$; or $R^1$ and $R^2$ together when attached to the same atom form a $(C_3-C_8)$ spiroheterocycloalkyl ring optionally substituted with one or more $R^8$; or $R^1$ and $R^2$ on adjacent atoms together with the atoms to which they are attached form a $(C_3-C_8)$ cycloalkyl ring optionally substituted with one or more $R^8$; or $R^1$ and $R^2$ on adjacent atoms together with the atoms to which they are attached form a heterocycloalkyl ring optionally substituted with one or more $R^8$; or $R^1$ and $R^2$ on adjacent atoms together with the atoms to which they are attached form an aryl ring optionally substituted with one or more $R^8$; or $R^1$ and $R^2$ on adjacent atoms together with the atoms to which they are attached form a heteroaryl ring optionally substituted with one or more $R^8$; or when A is cycloalkyl or heterocycloalkyl, $R^1$ and $R^2$ together with the atoms to which they are attached form a $(C_3-C_8)$ cycloalkyl ring optionally substituted with one or more $R^8$; or when cycloalkyl or heterocycloalkyl, $R^1$ and $R^2$ together with the atoms to which they are attached form a heterocycloalkyl ring optionally substituted with one or more $R^8$;

$R^3$ is $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, $(C_1-C_6)$ hydroxyalkyl, or $(C_3-C_7)$ cycloalkyl optionally substituted with one or more substituents each independently selected from the group consisting of halogen, $(C_1-C_6)$ alkyl, $(C_1-C_6)$ alkoxy, $(C_1-C_6)$ haloalkyl, $(C_1-C_6)$ haloalkoxy, and —OH;

$R^4$ is $COOR^{6a}$, $CONR^{6b}R^{6c}$, $CONH(CH_2)_nCOOR^{6a}$, $CONR^{6b}SO_2R^{6d}$, $CONH(CH_2)_nSO_2R^{6e}$, CN, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S;

each $R^5$ is independently at each occurrence halogen, $(C_1-C_6)$ alkyl, $(C_1-C_6)$ haloalkyl, $(C_1-C_6)$ alkoxy, $(C_1-C_6)$ haloalkoxy, CN, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the cycloalkyl, aryl, heterocycloalkyl or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy;

$R^{6a}$ is H, $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH;

$R^{6b}$ and $R^{6c}$ are each independently H, $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH;

$R^{6d}$ is $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH;

$R^{6e}$ is —OH, $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH;

each $R^7$ is independently at each occurrence $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, or CN;

each $R^8$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or OH;

each $R^9$ is independently at each occurrence $(C_1-C_6)$ alkyl, $(C_1-C_6)$ alkoxy, $(C_1-C_6)$ haloalkyl, $(C_1-C_6)$ haloalkoxy, halogen, or OH;

m is 0, 1, or 2; and p is 1 or 2.

In some embodiments of the Formulae above, $X_1$ is $CHR_y$ or C(O) and $X_2$ is $NR_x$ or $N^+(O^-)R_x$. In an embodiment, $X_1$ is $CHR_y$ and $X_2$ is $NR_x$ or $N^+(O^-)R_x$. In an embodiment, $X_1$ is C(O) and $X_2$ is $NR_x$ or $N^+(O^-)R_x$. In an embodiment, $X_1$ is $CHR_y$ and $X_2$ is $NR_x$. In an embodiment, $X_1$ is C(O) and $X_2$ is $NR_x$. In an embodiment, $X_1$ is $CHR_y$ and $X_2$ is $N^+(O^-)R_x$. In an embodiment, $X_1$ is C(O) and $X_2$ is $N^+(O^-)R_x$. In an embodiment, $X_1$ is $CH_2$ and $X_2$ is $NR_x$. In another embodiment, $X_1$ is $NR_x$ or $N^+(O^-)R_x$ and $X_2$ is $CHR_y$ or C(O). In another embodiment, $X_1$ is $NR_x$ and $X_2$ is $CHR_y$ or C(O). In another embodiment, $X_1$ is $N^+(O^-)R_x$ and $X_2$ is $CHR_y$ or C(O). In another embodiment, $X_1$ is $NR_x$ and $X_2$ is $CHR_y$. In another embodiment, $X_1$ is $NR_x$ and $X_2$ is C(O). In another embodiment, $X_1$ is $N^+(O^-)R_x$ and $X_2$ is $CHR_y$. In another embodiment, $X_1$ is $N^+(O^-)R_x$ and $X_2$ is C(O). In another embodiment, $X_1$ is $NR_x$ and $X_2$ is $CH_2$.

In some embodiments of the Formulae above, $L_1$ is —$(CH_2)_m(C=O)$—. In another embodiment $L_1$ is —$(CH_2)_p$—. In another embodiment $L_1$ is —$CH_2$—. In another embodiment $L_1$ is —$CH_2C(O)$—. In another embodiment $L_1$ is —C(O)—.

In some embodiments of the Formulae above, $L_2$ is a bond. In another embodiment $L_2$ is —$S(O)_2$—.

In some embodiments of the Formulae above, A is $(C_3-C_8)$ cycloalkyl optionally substituted with one or more $R^7$. In another embodiment, A is $(C_3-C_8)$ cycloalkyl. In yet another embodiment, A is $(C_3-C_8)$ cycloalkyl substituted with one or more $R^7$. In another embodiment, $(C_6-C_{10})$ aryl optionally substituted with one or more $R^7$. In yet another embodiment, A is $(C_6-C_{10})$ aryl. In another embodiment, A is $(C_6-C_{10})$ aryl substituted with one or more $R^7$. In an embodiment, A is phenyl optionally substituted with one or more $R^7$. In another embodiment, A is phenyl unsubstituted by $R^7$ while $R^1$ and $R^2$ are both a halogen. In another embodiment, A is phenyl unsubstituted by $R^7$ while $R^1$ and $R^2$ are both a Cl at the ortho positions relative to the isoxazole ring. In yet another embodiment, A is heterocycloalkyl wherein the heterocycloalkyl comprises one or two 5- to 7-membered rings and 1-4 heteroatoms selected from the group consisting of N, O and S, optionally substituted with one or more $R^7$. In another embodiment, A is heterocycloalkyl comprising one or two 5- to 7-membered rings and 1-4 heteroatoms selected from the group consisting of N, O and S. In yet another embodiment, A is heterocycloalkyl wherein the heterocycloalkyl comprises one or two 5- to 7-membered rings and 1-4 heteroatoms selected from the group consisting of N, O and S, substituted with one or more $R^7$. In another embodiment, A is heteroaryl wherein the heteroaryl comprises one or two 5- or 6-membered rings and 1-4 heteroatoms selected from the group consisting of N, O and S, optionally substituted with one or more $R^7$. In yet another embodiment, A is heteroaryl wherein the heteroaryl comprises one or two 5- or 6-membered rings and 1-4 heteroatoms selected from the group consisting of N, O and S.

In another embodiment, A is heteroaryl wherein the heteroaryl comprises one or two 5- or 6-membered rings and 1-4 heteroatoms selected from the group consisting of N, O and S, substituted with one or more $R^7$. In yet another embodiment, A is $(C_3-C_8)$ cycloalkyl or heterocycloalkyl wherein the heterocycloalkyl comprises one or two 5- to 7-membered rings and 1-4 heteroatoms selected from the group consisting of N, O and S, wherein the cycloalkyl or heterocycloalkyl are optionally substituted with one or more $R^7$. In another embodiment, A is $(C_6-C_{10})$ aryl or heteroaryl wherein the heteroaryl comprises one or two 5- or 6-membered rings and 1-4 heteroatoms selected from the group consisting of N, O and S, wherein the aryl or heteroaryl is optionally substituted with one or more $R^7$. In yet another embodiment, A is $(C_3-C_8)$ cycloalkyl, $(C_6-C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$. In another embodiment, A is $(C_3-C_8)$ cycloalkyl or $(C_6-C_{10})$ aryl, wherein the cycloalkyl or aryl are optionally substituted with one or more $R^7$. In yet another embodiment, A is $(C_6-C_{10})$ aryl or heterocycloalkyl wherein the heterocycloalkyl comprises one or two 5- to 7-membered rings and 1-4 heteroatoms selected from the group consisting of N, O and S, wherein the aryl or heterocycloalkyl are optionally substituted with one or more $R^7$.

In some embodiments of the Formulae above, B is $(C_6-C_{10})$ aryl optionally substituted with one or more $R^5$. In another embodiment, B is heteroaryl comprising one or two 5- or 6-member rings and 1-4 heteroatoms selected from the group consisting of N, O and S, optionally substituted with one or more $R^5$. In yet another embodiment, B is $(C_6-C_{10})$ aryl. In another embodiment, B is $(C_6-C_{10})$ aryl substituted with one or more $R^5$. In yet another embodiment, B is heteroaryl. In another embodiment, B is heteroaryl comprising one or two 5- or 6-member rings and 1-4 heteroatoms selected from the group consisting of N, O and S, substituted with one or more $R^5$. In another embodiment, B is $(C_6-C_{10})$ aryl or heteroaryl wherein the heteroaryl comprises one or two 5- or 6-member rings and 1-4 heteroatoms selected from the group consisting of N, O and S. In another embodiment, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl are substituted with one or more $R^5$.

In some embodiments of the Formulae above, $R^1$ is H, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, or halogen. In another embodiment, $R^1$ is halogen, CN, or $(C_3-C_7)$ cycloalkyl optionally substituted with one or more $R^9$. In yet another embodiment, $R^1$ is H, $(C_1-C_6)$ alkyl, $(C_1-C_6)$ alkoxy, $(C_1-C_6)$ haloalkyl, $(C_1-C_6)$ haloalkoxy, halogen, or $(C_3-C_7)$ cycloalkyl optionally substituted with one or more $R^9$. In another embodiment, $R^1$ is H, $(C_1-C_6)$ alkyl, $(C_1-C_6)$ alkoxy, halogen, or $(C_3-C_7)$ cycloalkyl optionally substituted with one or more $R^9$. In yet another embodiment, $R^1$ is $(C_1-C_6)$ alkyl, $(C_1-C_6)$ alkoxy, halogen, or $(C_3-C_7)$ cycloalkyl optionally substituted with one or more $R^9$. In another embodiment, $R^1$ is H, $(C_1-C_6)$ alkoxy, $(C_1-C_6)$ haloalkyl, $(C_1-C_6)$ haloalkoxy, or halogen. In yet another embodiment, $R^1$ is $(C_1-C_6)$ alkoxy, $(C_1-C_6)$ haloalkyl, $(C_1-C_6)$ haloalkoxy, or halogen. In another embodiment, $R^1$ is H, $(C_1-C_6)$ alkoxy, $(C_1-C_6)$ haloalkoxy, or halogen. In yet another embodiment, $R^1$ is $(C_1-C_6)$ alkoxy, $(C_1-C_6)$ haloalkoxy, or halogen. In another embodiment, $R^1$ is H, $(C_1-C_6)$ haloalkyl, $(C_1-C_6)$ haloalkoxy, or halogen. In yet another embodiment, $R^1$ is $(C_1-C_6)$ haloalkyl, $(C_1-C_6)$ haloalkoxy, or halogen. In another embodiment, $R^1$ is $(C_1-C_6)$ alkyl, $(C_1-C_6)$ alkoxy, $(C_1-C_6)$ haloalkyl, $(C_1-C_6)$ haloalkoxy, halogen, or $(C_3-C_7)$ cycloalkyl optionally substituted with one or more $R^9$. In yet another embodiment, $R^1$ is H, $(C_1-C_6)$ haloalkyl, or halogen. In another embodiment, $R^1$ is $(C_1-C_6)$ haloalkyl or halogen.

In some embodiments of the Formulae above, $R^2$ is H, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, or halogen. In another embodiment, $R^2$ is halogen, CN, or $(C_3-C_7)$ cycloalkyl optionally substituted with one or more $R^9$. In yet another embodiment, $R^2$ is H, $(C_1-C_6)$ alkyl, $(C_1-C_6)$ alkoxy, $(C_1-C_6)$ haloalkyl, $(C_1-C_6)$ haloalkoxy, halogen, or $(C_3-C_7)$ cycloalkyl optionally substituted with one or more $R^9$. In another embodiment, $R^2$ is H, $(C_1-C_6)$ alkyl, $(C_1-C_6)$ alkoxy, halogen, or $(C_3-C_7)$ cycloalkyl optionally substituted with one or more $R^9$. In yet another embodiment, $R^2$ is $(C_1-C_6)$ alkyl, $(C_1-C_6)$ alkoxy, halogen, or $(C_3-C_7)$ cycloalkyl optionally substituted with one or more $R^9$. In another embodiment, $R^2$ is H, $(C_1-C_6)$ alkoxy, $(C_1-C_6)$ haloalkyl, $(C_1-C_6)$ haloalkoxy, or halogen. In yet another embodiment, $R^2$ is $(C_1-C_6)$ alkoxy, $(C_1-C_6)$ haloalkyl, $(C_1-C_6)$ haloalkoxy, or halogen. In another embodiment, $R^2$ is H, $(C_1-C_6)$ alkoxy, $(C_1-C_6)$ haloalkoxy, or halogen. In yet another embodiment, $R^2$ is $(C_1-C_6)$ alkoxy, $(C_1-C_6)$ haloalkoxy, or halogen. In another embodiment, $R^2$ is H, $(C_1-C_6)$ haloalkyl, $(C_1-C_6)$ haloalkoxy, or halogen. In yet another embodiment, $R^2$ is $(C_1-C_6)$ haloalkyl, $(C_1-C_6)$ haloalkoxy, or halogen. In another embodiment, $R^2$ is $(C_1-C_6)$ alkyl, $(C_1-C_6)$ alkoxy, $(C_1-C_6)$ haloalkyl, $(C_1-C_6)$ haloalkoxy, halogen, or $(C_3-C_7)$ cycloalkyl optionally substituted with one or more $R^9$. In yet another embodiment, $R^2$ is H, $(C_1-C_6)$ haloalkyl, or halogen. In another embodiment, $R^2$ is $(C_1-C_6)$ haloalkyl or halogen.

In some embodiments of the Formulae above, $R^1$ and $R^2$ together when attached to the same carbon atom form a $(C_3-C_8)$ spirocycloalkyl ring optionally substituted with one or more $R^8$. In another embodiment, $R^1$ and $R^2$ together when attached to the same carbon atom form a $(C_3-C_8)$ spirocycloalkyl ring optionally substituted with one to three $R^8$. In yet another embodiment, $R^1$ and $R^2$ together when attached to the same carbon atom form a $(C_3-C_8)$ spirocycloalkyl ring. In another embodiment, $R^1$ and $R^2$ together when attached to the same carbon atom form a $(C_3-C_8)$ spirocycloalkyl ring substituted with one to three $R^8$.

In some embodiments of the Formulae above, $R^1$ and $R^2$ together when attached to the same atom form a $(C_3-C_8)$ spiroheterocycloalkyl ring optionally substituted with one or more $R^8$. In another embodiment, $R^1$ and $R^2$ together when attached to the same atom form a $(C_3-C_8)$ spiroheterocycloalkyl ring optionally substituted with one to three $R^8$. In yet another embodiment, $R^1$ and $R^2$ together when attached to the same atom form a $(C_3-C_8)$ spiroheterocycloalkyl ring. In another embodiment, $R^1$ and $R^2$ together when attached to the same atom form a $(C_3-C_8)$ spiroheterocycloalkyl ring substituted with one to three $R^8$.

In some embodiments of the Formulae above, $R^1$ and $R^2$ on adjacent atoms together with the atoms to which they are attached form a $(C_3-C_8)$ cycloalkyl ring optionally substituted with one or more $R^8$. In another embodiment, $R^1$ and $R^2$ on adjacent atoms together with the atoms to which they are attached form a $(C_3-C_8)$ cycloalkyl ring optionally substituted with one to three $R^8$. In yet another embodiment, $R^1$ and $R^2$ on adjacent atoms together with the atoms to which they are attached form a $(C_3-C_8)$ cycloalkyl ring. In another embodiment, $R^1$ and $R^2$ on adjacent atoms together with the atoms to which they are attached form a $(C_3-C_8)$ cycloalkyl ring substituted with one to three $R^8$.

In some embodiments of the Formulae above, $R^1$ and $R^2$ on adjacent atoms together with the atoms to which they are attached form a heterocycloalkyl ring optionally substituted with one or more $R^8$. In another embodiment, $R^1$ and $R^2$ on adjacent atoms together with the atoms to which they are attached form a heterocycloalkyl ring optionally substituted with one to three $R^8$. In yet another embodiment, $R^1$ and $R^2$ on adjacent atoms together with the atoms to which they are attached form a heterocycloalkyl ring. In another embodiment, $R^1$ and $R^2$ on adjacent atoms together with the atoms to which they are attached form a heterocycloalkyl ring substituted with one to three $R^8$.

In some embodiments of the Formulae above, $R^1$ and $R^2$ on adjacent atoms together with the atoms to which they are attached form an aryl ring optionally substituted with one or more $R^8$. In another embodiment, $R^1$ and $R^2$ on adjacent atoms together with the atoms to which they are attached form an aryl ring optionally substituted with one to three $R^8$. In yet another embodiment, $R^1$ and $R^2$ on adjacent atoms together with the atoms to which they are attached form an aryl ring. In another embodiment, $R^1$ and $R^2$ on adjacent atoms together with the atoms to which they are attached form an aryl ring substituted with one to three $R^8$.

In some embodiments of the Formulae above, $R^1$ and $R^2$ on adjacent atoms together with the atoms to which they are attached form a heteroaryl ring optionally substituted with one or more $R^8$. In another embodiment, $R^1$ and $R^2$ on adjacent atoms together with the atoms to which they are attached form a heteroaryl ring optionally substituted with one to three $R^8$. In yet another embodiment, $R^1$ and $R^2$ on adjacent atoms together with the atoms to which they are attached form a heteroaryl ring. In another embodiment, $R^1$ and $R^2$ on adjacent atoms together with the atoms to which they are attached form a heteroaryl ring substituted with one to three $R^8$.

In some embodiments of the Formulae above, when A is cycloalkyl or heterocycloalkyl, $R^1$ and $R^2$ together with the atoms to which they are attached form a $(C_4-C_8)$ cycloalkyl ring optionally substituted with one or more $R^8$. In another embodiment, when A is cycloalkyl or heterocycloalkyl, $R^1$ and $R^2$ together with the atoms to which they are attached form a ($C_4$-$C_8$) cycloalkyl ring optionally substituted with one to three $R^8$. In yet another embodiment, when A is cycloalkyl or heterocycloalkyl, $R^1$ and $R^2$ together with the atoms to which they are attached form a ($C_4$-$C_8$) cycloalkyl ring. In another embodiment, when A is cycloalkyl or heterocycloalkyl, $R^1$ and $R^2$ together with the atoms to which they are attached form a ($C_4$-$C_8$) cycloalkyl ring substituted with one to three $R^8$.

In some embodiments of the Formulae above, when cycloalkyl or heterocycloalkyl, $R^1$ and $R^2$ together with the atoms to which they are attached form a heterocycloalkyl ring optionally substituted with one or more $R^8$. In another embodiment, when cycloalkyl or heterocycloalkyl, $R^1$ and $R^2$ together with the atoms to which they are attached form a heterocycloalkyl ring optionally substituted with one to three $R^8$. In yet another embodiment, when cycloalkyl or heterocycloalkyl, $R^1$ and $R^2$ together with the atoms to which they are attached form a heterocycloalkyl ring. In another embodiment, when cycloalkyl or heterocycloalkyl, $R^1$ and $R^2$ together with the atoms to which they are attached form a heterocycloalkyl ring substituted with one to three $R^8$.

In some embodiments of the Formulae above, $R^3$ is ($C_1$-$C_4$) alkyl, ($C_2$-$C_4$) alkenyl, ($C_2$-$C_4$) alkynyl, ($C_1$-$C_4$) alkoxy, ($C_1$-$C_4$) haloalkyl, ($C_1$-$C_4$) haloalkoxy, ($C_1$-$C_4$) hydroxyalkyl, or ($C_3$-$C_7$) cycloalkyl optionally substituted with one or more substituents each independently selected from the group consisting of halogen, ($C_1$-$C_6$) alkyl, ($C_1$-$C_6$) alkoxy, ($C_1$-$C_6$) haloalkyl, ($C_1$-$C_6$) haloalkoxy, and —OH. In another embodiment, $R^3$ is ($C_1$-$C_4$) alkyl, ($C_2$-$C_4$) alkenyl, ($C_2$-$C_4$) alkynyl, or ($C_1$-$C_4$) alkoxy. In yet another embodiment, $R^3$ is ($C_1$-$C_4$) haloalkyl, ($C_1$-$C_4$) haloalkoxy, or ($C_1$-$C_4$) hydroxyalkyl. In another embodiment, $R^3$ is ($C_1$-$C_4$) alkyl, ($C_1$-$C_4$) alkoxy, ($C_1$-$C_4$) haloalkyl, ($C_1$-$C_4$) haloalkoxy, ($C_1$-$C_4$) hydroxyalkyl, or ($C_3$-$C_7$) cycloalkyl optionally substituted with one or more substituents each independently selected from the group consisting of halogen, ($C_1$-$C_6$) alkyl, ($C_1$-$C_6$) alkoxy, ($C_1$-$C_6$) haloalkyl, ($C_1$-$C_6$) haloalkoxy, and —OH. In yet another embodiment, $R^3$ is ($C_1$-$C_4$) alkyl or ($C_3$-$C_7$) cycloalkyl optionally substituted with one or more substituents each independently selected from the group consisting of halogen, ($C_1$-$C_6$) alkyl, ($C_1$-$C_6$) alkoxy, ($C_1$-$C_6$) haloalkyl, ($C_1$-$C_6$) haloalkoxy, and —OH. In another embodiment, $R^3$ is ($C_1$-$C_4$) alkyl or ($C_3$-$C_7$) cycloalkyl optionally substituted with one or more substituents each independently selected from the group consisting of halogen and ($C_1$-$C_6$) alkyl. In yet another embodiment, $R^3$ is ($C_3$-$C_7$) cycloalkyl optionally substituted with one or more substituents each independently selected from the group consisting of halogen, ($C_1$-$C_6$) alkyl, ($C_1$-$C_6$) alkoxy, ($C_1$-$C_6$) haloalkyl, ($C_1$-$C_6$) haloalkoxy, and —OH. In another embodiment, $R^3$ is ($C_3$-$C_7$) cycloalkyl optionally substituted with one or more substituents each independently selected from the group consisting of halogen or ($C_1$-$C_6$) alkyl.

In some embodiments of the Formulae above, $R^4$ is $COOR^{6a}$, —$(CH_2)_n$—$COOR^{6a}$, $CONR^{6b}OH$, $CONR^{6b}R^{6c}$, $CONH(CH_2)_nCOOR^{6a}$, $CONH(CH_2)_nR^{6a}$, —$(CH_2)_nCONH(CH_2)_nR^{6a}$, $CONR^{6b}SO_2R^{6d}$, $CONR^{6b}SO_2(CH_2)_nR^{6d}$, —$(CH_2)_n$—$CONR^{6b}SO_2R^{6d}$, $CONR^{6b}SO_2(CH_2)_nN(CO)R^{6d}$ $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$, CN, —$(CH_2)_n$—$NR^{6b}C(O)R^{6c}$, —$(CH_2)_n$—N(OH)—$C(O)R^{6c}$, oxo, alkyl, cycloalkyl, —$(CH_2)_n$-cycloalkyl, heterocycloalkyl, —$(CH_2)_n$-heterocycloalkyl, heteroaryl and —$(CH_2)_n$-heteroaryl; wherein the heterocycloalkyl and —$(CH_2)_n$-heterocycloalkyl independently comprise one or two 5- to 7-membered rings and 1-4 heteroatoms selected from the group consisting of N, O and S, or heteroaryl wherein the heteroaryl and —$(CH_2)_n$-heteroaryl comprises one or two 5- or 6-membered rings and 1-4 heteroatoms selected from the group consisting of N, O and S; and said alkyl, cycloalkyl, —$(CH_2)_n$-cycloalkyl, heterocycloalkyl, —$(CH_2)_n$-heterocycloalkyl, heteroaryl and —$(CH_2)_n$-heteroaryl are optionally substituted with $COOR^{6a}$, —$(CH_2)_n$—$COOR^{6a}$, $CONR^{6b}OH$, $CONR^{6b}R^{6c}$, $CONH(CH_2)_nCOOR^{6a}$, $CONH(CH_2)_nR^{6a}$, —$(CH_2)_nCONH(CH_2)_nR^{6a}$, $CONR^{6b}SO_2R^{6d}$, $CONR^{6b}SO_2(CH_2)_nR^{6d}$, —$(CH_2)_n$—$CONR^{6b}SO_2R^{6d}$, $CONR^{6b}SO_2$ $(CH_2)_nN(CO)R^{6d}$ $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$, CN, —$(CH_2)_n$—$NR^{6b}C(O)R^{6c}$, —$(CH_2)_n$—N(OH)—$C(O)R^{6c}$.

In an embodiment, $R^4$ is $COOR^{6a}$. In an embodiment, $R^4$ is -alkyl-$COOR^{6a}$. In another embodiment, $R^4$ is —$(CH_2)_n$—$COOR^{6a}$. In an embodiment, $R^4$ is $CONR^{6b}OH$. In another embodiment, $R^4$ is $CONR^{6b}R^{6c}$. In yet another embodiment, $R^4$ is $CONH(CH_2)_nCOOR^{6a}$. In another embodiment, $R^4$ is $CONH(CH_2)_nSO_2R^{6e}$. In yet another embodiment, $R^4$ is $CONH(CH_2)_nCOOR^{6a}$, $CONH(CH_2)_nR^{6a}$, —$(CH_2)_nCONH(CH_2)_nR^{6a}$. In yet another embodiment, $R^4$ is $CONH(CH_2)_nR^{6a}$. In yet another embodiment, $R^4$ is —$(CH_2)_nCONH(CH_2)_nR^{6a}$. In yet another embodiment, $R^4$ is $CONR^{6b}SO_2R^{6d}$. In yet another embodiment, $R^4$ is —$(CH_2)_n$—$NR^{6b}C(O)R^{6c}$. In yet another embodiment, $R^4$ is —$(CH_2)_n$—N(OH)—$C(O)R^{6c}$. In yet another embodiment, $R^4$ is -alkyl-$CONR^{6b}SO_2R^{6d}$. In yet another embodiment, $R^4$ is $COR^{6f}$, $(CH_2)_nPO(OR^{6g})_2$. In yet another embodiment, $R^4$ is $COO(CH_2)_nPO(OR^{6g})_2$. In yet another embodiment, $R^4$ is $SO_2NR^{6b}(CH_2)_nCOOR^{6a}$. In yet another embodiment, $R^4$ is $SO_2R^{6e}$. In yet another embodiment, $R^4$ is oxo. In yet another embodiment, $R^4$ is ($C_3$-$C_8$) cycloalkyl optionally substituted with $(CH_2)_nCOOR^{6a}$, $COOR^{6a}$, $CONR^{6b}OH$, $CONR^{6b}R^{6c}$, $CONH(CH_2)_nCOOR^{6a}$, $CONR^{6b}SO_2R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$. In another embodiment, $R^4$ is heterocycloalkyl comprising one or two 5- to 7-membered rings and 1-4 heteroatoms selected from the group consisting of N, O and S; and said heterocycloalkyl is optionally substituted with $(CH_2)_nCOOR^{6a}$, $COOR^{6a}$, $CONR^{6b}OH$, $CONR^{6b}R^{6c}$, $CONH(CH_2)_nCOOR^{6a}$, $CONR^{6b}SO_2R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$. In yet another embodiment, $R^4$ is or heteroaryl wherein the heteroaryl comprises one or two 5- or 6-membered rings and 1-4 heteroatoms selected from the group consisting of N, O and S; and said said hetearyl is optionally substituted with $(CH_2)_nCOOR^{6a}$, $COOR^{6a}$, $CONR^{6b}OH$, $CONR^{6b}R^{6b}R^{6c}$, $CONH(CH_2)_nCOOR^{6a}$, $CONR^{6b}SO_2R^{6d}$, $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^6$. In another embodiment, $R^4$ is $COOR^{6a}$, $CONR^{6b}SO_2R^{6d}$, or $CONR^{6b}R^{6c}$. In yet another embodiment, $R^4$ is $COOR^{6a}$, $CONR^{6b}SO_2R^{6d}$, or $CONH(CH_2)_nSO_2R^{6e}$. In another embodiment, $R^4$ is $COOR^{6a}$, $CONR^{6b}SO_2R^{6d}$, or $CONH(CH_2)_nCOOR^{6a}$. In yet another embodiment, $R^4$ is $COOR^{6a}$, $CONR^{6b}SO_2R^{6d}$, or heterocycloalkyl comprising one or two 5- to 7-membered rings and 1-4 heteroatoms selected from the group consisting of N, O and S. In another embodiment, $R^4$ is $COOR^{6a}$, $CONR^{6b}SO_2R^{6d}$, $CONR^{6b}R^{6c}$, or heterocycloalkyl comprising one 5- to 7-membered ring and 1-4 heteroatoms selected from the group consisting of N, O and S. In another embodiment, $R^4$ is $COOR^{6a}$, $CONR^{6b}SO_2R^{6d}$, or heterocycloalkyl comprising one 5- to 7-membered ring and 1-4 heteroatoms selected from the group consisting of N, O and S. In another embodiment, $R^4$ is $CONH(CH_2)_n COOR^{6a}$ or $CONH(CH_2)_n SO_2R^{6e}$. In yet another embodiment, $R^4$ is $CONR^{6b}R^{6c}$ or $CONH(CH_2)_n COOR^{6a}$. In another embodiment, $R^4$ is $CONR^{6b}SO_2R^{6d}$ or $CONH(CH_2)_n SO_2R^{6e}$.

In some embodiments, n is 1. In another embodiment, n is 2. In another embodiment, n is 3. In another embodiment, n is 4.

In some embodiments of the Formulae above, $R^5$ is halogen, $(C_1-C_4)$ alkyl, $(C_1-C_4)$ haloalkyl, $(C_1-C_4)$ alkoxy, $(C_1-C_4)$ haloalkoxy, CN, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment, $R^5$ is halogen, $(C_1-C_4)$ alkyl, $(C_1-C_4)$ haloalkyl, $(C_1-C_4)$ alkoxy, $(C_1-C_4)$ haloalkoxy, or $(C_3-C_8)$ cycloalkyl optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment, $R^5$ is $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl or heteroaryl are optionally substituted with one or more substituents each independently selected from the group consisting of halogen, $(C_1-C_6)$ alkyl, $(C_1-C_6)$ haloalkyl, $(C_1-C_6)$ alkoxy, and $(C_1-C_6)$ haloalkoxy. In another embodiment, $R^5$ is halogen, $(C_1-C_4)$ alkyl, $(C_1-C_4)$ haloalkyl, $(C_1-C_4)$ alkoxy, $(C_1-C_4)$ haloalkoxy, or $(C_3-C_8)$ cycloalkyl. In another embodiment, $R^5$ is halogen, $(C_1-C_4)$ alkyl, $(C_1-C_4)$ haloalkyl, $(C_1-C_4)$ alkoxy, or $(C_1-C_4)$ haloalkoxy.

In some embodiments of the Formulae above, $R_y$ is H, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy or halogen. In an embodiment $R_y$ is H. In an embodiment $R_y$ is methyl. In an embodiment $R_y$ is ethyl. In an embodiment $R_y$ is $CF_3$. In an embodiment $R_y$ is $(C_1-C_6)$ alkyl. In an embodiment $R_y$ is $(C_1-C_6)$ haloalkyl. In an embodiment $R_y$ is alkoxyalkyl. In some embodiments of the Formulae above, $R^{6a}$ is H, $(C_1-C_4)$ alkyl, $(C_1-C_4)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the alkyl, cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, $NR^{6b}R^{6c}$ and OH. In another embodiment, $R^{6a}$ is H, $(C_1-C_4)$ alkyl, or $(C_1-C_4)$ haloalkyl. In yet another embodiment, $R^{6a}$ is H, $(C_1-C_4)$ haloalkyl, or $(C_1-C_4)$ alkyl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6a}$ is $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and OH. In yet another embodiment, $R^{6a}$ is H or $(C_1-C_4)$ alkyl.

In some embodiments of the Formulae above, $R^{6b}$ is H, $(C_1-C_4)$ alkyl, $(C_1-C_4)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the alkyl, cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and OH. In yet another embodiment, $R^{6b}$ is H, $(C_1-C_4)$ alkyl, or $(C_1-C_4)$ haloalkyl. In another embodiment, $R^{6b}$ is H, $(C_1-C_4)$ haloalkyl, or $(C_1-C_4)$ alkyl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and OH. In yet another embodiment, $R^{6b}$ is $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6b}$ is H or $(C_1-C_4)$ alkyl. In yet another embodiment, $R^{6b}$ is H.

In some embodiments of the Formulae above, $R^{6c}$ is H, $(C_1-C_4)$ alkyl, $(C_1-C_4)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the alkyl, cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and OH. In another embodiment, $R^{6c}$ is H, $(C_1-C_4)$ alkyl, or $(C_1-C_4)$ haloalkyl. In yet another embodiment, $R^{6c}$ is H, $(C_1-C_4)$ haloalkyl, or $(C_1-C_4)$ alkyl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and OH. In another embodiment, $R^{6c}$ is $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and OH. In yet another embodiment, $R^{6c}$ is H or $(C_1-C_4)$ alkyl. In another embodiment, $R^{6c}$ is H.

In some embodiments of the Formulae above, $R^{6d}$ is $(C_1-C_6)$ alkyl, $(C_1-C_6)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, and wherein the alkyl, cycloalkyl, aryl, heterocycloalkyl, or heteroaryl is optionally substituted with one or more substituents each independently selected from the group consisting of halogen, COOH, $(C_1-C_6)$ alkyl, $(C_1-C_6)$ haloalkyl, $(C_1-C_6)$ alkoxy, $(C_1-C_6)$ haloalkoxy, $(C_1-C_6)$ alkoxyalkoxy, —O—CO—$(C_1-C_6)$ alkyl, —O—CO—$(C_3-C_8)$ cycloalkyl, —O—CO—$(C_1-C_6)$ alkyl-COOH, $NR^{6b}R^{6c}$, $NR^{6f}$CO—$(C_1-C_6)$ alkyl, $NR^{6f}$CO—$(C_1-C_6)$ alkoxy, cycloalkyl, heterocycloalkyl and —OH. In an embodiment, $R^{6d}$ is $(C_1-C_4)$ alkyl, $(C_1-C_4)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the alkyl, cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and OH. In another embodiment, $R^{6d}$ is $(C_1-C_4)$ alkyl, or $(C_1-C_4)$ haloalkyl. In yet another embodiment, $R^{6d}$ is $(C_1-C_4)$ haloalkyl, or $(C_1-C_4)$ alkyl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and OH. In yet another embodiment, $R^{6d}$ is $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and OH. In another embodiment, $R^{6d}$ is $(C_1-C_4)$ alkyl or $(C_3-C_8)$ cycloalkyl, wherein the alkyl or cycloalkyl are optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and OH. In yet another embodiment, $R^{6d}$ is $(C_1-C_4)$ alkyl or $(C_3-C_8)$ cycloalkyl, wherein the alkyl or cycloalkyl are optionally substituted with one or more OH. In another embodiment, $R^{6d}$ is $(C_1-C_4)$ alkyl or $(C_3-C_8)$ cycloalkyl.

In some embodiments of the Formulae above, $R^{6e}$ is —OH, $(C_1-C_4)$ alkyl, $(C_1-C_4)$ haloalkyl, $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the alkyl, cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is —OH, $(C_1-C_4)$ haloalkyl, $(C_1-C_4)$ alkyl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is $(C_3-C_8)$ cycloalkyl, $(C_6-C_{10})$ aryl, heterocycloalkyl wherein the heterocycloalkyl comprises one or two 5- to 7-membered rings and 1-4 heteroatoms selected from the group consisting of N, O and S, or heteroaryl wherein the heteroaryl comprises one or two 5- or 6-membered rings and 1-4 heteroatoms selected from the group consisting of N, O and S, wherein the cycloalkyl, aryl, heterocycloalkyl, or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is $(C_3-C_8)$ cycloalkyl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is $(C_6-C_{10})$ aryl optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is heterocycloalkyl wherein the heterocycloalkyl comprises one or two 5- to 7-membered rings and 1-4 heteroatoms selected from the group consisting of N, O and S, optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is heteroaryl wherein the heteroaryl comprises one or two 5- or 6-membered rings and 1-4 heteroatoms selected from the group consisting of N, O and S, optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH.

In another embodiment, $R^{6e}$ is $(C_3-C_8)$ cycloalkyl or heterocycloalkyl wherein the heterocycloalkyl comprises one or two 5- to 7-membered rings and 1-4 heteroatoms selected from the group consisting of N, O and S, wherein the cycloalkyl or heterocycloalkyl are optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is $(C_6-C_{10})$ aryl or heteroaryl wherein the heteroaryl comprises one or two 5- or 6-membered rings and 1-4 heteroatoms selected from the group consisting of N, O and S, wherein the aryl or heteroaryl is optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and —OH. In another embodiment, $R^{6e}$ is $(C_1-C_4)$ alkyl or $(C_3-C_8)$ cycloalkyl, wherein the alkyl or cycloalkyl are optionally substituted with one or more substituents each independently selected from the group consisting of halogen, $(C_1-C_6)$ alkyl, $(C_1-C_6)$ haloalkyl, $(C_1-C_6)$ alkoxy, $(C_1-C_6)$ haloalkoxy, and OH. In yet another embodiment, $R^{6e}$ is $(C_1-C_4)$ alkyl or $(C_3-C_8)$ cycloalkyl, wherein the alkyl or cycloalkyl are optionally substituted with one or more OH. In another embodiment, $R^{6e}$ is $(C_1-C_4)$ alkyl or $(C_3-C_8)$ cycloalkyl. In another embodiment, $R^{6e}$ is OH, $(C_1-C_4)$ alkyl or $(C_3-C_8)$ cycloalkyl.

In some embodiments, $R^{6f}$ is $(C_1-C_6)$ alkyl or $(C_1-C_6)$ haloalkyl. In another embodiment, $R^{6f}$ is $(C_1-C_6)$ alkyl. In another embodiment, $R^{6f}$ is methyl. In another embodiment, $R^{6f}$ is $(C_1-C_6)$ haloalkyl. In another embodiment, $R^{6f}$ trifluoromethyl.

In some embodiments, leg is H or $(C_1-C_6)$ alkyl optionally substituted with —O—CO—$(C_1-C_6)$ alkyl. In an embodiment, $R^{6g}$ is H. In an embodiment, $R^{6g}$ is $(C_1-C_6)$ alkyl optionally substituted with —O—CO—$(C_1-C_6)$ alkyl. In an embodiment, $R^{6g}$ is —$CH_2$—O—C(O)—C$(CH_3)_3$.

In some embodiments of the Formulae above, $R^7$ is $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, $(C_1-C_4)$ haloalkoxy, halogen, or CN. In another embodiment, $R^7$ is $(C_1-C_4)$ alkyl, $(C_1-C_4)$ alkoxy, $(C_1-C_4)$ haloalkyl, $(C_1-C_4)$ haloalkoxy, halogen, or CN. In yet another embodiment, $R^7$ is $(C_1-C_4)$ alkyl, $(C_2-C_4)$ alkenyl, $(C_2-C_4)$ alkynyl, $(C_1-C_4)$ alkoxy, $(C_1-C_4)$ haloalkyl, or $(C_1-C_4)$ haloalkoxy. In another embodiment, $R^7$ is $(C_1-C_4)$ alkyl, $(C_2-C_4)$ alkenyl, $(C_2-C_4)$ alkynyl, or $(C_1-C_4)$ alkoxy. In yet another embodiment, $R^7$ is $(C_1-C_4)$ alkyl, $(C_2-C_4)$ alkenyl, $(C_2-C_4)$ alkynyl, $(C_1-C_4)$ alkoxy, or halogen. In another embodiment, $R^7$ is $(C_1-C_4)$ alkyl, $(C_1-C_4)$ alkoxy, $(C_1-C_4)$ haloalkyl, $(C_1-C_4)$ haloalkoxy, or halogen. In yet another embodiment, $R^7$ is $(C_1-C_4)$ alkoxy, $(C_1-C_4)$ haloalkyl, $(C_1-C_4)$ haloalkoxy, or halogen. In another embodiment, $R^7$ is $(C_1-C_4)$ haloalkyl, $(C_1-C_4)$ haloalkoxy, or halogen.

In some embodiments of the Formulae above, $R^8$ is $(C_1-C_4)$ alkyl, $(C_1-C_4)$ alkoxy, $(C_1-C_4)$ haloalkyl, $(C_1-C_4)$ haloalkoxy, halogen, or OH. In another embodiment, $R^8$ is $(C_1-C_4)$ alkyl, $(C_1-C_4)$ alkoxy, $(C_1-C_4)$ haloalkyl, $(C_1-C_4)$ haloalkoxy, or halogen. In yet another embodiment, $R^8$ is $(C_1-C_4)$ alkyl, $(C_1-C_4)$ alkoxy, $(C_1-C_4)$ haloalkyl, or $(C_1-C_4)$ haloalkoxy. In another embodiment, $R^8$ is $(C_1-C_4)$ haloalkyl, $(C_1-C_4)$ haloalkoxy, halogen, or OH. In yet another embodiment, $R^8$ is $(C_1-C_4)$ alkyl, $(C_1-C_4)$ alkoxy, halogen, or OH. In another embodiment, $R^8$ is halogen, or OH. In yet another embodiment, $R^8$ is $(C_1-C_4)$ alkoxy, $(C_1-C_4)$ haloalkyl, $(C_1-C_4)$ haloalkoxy, halogen, or OH. In another embodiment, $R^8$ is $(C_1-C_4)$ alkyl, $(C_1-C_4)$ haloalkyl, $(C_1-C_4)$ haloalkoxy, halogen, or OH. In yet another embodiment, $R^8$ is $(C_1-C_4)$ alkyl, $(C_1-C_4)$ alkoxy, $(C_1-C_4)$ haloalkoxy, halogen, or OH. In another embodiment, $R^8$ is $(C_1-C_4)$ alkyl, $(C_1-C_4)$ alkoxy, $(C_1-C_4)$ haloalkyl, halogen, or OH. In yet another embodiment, $R^8$ is $(C_1-C_4)$ alkyl, $(C_1-C_4)$ alkoxy, $(C_1-C_4)$ haloalkyl, $(C_1-C_4)$ haloalkoxy, or OH.

In some embodiments of the Formulae above, $R^9$ is $(C_1-C_4)$ alkyl, $(C_1-C_4)$ alkoxy, $(C_1-C_4)$ haloalkyl, $(C_1-C_4)$ haloalkoxy, halogen, or OH. In another embodiment, $R^9$ is $(C_1-C_4)$ alkyl, $(C_1-C_4)$ alkoxy, $(C_1-C_4)$ haloalkyl, $(C_1-C_4)$ haloalkoxy, or halogen. In yet another embodiment, $R^9$ is $(C_1-C_4)$ alkyl, $(C_1-C_4)$ alkoxy, $(C_1-C_4)$ haloalkyl, or $(C_1-C_4)$ haloalkoxy. In another embodiment, $R^9$ is $(C_1-C_4)$ haloalkyl, $(C_1-C_4)$ haloalkoxy, halogen, or OH. In yet another embodiment, $R^9$ is $(C_1-C_4)$ alkyl, $(C_1-C_4)$ alkoxy, halogen, or OH. In another embodiment, $R^9$ is halogen, or OH. In yet another embodiment, $R^9$ is $(C_1-C_4)$ alkoxy, $(C_1-C_4)$ haloalkyl, $(C_1-C_4)$ haloalkoxy, halogen, or OH. In another embodiment, $R^9$ is $(C_1-C_4)$ alkyl, $(C_1-C_4)$ haloalkyl, $(C_1-C_4)$ haloalkoxy, halogen, or OH. In yet another embodiment, $R^9$ is $(C_1-C_4)$ alkyl, $(C_1-C_4)$ alkoxy, $(C_1-C_4)$ haloalkoxy, halogen, or OH. In another embodiment, $R^9$ is $(C_1-C_4)$ alkyl, $(C_1-C_4)$ alkoxy, $(C_1-C_4)$ haloalkyl, halogen, or OH. In yet another embodiment, $R^9$ is $(C_1-C_4)$ alkyl, $(C_1-C_4)$ alkoxy, $(C_1-C_4)$ haloalkyl, $(C_1-C_4)$ haloalkoxy, or —OH.

In some embodiments of the Formulae above, m is 0. In another embodiment, m is 1. In another embodiment, m is 2. In another embodiment, m is 1 or 2. In another embodiment, m is 0 or 1.

In some embodiments of the Formulae above, p is 1. In another embodiment, p is 2.

In some embodiments of the Formulae above, A is $(C_6-C_{10})$ aryl, $(C_3-C_8)$ cycloalkyl or heterocycloalkyl wherein the heterocycloalkyl comprises one or two 5- to 7-membered rings and 1-4 heteroatoms selected from the group consisting of N, O and S. In another embodiment, A is $(C_6-C_{10})$ aryl or $(C_3-C_8)$ cycloalkyl. In yet another embodiment, A is $(C_6-C_{10})$ aryl or heterocycloalkyl wherein the heterocycloalkyl comprises one or two 5- to 7-membered rings and 1-4 heteroatoms selected from the group consisting of N, O and S. In another embodiment, A is $(C_3-C_8)$ cycloalkyl or heterocycloalkyl wherein the heterocycloalkyl comprises one or two 5- to 7-membered rings and 1-4 heteroatoms selected from the group consisting of N, O and S. In yet another embodiment, A is phenyl or $(C_3-C_8)$ cycloalkyl. In another embodiment, A is phenyl or heterocycloalkyl wherein the heterocycloalkyl comprises one or two 5- to 7-membered rings and 1-4 heteroatoms selected from the group consisting of N, O and S. In yet another embodiment, A is phenyl. In another embodiment, A is cyclohexyl, bicyclo[2.2.2.]octanyl, or spiro[2.5]octanyl. In yet another embodiment, A is cyclohexyl or bicyclo[2.2.2.]octanyl. In another embodiment, A is bicyclo[2.2.2.]octanyl, or spiro [2.5]octanyl. In yet another embodiment, A is cyclohexyl, bicyclo[2.2.2.]octanyl, or tetrahydropyranyl. In another embodiment, A is cyclohexyl. In yet another embodiment, A is bicyclo[2.2.2.]octanyl. In another embodiment, A is tetrahydropyranyl.

In some embodiments of the Formulae above, $R^1$ and $R^2$ are each independently H, halogen, $(C_1-C_6)$ alkoxy, or $(C_1-C_6)$ haloalkoxy. In another embodiment, $R^1$ and $R^2$ are each independently H, halogen, or $(C_1-C_6)$ haloalkyl. In yet another embodiment, $R^1$ and $R^2$ are each independently halogen or $(C_1-C_6)$ haloalkyl. In another embodiment, $R^1$ is H and $R^2$ is halogen, $(C_1-C_6)$ haloalkyl, or $(C_1-C_6)$ haloalkoxy. In yet another embodiment, $R^1$ is H and $R^2$ is $(C_1-C_6)$ haloalkyl or $(C_1-C_6)$ haloalkoxy. In another embodiment, $R^1$ is H and $R^2$ is $(C_1-C_6)$ haloalkyl. In yet another embodiment, $R^1$ is H and $R^2$ is $(C_1-C_6)$ haloalkoxy. In another embodiment, $R^1$ is halogen and $R^2$ is halogen, $(C_1-C_6)$ haloalkyl, or $(C_1-C_6)$ haloalkoxy. In yet another embodiment, $R^1$ is halogen and $R^2$ is $(C_1-C_6)$ haloalkoxy. In another embodiment, $R^1$ is halogen and $R^2$ is $(C_1-C_6)$ haloalkyl. In yet another embodiment, $R^1$ is halogen and $R^2$ is halogen.

In some embodiments of the Formulae above, B is unsubstituted heteroaryl comprising one or two 5- or 6-member rings and 1-4 heteroatoms selected from the group consisting of N, O and S.

In some embodiments of the Formulae above, B is heteroaryl comprising one or two 5- or 6-member rings and 1-4 heteroatoms selected from the group consisting of N, O and S, substituted with one or more halogen, $(C_1-C_6)$ alkyl, $(C_1-C_6)$ alkoxy, $(C_1-C_6)$ haloalkoxy, or $(C_3-C_8)$ cycloalkyl.

In some embodiments of the Formulae above, B is unsubstituted $(C_6-C_{10})$ aryl. In some embodiments of the Formulae above, B is $(C_6-C_{10})$ aryl optionally substituted with $(C_1-C_6)$ alkyl, halogen, $(C_1-C_6)$ alkoxy, $(C_1-C_6)$ haloalkoxy, or $(C_3-C_8)$ cycloalkyl.

In some embodiments of the Formulae above, B is pyrimidinyl, furanyl, benzo[d]thiazolyl, 1-methyl-1H-benzo[d]imidazolyl, 1-methyl-1H-indolyl, benzo[d]isoxazolyl, 2,2-difluoro-1-methylindolin-3-onyl, or 7-fluoro-1-methyl-1H-benzo[d]imidazolyl, wherein each B is optionally substituted with one or more halogen, $(C_1-C_6)$ alkyl, $(C_1-C_6)$ alkoxy, or $(C_1-C_6)$ haloalkyl.

In some embodiments of the Formulae above, $R^3$ is $(C_3-C_8)$ cycloalkyl optionally substituted with halogen or $(C_1-C_6)$ alkyl. In another embodiment, $R^3$ is $(C_3-C_8)$ cycloalkyl optionally substituted with halogen. In another embodiment, $R^3$ is unsubstituted $(C_3-C_8)$ cycloalkyl.

In some embodiments of the Formulae above, $L_1$ is —$(CH_2)_m(C=O)$— and $L_2$ is a bond. In another embodiment, $L_1$ is —$(CH_2)_m(C=O)$—, $L_2$ is a bond and A is $(C_3-C_8)$ cycloalkyl, $(C_6-C_{10})$ aryl or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$. In another embodiment, $L_1$ is —$(CH_2)_m(C=O)$—, $L_2$ is a bond, A is $(C_3-C_8)$ cycloalkyl, $(C_6-C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, and B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m(C=O)$—, $L_2$ is a bond, A is $(C_3-C_8)$ cycloalkyl, $(C_6-C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or $(C_1-C_4)$ haloalkyl.

In another embodiment, $L_1$ is —$(CH_2)_m(C=O)$—, $L_2$ is a bond, A is $(C_3-C_8)$ cycloalkyl, $(C_6-C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, and $R^2$ is H, halogen, or $(C_1-C_4)$ haloalkyl. In another embodiment, $L_1$ is —$(CH_2)_m(C=O)$—, $L_2$ is a bond, A is $(C_3-C_8)$ cycloalkyl, $(C_6-C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, $R^2$ is H, halogen, or $(C_1-C_4)$ haloalkyl, and $R^3$ is $(C_3-C_7)$ cycloalkyl optionally substituted with one or more substituents each independently selected from the group consisting of halogen or $(C_1-C_4)$ alkyl.

In another embodiment, $L_1$ is a —$(CH_2)_m(C=O)$—, $L_2$ is a bond, A is $(C_3-C_8)$ cycloalkyl, $(C_6-C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, and $R^2$ is halogen or $(C_1-C_4)$ haloalkyl. In another embodiment, $L_1$ is —$(CH_2)_m(C=O)$—, $L_2$ is a bond, A is $(C_3-C_8)$ cycloalkyl, $(C_6-C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, $R^2$ is halogen or $(C_1-C_4)$ haloalkyl, and $R^3$ is $(C_3-C_7)$ cycloalkyl optionally substituted with one or more substituents each independently selected from the group consisting of halogen or $(C_1-C_4)$ alkyl.

In some embodiments of the Formulae above, $L_1$ is —$(CH_2)_m(C=O)$— and $L_2$ is a bond. In another embodiment, $L_1$ is —$(CH_2)_m(C=O)$—, $L_2$ is a bond and A is $(C_3-C_8)$ cycloalkyl or $(C_6-C_{10})$ aryl wherein the cycloalkyl or aryl are optionally substituted with one or more $R^7$. In another embodiment, $L_1$ is —$(CH_2)_m(C=O)$—, $L_2$ is a bond, A is $(C_3-C_8)$ cycloalkyl or $(C_6-C_{10})$ aryl wherein the cycloalkyl or aryl are optionally substituted with one or more $R^7$, and B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m(C=O)$—, $L_2$ is a bond, A is $(C_3-C_8)$ cycloalkyl or $(C_6-C_{10})$ aryl wherein the cycloalkyl or aryl are optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or $(C_1-C_4)$ haloalkyl.

In another embodiment, $L_1$ is a —$(CH_2)_m(C=O)$—, $L_2$ is a bond, A is $(C_3-C_8)$ cycloalkyl or $(C_6-C_{10})$ aryl wherein the cycloalkyl or aryl are optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, and $R^2$ is H, halogen, or $(C_1-C_4)$ haloalkyl. In another embodiment, $L_1$ is —$(CH_2)_m(C=O)$—, $L_2$ is a bond, A is $(C_3-C_8)$ cycloalkyl or $(C_6-C_{10})$ aryl wherein the cycloalkyl or aryl are optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, $R^2$ is H, halogen, or $(C_1\text{-}C_4)$ haloalkyl, and $R^3$ is $(C_3\text{-}C_7)$ cycloalkyl optionally substituted with one or more substituents each independently selected from the group consisting of halogen or $(C_1\text{-}C_4)$ alkyl.

In another embodiment, $L_1$ is —$(CH_2)_m(C{=}O)$—, $L_2$ is a bond, A is $(C_3\text{-}C_8)$ cycloalkyl or $(C_6\text{-}C_{10})$ aryl, wherein the cycloalkyl or aryl are optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, and $R^2$ is halogen or $(C_1\text{-}C_4)$ haloalkyl, or $(C_1\text{-}C_4)$ haloalkoxy. In another embodiment, $L_1$ is —$(CH_2)_m(C{=}O)$—, $L_2$ is a bond, A is $(C_3\text{-}C_8)$ cycloalkyl or $(C_6\text{-}C_{10})$ aryl wherein the cycloalkyl or aryl are optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, $R^2$ is halogen or $(C_1\text{-}C_4)$ haloalkyl, and $R^3$ is $(C_3\text{-}C_7)$ cycloalkyl optionally substituted with one or more substituents each independently selected from the group consisting of halogen or $(C_1\text{-}C_4)$ alkyl.

In some embodiments of the Formulae above, $L_1$ is —$(CH_2)_m(C{=}O)$—, $L_2$ is a bond and A is $(C_3\text{-}C_8)$ cycloalkyl optionally substituted with one or more $R^7$. In another embodiment, $L_1$ is —$(CH_2)_m(C{=}O)$—, $L_2$ is a bond, A is $(C_3\text{-}C_8)$ cycloalkyl optionally substituted with one or more $R^7$, and B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$ $(C{=}O)$—, $L_2$ is a bond, A is $(C_3\text{-}C_8)$ cycloalkyl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and H, halogen, or $(C_1\text{-}C_4)$ haloalkyl.

In another embodiment, $L_1$ is —$(CH_2)_m(C{=}O)$—, $L_2$ is a bond, A is $(C_3\text{-}C_8)$ cycloalkyl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, and $R^2$ is H, halogen, or $(C_1\text{-}C_4)$ haloalkyl. In another embodiment, $L_1$ is —$(CH_2)_m(C{=}O)$—, $L_2$ is a bond, A is $(C_3\text{-}C_8)$ cycloalkyl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, $R^2$ is H, halogen, or $(C_1\text{-}C_4)$ haloalkyl, and $R^3$ is $(C_3\text{-}C_7)$ cycloalkyl optionally substituted with one or more substituents each independently selected from the group consisting of halogen or $(C_1\text{-}C_4)$ alkyl.

In another embodiment, $L_1$ is —$(CH_2)_m(C{=}O)$—, $L_2$ is a bond, A is $(C_3\text{-}C_8)$ cycloalkyl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, and $R^2$ is halogen or $(C_1\text{-}C_4)$ haloalkyl. In another embodiment, $L_1$ is —$(CH_2)_m(C{=}O)$—, $L_2$ is a bond, A is $(C_3\text{-}C_8)$ cycloalkyl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, $R^2$ is halogen or $(C_1\text{-}C_4)$ haloalkyl, and $R^3$ is $(C_3\text{-}C_7)$ cycloalkyl optionally substituted with one or more substituents each independently selected from the group consisting of halogen or $(C_1\text{-}C_4)$ alkyl.

In some embodiments of the Formulae above, $L_1$ is —$(CH_2)_m(C{=}O)$—, $L_2$ is a bond, and A is $(C_6\text{-}C_{10})$ aryl optionally substituted with one or more $R^7$. In another embodiment, $L_1$ is —$(CH_2)_m(C{=}O)$—, $L_2$ is a bond, A is $(C_6\text{-}C_{10})$ aryl optionally substituted with one or more $R^7$, and B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$ $(C{=}O)$—, $L_2$ is a bond, A is $(C_6\text{-}C_{10})$ aryl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1\text{-}C_4)$ alkoxy, $(C_1\text{-}C_4)$ haloalkyl, or $(C_1\text{-}C_4)$ haloalkoxy.

In another embodiment, $L_1$ is —$(CH_2)_m(C{=}O)$—, $L_2$ is a bond, A is $(C_6\text{-}C_{10})$ aryl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy, $(C_1\text{-}C_4)$ haloalkyl, or $(C_1\text{-}C_4)$ haloalkoxy, and $R^2$ is H, halogen, $(C_1\text{-}C_4)$ alkoxy, $(C_1\text{-}C_4)$ haloalkyl, or $(C_1\text{-}C_4)$ haloalkoxy. In another embodiment, $L_1$ is —$(CH_2)_m(C{=}O)$—, $L_2$ is a bond, A is $(C_6\text{-}C_{10})$ aryl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy, $(C_1\text{-}C_4)$ haloalkyl, or $(C_1\text{-}C_4)$ haloalkoxy, $R^2$ is H, halogen, $(C_1\text{-}C_4)$ alkoxy, $(C_1\text{-}C_4)$ haloalkyl, or $(C_1\text{-}C_4)$ haloalkoxy, and $R^3$ is $(C_1\text{-}C_4)$ alkyl or $(C_3\text{-}C_7)$ cycloalkyl optionally substituted with one or more substituents each independently selected from the group consisting of halogen or $(C_1\text{-}C_4)$ alkyl.

In another embodiment, $L_1$ is —$(CH_2)_m(C{=}O)$—, $L_2$ is a bond, A is $(C_6\text{-}C_{10})$ aryl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy, $(C_1\text{-}C_4)$ haloalkyl, or $(C_1\text{-}C_4)$ haloalkoxy, and $R^2$ is halogen, $(C_1\text{-}C_4)$ alkoxy, $(C_1\text{-}C_4)$ haloalkyl, or $(C_1\text{-}C_4)$ haloalkoxy. In another embodiment, $L_1$ is —$(CH_2)_m$ (C=O)—, $L_2$ is a bond, A is ($C_6$-$C_{10}$) aryl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_m$(C=O)—, $L_2$ is a bond, and A is heterocycloalkyl wherein the heterocycloalkyl comprises one or two 5- to 7-membered rings and 1-4 heteroatoms selected from the group consisting of N, O and S, optionally substituted with one or more $R^7$. In another embodiment, $L_1$ is —$(CH_2)_m$(C=O)—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m$(C=O)—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, ($C_1$-$C_4$) alkoxy, ($C_1$-$C_4$) haloalkyl, or ($C_1$-$C_4$) haloalkoxy.

In another embodiment, $L_1$ is —$(CH_2)_m$(C=O)—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is H, halogen, ($C_1$-$C_4$) alkoxy, ($C_1$-$C_4$) haloalkyl, or ($C_1$-$C_4$) haloalkoxy. In another embodiment, $L_1$ is —$(CH_2)_m$(C=O)—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is H, halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_m$(C=O)—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is halogen, ($C_1$-$C_4$) alkoxy, ($C_1$-$C_4$) haloalkyl, or ($C_1$-$C_4$) haloalkoxy. In another embodiment, $L_1$ is —$(CH_2)_m$(C=O)—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$— and $L_2$ is a bond. In another embodiment, $L_1$ is —$(CH_2)_p$—, $L_2$ is a bond and A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$. In another embodiment, $L_1$ is —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is a —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl. In another embodiment, $L_1$ is —$(CH_2)_p$—, $L_2$ is a bond, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$— and $L_2$ is a bond. In another embodiment, $L_1$ is —$(CH_2)_p$—, $L_2$ is a bond and A is ($C_3$-$C_8$) cycloalkyl or ($C_6$-$C_{10}$) aryl wherein the cycloalkyl or aryl are optionally substituted with one or more $R^7$. In another embodiment, $L_1$ is —$(CH_2)_p$—, $L_2$ is a bond, A is ($C_3$-$C_8$) cycloalkyl or ($C_6$-$C_{10}$) aryl wherein the cycloalkyl or aryl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is a —$(CH_2)_p$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_p$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_p$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl, or ($C_1$-$C_4$) haloalkoxy. In another embodiment, $L_1$ is —$(CH_2)_p$—, $L_2$ is a bond, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$—, $L_2$ is a bond and A is ($C_3$-$C_8$) cycloalkyl optionally substituted with one or more $R^7$. In another embodiment, $L_1$ is —$(CH_2)_p$—, $L_2$ is a bond, A is ($C_3$-$C_8$) cycloalkyl optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and H, halogen, or ($C_1$-$C_4$) haloalkyl.

In another embodiment, $L_1$ is —$(CH_2)_p$—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_p$—, $L_2$ is a bond, A is ($C_3$-$C_8$) cycloalkyl optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, $R^2$ is H, halogen, or $(C_1-C_4)$ haloalkyl, and $R^3$ is $(C_3-C_7)$ cycloalkyl optionally substituted with one or more substituents each independently selected from the group consisting of halogen or $(C_1-C_4)$ alkyl.

In another embodiment, $L_1$ is —$(CH_2)_p$—, $L_2$ is a bond, A is $(C_3-C_8)$ cycloalkyl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, and $R^2$ is halogen or $(C_1-C_4)$ haloalkyl. In another embodiment, $L_1$ is —$(CH_2)_p$—, $L_2$ is a bond, A is $(C_3-C_8)$ cycloalkyl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, $R^2$ is halogen or $(C_1-C_4)$ haloalkyl, and $R^3$ is $(C_3-C_7)$ cycloalkyl optionally substituted with one or more substituents each independently selected from the group consisting of halogen or $(C_1-C_4)$ alkyl.

In some embodiments of the Formulae above, $L_1$ is —$(CH_2)_p$—, $L_2$ is a bond, and A is $(C_6-C_{10})$ aryl optionally substituted with one or more $R^7$. In another embodiment, $L_1$ is —$(CH_2)_p$—, $L_2$ is a bond, A is $(C_6-C_{10})$ aryl optionally substituted with one or more $R^7$, and B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is a bond, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is —$(CH_2)_p$—, $L_2$ is a bond, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is —$(CH_2)_p$—, $L_2$ is a bond, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is —$(CH_2)_p$—, $L_2$ is a bond, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy. In another embodiment, $L_1$ is —$(CH_2)_p$—, $L_2$ is a bond, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In some embodiments of the Formulae above, $L_1$ is —$(CH_2)_p$—, $L_2$ is a bond, and A is heterocycloalkyl wherein the heterocycloalkyl comprises one or two 5- to 7-membered rings and 1-4 heteroatoms selected from the group consisting of N, O and S, optionally substituted with one or more $R^7$. In another embodiment, $L_1$ is —$(CH_2)_p$—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, and B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is —$(CH_2)_p$—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is —$(CH_2)_p$—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or ($C_1$-$C_4$) alkyl.

In another embodiment, $L_1$ is —$(CH_2)_p$—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, and $R^2$ is halogen, ($C_1$-$C_4$) alkoxy, ($C_1$-$C_4$) haloalkyl, or ($C_1$-$C_4$) haloalkoxy. In another embodiment, $L_1$ is —$(CH_2)_p$—, $L_2$ is a bond, A is heterocycloalkyl wherein the heterocycloalkyl comprises one or two 5- to 7-membered rings and 1-4 heteroatoms selected from the group consisting of N, O and S, optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, ($C_1$-$C_4$) alkoxy, ($C_1$-$C_4$) haloalkyl, or ($C_1$-$C_4$) haloalkoxy, $R^2$ is halogen, ($C_1$-$C_4$) alkoxy, ($C_1$-$C_4$) haloalkyl, or ($C_1$-$C_4$) haloalkoxy, and $R^3$ is ($C_1$-$C_4$) alkyl or ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_m(C=O)$— and $L_2$ is —$S(O)_2$—. In another embodiment, $L_1$ is —$(CH_2)_m(C=O)$—, $L_2$ is —$S(O)_2$- and A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$. In another embodiment, $L_1$ is —$(CH_2)_m(C=O)$—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m(C=O)$—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is —$(CH_2)_m(C=O)$—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_m(C=O)$—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is a —$(CH_2)_m(C=O)$—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl. In another embodiment, $L_1$ is —$(CH_2)_m(C=O)$—, $L_2$ is —$S(O)_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_m(C=O)$—, $L_2$ is —$S(O)_2$— and A is ($C_3$-$C_8$) cycloalkyl or ($C_6$-$C_{10}$) aryl wherein the cycloalkyl or aryl are optionally substituted with one or more $R^7$. In another embodiment, $L_1$ is —$(CH_2)_m(C=O)$—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m(C=O)$—, $L_2$ is —$S(O)_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or $(C_1\text{-}C_4)$ haloalkyl.

In another embodiment, $L_1$ is a —$(CH_2)_m(C=O)$—, $L_2$ is —$S(O)_2$—, A is $(C_3\text{-}C_8)$ cycloalkyl or $(C_6\text{-}C_{10})$ aryl wherein the cycloalkyl or aryl are optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, and $R^2$ is H, halogen, or $(C_1\text{-}C_4)$ haloalkyl. In another embodiment, $L_1$ is —$(CH_2)_m(C=O)$—, $L_2$ is —$S(O)_2$—, A is $(C_3\text{-}C_8)$ cycloalkyl or $(C_6\text{-}C_{10})$ aryl wherein the cycloalkyl or aryl are optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, $R^2$ is H, halogen, or $(C_1\text{-}C_4)$ haloalkyl, and $R^3$ is $(C_3\text{-}C_7)$ cycloalkyl optionally substituted with one or more substituents each independently selected from the group consisting of halogen or $(C_1\text{-}C_4)$ alkyl.

In another embodiment, $L_1$ is —$(CH_2)_m(C=O)$—, $L_2$ is —$S(O)_2$—, A is $(C_3\text{-}C_8)$ cycloalkyl or $(C_6\text{-}C_{10})$ aryl wherein the cycloalkyl or aryl are optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, and $R^2$ is halogen or $(C_1\text{-}C_4)$ haloalkyl, or $(C_1\text{-}C_4)$ haloalkoxy. In another embodiment, $L_1$ is —$(CH_2)_m(C=O)$—, $L_2$ is —$S(O)_2$—, A is $(C_3\text{-}C_8)$ cycloalkyl or $(C_6\text{-}C_{10})$ aryl wherein the cycloalkyl or aryl are optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, $R^2$ is halogen or $(C_1\text{-}C_4)$ haloalkyl, and $R^3$ is $(C_3\text{-}C_7)$ cycloalkyl optionally substituted with one or more substituents each independently selected from the group consisting of halogen or $(C_1\text{-}C_4)$ alkyl.

In some embodiments of the Formulae above, $L_1$ is —$(CH_2)_m(C=O)$—, $L_2$ is —$S(O)_2$—, and A is $(C_3\text{-}C_8)$ cycloalkyl optionally substituted with one or more $R^7$. In another embodiment, $L_1$ is —$(CH_2)_m(C=O)$—, $L_2$ is —$S(O)_2$—, A is $(C_3\text{-}C_8)$ cycloalkyl optionally substituted with one or more $R^7$, and B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m(C=O)$—, $L_2$ is —$S(O)_2$—, A is $(C_3\text{-}C_8)$ cycloalkyl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and H, halogen, or $(C_1\text{-}C_4)$ haloalkyl.

In another embodiment, $L_1$ is —$(CH_2)_m(C=O)$—, $L_2$ is —$S(O)_2$—, A is $(C_3\text{-}C_8)$ cycloalkyl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, and $R^2$ is H, halogen, or $(C_1\text{-}C_4)$ haloalkyl. In another embodiment, $L_1$ is —$(CH_2)_m(C=O)$—, $L_2$ is —$S(O)_2$—, A is $(C_3\text{-}C_8)$ cycloalkyl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, $R^2$ is H, halogen, or $(C_1\text{-}C_4)$ haloalkyl, and $R^3$ is $(C_3\text{-}C_7)$ cycloalkyl optionally substituted with one or more substituents each independently selected from the group consisting of halogen or $(C_1\text{-}C_4)$ alkyl.

In another embodiment, $L_1$ is —$(CH_2)_m(C=O)$—, $L_2$ is —$S(O)_2$—, A is $(C_3\text{-}C_8)$ cycloalkyl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, and $R^2$ is halogen or $(C_1\text{-}C_4)$ haloalkyl. n another embodiment, $L_1$ is —$(CH_2)_m(C=O)$—, $L_2$ is —$S(O)_2$—, A is $(C_3\text{-}C_8)$ cycloalkyl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1\text{-}C_4)$ haloalkyl, $R^2$ is halogen or $(C_1\text{-}C_4)$ haloalkyl, and $R^3$ is $(C_3\text{-}C_7)$ cycloalkyl optionally substituted with one or more substituents each independently selected from the group consisting of halogen or $(C_1\text{-}C_4)$ alkyl.

In some embodiments of the Formulae above, $L_1$ is —$(CH_2)_m(C=O)$—, $L_2$ is —$S(O)_2$—, and A is $(C_6\text{-}C_{10})$ aryl optionally substituted with one or more $R^7$. In another embodiment, $L_1$ is —$(CH_2)_m(C=O)$—, $L_2$ is —$S(O)_2$—, A is $(C_6\text{-}C_{10})$ aryl optionally substituted with one or more $R^7$, and B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m(C=O)$—, $L_2$ is —$S(O)_2$—, A is $(C_6\text{-}C_{10})$ aryl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1\text{-}C_4)$ alkoxy, $(C_1\text{-}C_4)$ haloalkyl, or $(C_1\text{-}C_4)$ haloalkoxy.

In another embodiment, $L_1$ is —$(CH_2)_m(C=O)$—, $L_2$ is —$S(O)_2$—, A is $(C_6\text{-}C_{10})$ aryl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1\text{-}C_4)$ alkoxy, $(C_1\text{-}C_4)$ haloalkyl, or $(C_1\text{-}C_4)$ haloalkoxy, and $R^2$ is H, halogen, $(C_1\text{-}C_4)$ alkoxy, $(C_1\text{-}C_4)$ haloalkyl, or $(C_1\text{-}C_4)$ haloalkoxy. In another embodiment, $L_1$ is —$(CH_2)_m(C=O)$—, $L_2$ is —$S(O)_2$—, A is $(C_6\text{-}C_{10})$ aryl optionally substituted with one or more $R^7$, B is $(C_6\text{-}C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1$-$C_4)$ alkoxy, $(C_1$-$C_4)$ haloalkyl, or $(C_1$-$C_4)$ haloalkoxy, $R^2$ is H, halogen, $(C_1$-$C_4)$ alkoxy, $(C_1$-$C_4)$ haloalkyl, or $(C_1$-$C_4)$ haloalkoxy, and $R^3$ is $(C_1$-$C_4)$ alkyl or $(C_3$-$C_7)$ cycloalkyl optionally substituted with one or more substituents each independently selected from the group consisting of halogen or $(C_1$-$C_4)$ alkyl.

In another embodiment, $L_1$ is —$(CH_2)_m(C=O)$—, $L_2$ is —$S(O)_2$—, A is $(C_6$-$C_{10})$ aryl optionally substituted with one or more $R^7$, B is $(C_6$-$C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1$-$C_4)$ alkoxy, $(C_1$-$C_4)$ haloalkyl, or $(C_1$-$C_4)$ haloalkoxy, and $R^2$ is halogen, $(C_1$-$C_4)$ alkoxy, $(C_1$-$C_4)$ haloalkyl, or $(C_1$-$C_4)$ haloalkoxy. In another embodiment, $L_1$ is —$(CH_2)_m(C=O)$—, $L_2$ is —$S(O)_2$—, A is $(C_6$-$C_{10})$ aryl optionally substituted with one or more $R^7$, B is $(C_6$-$C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1$-$C_4)$ alkoxy, $(C_1$-$C_4)$ haloalkyl, or $(C_1$-$C_4)$ haloalkoxy, $R^2$ is halogen, $(C_1$-$C_4)$ alkoxy, $(C_1$-$C_4)$ haloalkyl, or $(C_1$-$C_4)$ haloalkoxy, and $R^3$ is $(C_1$-$C_4)$ alkyl or $(C_3$-$C_7)$ cycloalkyl optionally substituted with one or more substituents each independently selected from the group consisting of halogen or $(C_1$-$C_4)$ alkyl.

In some embodiments of the Formulae above, $L_1$ is —$(CH_2)_m(C=O)$—, $L_2$ is —$S(O)_2$—, and A is heterocycloalkyl wherein the heterocycloalkyl comprises one or two 5- to 7-membered rings and 1-4 heteroatoms selected from the group consisting of N, O and S, optionally substituted with one or more $R^7$. In another embodiment, $L_1$ is —$(CH_2)_m(C=O)$—, $L_2$ is —$S(O)_2$—, A is heterocycloalkyl wherein the heterocycloalkyl comprises one or two 5- to 7-membered rings and 1-4 heteroatoms selected from the group consisting of N, O and S, optionally substituted with one or more $R^7$, and B is $(C_6$-$C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_m(C=O)$—, $L_2$ is —$S(O)_2$—, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6$-$C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1$-$C_4)$ alkoxy, $(C_1$-$C_4)$ haloalkyl, or $(C_1$-$C_4)$ haloalkoxy.

In another embodiment, $L_1$ is —$(CH_2)_m(C=O)$—, $L_2$ is —$S(O)_2$—, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6$-$C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1$-$C_4)$ alkoxy, $(C_1$-$C_4)$ haloalkyl, or $(C_1$-$C_4)$ haloalkoxy, and $R^2$ is H, halogen, $(C_1$-$C_4)$ alkoxy, $(C_1$-$C_4)$ haloalkyl, or $(C_1$-$C_4)$ haloalkoxy.

$L_1$ is —$(CH_2)_m(C=O)$—, $L_2$ is —$S(O)_2$—, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6$-$C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1$-$C_4)$ alkoxy, $(C_1$-$C_4)$ haloalkyl, or $(C_1$-$C_4)$ haloalkoxy, $R^2$ is H, halogen, $(C_1$-$C_4)$ alkoxy, $(C_1$-$C_4)$ haloalkyl, or $(C_1$-$C_4)$ haloalkoxy, and $R^3$ is $(C_1$-$C_4)$ alkyl or $(C_3$-$C_7)$ cycloalkyl optionally substituted with one or more substituents each independently selected from the group consisting of halogen or $(C_1$-$C_4)$ alkyl.

In another embodiment, $L_1$ is —$(CH_2)_m(C=O)$—, $L_2$ is —$S(O)_2$—, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6$-$C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1$-$C_4)$ alkoxy, $(C_1$-$C_4)$ haloalkyl, or $(C_1$-$C_4)$ haloalkoxy, $R^2$ is halogen, $(C_1$-$C_4)$ alkoxy, $(C_1$-$C_4)$ haloalkyl, or $(C_1$-$C_4)$ haloalkoxy, and $R^3$ is $(C_1$-$C_4)$ alkyl or $(C_3$-$C_7)$ cycloalkyl optionally substituted with one or more substituents each independently selected from the group consisting of halogen or $(C_1$-$C_4)$ alkyl.

In some embodiments of the Formulae above, $L_1$ is —$(CH_2)_p$— and $L_2$ is —$S(O)_2$—. In another embodiment, $L_1$ is —$(CH_2)_p$—, $L_2$ is —$S(O)_2$— and A is $(C_3$-$C_8)$ cycloalkyl, $(C_6$-$C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$. In another embodiment, $L_1$ is —$(CH_2)_p$—, $L_2$ is —$S(O)_2$—, A is $(C_3$-$C_8)$ cycloalkyl, $(C_6$-$C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, and B is $(C_6$-$C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is —$S(O)_2$—, A is $(C_3$-$C_8)$ cycloalkyl, $(C_6$-$C_{10})$ aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is $(C_6$-$C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is —$(CH_2)_p$—, $L_2$ is —S(O)$_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_p$—, $L_2$ is S(O)$_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is a —$(CH_2)_p$—, $L_2$ is —S(O)$_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl. In another embodiment, $L_1$ is —$(CH_2)_p$—, $L_2$ is —S(O)$_2$—, A is ($C_3$-$C_8$) cycloalkyl, ($C_6$-$C_{10}$) aryl, or heterocycloalkyl wherein the heterocycloalkyl comprises one or two 5- to 7-membered rings and 1-4 heteroatoms selected from the group consisting of N, O and S, wherein the cycloalkyl, aryl, or heterocycloalkyl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$— and $L_2$ is —S(O)$_2$—. In another embodiment, $L_1$ is —$(CH_2)_p$—, $L_2$ is —S(O)$_2$—, and A is ($C_3$-$C_8$) cycloalkyl or ($C_6$-$C_{10}$) aryl wherein the cycloalkyl or aryl are optionally substituted with one or more $R^7$. In another embodiment, $L_1$ is —$(CH_2)_p$—, $L_2$ is —S(O)$_2$—, A is ($C_3$-$C_8$) cycloalkyl or ($C_6$-$C_{10}$) aryl wherein the cycloalkyl or aryl are optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is S(O)$_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, or ($C_1$-$C_4$) haloalkyl.

In another embodiment, $L_1$ is a —$(CH_2)_p$—, $L_2$ is —S(O)$_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is H, halogen, or ($C_1$-$C_4$) haloalkyl. In another embodiment, $L_1$ is —$(CH_2)_p$—, $L_2$ is S(O)$_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is H, halogen, or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In another embodiment, $L_1$ is —$(CH_2)_p$—, $L_2$ is —S(O)$_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, and $R^2$ is halogen or ($C_1$-$C_4$) haloalkyl, or ($C_1$-$C_4$) haloalkoxy. In another embodiment, $L_1$ is —$(CH_2)_p$—, $L_2$ is S(O)$_2$—, A is ($C_3$-$C_8$) cycloalkyl or ($C_6$-$C_{10}$) aryl wherein the cycloalkyl or aryl are optionally substituted with one or more $R^7$, B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or ($C_1$-$C_4$) haloalkyl, $R^2$ is halogen or ($C_1$-$C_4$) haloalkyl, and $R^3$ is ($C_3$-$C_7$) cycloalkyl optionally substituted with one or more substituents each independently selected from the group consisting of halogen or ($C_1$-$C_4$) alkyl.

In some embodiments of the Formulae above, $L_1$ is —$(CH_2)_p$—, $L_2$ is —S(O)$_2$—, and A is ($C_3$-$C_8$) cycloalkyl optionally substituted with one or more $R^7$. In another embodiment, $L_1$ is —$(CH_2)_p$—, $L_2$ is —S(O)$_2$—, A is ($C_3$-$C_8$) cycloalkyl optionally substituted with one or more $R^7$, and B is ($C_6$-$C_{10}$) aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is —S(O)$_2$—, A is ($C_3$-$C_8$) cycloalkyl optionally substituted with one or more $R^7$, B is ($C_6$-$C_{10}$)

aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and H, halogen, or $(C_1-C_4)$ haloalkyl.

In another embodiment, $L_1$ is —$(CH_2)_p$—, $L_2$ is —$S(O)_2$—, A is $(C_3-C_8)$ cycloalkyl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, and $R^2$ is H, halogen, or $(C_1-C_4)$ haloalkyl. In another embodiment, $L_1$ is —$(CH_2)_p$—, $L_2$ is —$S(O)_2$—, A is $(C_3-C_8)$ cycloalkyl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, $R^2$ is H, halogen, or $(C_1-C_4)$ haloalkyl, and $R^3$ is $(C_3-C_7)$ cycloalkyl optionally substituted with one or more substituents each independently selected from the group consisting of halogen or $(C_1-C_4)$ alkyl.

In another embodiment, $L_1$ is —$(CH_2)_p$—, $L_2$ is —$S(O)_2$—, A is $(C_3-C_8)$ cycloalkyl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, and $R^2$ is halogen or $(C_1-C_4)$ haloalkyl. In another embodiment, $L_1$ is —$(CH_2)_p$—, $L_2$ is —$S(O)_2$—, A is $(C_3-C_8)$ cycloalkyl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, or $(C_1-C_4)$ haloalkyl, $R^2$ is halogen or $(C_1-C_4)$ haloalkyl, and $R^3$ is $(C_3-C_7)$ cycloalkyl optionally substituted with one or more substituents each independently selected from the group consisting of halogen or $(C_1-C_4)$ alkyl.

In some embodiments of the Formulae above, $L_1$ is —$(CH_2)_p$—, $L_2$ is —$S(O)_2$—, and A is $(C_6-C_{10})$ aryl optionally substituted with one or more $R^7$. In another embodiment, $L_1$ is —$(CH_2)_p$—, $L_2$ is —$S(O)_2$—, A is $(C_6-C_{10})$ aryl optionally substituted with one or more $R^7$, and B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is $S(O)_2$—, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is —$(CH_2)_p$—, $L_2$ is —$S(O)_2$—, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is —$(CH_2)_p$—, $L_2$ is —$S(O)_2$—, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is —$(CH_2)_p$—, $L_2$ is —$S(O)_2$—, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is halogen, $(C_1-C_4)$ alkoxy, $(C_1-C_4)$ haloalkyl, or $(C_1-C_4)$ haloalkoxy. In another embodiment, $L_1$ is —$(CH_2)_p$—, $L_2$ is —$S(O)_2$—, A is $(C_6-C_{10})$ aryl optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In some embodiments of the Formulae above, $L_1$ is —$(CH_2)_p$—, $L_2$ is —$S(O)_2$—, and A is heterocycloalkyl wherein the heterocycloalkyl comprises one or two 5- to 7-membered rings and 1-4 heteroatoms selected from the group consisting of N, O and S, optionally substituted with one or more $R^7$. In another embodiment, $L_1$ is —$(CH_2)_p$—, $L_2$ is —$S(O)_2$—, A is heterocycloalkyl wherein the heterocycloalkyl comprises one or two 5- to 7-membered rings and 1-4 heteroatoms selected from the group consisting of N, O and S, optionally substituted with one or more $R^7$, and B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$. In another embodiment, $L_1$ is —$(CH_2)_p$—, $L_2$ is —$S(O)_2$—, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, and $R^1$ is H, halogen, $(C_1-C_4)$ alkoxy, $(C_1-C_4)$ haloalkyl, or $(C_1-C_4)$ haloalkoxy.

In another embodiment, $L_1$ is —$(CH_2)_p$—, $L_2$ is —$S(O)_2$—, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is H, halogen, $(C_1-C_4)$ alkoxy, $(C_1-C_4)$ haloalkyl, or $(C_1-C_4)$ haloalkoxy. In another embodiment, $L_1$ is $—(CH_2)_p—$, $L_2$ is $—S(O)_2—$, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is H, halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In another embodiment, $L_1$ is $—(CH_2)_p—$, $L_2$ is $—S(O)_2—$, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, and $R^2$ is halogen, $(C_1-C_4)$ alkoxy, $(C_1-C_4)$ haloalkyl, or $(C_1-C_4)$ haloalkoxy. In another embodiment, $L_1$ is $—(CH_2)_p—$, $L_2$ is $—S(O)_2—$, A is heterocycloalkyl wherein the heterocycloalkyl comprises one or two 5- to 7-membered rings and 1-4 heteroatoms selected from the group consisting of N, O and S, optionally substituted with one or more $R^7$, B is $(C_6-C_{10})$ aryl or heteroaryl wherein the heteroaryl comprises one or two 5- or 6-member rings and 1-4 heteroatoms selected from the group consisting of N, O and S, and wherein the aryl or heteroaryl is optionally substituted with one or more $R^5$, $R^1$ is H, halogen, $(C_1-C_4)$ alkoxy, $(C_1-C_4)$ haloalkyl, or $(C_1-C_4)$ haloalkoxy, $R^2$ is halogen, $(C_1-C_4)$ alkoxy, $(C_1-C_4)$ haloalkyl, or $(C_1-C_4)$ haloalkoxy, and $R^3$ is $(C_1-C_4)$ alkyl or $(C_3-C_7)$ cycloalkyl optionally substituted with one or more substituents each independently selected from the group consisting of halogen or $(C_1-C_4)$ alkyl.

In some embodiments, compounds of Formula (I) have the structure of Formula (Ia)-(Id):

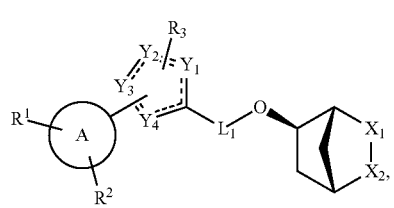
(Ia)

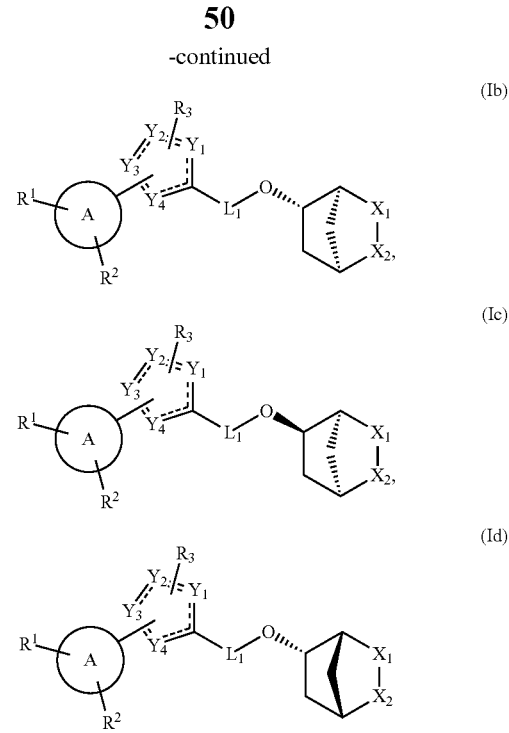

and pharmaceutically acceptable salts, hydrates, solvates, prodrugs, stereoisomers, and tautomers thereof. In an embodiment, the compounds of the invention have the stereochemical configuration of Formula (Ia). In an embodiment, the compounds of the invention have the stereochemical configuration of Formula (Ib). In an embodiment, the compounds of the invention have the stereochemical configuration of Formula (Ic). In an embodiment, the compounds of the invention have the stereochemical configuration of Formula (Id).

In one embodiment, the compounds of Formula (I) have the structure of Formula (IIa)-(IId):

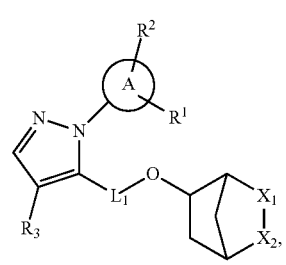
(IIa)

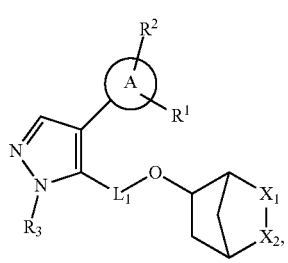
(IIb)

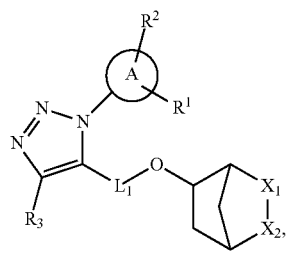

(IIc)

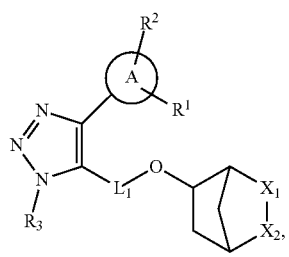

(IId)

and pharmaceutically acceptable salts, hydrates, solvates, prodrugs, stereoisomers, and tautomers thereof. In an embodiment, the compounds of the invention have the structure of Formula (IIa). In an embodiment, the compounds of the invention have the structure of Formula (IIb). In an embodiment, the compounds of the invention have the structure of Formula (IIc). In an embodiment, the compounds of the invention have the structure of Formula (IId).

In one embodiment, the compounds of Formula (I) have the structure of Formula (IIa1)-(IId1):

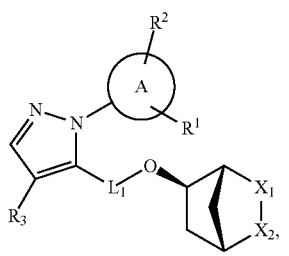

(IIa1)

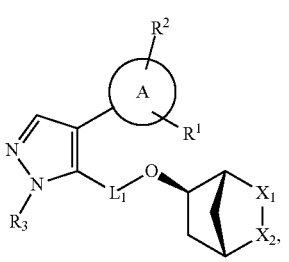

(IIb1)

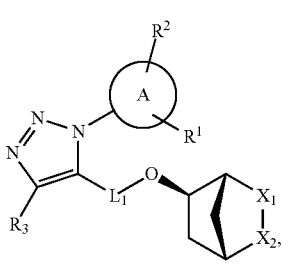

(IIc1)

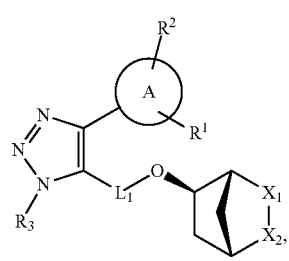

(IId1)

and pharmaceutically acceptable salts, hydrates, solvates, prodrugs, stereoisomers, and tautomers thereof. In an embodiment, the compounds of the invention have the structure of Formula (IIa1). In an embodiment, the compounds of the invention have the structure of Formula (IIb1). In an embodiment, the compounds of the invention have the structure of Formula (IIc1). In an embodiment, the compounds of the invention have the structure of Formula (IId1).

In another embodiment, the compounds of Formula (I) have the structure of Formula (IIIa) or (IIIg):

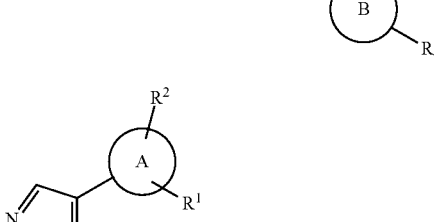

(IIIa)

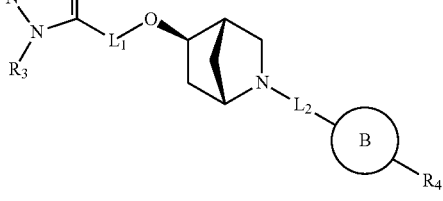

(IIIb)

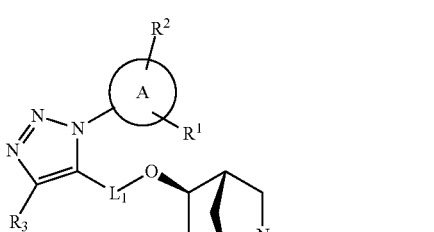

(IIIc)

(IIId)

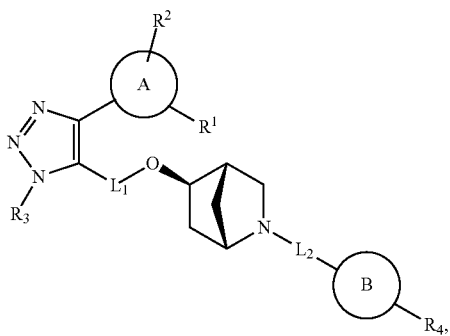

and pharmaceutically acceptable salts, hydrates, solvates, prodrugs, stereoisomers, and tautomers thereof. In an embodiment, the compounds of the invention have the structure of Formula (IIIa). In an embodiment, the compounds of the invention have the structure of Formula (IIIb). In an embodiment, the compounds of the invention have the structure of Formula (IIIc). In an embodiment, the compounds of the invention have the structure of Formula (IIId).

In another embodiment, the compounds of Formula (I) have the structure of Formula (IVa) or (IVd):

(IVa)

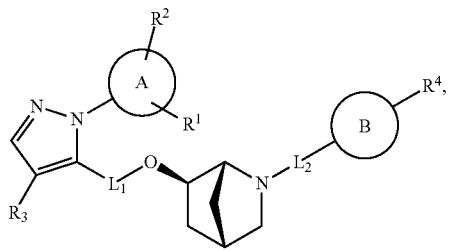

(IVb)

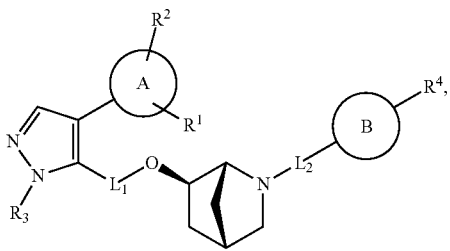

(IVc)

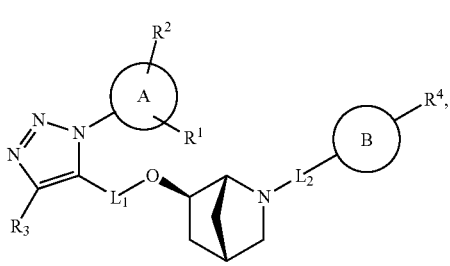

(IVd)

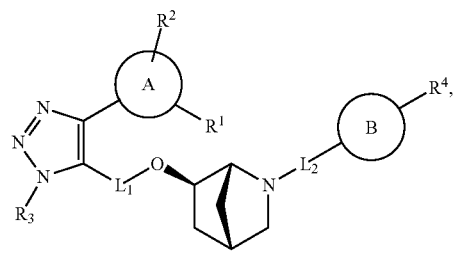

and pharmaceutically acceptable salts, hydrates, solvates, prodrugs, stereoisomers, and tautomers thereof. In an embodiment, the compounds of the invention have the structure of Formula (IVa). In an embodiment, the compounds of the invention have the structure of Formula (IVb). In an embodiment, the compounds of the invention have the structure of Formula (IVc). In an embodiment, the compounds of the invention have the structure of Formula (IVd).

In another embodiment, the compounds of Formula (I) have the structure of Formula (Va) or (Vd):

(Va)

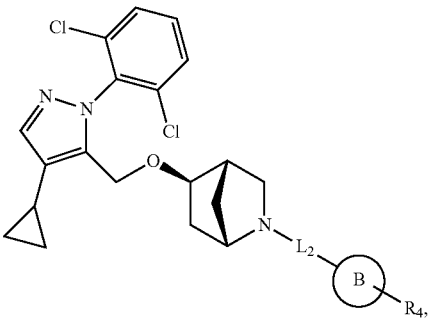

(Vb)

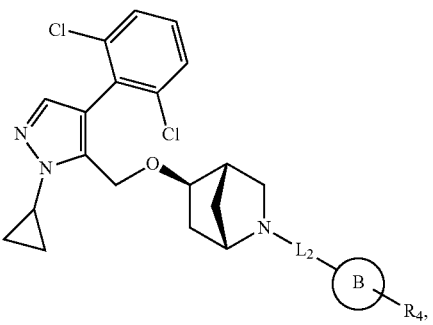

(Vc)

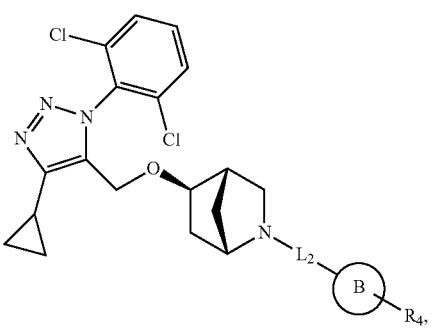

(Vd)

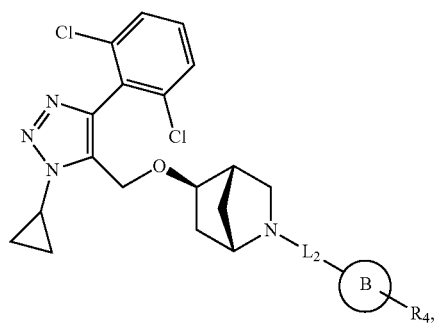

and pharmaceutically acceptable salts, hydrates, solvates, prodrugs, stereoisomers, and tautomers thereof. In an embodiment, the compounds of the invention have the structure of Formula (Va). In an embodiment, the compounds of the invention have the structure of Formula (Vb). In an embodiment, the compounds of the invention have the structure of Formula (Vc). In an embodiment, the compounds of the invention have the structure of Formula (Vd).

In another embodiment, the compounds of Formula (I) have the structure of Formula (VIa) or (VId):

(VIa)

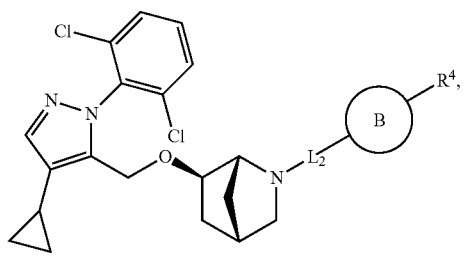

(VIb)

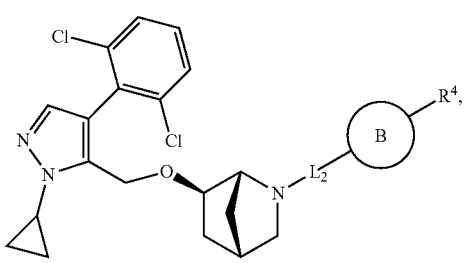

(VIc)

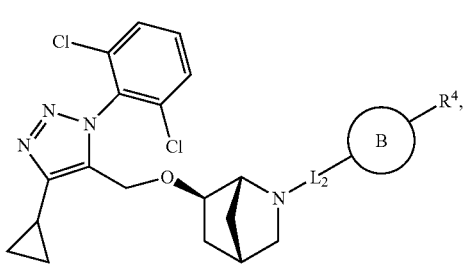

(VId)

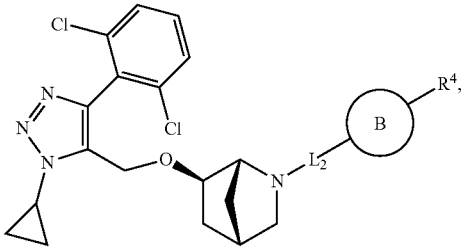

and pharmaceutically acceptable salts, hydrates, solvates, prodrugs, stereoisomers, and tautomers thereof. In an embodiment, the compounds of the invention have the structure of Formula (VIa). In an embodiment, the compounds of the invention have the structure of Formula (VIb). In an embodiment, the compounds of the invention have the structure of Formula (VIc). In an embodiment, the compounds of the invention have the structure of Formula (VId).

In another embodiment, the compounds of Formula (I) have the structure of Formula (VIIa) or (VIId):

(VIIa)

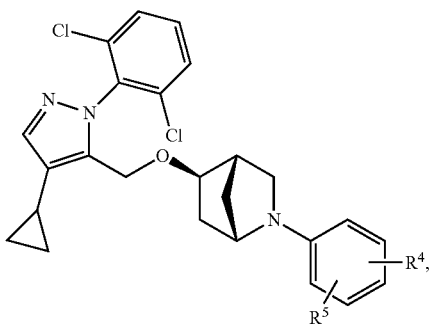

(VIIb)

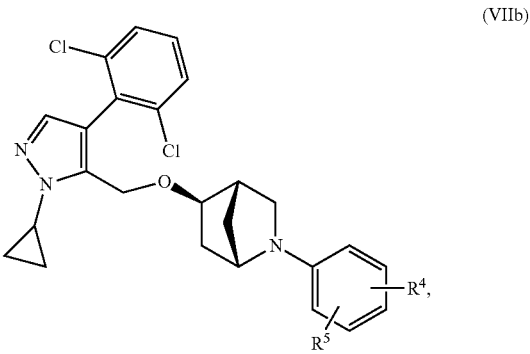

(VIIc)

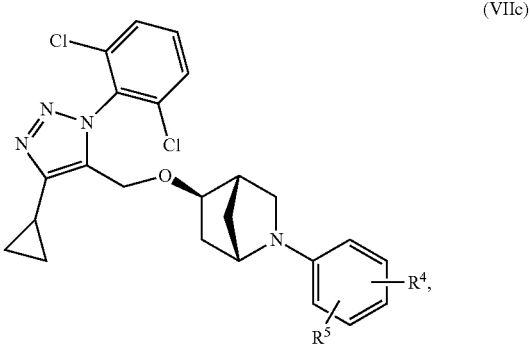

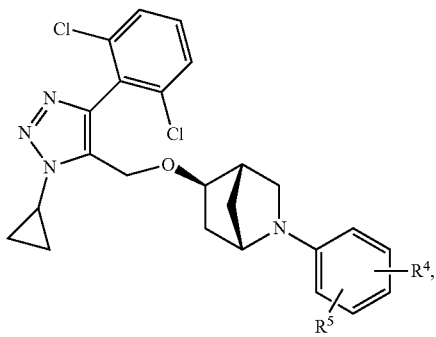
(VIId)

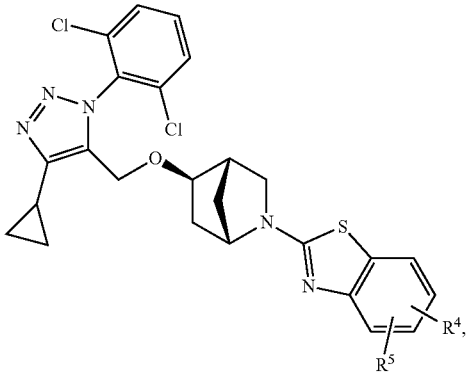
(VIIIc)

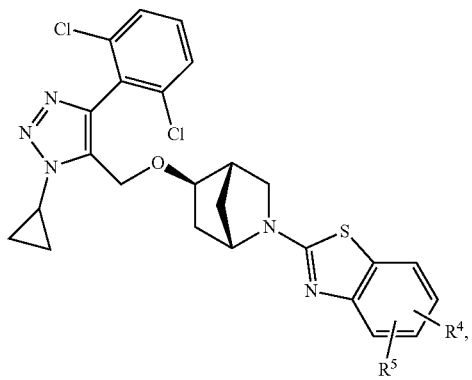
(VIIId)

and pharmaceutically acceptable salts, hydrates, solvates, prodrugs, stereoisomers, and tautomers thereof. In an embodiment, the compounds of the invention have the structure of Formula (VIIa). In an embodiment, the compounds of the invention have the structure of Formula (VIIb). In an embodiment, the compounds of the invention have the structure of Formula (VIIc). In an embodiment, the compounds of the invention have the structure of Formula (VIId).

In another embodiment, the compounds of Formula (I) have the structure of Formula (VIIIa) or (VIIId):

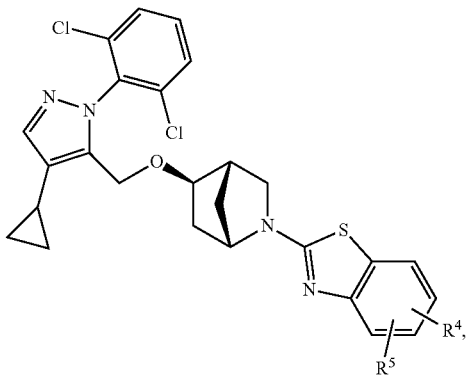
(VIIIa)

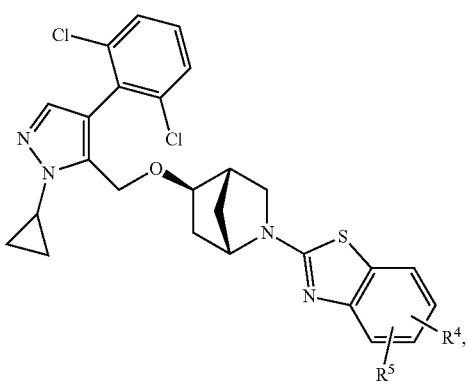
(VIIIb)

and pharmaceutically acceptable salts, hydrates, solvates, prodrugs, stereoisomers, and tautomers thereof. In an embodiment, the compounds of the invention have the structure of Formula (VIIIa). In an embodiment, the compounds of the invention have the structure of Formula (VIIIb). In an embodiment, the compounds of the invention have the structure of Formula (VIIIc). In an embodiment, the compounds of the invention have the structure of Formula (VIIId).

In an embodiment, the compound is selected from the group consisting of the group consisting of:

4-[(1S,4S,5R)-5-{[4-cyclopropyl-1-(2,6-dichlorophenyl)-1H-pyrazol-5-yl]methoxy}-2-azabicyclo[2.2.1]heptan-2-yl]benzoic acid (I-1);

4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-2-fluorobenzoic acid (I-2);

4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-2,6-difluorobenzoic acid (I-3);

6-[(1S,4S,5R)-5-{[4-cyclopropyl-1-(2,6-dichlorophenyl)-1H-pyrazol-5-yl]methoxy}-2-azabicyclo[2.2.1]heptan-2-yl]pyridine-3-carboxylic acid (I-4);

5-[(1S,4S,5R)-5-{[4-cyclopropyl-1-(2,6-dichlorophenyl)-1H-pyrazol-5-yl]methoxy}-2-azabicyclo[2.2.1]heptan-2-yl]pyridine-2-carboxylic acid (I-5);

5-[(1S,4S,5R)-5-{[4-cyclopropyl-1-(2,6-dichlorophenyl)-1H-pyrazol-5-yl]methoxy}-2-azabicyclo[2.2.1]heptan-2-yl]pyrimidine-2-carboxylic acid (I-6);

4-[(1S,4S,5R)-5-{[4-cyclopropyl-1-(2,6-dimethylphenyl)-1H-pyrazol-5-yl]m ethoxy}-2-azabicyclo[2.2.1]heptan-2-yl]-2-fluorobenzoic acid (I-7);

4-[(1S,4S,5R)-5-{[1-(2-chloro-6-methylphenyl)-4-cyclopropyl-1H-pyrazol-5-yl]methoxy}-2-azabicyclo[2.2.1]heptan-2-yl]-2-fluorobenzoic acid (I-8);

4-[(1S,4S,5R)-5-{[1-(2-chloro-6-fluorophenyl)-4-cyclopropyl-1H-pyrazol-5-yl]methoxy}-2-azabicyclo[2.2.1]heptan-2-yl]-2-fluorobenzoic acid (I-9);

4-[(1S,4S,5R)-5-{[4-cyclopropyl-1-(2,6-difluorophenyl)-1H-pyrazol-5-yl]methoxy}-2-azabicyclo[2.2.1]heptan-2-yl]-2-fluorobenzoic acid (I-10);

4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]benzoic acid (I-11);

4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-2-fluorobenzoic acid (I-12);

4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-3-fluorobenzoic acid (I-13);

4-[(1S,3R,4S,5R)-5-{[4-cyclopropyl-1-(2,6-dichlorophenyl)-1H-pyrazol-5-yl]methoxy}-3-methyl-2-azabicyclo[2.2.1]heptan-2-yl]benzoic acid (I-14);

4-[(1S,3R,4S,5R)-5-{[4-cyclopropyl-1-(2,6-dichlorophenyl)-1H-pyrazol-5-yl]methoxy}-3-methyl-2-azabicyclo[2.2.1]heptan-2-yl]-2-fluorobenzoic acid (I-15);

4-[(1S,3R,4S,5R)-5-{[4-cyclopropyl-1-(2,6-dichlorophenyl)-1H-pyrazol-5-yl]methoxy}-3-ethyl-2-azabicyclo[2.2.1]heptan-2-yl]benzoic acid (I-16);

4-[(1R,3S,4R,5S)-5-{[4-cyclopropyl-1-(2,6-dichlorophenyl)-1H-pyrazol-5-yl]methoxy}-3-ethyl-2-azabicyclo[2.2.1]heptan-2-yl]benzoic acid (I-17);

4-[(1S,3R,4S,5R)-5-{[4-cyclopropyl-1-(2,6-dichlorophenyl)-1H-pyrazol-5-yl]methoxy}-3-ethyl-2-azabicyclo[2.2.1]heptan-2-yl]-2-fluorobenzoic acid (I-18);

4-[(1R,3S,4R,5S)-5-{[4-cyclopropyl-1-(2,6-dichlorophenyl)-1H-pyrazol-5-yl]methoxy}-3-ethyl-2-azabicyclo[2.2.1]heptan-2-yl]-2-fluorobenzoic acid (I-19);

4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-N-(oxane-4-sulfonyl)benzamide (I-20);

4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-N-[(2,2-dimethyloxan-4-yl)sulfonyl]benzamide (I-21);

4-((1S,4S,5R)-5-((4-cyclopropyl-1-(2,6-dichlorophenyl)-1H-pyrazol-5-yl)methoxy)-2-azabicyclo[2.2.1]heptan-2-yl)-N-(cyclopropylsulfonyl)benzamide (I-22);

4-((1S,4S,5R)-5-((4-cyclopropyl-1-(2,6-dichlorophenyl)-1H-pyrazol-5-yl)methoxy)-2-azabicyclo[2.2.1]heptan-2-yl)-N-((tetrahydrofuran-3-yl)sulfonyl)benzamide (I-23);

4-((1S,4S,5R)-5-((4-cyclopropyl-1-(2,6-dichlorophenyl)-1H-pyrazol-5-yl)methoxy)-2-azabicyclo[2.2.1]heptan-2-yl)-N-(((tetrahydrofuran-3-yl)methyl)sulfonyl)benzamide (I-24);

5-((1S,4S,5R)-5-((4-cyclopropyl-1-(2,6-dichlorophenyl)-1H-pyrazol-5-yl)methoxy)-2-azabicyclo[2.2.1]heptan-2-yl)-N-((tetrahydro-2H-pyran-4-yl)sulfonyl)picolinamide (I-25);

4-((1S,4R,5R)-5-((4-cyclopropyl-1-(2,6-dichlorophenyl)-1H-pyrazol-5-yl)methoxy)-3-oxo-2-azabicyclo[2.2.1]heptan-2-yl)-N-((tetrahydro-2H-pyran-4-yl)sulfonyl)benzamide (I-26);

4-((1S,4R,5R)-5-((4-cyclopropyl-1-(2,6-dichlorophenyl)-1H-pyrazol-5-yl)methoxy)-3-oxo-2-azabicyclo[2.2.1]heptan-2-yl)-2-fluoro-N-((tetrahydro-2H-pyran-4-yl)sulfonyl)benzamide (I-27);

4-((1S,3R,4S,5R)-5-((4-cyclopropyl-1-(2,6-dichlorophenyl)-1H-pyrazol-5-yl)methoxy)-3-methyl-2-azabicyclo[2.2.1]heptan-2-yl)-2-fluoro-N-((tetrahydro-2H-pyran-4-yl)sulfonyl)benzamide (I-28);

N-(cyclopropanesulfonyl)-4-[(1S,3R,4S,5R)-5-{[4-cyclopropyl-1-(2,6-dichlorophenyl)-1H-pyrazol-5-yl]methoxy}-3-methyl-2-azabicyclo[2.2.1]heptan-2-yl]-2-fluorobenzamide (I-29);

2-[(1S,4S,5R)-5-{[4-cyclopropyl-1-(2,6-dichlorophenyl)-1H-pyrazol-5-yl]methoxy}-2-azabicyclo[2.2.1]heptan-2-yl]-4-fluoro-1,3-benzothiazole-6-carboxylic acid (I-30);

4-cyclopropoxy-2-[(1S,4S,5R)-5-{[4-cyclopropyl-1-(2,6-dichlorophenyl)-1H-pyrazol-5-yl]methoxy}-2-azabicyclo[2.2.1]heptan-2-yl]-1,3-benzothiazole-6-carboxylic acid (I-31);

2-[(1S,4S,5R)-5-{[4-cyclopropyl-1-(2,6-dichlorophenyl)-1H-pyrazol-5-yl]methoxy}-2-azabicyclo[2.2.1]heptan-2-yl]-4-(oxan-4-yl)-1,3-benzothiazole-6-carboxylic acid (I-32);

3-{4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-3-fluorophenyl}propanoic acid (I-33);

3-{4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-2-fluorophenyl}propanoic acid (I-34);

3-{4-[(1S,4S,5R)-5-{[4-cyclopropyl-1-(2,6-difluorophenyl)-1H-pyrazol-5-yl]methoxy}-2-azabicyclo[2.2.1]heptan-2-yl]-3-fluorophenyl}propanoic acid (I-35);

3-{4-[(1S,4S,5R)-5-{[4-cyclopropyl-1-(2,6-dimethylphenyl)-1H-pyrazol-5-yl]methoxy}-2-azabicyclo[2.2.1]heptan-2-yl]-3-fluorophenyl}propanoic acid (I-36);

3-{4-[(1S,4S,5R)-5-{[1-(2-chloro-6-methylphenyl)-4-cyclopropyl-1H-pyrazol-5-yl]methoxy}-2-azabicyclo[2.2.1]heptan-2-yl]-3-fluorophenyl}propanoic acid (I-37);

3-{4-[(1S,4S,5R)-5-{[1-(2-chloro-6-fluorophenyl)-4-cyclopropyl-1H-pyrazol-5-yl]methoxy}-2-azabicyclo[2.2.1]heptan-2-yl]-3-fluorophenyl}propanoic acid (I-38);

3-{4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-3-fluorophenyl}propanoic acid (I-39);

3-{4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-3-fluorophenyl}cyclobutane-1-carboxylic acid (I-40);

4-[(1S,4S,5R)-5-{[1-cyclopropyl-4-(2,6-dichlorophenyl)-1H-pyrazol-5-yl]methoxy}-2-azabicyclo[2.2.1]heptan-2-yl]benzoic acid (I-41);

4-[(1S,4S,5R)-5-{[1-cyclopropyl-4-(2,6-dichlorophenyl)-1H-pyrazol-5-yl]methoxy}-2-azabicyclo[2.2.1]heptan-2-yl]-2-fluorobenzoic acid (I-42);

3-{4-[(1S,4S,5R)-5-{[1-cyclopropyl-4-(2,6-dichlorophenyl)-1H-pyrazol-5-yl]methoxy}-2-azabicyclo[2.2.1]heptan-2-yl]phenyl}propanoic acid (I-43);

3-{4-[(1S,4S,5R)-5-{[1-cyclopropyl-4-(2,6-dichlorophenyl)-1H-pyrazol-5-yl]methoxy}-2-azabicyclo[2.2.1]heptan-2-yl]-3-fluorophenyl}propanoic acid (I-44);

4-[(1S,4S,5R)-5-{[1-cyclopropyl-4-(2,6-dichlorophenyl)-1H-pyrazol-5-yl]methoxy}-2-azabicyclo[2.2.1]heptan-2-yl]-2-fluoro-N-(2-methanesulfonylethyl)benzamide (I-45);

4-[(1S,4S,5R)-5-{[1-cyclopropyl-4-(2,6-dichlorophenyl)-1H-pyrazol-5-yl]methoxy}-2-azabicyclo[2.2.1]heptan-2-yl]-N-(oxane-4-sulfonyl)benzamide (I-46);

2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-fluoro-1,3-benzothiazole-6-carboxylic acid (I-47);

4-cyclopropoxy-2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-1,3-benzothiazole-6-carboxylic acid (I-48);

2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-(oxan-4-yl)-1,3-benzothiazole-6-carboxylic acid (I-49);

2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-[(3S)-oxolan-3-yl]-1,3-benzothiazole-6-carboxylic acid (I-50);

2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-[(3R)-oxolan-3-yl]-1,3-benzothiazole-6-carboxylic acid (I-51);

4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]benzoic acid (I-52);

4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-2-fluorobenzoic acid (I-53);

3-{4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-3-fluorophenyl}propanoic acid (I-54);

3-{4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-2-fluorophenyl}propanoic acid (I-55);

4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-N-(oxane-4-sulfonyl)benzamide (I-56);

4-cyclopropoxy-2-((1S,4S,5R)-5-((4-cyclopropyl-1-(2,6-dichlorophenyl)-1H-1,2,3-triazol-5-yl)methoxy)-2-azabicyclo[2.2.1]heptan-2-yl)benzo[d]thiazole-6-carboxylic acid (I-57);

2-((1S,4S,5R)-5-((4-cyclopropyl-1-(2,6-dichlorophenyl)-1H-1,2,3-triazol-5-yl)methoxy)-2-azabicyclo[2.2.1]heptan-2-yl)-4-((R)-tetrahydrofuran-3-yl)benzo[d]thiazole-6-carboxylic acid (I-58);

2-((1S,4S,5R)-5-((4-cyclopropyl-1-(2,6-dichlorophenyl)-1H-1,2,3-triazol-5-yl)methoxy)-2-azabicyclo[2.2.1]heptan-2-yl)-4-((S)-tetrahydrofuran-3-yl)benzo[d]thiazole-6-carboxylic acid (I-59);

2-((1S,4S,5R)-5-((4-cyclopropyl-1-(2,6-dichlorophenyl)-1H-1,2,3-triazol-5-yl)methoxy)-2-azabicyclo[2.2.1]heptan-2-yl)-4-(tetrahydro-2H-pyran-4-yl)benzo[d]thiazole-6-carboxylic acid (I-60);

2-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-4-[(3S)-oxolan-3-yloxy]-1,3-benzothiazole-6-carboxylic acid (I-61);

2-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-4-[(3R)-oxolan-3-yloxy]-1,3-benzothiazole-6-carboxylic acid (I-62);

2-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]-4-(trifluoromethoxy)-1,3-benzothiazole-6-carboxylic acid (I-63);

4-cyclopropoxy-2-((1S,4S,5R)-5-((1-cyclopropyl-4-(2,6-dichlorophenyl)-1H-1,2,3-triazol-5-yl)methoxy)-2-azabicyclo[2.2.1]heptan-2-yl)benzo[d]thiazole-6-carboxylic acid (I-64);

2-((1S,4S,5R)-5-((1-cyclopropyl-4-(2,6-dichlorophenyl)-1H-1,2,3-triazol-5-yl)methoxy)-2-azabicyclo[2.2.1]heptan-2-yl)-4-((R)-tetrahydrofuran-3-yl)benzo[d]thiazole-6-carboxylic acid (I-65);

2-((1S,4S,5R)-5-((1-cyclopropyl-4-(2,6-dichlorophenyl)-1H-1,2,3-triazol-5-yl)methoxy)-2-azabicyclo[2.2.1]heptan-2-yl)-4-((S)-tetrahydrofuran-3-yl)benzo[d]thiazole-6-carboxylic acid (I-66);

2-((1S,4S,5R)-5-((1-cyclopropyl-4-(2,6-dichlorophenyl)-1H-1,2,3-triazol-5-yl)methoxy)-2-azabicyclo[2.2.1]heptan-2-yl)-4-(tetrahydro-2H-pyran-4-yl)benzo[d]thiazole-6-carboxylic acid (I-67);

4-cyclobutyl-2-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]-1,3-benzothiazole-6-carboxylic acid (I-68)

4-cyclopentyl-2-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]-1,3-benzothiazole-6-carboxylic acid (I-69); and 4-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]benzoic acid (I-70).

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain further asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

The compounds of Formula I may form salts, solvates, polymorphs and isotopologues which are also within the scope of this invention. Reference to a compound of the Formula herein is understood to include reference to salts thereof, unless otherwise indicated.

Method of Synthesizing the Compounds

The compounds of the present invention can be prepared in a number of ways from commercially available starting materials or synthesized using known organic, inorganic, and/or enzymatic processes well known to those skilled in the art of organic synthesis. By way of example, compounds of the present invention can be synthesized using the methods described below, together with synthetic methods known in the art of synthetic organic chemistry, or variations thereof as appreciated by those skilled in the art. Preferred methods include but are not limited to those methods described below. Compounds of the present invention can be synthesized by the steps outlined in the General Schemes below which comprise different sequences of assembling intermediates. Starting materials are either commercially available or made by known procedures in the reported literature or as illustrated.

Compounds of Formula (I) wherein $L_1$ is —$(CH_2)_p$— and the bridged bicycle is 2-azabicyclo[2.2.1]heptane, can be prepared using intermediates 1a, 1b and 1e as outlined in the following General Scheme A.

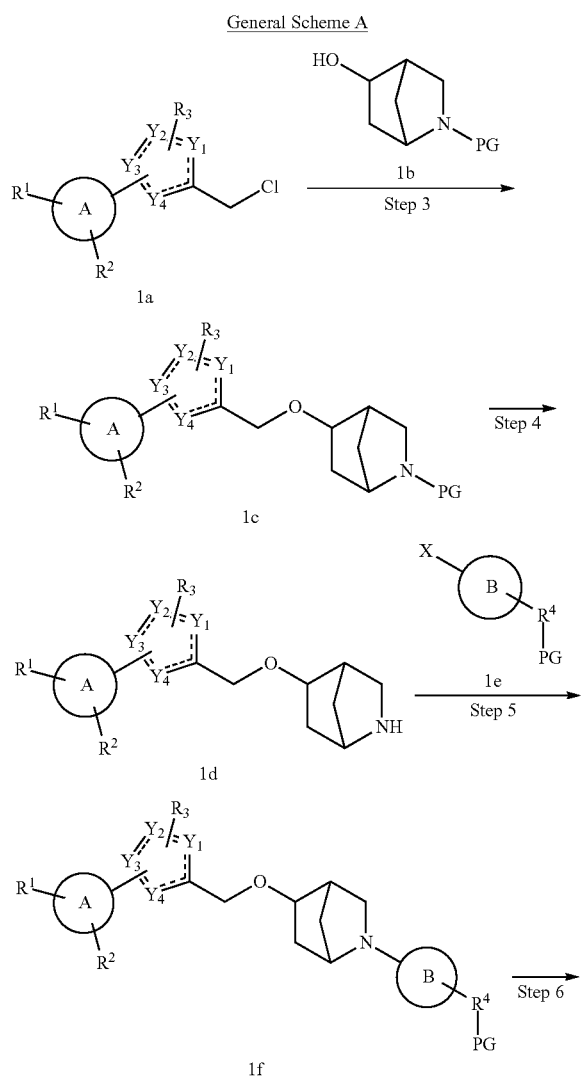

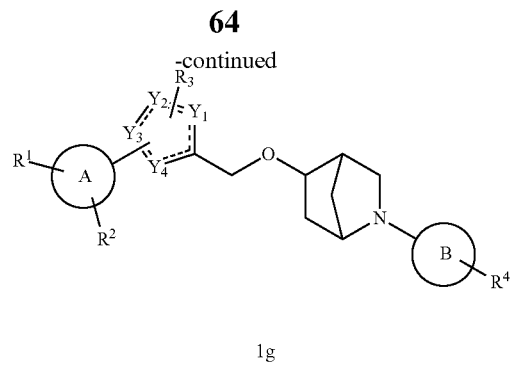

wherein $Y_1$-$Y_4$, A, B, and $R^1$-$R^4$ are defined as in herein.

Nucleophilic addition of 1b to 1a in the presence of a base (i.e., sodium hydride (NaH)) and in a solvent (i.e., THF) provides 1c. Deprotection of intermediate 1c (i.e., when PG is an acid labile group, i.e., BOC) in the presence of a strong acid (i.e., trifluoroacetic acid (TFA)) and in a solvent (i.e., dichloromethane (DCM)) affords the intermediate 1d. Alternatively deprotection of intermediate 1c when PG is benzylcarbamate (Cbz) in the presence of a palladium catalyst (i.e., palladium on carbon), hydrogen gas, and in a solvent (i.e., dichloromethane (DCM)) also affords the intermediate 1d. Coupling of 1d with 1e, wherein $R^4$ in reagent 1e is optionally protected, using a catalytic amount of a palladium catalyst and ligand (i.e., palladium (II) acetate (Pd(OAc)$_2$) and 1,1'-Ferrocenediyl-bis(diphenylphosphine) (dppf)) and acetic anhydride in a solvent, e.g., DMF, at elevated temperature provides intermediate 1f. Deprotection intermediate 1f provides the desired product 1g of Formula (I). Analogous compounds of Formula (I) wherein the azabicyclo[2.2.1]heptane is attached at the 6-position can also be synthesized as described in General Scheme 1 by using an N-protected-2-azabicyclo[2.2.1]heptan-6-ol in place of intermediate 1b.

Compounds of the invention in which $Y_1$ is C—$R_3$, $Y_2$ is CH, $Y_3$ is N, and $Y_4$ is N-A and wherein A, B, and $R_1$-$R_4$, are as defined herein, $R^{3b}$ is an alkyl group, X is halogen (i.e., F, Cl, Br, I) or another suitable leaving group (i.e., mesylate), and PG is a protecting group (i.e., tert-butylcarbamate (BOC), benzylcarbamate (Cbz)) may be prepared by the procedures described in General Scheme 2 using intermediates g1a-g1f, g1g1, g1g2, g1h1, g1h2, g1i1, g1i2, g1j, g1k1, and g1k2.

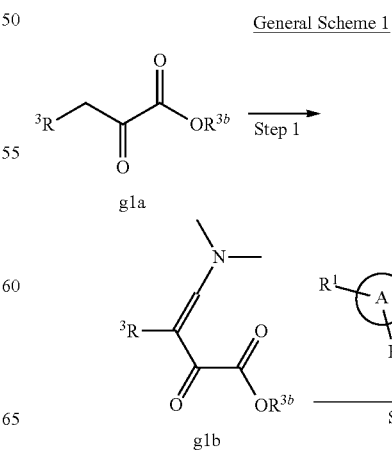

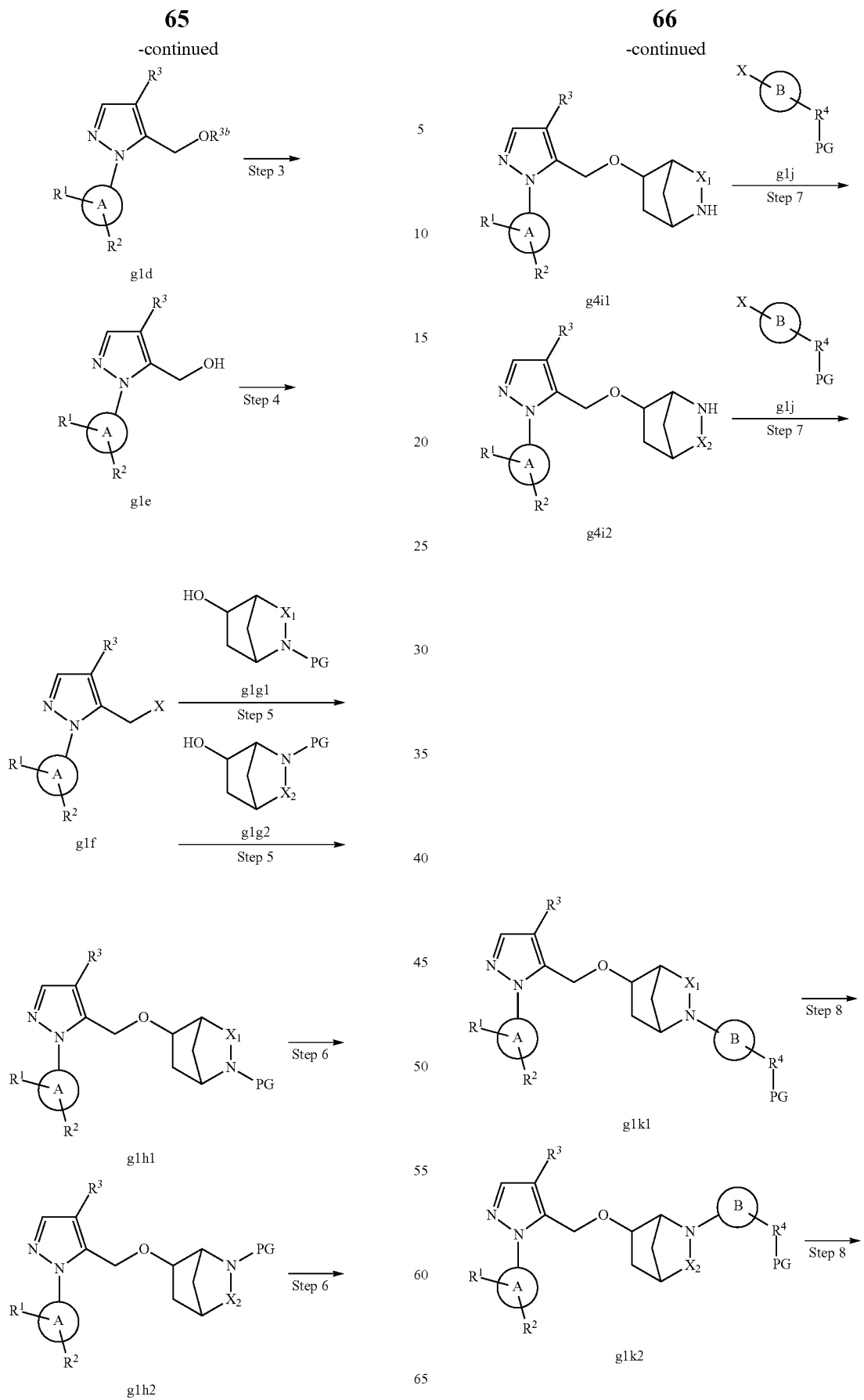

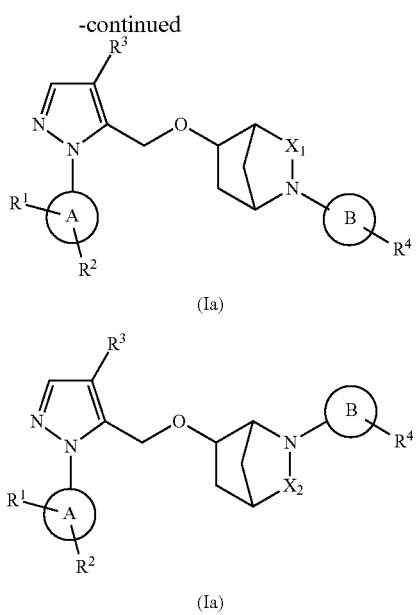

(Ia)

(Ia)

Condensation of β-substituted-α-ketoester g1a with N,N-dimethylformamide dimethylacetal at room temperature or optionally at elevated temperature provides intermediate enaminone g1b. Intermediate g1b undergoes acid-catalyzed facile vinylogous dimethylamine substitution with hydrazine g1c followed by condensation to the keto group to form pyrazole-carboxylate intermediate g1d. Reduction of the ester functional group in g1d with a reducing agent (i.e. lithium aluminumhydride) provides alcoholic intermediate g1e. Alcohol g1e is converted to the corresponding halide g1f using a chlorinating agent (i.e. thionyl chloride in the presence of benzotriazole), a brominating agent (i.e. $CBr_4$ in the presence of triphenylphosphine), and or iodination agent (i.e. methyltriphenylphosphine iodide) in a solvent (i.e., DCM, THF, DMF). Under a basic condition (i.e. NaH) in a solvent (i.e. DMF) at room temperature or below (sometimes, elevated temperature may be necessary), protected 5-hydroxy-aza-bicycloheptane intermediate g1g1 or 6-hydroxy-aza-bicycloheptane intermediate g1g2 reacts with halide intermediate g1f to form the ether g1h1 or g1h2. Deprotection of intermediate g1h1 or g1h2 (i.e., when PG is an acid labile group, i.e., Cbz) in the presence of a strong acid (i.e., HCl) or a Lewis acid (i.e. TMSI) and in a solvent (i.e., dichloromethane (DCM)) affords the intermediate g1i1 or g1i2. Coupling of g1i1 or g1i2 with g1j, wherein $R^4$ in reagent g1j is optionally protected, using a catalytic amount of a palladium catalyst and ligand (i.e., palladium (II) acetate ($Pd(OAc)_2$) and Xantphos) and mild base (i.e. $Cs_2CO_3$) in a solvent, e.g., toluene, at elevated temperature affords the desired product of Formula (Ia) when $R^4$ is unprotected, or advanced intermediate g1k1 or g1k2 when $R^4$ is protected. Alternatively, the coupling of g1i1 or g1i2 with g1j, wherein $R^4$ in reagent g1j is optionally protected, is effected by the treatment with a base (i.e. CsF, $Cs_2CO_3$) in a solvent (i.e. DMSO, DMF) at optionally at elevated temperature to afford the desired product of Formula (I) when $R^4$ is unprotected, or advanced intermediate g1k1 or g1k2 when $R^4$ is protected. Deprotection of intermediate g1k1 or g1k2 provides the desired product of Formula (I).

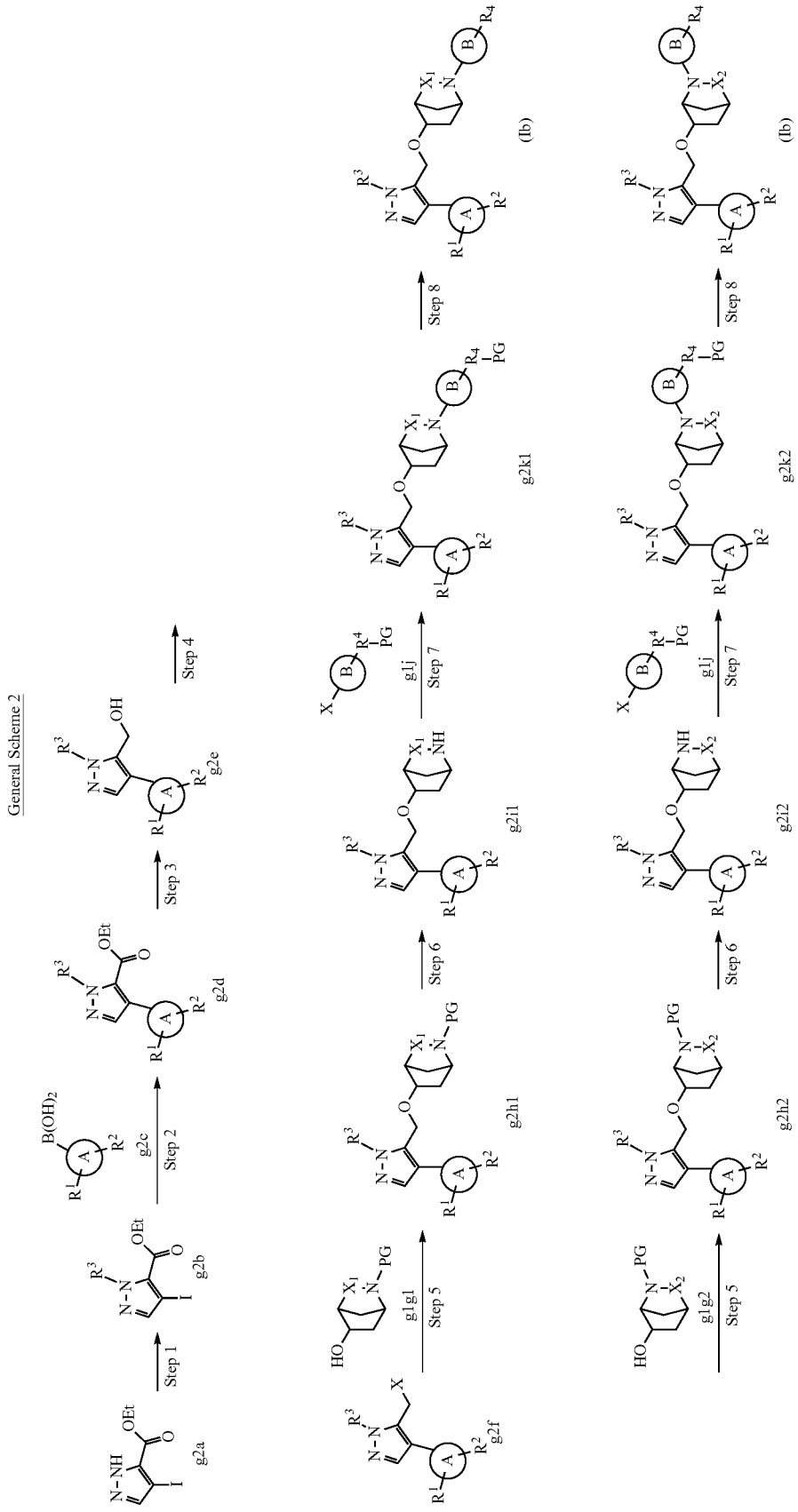

Wherein A, B, and $R_1$-$R_4$, are defined as in Formula (I), $R^{3b}$ is an alkyl group, X is halogen (i.e., F, Cl, Br, I) or another suitable leaving group (i.e., mesylate), and PG is a protecting group (i.e., tert-butylcarbamate (BOC), benzylcarbamate (Cbz)).

The general manner of preparing target compounds of Formula (Ib) by using intermediates g2a-g2f, g1g1, g1g2, g2h1, g2h2, g1i1, g1i2, g1j, g2k1, and g2k2, is outlined above in General Scheme 2. N-alkylation of 4-iodo-1H-pyrazole-5-carboxylate g2a with $R^3B(OH)_2$ under copper mediated condition (i.e. $Cu(OAc)_2$, $Cs_2CO_3$, 4-dimethylaminopyridine) in a solvent (i.e. dioxane) at mildly elevated temperature produces intermediate g2b. Boronic acid g2c couples with iodo-pyrazole intermediate g2b in the presence of a palladium catalyst and ligand (i.e. $Pd_2(dba)_3$, Sphos) under mild basic condition (i.e. $K_3PO_4$) in a solvent (i.e. toluene) at an elevated temperature affords pyrazole carboxylate g2d. Following similar procedures described in General Scheme 1 steps 3 and 4, intermediate g2d is converted to halide g2f after reduction and halogenation. Under a basic condition (i.e. NaH) in a solvent (i.e. DMF) at room temperature or below (sometimes, elevated temperature may be necessary), protected 5-hydroxy-aza-bicycloheptane intermediate g1g1 or 6-hydroxy-aza-bicycloheptane intermediate g1g2 reacts with halide intermediate g2f to form the ether g2h1 or g2h2. Deprotection of intermediate g2h1 or g2h2 (i.e., when PG is an acid labile group, i.e., Cbz) in the presence of a strong acid (i.e. HCl) or a Lewis acid (i.e. TMSI) and in a solvent (i.e., dichloromethane (DCM)) affords the intermediate g2i1 or g2i2. Following the procedures described in General Scheme 1 steps 7 and 8, intermediates g2i1 or g2i2 is reacting with g1j and subsequently converted into the desired compounds of Formula (Ib).

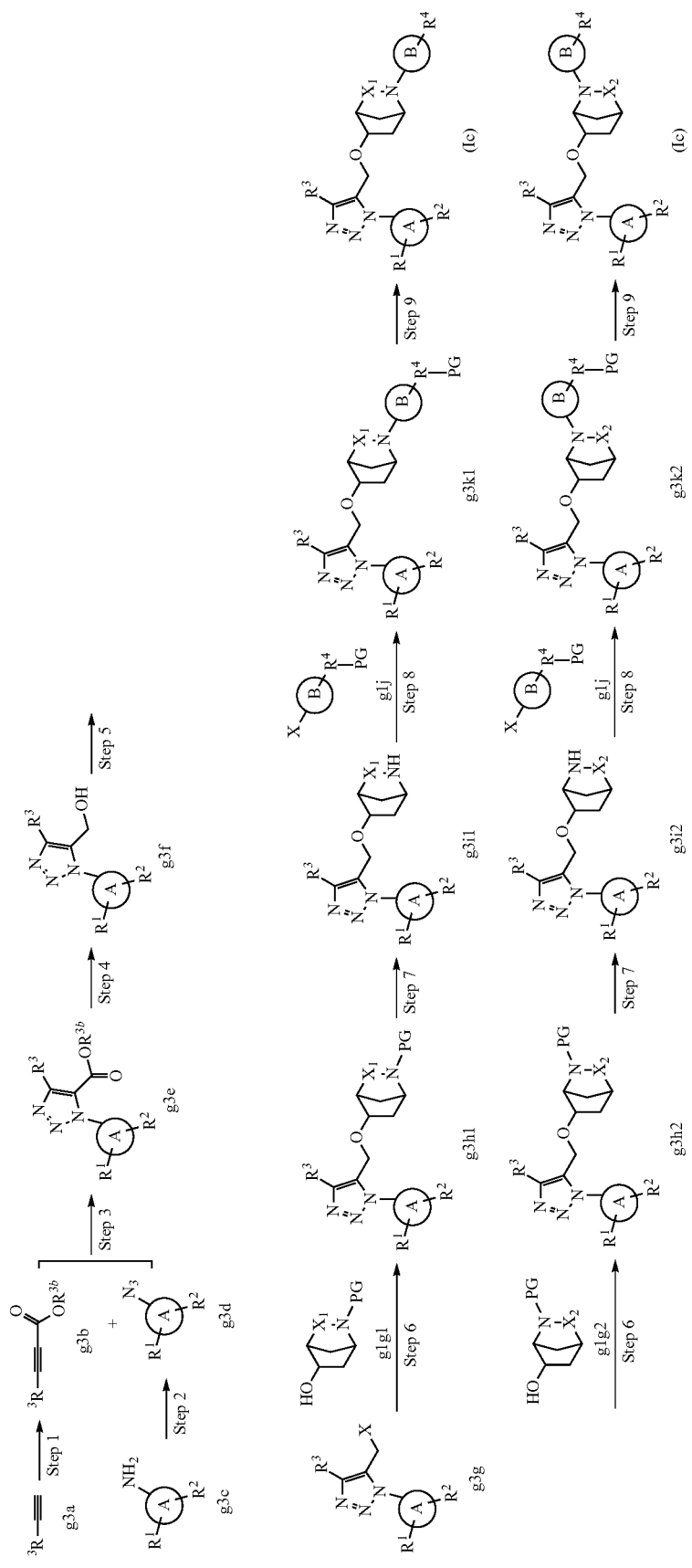

Wherein A, B, and $R_1$-$R_4$, are defined as in Formula (I), $R^{3b}$ is an alkyl group, X is halogen (i.e., F, Cl, Br, I) or another suitable leaving group (i.e., mesylate), and PG is a protecting group (i.e., tert-butylcarbamate (BOC), benzylcarbamate (Cbz)).

The general manner of preparing target compounds of Formula (Ic) by using intermediates g3a-g3g, g1g1, g1g2, g3h1, g3h2, g3i1, g3i2, g1j, g3k1, and g3k2, is outlined above in General Scheme 3. Substituted terminal alkyne g3a is lithiated and elaborated to alkynyl ester g3b under the conditions of n-butyl lithium followed by alkyl formate. Amine g3c is converted to the corresponding azide g3d using $TMSN_3$ and $tBuNO_2$ in a solvent (i.e. $CH_3CN$). Cyclization of alkynyl ester g3b and azide g3d under elevated temperature in a solvent (i.e. toluene) provides triazole carboxylate g3e. Reduction of g3e and further halogenation, following similar procedures used in General Scheme 1 steps 3 and 4, generates halide g3g. Under a basic condition (i.e. NaH) in a solvent (i.e. DMF) at room temperature or below (sometimes, elevated temperature may be necessary), protected 5-hydroxy-aza-bicycloheptane intermediate g1g1 or 6-hydroxy-aza-bicycloheptane intermediate g1g2 reacts with halide intermediate g3g to form the ether g3h1 or g3h2. Deprotection of intermediate g3h1 or g3h2 (i.e., when PG is an acid labile group, i.e., Cbz) in the presence of a strong acid (i.e., HCl) or a Lewis acid (i.e. TMSI) and in a solvent (i.e., dichloromethane (DCM)) affords the intermediate g3i1 or g3i2. Following the procedures described in General Scheme 1 steps 7 and 8, intermediates g3i1 or g3i2 is reacting with g1j and subsequently converted into the desired compounds of Formula (Ic).

General Scheme 4

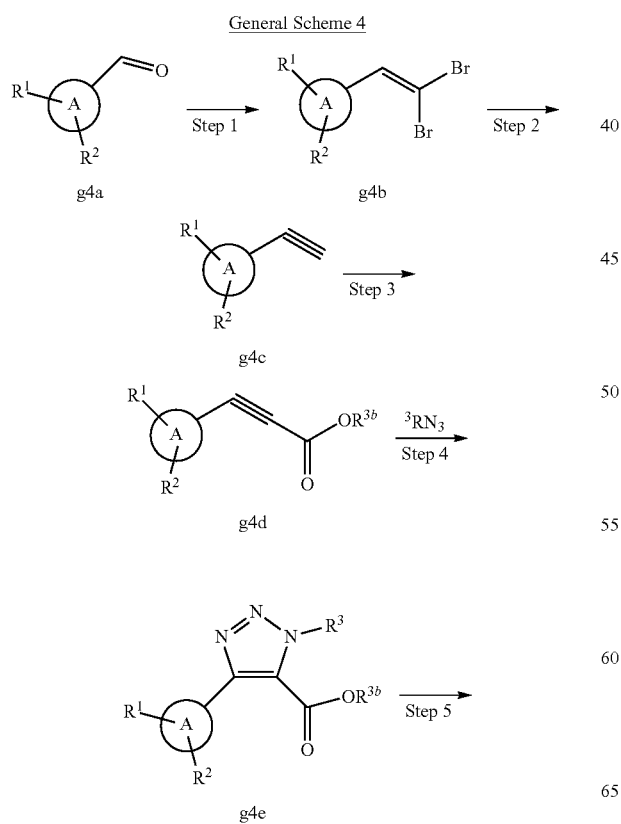

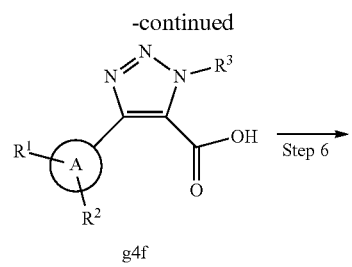

g4f

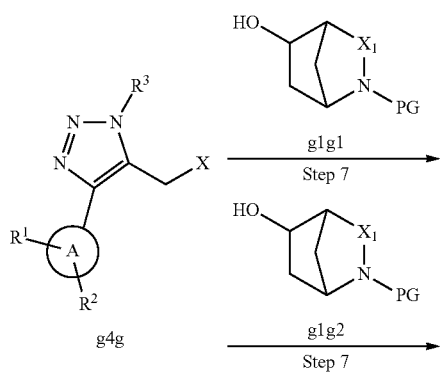

g4g

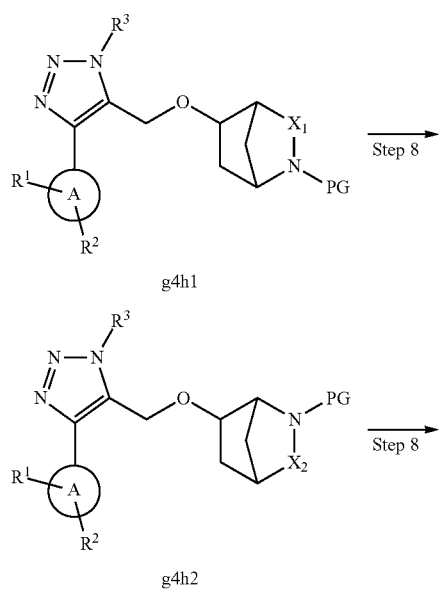

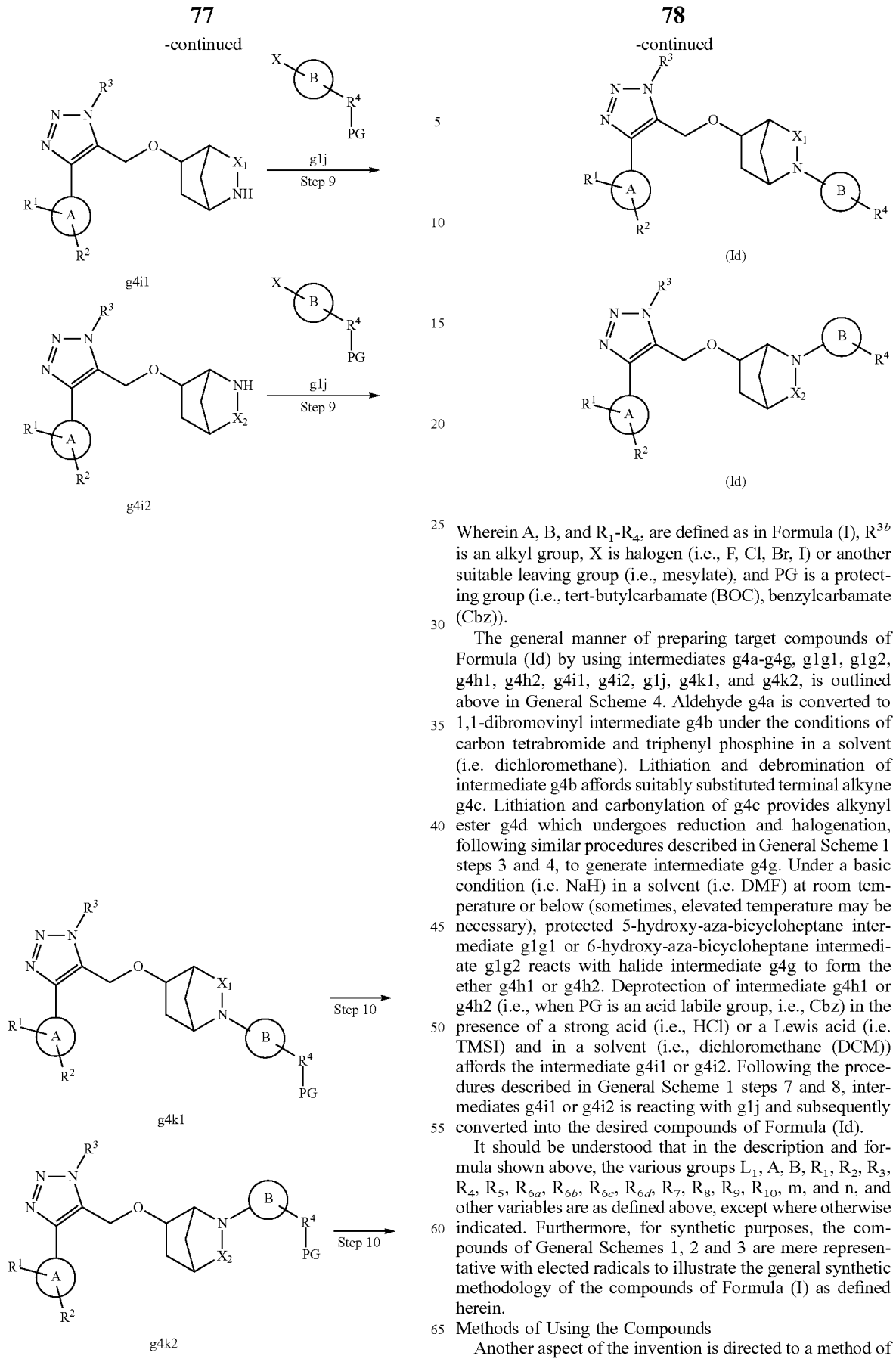

Wherein A, B, and $R_1$-$R_4$, are defined as in Formula (I), $R^{3b}$ is an alkyl group, X is halogen (i.e., F, Cl, Br, I) or another suitable leaving group (i.e., mesylate), and PG is a protecting group (i.e., tert-butylcarbamate (BOC), benzylcarbamate (Cbz)).

The general manner of preparing target compounds of Formula (Id) by using intermediates g4a-g4g, g1g1, g1g2, g4h1, g4h2, g4i1, g4i2, g1j, g4k1, and g4k2, is outlined above in General Scheme 4. Aldehyde g4a is converted to 1,1-dibromovinyl intermediate g4b under the conditions of carbon tetrabromide and triphenyl phosphine in a solvent (i.e. dichloromethane). Lithiation and debromination of intermediate g4b affords suitably substituted terminal alkyne g4c. Lithiation and carbonylation of g4c provides alkynyl ester g4d which undergoes reduction and halogenation, following similar procedures described in General Scheme 1 steps 3 and 4, to generate intermediate g4g. Under a basic condition (i.e. NaH) in a solvent (i.e. DMF) at room temperature or below (sometimes, elevated temperature may be necessary), protected 5-hydroxy-aza-bicycloheptane intermediate g1g1 or 6-hydroxy-aza-bicycloheptane intermediate g1g2 reacts with halide intermediate g4g to form the ether g4h1 or g4h2. Deprotection of intermediate g4h1 or g4h2 (i.e., when PG is an acid labile group, i.e., Cbz) in the presence of a strong acid (i.e., HCl) or a Lewis acid (i.e. TMSI) and in a solvent (i.e., dichloromethane (DCM)) affords the intermediate g4i1 or g4i2. Following the procedures described in General Scheme 1 steps 7 and 8, intermediates g4i1 or g4i2 is reacting with g1j and subsequently converted into the desired compounds of Formula (Id).

It should be understood that in the description and formula shown above, the various groups $L_1$, A, B, $R_1$, $R_2$, $R_3$, $R_4$, $R_5$, $R_{6a}$, $R_{6b}$, $R_{6c}$, $R_{6d}$, $R_7$, $R_8$, $R_9$, $R_{10}$, m, and n, and other variables are as defined above, except where otherwise indicated. Furthermore, for synthetic purposes, the compounds of General Schemes 1, 2 and 3 are mere representative with elected radicals to illustrate the general synthetic methodology of the compounds of Formula (I) as defined herein.

Methods of Using the Compounds

Another aspect of the invention is directed to a method of modulating FXR. The method comprises administering to a patient in need thereof an effective amount of a compound of Formula (I), or a pharmaceutically acceptable salt, hydrate, solvate, prodrug, stereoisomer, or tautomer thereof.

Another aspect of the invention is directed to a method of modulating FXR. The method comprises administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the invention is directed to a method of activating FXR. The method involves administering to a patient in need thereof an effective amount of a compound of Formula (I), or a pharmaceutically acceptable salt, hydrate, solvate, prodrug, stereoisomer, or tautomer thereof.

In another aspect, the invention is directed to a method of activating FXR. The method involves administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

Another aspect of the invention relates to a method of treating, preventing, inhibiting, or eliminating a disease or disorder in which FXR plays a role. The method comprises administering to a patient in need of a treatment for diseases or disorders in which FXR plays a role an effective amount of a compound of Formula (I), or a pharmaceutically acceptable salt, hydrate, solvate, prodrug, stereoisomer, or tautomer thereof. In one embodiment, the disease or disorder is a liver disease, an intestinal disease, a kidney disease, an autoimmune disorder, or cancer.

Another aspect of the invention relates to a method of treating, preventing, inhibiting, or eliminating a disease or disorder in which FXR plays a role. The method comprises administering to a patient in need of a treatment for diseases or disorders in which FXR plays a role an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier. In one embodiment, the disease or disorder is a liver disease, an intestinal disease, a kidney disease, an autoimmune disorder, or cancer.

Another aspect of the invention relates to a method of modulating FXR. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of modulating FXR. The method comprises administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

Another aspect of the present invention relates to a method of treating, preventing, inhibiting, or eliminating a disease or disorder in a patient associated with the activation of FXR, the method comprising administering to a patient in need thereof an effective amount of a compound of Formula (I), or a pharmaceutically acceptable salt, hydrate, solvate, prodrug, stereoisomer, or tautomer thereof. In one embodiment, the disease or disorder is a liver disease, an intestinal disease, a kidney disease, an autoimmune disorder, or cancer.

Another aspect of the present invention relates to a method of treating, preventing, inhibiting, or eliminating a disease or disorder in a patient associated with the activation of FXR, the method comprising administering to a patient in need thereof an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier. In one embodiment, the disease or disorder is a liver disease, an intestinal disease, a kidney disease, an autoimmune disorder, or cancer.

In another aspect, the present invention relates to a method of treating, preventing, inhibiting, or eliminating a liver disease. The method comprises administering to a patient in need of a treatment for a liver disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating a liver disease. The method comprises administering to a patient in need of a treatment for a liver disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating an intestinal disease. The method comprises administering to a patient in need of a treatment for an intestinal disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating an intestinal disease. The method comprises administering to a patient in need of a treatment for an intestinal disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating a kidney disease. The method comprises administering to a patient in need of a treatment for a kidney disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating a kidney disease. The method comprises administering to a patient in need of a treatment for a kidney disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating an autoimmune disease. The method comprises administering to a patient in need of a treatment for an autoimmune disease an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating an autoimmune disease. The method comprises administering to a patient in need of a treatment for an autoimmune disease an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

In another aspect, the present invention relates to a method of treating, preventing, inhibiting, or eliminating cancer. The method comprises administering to a patient in need of a treatment for cancer an effective amount of a compound of Formula (I), or a pharmaceutically acceptable salt, hydrate, solvate, prodrug, stereoisomer, or tautomer thereof.

In another aspect, the present invention relates to a method of treating, preventing, inhibiting, or eliminating cancer. The method comprises administering to a patient in need of a treatment for cancer an effective amount of a pharmaceutical composition comprising a compound of Formula (I), or a pharmaceutically acceptable salt, hydrate, solvate, prodrug, stereoisomer, or tautomer thereof, and a pharmaceutically acceptable carrier.

Another aspect of the present invention relates to a compound of Formula (I), or a pharmaceutically acceptable salt, hydrate, solvate, prodrug, stereoisomer, or tautomer thereof, for use in the treatment, prevention, inhibition, or elimination of a disease or disorder in which FXR plays a role. In one embodiment, the disease or disorder is a liver disease, an intestinal disease, a kidney disease, an autoimmune disorder, or cancer.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of a disease or disorder in which FXR plays a role. In one embodiment, the disease or disorder is a liver disease, an intestinal disease, a kidney disease, an autoimmune disorder, or cancer.

In another aspect, the present invention relates to a compound of Formula (I), or a pharmaceutically acceptable salt, hydrate, solvate, prodrug, stereoisomer, or tautomer thereof, for use in the treatment, prevention, inhibition, or elimination of a liver disease.

Another aspect of the present invention relates to a compound of Formula (I), or a pharmaceutically acceptable salt, hydrate, solvate, prodrug, stereoisomer, or tautomer thereof, for use in the treatment, prevention, inhibition, or elimination of a disease associated with activating FXR.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of a liver disease.

In another aspect, the present invention relates to a compound of Formula (I) or (Ia), or a pharmaceutically acceptable salt, hydrate, solvate, prodrug, stereoisomer, or tautomer thereof, for use in the treatment, prevention, inhibition, or elimination of an intestinal disease.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of an intestinal disease.

In another aspect, the present invention relates to a compound of Formula (I), or a pharmaceutically acceptable salt, hydrate, solvate, prodrug, stereoisomer, or tautomer thereof, for use in the treatment, prevention, inhibition, or elimination of a kidney disease.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of a kidney disease.

In another aspect, the present invention relates to a compound of Formula (I) or (Ia), or a pharmaceutically acceptable salt, hydrate, solvate, prodrug, stereoisomer, or tautomer thereof, for use in the treatment, prevention, inhibition, or elimination of an autoimmune disorder.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of an autoimmune disorder.

In another aspect, the present invention relates to a compound of Formula (I) or (Ia), or a pharmaceutically acceptable salt, hydrate, solvate, prodrug, stereoisomer, or tautomer thereof, for use in the treatment, prevention, inhibition, or elimination of cancer.

In another aspect, the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the treatment, prevention, inhibition, or elimination of cancer.

Another aspect of the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a disease or disorder in which FXR plays a role. In one embodiment, the disease or disorder is a liver disease, an intestinal disease, a kidney disease, an autoimmune disorder or cancer.

Another aspect of the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a disease or disorder in which FXR plays a role. In one embodiment, the disease or disorder is a liver disease, an intestinal disease, a kidney disease, an autoimmune disorder or cancer.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a liver disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a liver disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating an intestinal disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating an intestinal disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a kidney disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a kidney disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating an autoimmune disease.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating an autoimmune disease.

In another aspect, the present invention relates to the use of a compound of Formula (I), or a pharmaceutically acceptable salt, hydrate, solvate, prodrug, stereoisomer, or tautomer thereof, in the manufacture of a medicament for treating, preventing, inhibiting, or eliminating a cancer.

In another aspect, the present invention relates to the use of a pharmaceutical composition comprising a compound of Formula (I), or a pharmaceutically acceptable salt, hydrate, solvate, prodrug, stereoisomer, or tautomer thereof, and a pharmaceutically acceptable carrier, in the manufacture of a medicament for treating, preventing, inhibiting, or eliminating a cancer.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with activating FXR.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a disease associated with activating FXR.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease in which FXR plays a role.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a disease in which FXR plays a role.

Another aspect of the present invention relates to a compound of Formula (I), or a pharmaceutically acceptable salt, hydrate, solvate, prodrug, stereoisomer, or tautomer thereof, for use in the manufacture of a medicament for treating a liver disease.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a liver disease.

Another aspect of the present invention relates to a compound of Formula (I), or a pharmaceutically acceptable salt, hydrate, solvate, prodrug, stereoisomer, or tautomer thereof, for use in the manufacture of a medicament for treating an intestinal disease.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating an intestinal disease.

Another aspect of the present invention relates to a compound of Formula (I), or a pharmaceutically acceptable salt, hydrate, solvate, prodrug, stereoisomer, or tautomer thereof, for use in the manufacture of a medicament for treating a kidney disease.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating a kidney disease.

Another aspect of the present invention relates to a compound of Formula (I), or a pharmaceutically acceptable salt, hydrate, solvate, prodrug, stereoisomer, or tautomer thereof, for use in the manufacture of a medicament for treating an autoimmune disorder.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating an autoimmune disorder.

Another aspect of the present invention relates to a compound of Formula (I), or a pharmaceutically acceptable salt, hydrate, solvate, prodrug, stereoisomer, or tautomer thereof, for use in the manufacture of a medicament for treating cancer.

Another aspect of the present invention relates to a pharmaceutical composition comprising a compound of Formula (I), or a pharmaceutically acceptable salt, hydrate, solvate, prodrug, stereoisomer, or tautomer thereof, and a pharmaceutically acceptable carrier, for use in the manufacture of a medicament for treating cancer.

In other embodiments, the present invention relates to the use of an activator of FXR for the preparation of a medicament used in the treatment, prevention, inhibition or elimination of a liver disease.

In other embodiments, the present invention relates to the use of an activator of FXR for the preparation of a medicament used in the treatment, prevention, inhibition or elimination of an intestinal disease.

In other embodiments, the present invention relates to the use of an activator of FXR for the preparation of a medicament used in the treatment, prevention, inhibition or elimination of a kidney disease.

In other embodiments, the present invention relates to the use of an activator of FXR for the preparation of a medicament used in the treatment, prevention, inhibition or elimination of an autoimmune disorder.

In other embodiments, the present invention relates to the use of an activator of FXR for the preparation of a medicament used in the treatment, prevention, inhibition or elimination of a cancer.

The present invention also relates to the use of an activator of FXR for the preparation of a medicament used in the treatment, prevention, inhibition, or elimination of a disease or condition in which FXR plays a role, wherein the medicament comprises a compound of Formula (I).

In another aspect, the present invention relates to a method for the manufacture of a medicament for treating, preventing, inhibiting, or eliminating a disease or condition mediated by FXR, wherein the medicament comprises a compound of Formula (I), or a pharmaceutically acceptable salt, hydrate, solvate, prodrug, stereoisomer, or tautomer thereof.

In some embodiments of the methods described herein, the disease or condition is selected from the group consisting of liver disease, intestinal disease, kidney disease, an autoimmune disorder, or cancer. In other embodiments, the disease can be any disease including, but not limited to, Alagille syndrome (ALGS), atherosclerosis, biliary atresia, Byler disease, gallstone disease, hyperlipidemia, hepatocellular carcinoma, hepatocellular adenoma, cholangiocarcinoma, colorectal cancer, colorectal adenoma, ileal adenoma, renal cancer, oesophageal cancer, obesity, type-2 diabetes mellitus, and gastric cancer.

In any of the embodiments of the invention, the liver disease can be any liver diseases, including, but not limited to, primary biliary cirrhosis (PBC), primary sclerosing cholangitis (PSC), non-alcoholic fatty liver disease (NAFLD), non-alcoholic steatohepatitis (NASH), alcoholic liver disease, intra- and extra-cholestasis, biliary atresia, portal vein hypertension (PAH), spontaneous bacterial peritonitis (SBP), acute decompensation liver failure, hepatorenal syndrome and hepatic encephalopathy. In an embodiment, the liver disease is NASH. In an embodiment, the liver disease is NAFLD. In an embodiment, the liver disease is NASH and the compound of the invention is administered in combination with an anti-inflammatory agent or anti-fibrotic agent.

In any of the embodiments of the invention, the intestinal disease can be any intestinal disease, including, but not limited to, inflammatory bowel disease, Crohn's disease, ulcerative colitis, proctitis, pouchitis, Celiac's disease and bile acid diarrhea.

In an embodiment, the disease is an intestinal permeability disease, disorder or condition mediated by tight junction dysfunction. In an embodiment the disease, disorder or condition is gastric ulcers, infectious diarrhea, irritable bowel syndrome, functional GI diseases (IBS, IBS-C, IBS-D, IBS-M, post infectious IBS), inflammatory bowel disease (CD, UC), Celiac's, cancer (colorectal), Leaky Gut Syndrome, cystic fibrosis GI manifestations, multi-organ failure, microscopic colitis or necrotizing enterocolitis.

In another embodiment, compounds of the invention are used to treat one of the following disease, disorder or condition: allergy e.g. atopy, food allergy; infections e.g. respiratory infections; acute inflammation e.g. sepsis, SIRS, MOF); chronic inflammation e.g. arthritis; obesity-induced metabolic diseases e.g. NASH, diabetes, T1D/T2D, CVD; kidney disease e.g. chronic kidney disease, diabetic kidney disease; heart disease e.g. heart failure, congestive heart failure; liver disease e.g. cirrhosis, NASH, NAFLD, steatosis, PSC, PBC, portal hypertension; autoimmune disease e.g. type 1 diabetes, celiac disease, multiple sclerosis, IBD, ankylosing spondylitis, RA, lupus, alopecia areata, rheumatoid arthritis, polymyalgia rheumatica, multiple sclerosis, fibromyalgia, chronic fatigue syndrome, Sjogren's syndrome, vitiligo, thyroiditis, vasculitis, Crohn's disease, ulcerative colitis, urticaria (hives) and Raynaud's syndrome; neurological e.g. schizophrenia, autism spectrum disorders, multiple sclerosis, hepatic encephalopathy; and chronic alcoholism.

In any of the embodiments of the invention, the kidney disease can be any kidney disease, including, but not limited to, fibrotic renal disease and diabetic nephrophathy.

In any of the embodiments of the invention, the autoimmune disorder can be any autoimmune disorder, including, but not limited to, inflammatory bowel disease, autoimmune hepatitis, autoimmune liver disease (primary biliary cirrhosis (PBC) and primary sclerosing cholangitis (PSC)), and multiple sclerosis.

In any of the embodiments of the invention, the cancer can be any cancer including, but not limited to, a cancer is selected from the group consisting of hepatocellular carcinoma, hepatocellular adenoma, cholangiocarcinoma, colorectal cancer, colorectal adenoma, ileal adenoma, renal cancer, oesophageal cancer, or gastric cancer.

In another embodiment, the present invention relates to a compound of Formula (I), or a pharmaceutically acceptable salt, hydrate, solvate, prodrug, stereoisomer, or tautomer thereof, or a pharmaceutical composition comprising a compound, or a pharmaceutically acceptable salt, hydrate, solvate, prodrug, stereoisomer, or tautomer thereof, of the present invention and a pharmaceutically acceptable carrier used for the treatment of diseases including, but not limited to liver diseases, intestinal diseases, kidney diseases, autoimmune disorders or cancer.

Another aspect of the invention is directed to pharmaceutical compositions comprising a compound of Formula (I), or a pharmaceutically acceptable salt, hydrate, solvate, prodrug, stereoisomer, or tautomer thereof, and a pharmaceutically acceptable carrier. The pharmaceutical acceptable carrier may further include an excipient, diluent, or surfactant.

In one embodiment, are provided methods of treating a disease or disorder in which FXR plays a role including a liver disease, an intestinal disease, a kidney disease or an autoimmune disorder comprising administering to a patient suffering from at least one of said diseases or disorder a compound of Formula (I).

One therapeutic use of the compounds or compositions of the present invention which activate FXR is to provide treatment to patients or subjects suffering from a liver disease, an intestinal disease, a kidney disease, an autoimmune disorder, or cancer.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The invention is further illustrated by the following examples and synthesis schemes, which are not to be construed as limiting this invention in scope or spirit to the specific procedures herein described. It is to be understood that the examples are provided to illustrate certain embodiments and that no limitation to the scope of the invention is intended thereby. It is to be further understood that resort may be had to various other embodiments, modifications, and equivalents thereof which may suggest themselves to those skilled in the art without departing from the spirit of the present invention and/or scope of the appended claims.

Analytical Methods, Materials, and Instrumentation

Unless otherwise noted, reagents and solvents were used as received from commercial suppliers. Proton nuclear magnetic resonance (NMR) spectra were obtained with a Varian spectrometer at 400 MHz, a Bruker spectrometer at 300 MHz or 400 MHz. Spectra are given in ppm (δ) and coupling constants, J, are reported in Hertz. Tetramethylsilane (TMS)

or the solvent peak was used as an internal standard. If not otherwise specified, purity and low resolution mass spectral data were measured using a Thermo Finnigan Surveyor HPLC system with Surveyor photo diode array (PDA) detection and a Thermo LCQ Fleet™ ion trap mass spectrometer. Column: Synergi 4 micron, hydro-RP80A, 30×2.0 mm, Flow rate: 0.500 mL/min; Solvent A (water+0.1% formic acid), Solvent B (acetonitrile+0.1% formic acid); Gradient: 2% B at t=0 to 95% B at 3 min to 95% B at 3.3 min.

Abbreviations used in the following examples and elsewhere herein are:
AcOH acetic acid
ACN acetonitrile
aq. Aqueous
BINAP 2,2'-Bis(diphenylphosphino)-1,1'-binaphthyl
Boc tert-butyl carbamate
tert-BuONO tert-butyl nitrite
CbzCl benzyl chloroformate
CDI carbonyldiimidazole
$Cs_2CO_3$ cesium carbonate
$CuBr_2$ copper(II)bromide
DCM dichloromethane
DIAD diisopropyl azodicarboxylate
DIEA N,N-diisopropylethylamine
DMA dimethylacetamide
DMAP 4-dimethylaminopyridine
DMF N,N-dimethylformamide
DMSO dimethylsulfoxide
dppf bis(diphenylphosphino)ferrocene
EDCI 1-ethyl-3-(3-dimethylaminopropyl)carbodiimide
equiv. equivalents
ESI electrospray ionization
$Et_2O$ diethylether
EtOAc ethyl acetate
EtOH ethanol
h hours
HATU 1-[bis(dimethylamino)methylene]-1H-1,2,3-triazolo[4,5-b]pyridinium 3-oxid hexafluorophosphate
HCl hydrogen chloride
HPLC high performance liquid chromatography
LCMS liquid chromatography-mass spectrometry
LAH lithium aluminium hydride
LiOH lithium hydroxide
MeOH methanol
min minutes
MeCN acetonitrile
MeI methyl iodide
MS mass spectrometry
NaOMe sodium methoxide
NaOH sodium hydroxide
NaSCN sodium thiocyanate
$NEt_3$ triethylamine
$NH_2OH \cdot HCl$ hydroxylamine hydrochloride
NCS N-chlorosuccinimide
NIS N-Iodosuccinimide
$Pd(OAc)_2$ palladium (II) acetate
$Pd_2(dba)_3$ tris(dibenzylideneacetone)dipalladium
PE petroleum ether
$P(Cy)_3$ tricyclohexyl phosphine
$PPh_3$ triphenyl phosphine
RT room temperature
TEA triethylamine
$TMSCH_2N_2$ trimethylsilyldiazomethane
THF tetrahydrofuran
TFA trifluoroacetic acid Example 1: Intermediate. Benzyl (1S,4S,5R)-5-hydroxy-2-azabicyclo[2.2.1]heptane-2-carboxylate (C-1) and (1S,4R,6S)-Benzyl 6-hydroxy-2-aza-bicyclo[2.2.1]heptane-2-carboxylate (C-2)

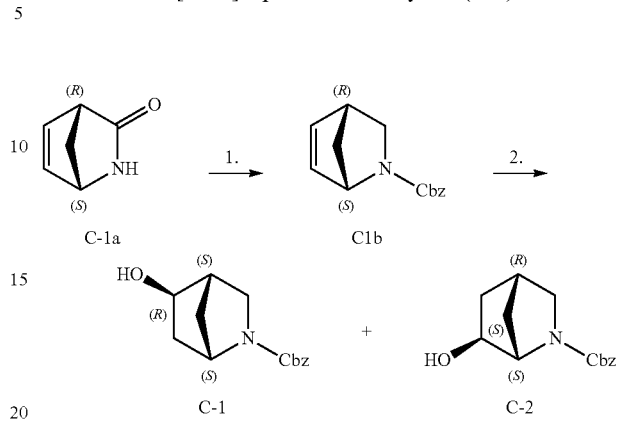

Step 1. Benzyl (1S,4R)-2-azabicyclo[2.2.1]hept-5-ene-2-carboxylate (C-1b)

To a 250-mL 3-necked round-bottom flask purged and maintained under an inert atmosphere of nitrogen was added a solution of $LiAlH_4$ (2.15 g, 56.65 mmol, 1.25 equiv.) in tetrahydrofuran (80 mL). A solution of (1S,4R)-2-azabicyclo[2.2.1]hept-5-en-3-one C-1a (5 g, 45.82 mmol, 1.0 equiv.) in tetrahydrofuran (45 mL) was added dropwise with stirring at 0° C. The mixture was stirred at 23° C. for 3 h, and then continued at 60° C. for 24 h. After cooling to room temperature, water (5 mL) was added. The resulting mixture was diluted with 250 mL of tetrahydrofuran, and the solids were removed by filtration. The filtrate was cooled to 0° C. and TEA was added (9.1 g, 89.93 mmol, 2.0 equiv.) dropwise followed by the dropwise addition of benzyl chloroformate (11.75 g, 68.88 mmol, 1.50 equiv.). The reaction mixture was stirred at 23° C. for 48 h and concentrated under reduced pressure. The crude product was purified by Flash-Prep-HPLC using the following conditions: Column, C18 silica gel; mobile phase, $CH_3CN:H_2O=0:100$ increasing to $CH_3CN:H_2O=30:70$ within 30 min; Detector, UV 254 nm. Removal of solvents provided benzyl (1S,4R)-2-azabicyclo[2.2.1]hept-5-ene-2-carboxylate C-1b in 5.6 g (53%) as a light yellow oil.

Step 2. Benzyl (1S,4S,5R)-5-hydroxy-2-azabicyclo[2.2.1]heptane-2-carboxylate (C-1) (1S,4R,6S)-Benzyl 6-hydroxy-2-aza-bicyclo[2.2.1]heptane-2-carboxylate (C-2)

To a 500-mL round-bottom flask purged and maintained under an inert atmosphere of nitrogen, was added a solution of benzyl (1S,4R)-2-azabicyclo[2.2.1]hept-5-ene-2-carboxylate (8.6 g, 24.42 mmol, 1.0 equiv.) C-1b in tetrahydrofuran (60 mL). $NaBH_4$ (1.17 g, 30.93 mmol, 0.80 equiv.) was added. The mixture was stirred 23° C. for 30 min then cooled in an ice bath. A solution of $Me_2SO_4$ (2.93 mL, 0.80 equiv.) in tetrahydrofuran (2 mL) was added dropwise with stirring at 0° C. Reaction was continued at 35° C. for 4 h. The mixture was cooled again at 0° C., a 1M sodium hydroxide aqueous solution (80 mL) was added dropwise with stirring followed by the dropwise addition of $H_2O_2$ (30%) (5 mL). The resulting mixture was stirred at 23° C. for 1 h. 250 mL of ethyl acetate was added. The mixture was washed with brine (150 mL), dried over anhydrous sodium sulfate, filtered, and concentrated under reduced pressure. The residue was purified by silica gel column chromatography eluting with ethyl acetate/petroleum ether (0-60% in 1 h, 100 ml/min). Removal of solvents provided 3.7 g (40%) of benzyl (1S,4S,5R)-5-hydroxy-2-azabicyclo[2.2.1]heptane-2-carboxylate C-1 as a colorless oil and 3.5 g (38%) its isomer (1S,4R,6S)-benzyl 6-hydroxy-2-aza-bicyclo[2.2.1]heptane-2-carboxylate C-2 also a colorless oil. Rf (C1)<Rf (C2).

C-1: $^1$H NMR (400 MHz, Methanol-$d_4$) δ 7.40-7.24 (m, 5H), 5.15-5.01 (m, 2H), 4.30-4.19 (m, 1H), 3.98-3.89 (m, 1H), 3.25 (ddd, J=18.3, 10.2, 4.0 Hz, 1H), 2.97-2.84 (m, 1H), 2.48-2.37 (m, 1H), 2.10-1.79 (m, 2H), 1.56 (ddt, J=9.9, 7.5, 2.1 Hz, 1H), 1.44 (dq, J=13.6, 2.9 Hz, 1H). Rf (C1)<Rf (C2).

C-2: $^1$H NMR (400 MHz, Methanol-$d_4$) δ 7.42-7.24 (m, 5H), 5.10 (dd, J=11.7, 3.1 Hz, 2H), 4.03 (d, J=9.9 Hz, 1H), 3.87 (tdt, J=8.4, 2.5, 1.3 Hz, 1H), 3.20 (ddt, J=15.2, 9.4, 2.8 Hz, 1H), 2.88 (ddd, J=20.8, 9.4, 1.6 Hz, 1H), 2.58-2.51 (m, 1H), 1.88-1.73 (m, 2H), 1.61-1.49 (m, 1H), 1.42 (ddt, J=13.4, 4.7, 2.4 Hz, 1H).

Example 2: Intermediate. Benzyl (1R,4R,5S)-5-hydroxy-2-azabicyclo[2.2.1]heptane-2-carboxylate (C-4) and Benzyl (1R,4S,6R)-6-hydroxy-2-azabicyclo[2.2.1]heptane-2-carboxylate (C-5)

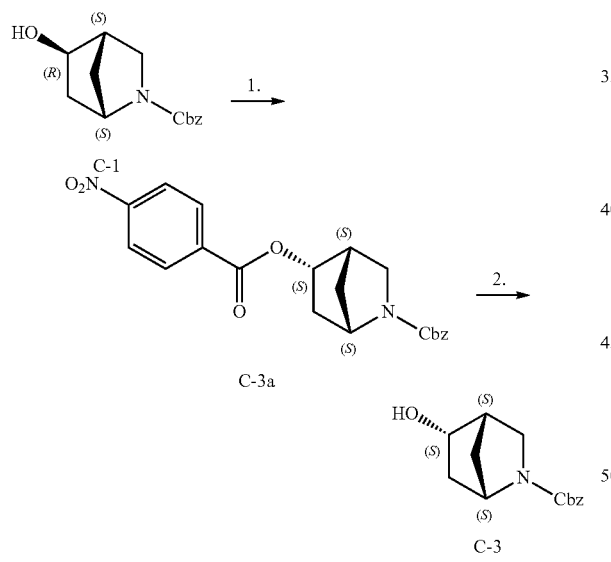

Step 1. Benzyl (1S,4S,5S)-5-[(4-nitrophenyl)carbonyloxy]-2-azabicyclo[2.2.1]heptane-2-carboxylate (C-3a)

To a 250-mL round-bottom flask was added a solution of benzyl (1S,4S,5R)-5-hydroxy-2-azabicyclo[2.2.1]heptane-2-carboxylate C-1 (1.03 g, 4.17 mmol, 1.0 equiv.) in tetrahydrofuran (50 mL) and 4-nitrobenzoic acid (1.05 g, 6.28 mmol, 1.50 equiv.). The reaction mixture was cooled to 0° C. and PPh$_3$ was added (1.64 g, 6.25 mmol, 1.50 equiv) in several batches followed by dropwise addition of DIAD (1.26 g, 6.23 mmol, 1.50 equiv). The resulting mixture was stirred at room temperature overnight and then concentrated under reduced pressure. The residue was purified by silica gel column chromatography eluting with ethyl acetate/petroleum ether (25:75) to give 1.6 g (97%) of benzyl (1S,4S,5S)-5-[(4-nitrophenyl)carbonyloxy]-2-azabicyclo[2.2.1]heptane-2-carboxylate C-3a as a colorless oil.

Step 2. Benzyl (1S,4S,5S)-5-hydroxy-2-azabicyclo[2.2.1]heptane-2-carboxylate (C-3)

To a 250-mL round-bottom flask was added a solution of benzyl (1S,4S,5S)-5-[(4-nitrophenyl)carbonyloxy]-2-azabicyclo[2.2.1]heptane-2-carboxylate C-3a (1.6 g, 4.04 mmol, 1.0 equiv.) in methanol/H$_2$O (20 mL/2 mL) and LiOH·H$_2$O (1.69 g, 40.28 mmol, 10.0 equiv.). The resulting mixture was stirred at 60° C. for 1 h, and then concentrated under reduced pressure. The crude product was purified by Flash-Prep-HPLC using the following conditions: Column, C18 silica gel; mobile phase, CH$_3$CN:H$_2$O=0:100 increasing to CH$_3$CN:H$_2$O=30:70 within 20 min; Detector, UV 254 nm. 0.6 g product was obtained. Removal of solvents afforded 0.6 g (60%) of benzyl (1S,4S,5S)-5-hydroxy-2-azabicyclo[2.2.1]heptane-2-carboxylate C-3 as a light yellow oil. $^1$H NMR (400 MHz, Methanol-$d_4$) δ 7.40-7.24 (m, 5H), 5.10 (t, J=2.5 Hz, 2H), 4.33 (dq, J=7.8, 3.6 Hz, 1H), 4.16 (dt, J=14.9, 2.5 Hz, 1H), 3.73 (ddd, J=19.9, 9.9, 1.4 Hz, 1H), 3.24-3.12 (m, 1H), 2.57 (t, J=3.7 Hz, 1H), 2.02 (dddd, J=12.9, 9.9, 4.7, 2.8 Hz, 1H), 1.76-1.65 (m, 1H), 1.58 (d, J=10.3 Hz, 1H), 1.31 (ddt, J=17.0, 12.9, 3.3 Hz, 1H).

Example 3: Intermediates. Benzyl (1R,4R,5S)-5-hydroxy-2-azabicyclo[2.2.1]heptane-2-carboxylate (C-4) and Benzyl (1R,4S,6R)-6-hydroxy-2-azabicyclo[2.2.1]heptane-2-carboxylate (C-5)

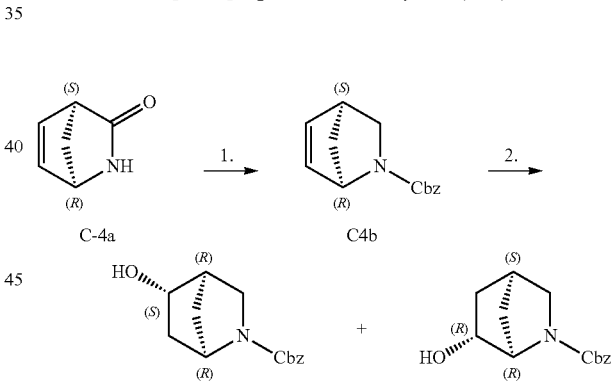

Step 1. Benzyl (1R,4S)-2-azabicyclo[2.2.1]hept-5-ene-2-carboxylate (C-2)

A solution of (1R,4S)-2-azabicyclo[2.2.1]hept-5-en-3-one C-4a (5.0 g, 45.8 mmol) in anhydrous THF (50 mL) was added slowly to a solution of LAH (28.7 mL, 57.3 mmol, 2M solution in THF) in anhydrous THF (50 mL) under a nitrogen atmosphere at 0° C. The resulting mixture was then stirred at room temperature for 3 h and then heated at 60° C. for 24 h. The mixture was cooled to 0° C. and H$_2$O (5.0 mL) was added carefully to the mixture. The resulting white suspension was filtered through a Celite pad and the pad was washed with anhydrous THF (250.0 mL). The clear filtrate was cooled to 0° C. and then treated with trimethylamine (12.8 mL, 91.6 mmol) and CbzCl (10.3 mL, 68.7 mmol).

The reaction mixture was slowly warmed to room temperature and stirred for 48 hours. The white precipitate was filtered and the resulting clear filtrate solution was concentrated to dryness. The crude material was purified by column chromatography (hexane:EtOAc 4:1) to give benzyl (1R,4S)-2-azabicyclo[2.2.1]hept-5-ene-2-carboxylate C-4b (7.06 g, 63%) as a clear oil. MS (ES, m/z): [M+1]=230.

Step 2. Benzyl (1R,4R,5S)-5-hydroxy-2-azabicyclo [2.2.1]heptane-2-carboxylate (C-4), Benzyl (1R,4S, 6R)-6-hydroxy-2-azabicyclo[2.2.1]heptane-2-carboxylate (C-5)

A mixture of benzyl (1R,4S)-2-azabicyclo[2.2.1]hept-5-ene-2-carboxylate C-4b (7.0 g, 30.8 mmol) and sodium borohydride (0.95 g, 25.1 mmol) in THF (50 mL) was stirred at 23° C. for 30 minutes under nitrogen atmosphere. The mixture was warmed to 35° C. and then dimethylsulfate (2.37 mL, 25.1 mmol) dissolved in THF (2.0 mL) was added dropwise. The resulting mixture was stirred at 35° C. for 4 hours, and then cooled to 0° C. and quenched by dropwise addition of H$_2$O (4.0 mL). A 1M aqueous solution of sodium hydroxide (70 mL, 70.0 mmol) was added at 0° C. followed by addition of hydrogen peroxide (4.0 mL, 30 wt % in H$_2$O). The mixture was warmed to room temperature and stirred for an additional hour. The resulting mixture was diluted with ethyl acetate (250 mL) and the organic layer was separated, washed with brine, and dried over MgSO$_4$, filtered and concentrated. The crude product was purified by column chromatography (hexane:ethyl acetate 1:1 v/v) to provide both benzyl (1R,4R,5S)-5-hydroxy-2-azabicyclo [2.2.1]heptane-2-carboxylate C-4 (3.0 g, Rf=0.22, clear oil) and Benzyl (1R,4S,6R)-6-hydroxy-2-azabicyclo[2.2.1]heptane-2-carboxylate C-5 (2.9 g, Rf=0.36, clear oil).

C-4: $^1$H NMR (400 MHz, CDCl$_3$) δ: 7.41-7.27 (m, 5H), 5.14-5.06 (m, 2H), 4.29 (d, J=21.5 Hz, 1H), 4.02 (d, J=6.6 Hz, 1H), 3.26 (dt, J=13.1, 6.5 Hz, 1H), 2.91 (t, J=9.8 Hz, 1H). 2.47 (s, 1H), 2.20-2.01 (m, 2H), 1.85 (t, J=10.8 Hz, 1H), 1.62-1.39 (m, 2H)

C-5: $^1$H NMR (400 MHz, CDCl$_3$) δ: 7.40-7.28 (m, 5H), 5.20-5.02 (m, 2H), 4.16-3.94 (m, 2H), 3.22 (ddd, J=9.5, 6.9, 2.9 Hz, 1H), 2.90 (dd, J=16.0, 6.1 Hz, 1H), 2.54 (s, 1H), 1.90-1.73 (m, 2H), 1.61-1.37 (m, 2H).

Example 4: Intermediate. Benzyl (1R,4R,5R)-5-hydroxy-2-azabicyclo[2.2.1]heptane-2-carboxylate (C-6)

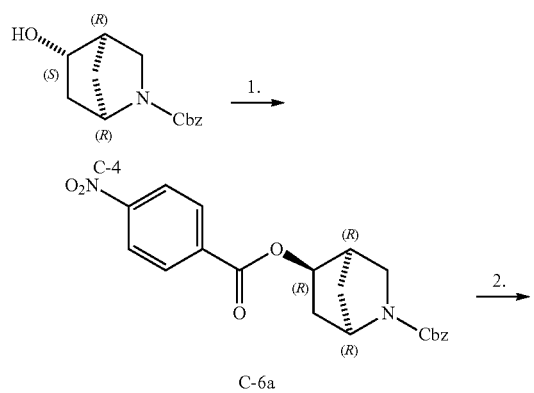

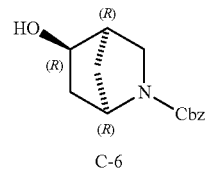

Step 1. Benzyl (1R,4R,5R)-5-((4-nitrobenzoyl)oxy)-2-azabicyclo[2.2.1]heptane-2-carboxylate (C-6a)

To a mixture of benzyl (1R,4R,5S)-5-hydroxy-2-azabicyclo[2.2.1]heptane-2-carboxylate C-4 (0.4 g, 2.4 mmol) and 4-nitrobenzoic acid (0.6 g, 2.4 mmol) in THF (10 mL) was added DIAD (1.0 mL, 4.8 mmol) and PPh$_3$ (1.28 g, 4.8 mmol) and the resulting mixture was stirred at room temperature overnight. The mixture was then partitioned between EtOAc and water. The organic layer was washed with brine, dried, filtered, concentrated, and purified by column chromatography (20-40% EtOAc in hexanes) to give benzyl (1R,4R,5R)-5-((4-nitrobenzoyl)oxy)-2-azabicyclo[2.2.1]heptane-2-carboxylate C-6a (0.85 g, 90%) as a yellow oil. MS (ES, m/z): [M+1]=397.

Step 2. Benzyl (1R,4R,5R)-5-hydroxy-2-azabicyclo [2.2.1]heptane-2-carboxylate (C-6)

To a solution of benzyl (1R,4R,5R)-5-((4-nitrobenzoyl)oxy)-2-azabicyclo[2.2.1]heptane-2-carboxylate C-6a (0.85 g, 2.1 mmol) in MeOH (6.0 mL) was added a 1M aqueous solution of NaOH (4.2 mL, 4.2 mmol) and the resulting mixture was heated at 50° C. for 2 hours. The reaction mixture was cooled to room temperature and partitioned between EtOAc and water. The organic layer was washed with 1M NaOH and brine, dried with MgSO$_4$, filtered, and concentrated. The crude product was purified by column chromatography (hexanes:EtOAc 1:1) to give benzyl (1R,4R,5R)-5-hydroxy-2-azabicyclo[2.2.1]heptane-2-carboxylate C-6 (0.32 g, 60%) as a clear oil. $^1$H NMR (400 MHz, CDCl$_3$) δ 7.43-7.21 (m, 5H), 5.20-5.02 (m, 2H), 4.35 (dt, J=18.3, 9.2 Hz, 1H), 4.21 (d, J=22.8 Hz, 1H), 3.76 (dt, J=16.5, 8.1 Hz, 1H), 3.25-3.15 (m, 1H), 2.59 (s, 1H), 2.09-1.94 (m, 1H), 1.69 (t, J=9.6 Hz, 1H), 1.53-1.31 (m, 2H). MS (ES, m/z): [M+1]=248.

Example 5: Intermediate. (1S,4R,5R)-5-hydroxy-2-[(4-methoxyphenyl)methyl]-2-azabicyclo[2.2.1]heptan-3-one (C-7) and (1S,4R,6S)-6-hydroxy-2-(4-methoxybenzyl)-2-azabicyclo[2.2.1]heptan-3-one (C-8)

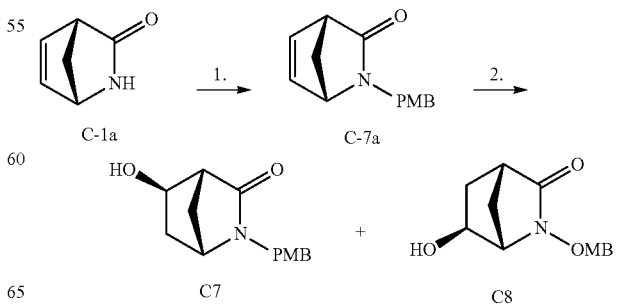

Step 1. To a 1 L round bottom flask was added a solution of (1S,4R)-2-azabicyclo[2.2.1]hept-5-en-3-one C-1a (30 g, 274.9 mmol, 1.00 equiv.) in N,N-dimethylformamide (500 mL). The solution was cooled to 0° C. Sodium hydride (12 g, 300.0 mmol, 1.10 equiv., 60% dispersion in mineral oil) was added in several batches at 0° C. The reaction mixture was stirred for another 30 min at 0° C. To this mixture was added TBAI (10 g, 27.1 mmol, 0.10 equiv.). 1-(chloromethyl)-4-methoxybenzene (47 g, 300.1 mmol, 1.10 equiv.) was added dropwise with stirring at 0° C.

The resulting mixture was stirred overnight at room temperature. The reaction was then quenched by the addition of 300 mL of chilled water. The aqueous mixture was extracted with ethyl acetate (400 mL×3). The combined organic extracts were washed with brine (200 mL×2), dried over anhydrous sodium sulfate and concentrated under vacuum. The residue was purified by silica gel column chromatography eluting with PE:EA (5:1) to afford (1S,4R)-2-[(4-methoxyphenyl)methyl]-2-azabicyclo[2.2.1]hept-5-en-3-one C-7a (56.6 g, 90%) as a yellow oil.

$^1$H NMR (400 MHz, CD$_3$OD): δ 7.14 (dd, J=8.5, 1.4 Hz, 2H), 6.88 (dq, J=9.4, 2.6, 2.1 Hz, 2H), 6.62-6.50 (m, 2H), 4.87-4.79 (m, OH), 4.26 (d, J=14.5 Hz, 1H), 4.19-4.05 (m, 2H), 3.77 (d, J=2.8 Hz, 3H), 2.98 (q, J=2.5, 1.7 Hz, 1H), 2.86 (d, J=2.9 Hz, 1H), 2.25 (ddd, J=7.3, 4.0, 1.8 Hz, 1H), 2.07 (tt, J=7.2, 1.8 Hz, 1H).

Step 2. To a 500 mL round bottom flask purged with and maintained under an inert atmosphere of nitrogen was added a solution of (1S,4R)-2-[(4-methoxyphenyl)methyl]-2-azabicyclo[2.2.1]hept-5-en-3-one C-7a (12.2 g, 53.21 mmol, 1.00 equiv.) in anhydrous dimethoxyethane (120 mL). The solution was cooled to 0° C. A solution of borane-dimethyl sulfide complex (11.6 mL, 10 M in DMS, 2.18 equiv.) was added dropwise with stirring at 0° C. After addition, the mixture was stirred at room temperature for 2 h, and then cooled to 0° C. An aqueous solution of sodium hydroxide (5.4 mL, 3 M aq, 0.30 equiv.) was added dropwise with stirring at 0° C. followed by dropwise addition of an aqueous solution of H$_2$O$_2$ (21.2 g, 3.50 equiv., 30%). The reaction was allowed to continue at room temperature overnight. The mixture was diluted with EA (500 mL), washed successively with water (500 mL×2) and brine (500 mL×2), dried over anhydrous sodium sulfate, and concentrated under vacuum. The crude product was purified by high pressure (maximum: 20 MPa) Prep-flash using the following conditions: Column, Welch Ultimate® XB-C18 OBD Column, 10 um, 50*250 mm (300 g); mobile phase, Water (0.05% TFA) and ACN (5.0% ACN up to 30.0% in 40 min); Detector, UV 254 nm, to provide (1S,4R,5R)-5-hydroxy-2-[(4-methoxyphenyl)methyl]-2-azabicyclo[2.2.1]heptan-3-one C-7 (4.6 g, 35%, with a longer retention time than isomer C-8 as a white solid. C-7: $^1$H NMR (300 MHz, CD$_3$OD): δ 7.26-7.14 (m, 2H), 6.97-6.85 (m, 2H), 4.42 (d, J=14.8 Hz, 1H), 4.16-3.98 (m, 2H), 3.80 (s, 4H), 2.73 (d, J=1.8 Hz, 1H), 2.08-1.84 (m, 3H), 1.46 (dt, J=13.2, 2.5 Hz, 1H). Isomeric compound (1S,4R,6S)-6-hydroxy-2-(4-methoxybenzyl)-2-azabicyclo[2.2.1]heptan-3-one C-8 was obtained also, in similar yield.

Example 6: 4-[(1S,4S,5R)-5-{[4-cyclopropyl-1-(2,6-dichlorophenyl)-1H-pyrazol-5-yl]methoxy}-2-azabicyclo[2.2.1]heptan-2-yl]benzoic acid (I-1)

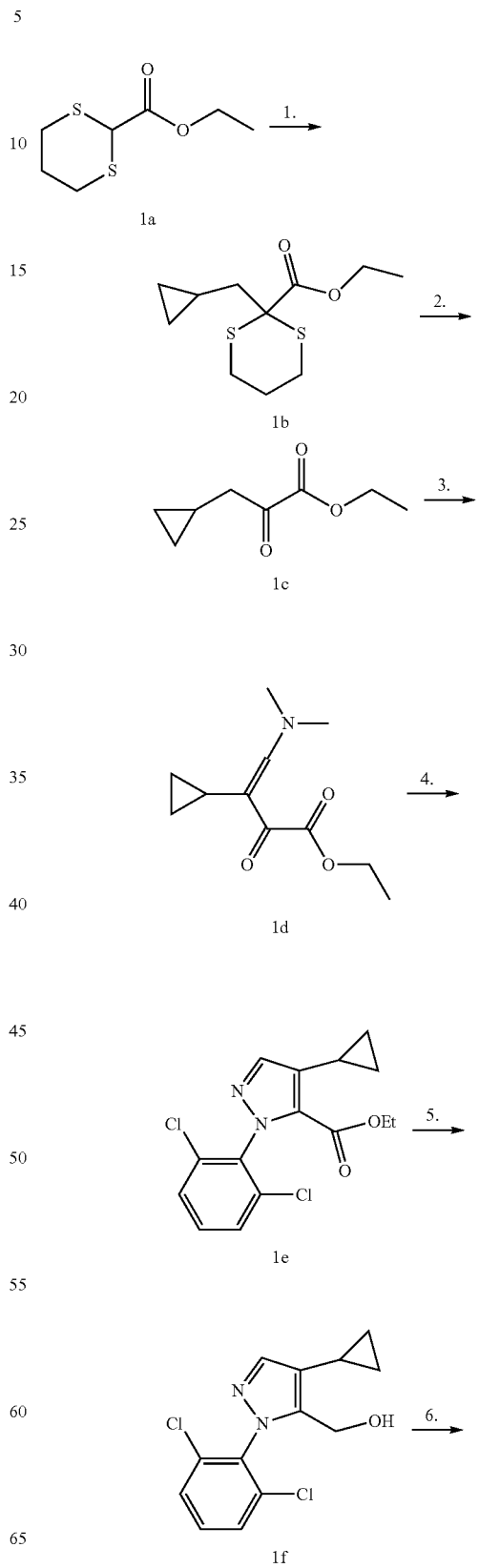

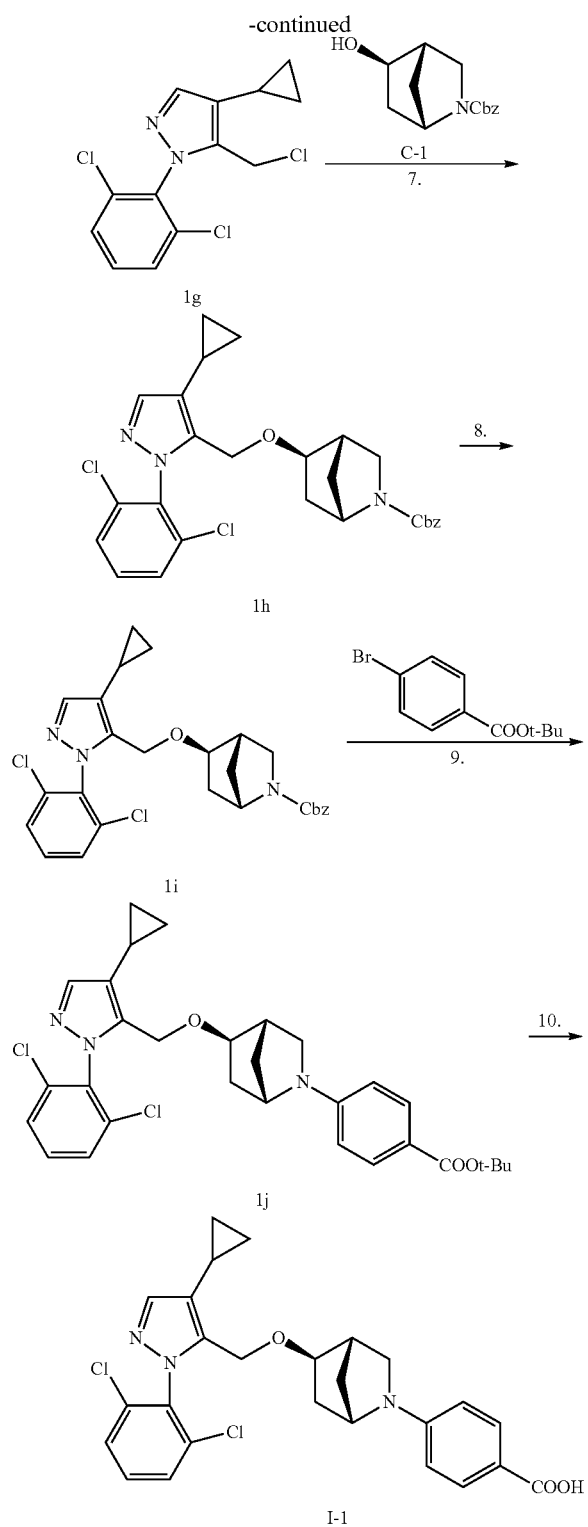

h at room temperature and then quenched by the addition of 20 mL of H₂O. The reaction mixture was extracted with ethyl acetate (300 mL×2), and the combined organic extracts were washed with brine (100 mL×2), dried over sodium sulfate and concentrated under vacuum. The residue was purified by silica gel column chromatography eluting with PE:EA (0%-10%) to give ethyl 2-(cyclopropylmethyl)-1,3-dithiane-2-carboxylate 1b (16 g, 84%) as a yellow oil.

Step 2. To a 100 mL round-bottom flask was added NBS (17 g, 95.52 mmol, 6.00 equiv.) followed by the addition of MeCN (88 mL) and H₂O (22 mL). The mixture was cooled to 0° C., and added with a solution of ethyl 2-(cyclopropylmethyl)-1,3-dithiane-2-carboxylate 1b (4 g, 16.23 mmol, 1.00 equiv.) in MeCN (10 mL) in 5 min. The resulting mixture was stirred for 2 h at room temperature and diluted with hexane (200 mL) and DCM (200 mL), then washed with Na₂SO₃(aq) (50 mL×2). The organic solution was dried over anhydrous sodium sulfate and concentrated under vacuum to afford ethyl 3-cyclopropyl-2-oxopropanoate 1c (2.5 g, 99%) as light yellow crude oil.

Step 3. To a 50 mL round-bottom flask was added ethyl 3-cyclopropyl-2-oxopropanoate 1c (5 g, 32.01 mmol, 1.00 equiv.) and (dimethoxymethyl)dimethylamine (10 mL). The resulting mixture was stirred for 18 h at 20° C. and concentrated under vacuum. The residue was purified by silica gel column chromatography eluting with ethyl acetate in petroleum ether (0% to 10%). Removal of solvents afforded ethyl 3-cyclopropyl-4-(dimethylamino)-2-oxobut-3-enoate 1d (2.7 g, 40%) as light yellow oil.

Step 4. To a 100 mL round-bottom flask purged and maintained under an inert atmosphere of nitrogen was added ethyl 3-cyclopropyl-4-(dimethylamino)-2-oxobut-3-enoate id (4.6 g, 21.77 mmol, 1.00 equiv.), ethanol (80 mL), and hydrogen chloride (0.32 mL, 1M). (2,6-Dichlorophenyl)hydrazine hydrochloride (4.7 g, 22.01 mmol, 1.10 equiv.) was added. The mixture was stirred at 20° C. for 4 h and continued at 85° C. for 18 h. After cooling to room temperature, the reaction mixture was quenched by the addition of 100 mL of water. The aqueous mixture was extracted with ethyl acetate (300 mL×2); and combined organic extracts were washed with brine (100 mL×2), dried over anhydrous sodium sulfate, and concentrated under vacuum. The residue was purified by silica gel column chromatography eluting with ethyl acetate/petroleum ether (0% to 15%) to afford ethyl 4-cyclopropyl-1-(2,6-dichlorophenyl)-1H-pyrazole-5-carboxylate R¹ (3.3 g, 47%) as a light yellow oil.

Step 5. To a 100 mL round-bottom flask was added ethyl 4-cyclopropyl-1-(2,6-dichlorophenyl)-1H-pyrazole-5-carboxylate R¹ (2.302 g, 7.08 mmol, 1.00 equiv.) and tetrahydrofuran (20 mL). The mixture was cooled at 0° C., LiAlH₄ (540 mg, 14.23 mmol, 2.00 equiv.) was added in several batches. The reaction mixture was stirred at room temperature for 2 h and then diluted with 20 mL of EA. The reaction was quenched by the addition of 30 mL of ice water. The aqueous mixture was extracted with ethyl acetate (100 mL×2), and the combined organic extracts were washed with an aqueous solution of sodium potassium tartrate (50 mL) and brine (30 mL×2). The organic solution was dried over anhydrous sodium sulfate and concentrated under vacuum. The residue was purified by silica gel column chromatography eluting with ethyl acetate/petroleum ether (1/3) to give [4-cyclopropyl-1-(2,6-dichlorophenyl)-1H-pyrazol-5-yl]methanol 1f (1.49 g, 74%) as a light yellow solid.

Step 6. To a 50 mL round-bottom flask was added benzotriazole (332 mg, 1.00 equiv.) and dichloromethane (10 mL). The mixture was cooled to 0° C., thionyl chloride Step 1. To a 100 mL round-bottom flask was added sodium hydride (6.25 g, 260.42 mmol, 2.00 equiv., 60% dispersed in mineral oil) followed by toluene (40 mL). The mixture was cooled to −10° C. A solution of ethyl 1,3-dithiane-2-carboxylate 1a (15 g, 78.00 mmol, 1.00 equiv.) and (bromomethyl)cyclopropane (11.5 g, 85.18 mmol, 1.10 equiv.) in N,N-dimethylformamide (20 mL) was added slowly with stirring. The resulting mixture was stirred for 18

(665 mg, 2.00 equiv.) was added slowly, and the reaction mixture was stirred for 30 min at 0° C. [4-cyclopropyl-1-(2,6-dichlorophenyl)-1H-pyrazol-5-yl]methanol 1f (790 mg, 2.79 mmol, 1.00 equiv.) was added. The resulting mixture was stirred at room temperature overnight. The mixture was diluted with DCM (20 mL), quenched by the addition water/ice (20 mL), and extracted with ethyl acetate (100 mL×2). The combined organic extracts were washed with brine (20 mL×2), dried over anhydrous sodium sulfate, and concentrated under vacuum. The residue was purified by silica gel column chromatography eluting with ethyl acetate/petroleum ether (1/5) to afford 5-(chloromethyl)-4-cyclopropyl-1-(2,6-dichlorophenyl)-1H-pyrazole 1g (790 mg, 94%) as a yellow solid.

Step 7. To a 100 mL round-bottom flask was added 5-(chloromethyl)-4-cyclopropyl-1-(2,6-dichlorophenyl)-1H-pyrazole 1g (470 mg, 1.56 mmol, 1.00 equiv.), N,N-dimethylformamide (10 mL), and TBAI (581 mg, 1.57 mmol, 1.00 equiv.). Benzyl (1S,4S,5R)-5-hydroxy-2-azabicyclo[2.2.1]heptane-2-carboxylate C-1 (464 mg, 1.88 mmol, 1.20 equiv.) was added. The mixture was cooled to 0° C., sodium hydride (126 mg, 5.25 mmol, 2.00 equiv., 60% dispersion in mineral oil) was added in several batches. The resulting mixture was stirred at 25° C. for 2 days, diluted with 50 mL of EA and quenched by the addition of 10 mL of water/ice. The aqueous mixture was extracted with ethyl acetate (50 mL×2), and the combined organic extracts were washed with brine (20 mL×4), dried over anhydrous sodium sulfate and concentrated under vacuum to give benzyl (1S,4S,5R)-5-[[4-cyclopropyl-1-(2,6-dichlorophenyl)-1H-pyrazol-5-yl]methoxy]-2-azabicyclo[2.2.1]heptane-2-carboxylate 1h (581 mg, 73%) as a light yellow crude oil.

Step 8. To a 100 mL round-bottom flask was added benzyl (1S,4S,5R)-5-[[4-cyclopropyl-1-(2,6-dichlorophenyl)-1H-pyrazol-5-yl]methoxy]-2-azabicyclo[2.2.1]heptane-2-carboxylate 1h (420 mg, 0.82 mmol, 1.00 equiv.), dichloromethane (4 mL), and TMSI (328 mg, 1.64 mmol, 2.00 equiv.). The resulting mixture was stirred for 10 min at room temperature and then quenched by the addition of 1 mL of a 1 M hydrogen chloride aqueous solution. The aqueous mixture was extracted with ethyl acetate (20 mL×2), dried over anhydrous sodium sulfate and concentrated under vacuum. The residue was purified by silica gel column chromatography eluting with dichloromethane/methanol (10:1) to give (1S,4S,5R)-5-[[4-cyclopropyl-1-(2,6-dichlorophenyl)-1H-pyrazol-5-yl]methoxy]-2-azabicyclo[2.2.1]heptane 1i (190 mg, 61%) as a light yellow oil.

Step 9. To a 50 mL round-bottom flask purged and maintained under an inert atmosphere of nitrogen was added (1S,4S,5R)-5-[[4-cyclopropyl-1-(2,6-dichlorophenyl)-1H-pyrazol-5-yl]methoxy]-2-azabicyclo[2.2.1]heptane 1i (110 mg, 0.29 mmol, 1.00 equiv.), toluene (2 mL), Pd$_2$(dba)$_3$ (53 mg, 0.06 mmol, 0.20 equiv.), BINAP (36 mg, 0.20 equiv.), tert-butyl 4-bromobenzoate (113 mg, 0.44 mmol, 1.50 equiv.), and Cs$_2$CO$_3$ (283 mg, 3.00 equiv.). The resulting mixture was heated at 110° C. overnight and concentrated under vacuum. The residue was purified by silica gel column chromatography eluting with ethyl acetate/petroleum ether (1/5) to afford tert-butyl 4-[(1S,4S,5R)-5-[[4-cyclopropyl-1-(2,6-dichlorophenyl)-1H-pyrazol-5-yl]methoxy]-2-azabicyclo[2.2.1]heptan-2-yl]benzoate 1j (102 mg, 63%) as a light yellow oil.

Step 10. To a 25 mL round-bottom flask was added tert-butyl 4-[(1S,4S,5R)-[[4-cyclopropyl-1-(2,6-dichlorophenyl)-1H-pyrazol-5-yl]methoxy]-2-azabicyclo[2.2.1]heptan-2-yl]benzoate (102 mg, 0.18 mmol, 1.00 equiv.), dichloromethane (1 mL), and trifluoroacetic acid (3 mL). The resulting mixture was stirred at room temperature for 3 h. The mixture was diluted with 10 mL of EA and treated with a 1M sodium bicarbonate aqueous solution to adjust the pH to 6. The aqueous mixture was extracted with ethyl acetate (50 mL×2), and the combined organic extracts were washed with brine (20 mL×2), dried over anhydrous sodium sulfate and concentrated under vacuum. The residue was purified by Prep-HPLC using the following conditions: Column, XBridge Shield RP18 OBD Column, 5 um, 19*150 mm; mobile phase, Water (0.05% TFA) and ACN (5.0% ACN up to 45.0% in 1 min, up to 63.0% in 7 min); Detector, UV 254 nm. After purification, 4-[(1S,4S,5R)-5-[[4-cyclopropyl-1-(2,6-dichlorophenyl)-1H-pyrazol-5-yl]methoxy]-2-azabicyclo[2.2.1]heptan-2-yl]benzoic acid I-1 (37.1 mg, 40%) was obtained as an off-white solid. $^1$H NMR (300 MHz, CD$_3$OD): δ 7.82 (d, J=8.7 Hz, 2H), 7.68-7.43 (m, 4H), 6.52 (d, J=8.6 Hz, 2H), 4.48 (d, J=2.4 Hz, 2H), 3.52 (d, J=6.5 Hz, 1H), 3.41 (dd, J=9.5, 4.2 Hz, 2H), 2.67-2.51 (m, 2H), 1.96-1.74 (m, 2H), 1.63 (t, J=7.7 Hz, 2H), 1.32 (d, J=13.5 Hz, 1H), 1.02-0.91 (m, 2H), 0.67 (dd, J=4.9, 1.9 Hz, 2H). MS (ES, m/z): [M+1]=498.25.

Example 7: 4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-2-fluorobenzoic acid (I-2)

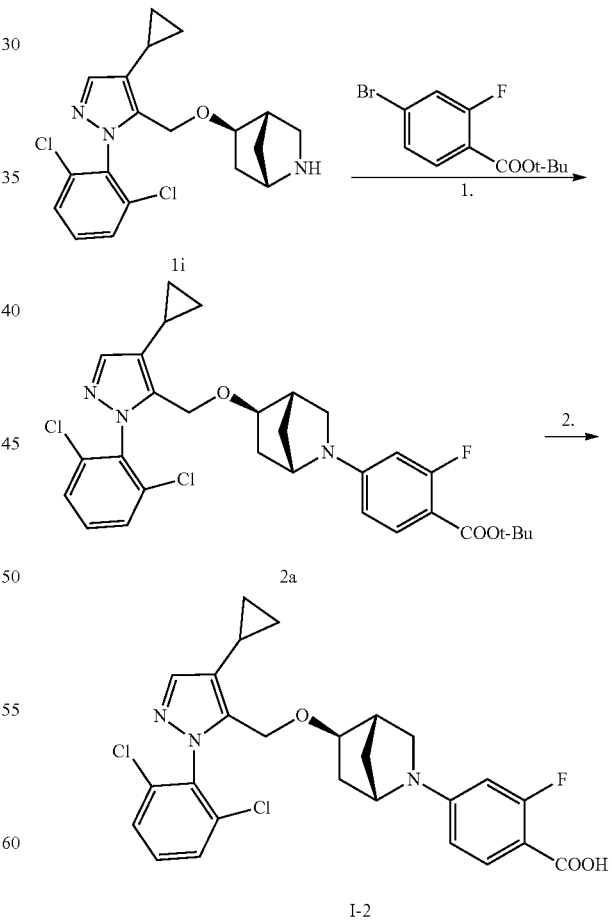

Step 1. To a 50 mL round-bottom flask purged and maintained under an inert atmosphere of nitrogen was added (1S,4S,5R)-5-[[4-cyclopropyl-1-(2,6-dichlorophenyl)-1H- pyrazol-5-yl]methoxy]-2-azabicyclo[2.2.1]heptane 1i (200 mg, 0.53 mmol, 1.00 equiv.), toluene (5 mL), Pd(OAc)₂ (25 mg, 0.11 mmol, 0.20 equiv.), Xantphos (64 mg, 0.11 mmol, 0.20 equiv.), Cs₂CO₃ (518 mg, 1.59 mmol, 3.00 equiv.), and tert-butyl 4-bromo-2-fluorobenzoate (134 mg, 0.49 mmol, 1.10 equiv.). The resulting mixture was heated at 90° C. overnight and concentrated under vacuum. The residue was purified by silica gel column chromatography eluting with ethyl acetate/petroleum ether (1/3) to give tert-butyl 4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-2-fluorobenzoate 2a (176 mg, 58%) as a yellow solid.

Step 2. To a 50 mL round-bottom flask was added tert-butyl 4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-2-fluorobenzoate 2a (176 mg, 0.31 mmol, 1.00 equiv.), dichloromethane (3 mL), and trifluoroacetic acid (1 mL). The resulting mixture was stirred at room temperature for 1 h, then diluted with EA (100 mL), and washed with a 1M sodium bicarbonate aqueous solution (20 mL×2). The organic layer was dried over anhydrous sodium sulfate and concentrated under vacuum. The residue was purified by Prep-HPLC using the following conditions: Column, XBridge Shield RP18 OBD Column, 5 um, 19*150 mm; mobile phase, Water (0.05% TFA) and ACN (46.0% ACN up to 66.0% in 8 min); Detector, uv 254 nm. After purification 4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-2-fluorobenzoic acid I-2 (73.2 mg, 46%) was obtained as an off-white solid. ¹H NMR (400 MHz, CD₃OD): δ 7.73 (t, J=8.8 Hz, 1H), 7.67-7.49 (m, 3H), 7.46 (s, 1H), 6.33 (dd, J=8.9, 2.3 Hz, 1H), 6.20 (dd, J=14.6, 2.3 Hz, 1H), 4.47 (d, J=2.1 Hz, 2H), 4.16 (s, 1H), 3.53 (d, J=6.1 Hz, 1H), 3.37 (d, J=4.1 Hz, 1H), 2.67-2.52 (m, 2H), 1.92-1.75 (m, 2H), 1.68-1.56 (m, 2H), 1.38-1.26 (m, 1H), 1.03-0.90 (m, 2H), 0.74-0.61 (m, 2H). MS (ES, m/z): [M+1]=516.25.

Example 8: 4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-2,6-difluorobenzoic acid (I-3)

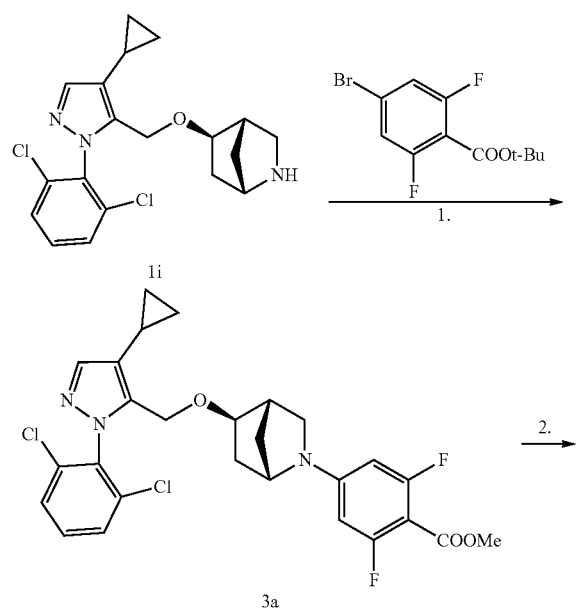

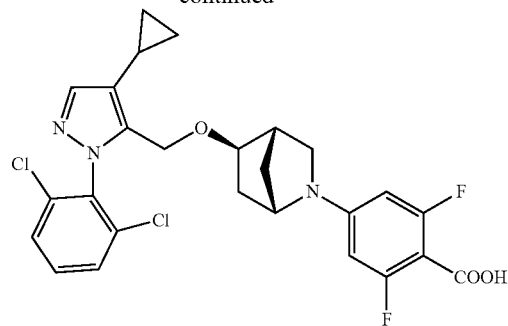

Step 1. To a 50 mL round-bottom flask was added (1S,4S,5R)-5-[[4-cyclopropyl-1-(2,6-dichlorophenyl)-1H-pyrazol-5-yl]methoxy]-2-azabicyclo[2.2.1]heptane 1i (117 mg, 0.31 mmol, 1.00 equiv.), toluene (3 mL), methyl 4-bromo-2,6-difluorobenzoate (85 mg, 0.34 mmol, 1.10 equiv.), Ruphos precatalyst (53 mg, 0.06 mmol, 0.20 equiv.), Ruphos (29 mg, 0.06 mmol, 0.20 equiv.), and Cs₂CO₃ (303 mg, 0.93 mmol, 3.00 equiv.). The resulting mixture was heated at 110° C. overnight and concentrated under vacuum. The residue was purified by silica gel column chromatography eluting with ethyl acetate/petroleum ether (1:1) to give methyl 4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-2,6-difluorobenzoate 3a (80 mg, 47%) as a light yellow solid.

Step 2. To a 50 mL round-bottom flask was added methyl 4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-2,6-difluorobenzoate 3a (100 mg, 0.18 mmol, 1.00 equiv.), LiOH (73 mg, 3.05 mmol, 10.00 equiv.), methanol (2 mL), and water (0.2 mL). The resulting mixture was stirred at 50° C. for 2 h. After cooling to room temperature, the mixture was diluted with 50 mL of H₂O, and extracted with ethyl acetate (100 mL×2). The combined organic extracts were washed with brine (100 mL×2), dried over anhydrous sodium sulfate and concentrated. The residue was purified by Prep-HPLC using the following conditions: Column, XBridge Shield RP18 OBD Column, 5 um, 19*150 mm; mobile phase, Water (0.05% TFA) and ACN (46.0% ACN up to 66.0% in 8 min); Detector, uv 254 nm. After purification 4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-2,6-difluorobenzoic acid I-3 (19.5 mg, 20%) was obtained as a colorless solid. ¹H NMR (300 MHz, CD₃OD): δ 7.68-7.43 (m, 4H), 6.11 (d, J=13.0 Hz, 2H), 4.90 (s, 2H), 4.47 (d, J=1.7 Hz, 1H), 3.53 (s, 1H), 2.65-2.51 (m, 2H), 1.81 (dd, J=9.7, 4.6 Hz, 2H), 1.60 (d, J=7.9 Hz, 2H), 1.31 (s, 2H), 1.01-0.92 (m, 2H), 0.67 (dd, J=5.1, 1.9 Hz, 2H). MS (ES, m/z): [M+1]=534.

Example 9: 6-[(1S,4S,5R)-5-{[4-cyclopropyl-1-(2,6-dichlorophenyl)-1H-pyrazol-5-yl]methoxy}-2-azabicyclo[2.2.1]heptan-2-yl]pyridine-3-carboxylic acid (I-4)

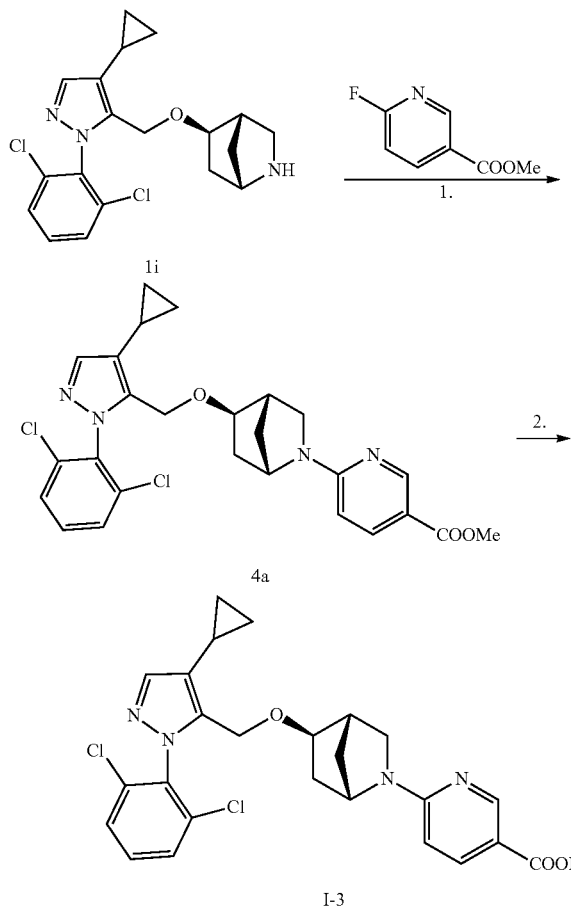

Step 1. To a 50 mL round-bottom flask was added (1S,4S,5R)-5-[[4-cyclopropyl-1-(2,6-dichlorophenyl)-1H-pyrazol-5-yl]methoxy]-2-azabicyclo[2.2.1]heptane 1i (100 mg, 0.26 mmol, 1.00 equiv.), MeCN (2 mL), TEA (53 mg, 0.52 mmol, 2.00 equiv.), and methyl 6-fluoropyridine-3-carboxylate (82 mg, 0.53 mmol, 2.00 equiv.). The resulting mixture was stirred at room temperature overnight, and quenched with the addition of water (30 mL). The aqueous mixture was extracted with ethyl acetate (50 mL×2), and the combined organic extracts were washed with brine (50 mL×2), dried over anhydrous sodium sulfate and concentrated under vacuum. The residue was purified by silica gel column chromatography eluting with ethyl acetate/petroleum ether (1:2) to give methyl 6-[(1S,4S,5R)-5-[[4-cyclopropyl-1-(2,6-dichlorophenyl)-1H-pyrazol-5-yl]methoxy]-2-azabicyclo[2.2.1]heptan-2-yl]pyridine-3-carboxylate 4a (110 mg, 81%) as a light yellow solid.

Step 2. To a 50 mL round-bottom flask was added methyl 6-[(1S,4S,5R)-5-[[4-cyclopropyl-1-(2,6-dichlorophenyl)-1H-pyrazol-5-yl]methoxy]-2-azabicyclo[2.2.1]heptan-2-yl]pyridine-3-carboxylate 4a (100 mg, 0.19 mmol, 1.00 equiv.), methanol (2 mL), LiOH (78 mg, 3.26 mmol, 10.00 equiv), and water (0.2 mL). The resulting mixture was heated at 60° C. for 2 h. After cooling to room temperature, the pH value of the solution was adjusted to 6 using a 1M HCl aqueous solution. The aqueous mixture was extracted with ethyl acetate (100 mL×2), and the combined organic extracts were washed with brine (100 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (22.0% ACN up to 42.0% in 8 min); Detector, uv 254/220 nm. After purification 6-[(1S,4S,5R)-5-[[4-cyclopropyl-1-(2,6-dichlorophenyl)-1H-pyrazol-5-yl]methoxy]-2-azabicyclo[2.2.1]heptan-2-yl]pyridine-3-carboxylic acid I-4 (52.9 mg, 54%) was obtained as a white solid. $^1$H NMR (300 MHz, CD$_3$OD): δ 8.41 (d, J=2.0 Hz, 1H), 8.24 (dd, J=9.5, 2.1 Hz, 1H), 7.69-7.50 (m, 3H), 7.48 (s, 1H), 7.11 (s, 1H), 4.63-4.44 (m, 3H), 3.71 (d, J=6.2 Hz, 1H), 3.55 (dd, J=10.4, 4.1 Hz, 1H), 3.13-2.85 (m, 2H), 2.75 (s, 1H), 2.13-1.94 (m, 1H), 1.91-1.66 (m, 3H), 1.45 (d, J=13.6 Hz, 1H), 1.04-0.92 (m, 2H), 0.74-0.63 (m, 2H). MS (ES, m/z): [M+1]=499.

Example 10: 5-[(1S,4S,5R)-5-{[4-cyclopropyl-1-(2,6-dichlorophenyl)-1H-pyrazol-5-yl]methoxy}-2-azabicyclo[2.2.1]heptan-2-yl]pyridine-2-carboxylic acid (I-5)

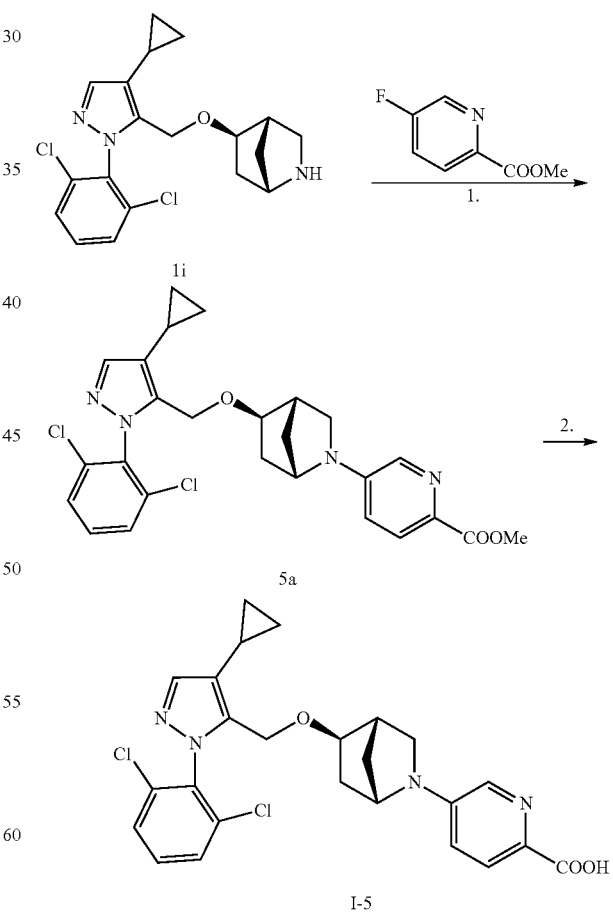

Step 1. To a 8 mL sealed tube was added (1S,4S,5R)-5-[[4-cyclopropyl-1-(2,6-dichlorophenyl)-1H-pyrazol-5-yl]methoxy]-2-azabicyclo[2.2.1]heptane 1i (270 mg, 0.71 mmol, 1.00 equiv.), methyl 5-fluoropyridine-2-carboxylate (222 mg, 1.43 mmol, 2.00 equiv.), MeCN (3 mL), and TEA (193 mg, 1.91 mmol, 2.00 equiv.). The resulting mixture was heated at 90° C. for 3 days. After cooling to room temperature, water (50 mL) was added. The aqueous mixture was extracted with ethyl acetate (200 mL×2), and the combined organic extracts were washed with brine (200 mL×2), dried over anhydrous sodium sulfate and concentrated under vacuum. The residue was purified by silica gel column chromatography eluting with dichloromethane/methanol (15:1) to give methyl 5-[(1S,4S,5R)-[[4-cyclopropyl-1-(2,6-dichlorophenyl)-1H-pyrazol-5-yl]methoxy]-2-azabicyclo[2.2.1]heptan-2-yl]pyridine-2-carboxylate 5a (140 mg, 38%) as a light yellow oil.

Step 2. To a 25 mL round-bottom flask was added methyl 5-[(1S,4S,5R)-5-[[4-cyclopropyl-1-(2,6-dichlorophenyl)-1H-pyrazol-5-yl]methoxy]-2-azabicyclo[2.2.1]heptan-2-yl]pyridine-2-carboxylate 5a (140 mg, 0.27 mmol, 1.00 equiv.), methanol (2 mL), water (1 mL), and lithium hydroxide monohydrate (115 mg, 2.74 mmol, 10.00 equiv.). The resulting mixture was stirred at 60° C. for 1 h. After cooling to room temperature, the pH value of the solution was adjusted to 4 using a 1M HCl aqueous solution. The aqueous mixture was extracted with ethyl acetate (150 mL×2), and the combined organic extracts were washed with brine (200 mL×2), dried over anhydrous sodium sulfate and concentrated under vacuum. The crude product was purified by Prep-HPLC using the following conditions: Column, XBridge Shield RP18 OBD Column 5 um, 19*150 mm; mobile phase, Water (0.05% TFA) and ACN (20.0% ACN up to 50.0% in 8 min); Detector, uv 254/220 nm. After purification 5-[(1S,4S,5R)-[[4-cyclopropyl-1-(2,6-dichlorophenyl)-1H-pyrazol-5-yl]methoxy]-2-azabicyclo[2.2.1]heptan-2-yl]pyridine-2-carboxylic acid I-5 (43.5 mg, 32%) was obtained as a light yellow solid. $^1$H NMR (300 MHz, CD$_3$OD): δ 8.10 (d, J=9.1 Hz, 1H), 7.90 (d, J=2.8 Hz, 1H), 7.68-7.49 (m, 3H), 7.47 (s, 1H), 7.37 (dd, J=9.0, 2.9 Hz, 1H), 4.50 (d, J=1.5 Hz, 2H), 4.38 (s, 1H), 3.62 (d, J=6.4 Hz, 1H), 3.46 (dd, J=10.0, 4.1 Hz, 1H), 2.80 (d, J=9.9 Hz, 1H), 2.66 (s, 1H), 1.91 (dt, J=11.5, 5.7 Hz, 1H), 1.81 (td, J=8.5, 4.3 Hz, 1H), 1.69 (q, J=10.4 Hz, 2H), 1.41 (d, J=13.4 Hz, 1H), 1.03-0.91 (m, 2H), 0.73-0.62 (m, 2H). MS (ES, m/z): [M+1]=499.12.

Example 11: 5-[(1S,4S,5R)-5-{[4-cyclopropyl-1-(2,6-dichlorophenyl)-1H-pyrazol-5-yl]methoxy}-2-azabicyclo[2.2.1]heptan-2-yl]pyrimidine-2-carboxylic acid (I-6)

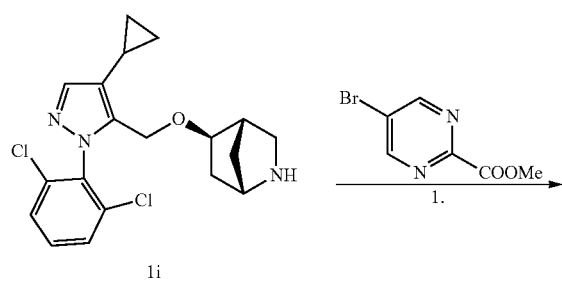

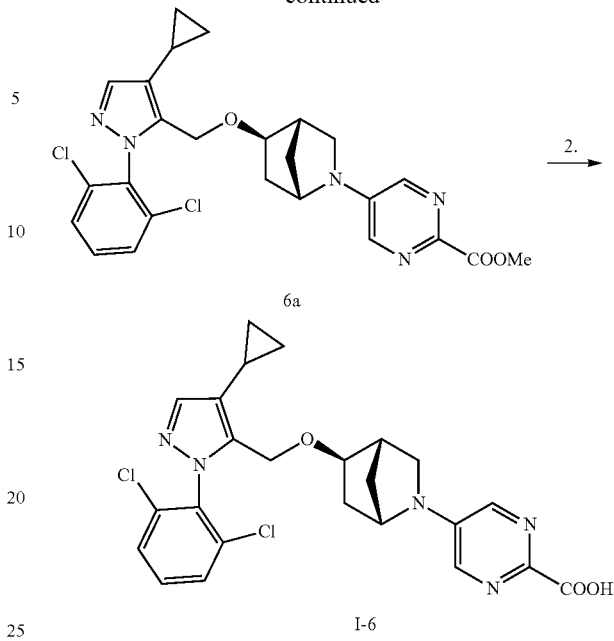

Step 1. To a 25 mL round-bottom flask was added (1S,4S,5R)-5-[[4-cyclopropyl-1-(2,6-dichlorophenyl)-1H-pyrazol-5-yl]methoxy]-2-azabicyclo[2.2.1]heptane 1i (156 mg, 0.41 mmol, 1.00 equiv.), Ruphos precatalyst (66 mg, 0.20 equiv.), Ruphos (37 mg, 0.20 equiv.), Cs$_2$CO$_3$ (390 mg, 1.20 mmol, 3.00 equiv.), methyl 5-bromopyrimidine-2-carboxylate (129 mg, 0.59 mmol, 1.50 equiv.), and toluene (2 mL). The resulting mixture was heated at 110° C. overnight. After cooling to room temperature, the mixture was diluted with 30 mL of H$_2$O, extracted with ethyl acetate (100 mL×2), and the combined organic extracts were washed with brine (100 mL×2), dried over anhydrous sodium sulfate and concentrated. The residue was purified by silica gel column chromatography eluting with ethyl acetate/petroleum ether (1:2) to afford methyl 5-[(1S,4S,5R)-5-[[4-cyclopropyl-1-(2,6-dichlorophenyl)-1H-pyrazol-5-yl]methoxy]-2-azabicyclo[2.2.1]heptan-2-yl]pyrimidine-2-carboxylate 6a (65 mg, 31%) as a reddish oil.

Step 2. To a 25 mL round-bottom flask was added methyl 5-[(1S,4S,5R)-5-[[4-cyclopropyl-1-(2,6-dichlorophenyl)-1H-pyrazol-5-yl]methoxy]-2-azabicyclo[2.2.1]heptan-2-yl]pyrimidine-2-carboxylate 6a (65 mg, 0.13 mmol, 1.00 equiv.), methanol (2 mL), water (0.5 mL), and LiOH—H$_2$O (53 mg, 2.21 mmol, 10.00 equiv.). The resulting mixture was stirred at 50° C. for 2 h. The mixture was diluted with 20 mL of H$_2$O, and the pH value of the solution was adjusted to 3 using a 1M hydrogen chloride aqueous solution. The aqueous mixture was extracted with ethyl acetate (100 mL×2), and the combined organic extracts were washed with brine (100 mL×2), dried over anhydrous sodium sulfate and concentrated under vacuum. The crude product was purified by Prep-HPLC using the following conditions Column, XBridge Shield RP18 OBD Column 5 um, 19*150 mm; mobile phase, Water (0.05% TFA) and ACN (30.0% ACN up to 50.0% in 8 min); Detector, UV 254/220 nm. After purification 5-[(1S,4S,5R)-[[4-cyclopropyl-1-(2,6-dichlorophenyl)-1H-pyrazol-5-yl]methoxy]-2-azabicyclo[2.2.1]heptan-2-yl]pyrimidine-2-carboxylic acid I-6 (22.9 mg, 36%) as a yellow green oil. $^1$H NMR (300 MHz, CD$_3$OD): δ 8.13 (s, 2H), 7.69-7.51 (m, 3H), 7.47 (s, 1H), 4.50 (d, J=1.7 Hz, 2H), 4.36 (s, 1H), 3.61 (s, 1H), 3.46 (dd, J=9.7, 4.1 Hz, 2H), 2.77 (d, J=9.8 Hz, 1H), 2.63 (s, 1H), 1.96-1.57 (m, 5H), 1.38 (d, J=13.6 Hz, 1H), 1.04-0.91 (m, 2H), 0.74-0.62 (m, 2H). MS (ES, m/z): [M+1]=500.

Example 12: 4-[(1S,4S,5R)-5-{[4-cyclopropyl-1-(2,6-dimethylphenyl)-1H-pyrazol-5-yl]methoxy}-2-azabicyclo[2.2.1]heptan-2-yl]-2-fluorobenzoic acid (I-7)

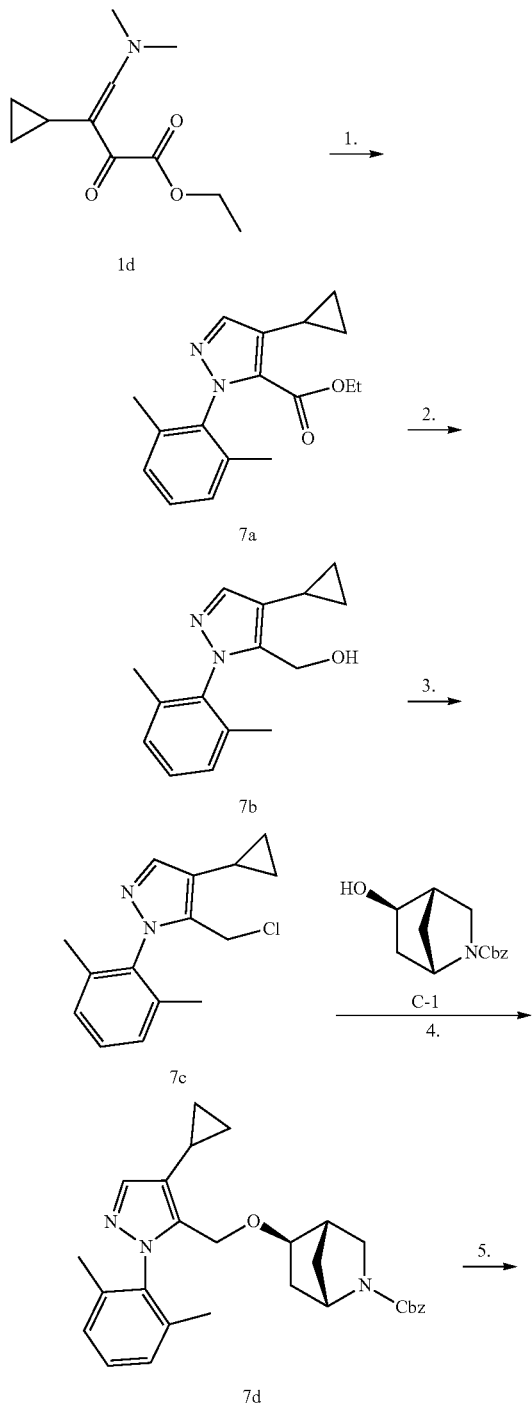

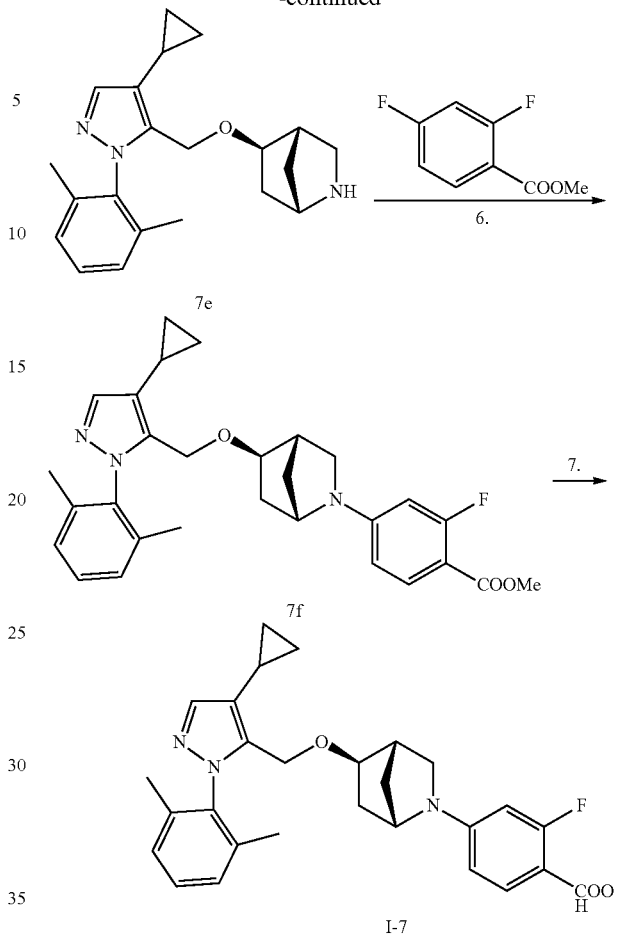

Step 1. To a 250 mL round-bottom flask was added (2,6-dimethylphenyl)hydrazine (1.25 g, 9.18 mmol, 1.00 equiv.), hydrogen chloride (0.9 mL), ethanol (10 mL), and ethyl (3Z)-3-cyclopropyl-4-(dimethylamino)-2-oxobut-3-enoate 1d (1.3 g, 6.15 mmol, 1.10 equiv.). The resulting mixture was heated at 85° C. overnight and concentrated under vacuum. The residue was diluted with 50 mL of H₂O, and extracted with ethyl acetate (100 mL×2). The combined organic extracts were washed with brine (100 mL×2), dried over anhydrous sodium sulfate, and concentrated. The residue was purified by silica gel column chromatography eluting with ethyl acetate/hexane (0 to 30%) to give ethyl 4-cyclopropyl-1-(2,6-dimethylphenyl)-1H-pyrazole-5-carboxylate 7a (600 mg, 23%) as a yellow oil.

Step 2. To a 250 mL round-bottom flask was added ethyl 4-cyclopropyl-1-(2,6-dimethylphenyl)-1H-pyrazole-5-carboxylate 7a (600 mg, 2.11 mmol, 1.00 equiv.), DIBAL (3.5 mL, 2.00 equiv.), and tetrahydrofuran (6 mL). The resulting mixture was stirred at room temperature overnight, and quenched by the addition of 10 mL of sodium hydroxide. The mixture was further diluted with H₂O (100 mL), extracted with ethyl acetate (100 mL×2), and the combined organic extracts were washed with brine (100 mL×2), dried over anhydrous sodium sulfate and concentrated under vacuum. The residue was purified by silica gel column chromatography eluting with ethyl acetate/hexane (4:1) to afford [4-cyclopropyl-1-(2,6-dimethylphenyl)-1H-pyrazol-5-yl]methanol 7b (380 mg, 74%) as a white solid.

Step 3. To a 250 mL round-bottom flask was added [4-cyclopropyl-1-(2,6-dimethylphenyl)-1H-pyrazol-5-yl] methanol 7b (380 mg, 1.57 mmol, 1.00 equiv.), thionyl chloride (371 mg, 2.00 equiv), benzotriazole (185 mg, 1.00 equiv), and dichloromethane (4 mL). The reaction mixture was stirred at room temperature for 2 h. The mixture was diluted with H₂O (50 mL), extracted with ethyl acetate (100 mL×2), and the combined organic extracts were washed with brine (100 mL×2), dried over anhydrous sodium sulfate and concentrated under vacuum. The residue was purified by silica gel column chromatography eluting with ethyl acetate/hexane (2:1) to give 5-(chloromethyl)-4-cyclopropyl-1-(2,6-dimethylphenyl)-1H-pyrazole 7c (340 mg, 83%) as a yellow oil.

Step 4. To a 50 mL round-bottom flask was added 5-(chloromethyl)-4-cyclopropyl-1-(2,6-dimethylphenyl)-1H-pyrazole 7c (100 mg, 0.38 mmol, 1.00 equiv.), benzyl (1S,4S,5R)-5-hydroxy-2-azabicyclo[2.2.1]heptane-2-carboxylate C-1 (114 mg, 0.46 mmol, 1.20 equiv.), N,N-dimethylformamide (2 mL), and sodium hydride (20 mg, 60% dispersion in mineral oil, 0.83 mmol, 2.00 equiv.). The reaction mixture was stirred at room temperature overnight, then quenched by the addition of 10 mL of water. The aqueous mixture was extracted with ethyl acetate (100 mL×2), and the combined organic extracts were washed with brine (100 mL×2), dried over anhydrous sodium sulfate, and concentrated. The residue was purified by silica gel column chromatography eluting with ethyl acetate/hexane (1:1) to afford benzyl (1S,4S,5R)-5-[[4-cyclopropyl-1-(2,6-dimethylphenyl)-1H-pyrazol-5-yl]methoxy]-2-azabicyclo [2.2.1]heptane-2-carboxylate 7d (100 mg, 55%) as a yellow oil.

Step 5. To a 50 mL round-bottom flask was added benzyl (1S,4S,5R)-[[4-cyclopropyl-1-(2,6-dimethylphenyl)-1H-pyrazol-5-yl]methoxy]-2-azabicyclo[2.2.1]heptane-2-carboxylate 7d (250 mg, 0.53 mmol, 1.00 equiv.), TMSI (220 mg, 2.00 equiv.), and dichloromethane (5 mL). The resulting mixture was stirred at room temperature for 2 h. The reaction was quenched by the addition of 5 mL of a 1M hydrogen chloride aqueous solution, and the mixture was concentrated under vacuum. The crude product was purified by Flash-Prep-HPLC using the following conditions (IntelFlash-1): Column, silica gel; mobile phase, H₂O:MeCN=100:0 increasing to H₂O:MeCN=0:100 within 25 min; Detector, UV 254 nm. Removal of solvents afforded (1S,4S,5R)-[[4-cyclopropyl-1-(2,6-dimethylphenyl)-1H-pyrazol-5-yl]methoxy]-2-azabicyclo[2.2.1]heptane 7e (150 mg, 84%) as a yellow oil.

Step 6. To a 50 mL round-bottom flask was added (1S,4S,5R)-5-[[4-cyclopropyl-1-(2,6-dimethylphenyl)-1H-pyrazol-5-yl]methoxy]-2-azabicyclo[2.2.1]heptane 7e (200 mg, 0.59 mmol, 1.00 equiv.), methyl 2,4-difluorobenzoate (153 mg, 0.89 mmol, 1.50 equiv.), CsF (283 mg, 3.00 equiv), and 1-Ethyl-3-methylimidazolium dimethyl phosphate (2 mL). The resulting mixture was heated at 90° C. overnight. After cooling to room temperature, the mixture was diluted with 50 mL of H₂O, and extracted with ethyl acetate (100 mL×2). The combined organic extracts were washed with brine (100 mL×2), dried over anhydrous sodium sulfate and concentrated under vacuum. The residue was purified by silica gel column chromatography eluting with ethyl acetate/hexane (1:2) to give methyl 4-[(1S,4S,5R)-[[4-cyclopropyl-1-(2,6-dimethylphenyl)-1H-pyrazol-5-yl]methoxy]-2-azabicyclo[2.2.1]heptan-2-yl]-2-fluorobenzoate 7f (280 mg, 96%) as a yellow oil.

Step 7. To a 50 mL round-bottom flask was added methyl 4-[(1S,4S,5R)-5-[[4-cyclopropyl-1-(2,6-dimethylphenyl)-1H-pyrazol-5-yl]methoxy]-2-azabicyclo[2.2.1]heptan-2-yl]-2-fluorobenzoate 7f (280 mg, 0.57 mmol, 1.00 equiv.), methanol (2 mL), LiOH (230 mg, 9.60 mmol, 10.00 equiv.), and water (0.2 mL). The resulting mixture was heated at 50° C. for 2 h. After cooling to room temperature, the mixture was diluted with 50 mL of H₂O, and extracted with ethyl acetate (100 mL×2). The combined organic extracts were washed with brine, dried over anhydrous sodium sulfate, and concentrated. The residue was purified by silica gel column chromatography eluting with ethyl acetate/hexane (2:1) to afford 4-[(1S,4S,5R)-5-[[4-cyclopropyl-1-(2,6-dimethylphenyl)-1H-pyrazol-5-yl]methoxy]-2-azabicyclo[2.2.1] heptan-2-yl]-2-fluorobenzoic acid I-7 (72.5 mg, 27%) as a white solid. $^1$H NMR (300 MHz, CD₃OD): δ 7.71 (t, J=8.8 Hz, 1H), 7.44-7.27 (m, 1H), 7.25 (d, J=7.6 Hz, 1H), 7.21 (d, J=7.6 Hz, 2H), 6.31 (dd, J=8.9, 2.3 Hz, 1H), 6.25-6.13 (m, 1H), 4.39-4.22 (m, 2H), 4.14 (s, 1H), 3.49 (d, J=5.8 Hz, 1H), 3.36 (s, 1H), 2.60 (d, J=9.6 Hz, 1H), 2.49 (s, 1H), 2.04 (s, 2H), 1.95 (d, J=1.6 Hz, 6H), 8.00--0.00 (m, 2H), 1.59 (s, 2H), 1.25 (d, J=13.3 Hz, 1H), 1.01-0.88 (m, 2H), 0.71-0.59 (m, 2H). MS (ES, m/z): [M+1]=476.

Example 13: 4-[(1S,4S,5R)-5-{[1-(2-chloro-6-methylphenyl)-4-cyclopropyl-1H-pyrazol-5-yl]methoxy}-2-azabicyclo[2.2.1]heptan-2-yl]-2-fluorobenzoic acid (I-8)

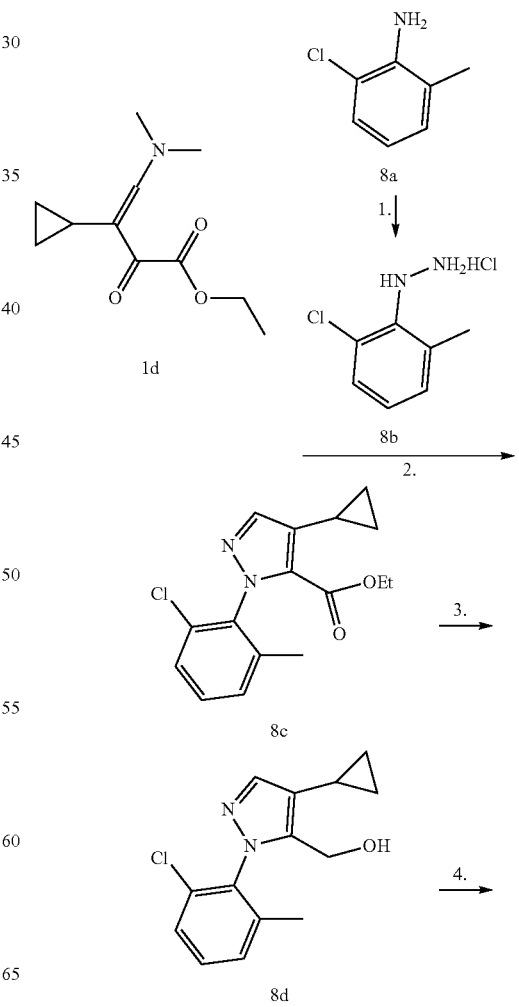

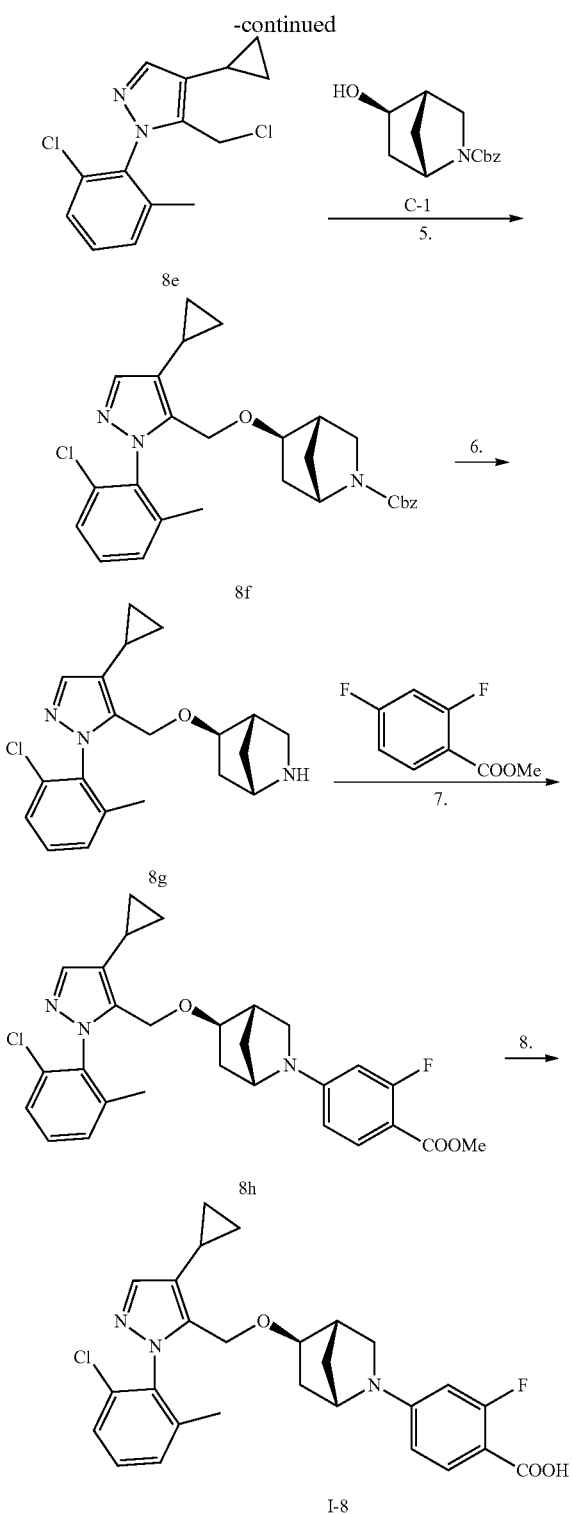

(IntelFlash-1): Column, C18 silica gel; mobile phase, MeCN:H₂O=0:100; Detector, UV 254 nm. Removal of solvents afforded (2-chloro-6-methylphenyl)hydrazine hydrochloride 8b (3.0, 22%) as a light yellow solid.

Step 2. To a 100 mL round-bottom flask was added (2-chloro-6-methylphenyl)hydrazine hydrochloride 8b (1.3 g, 6.73 mmol, 1.10 equiv.), ethyl 3-cyclopropyl-4-(dimethylamino)-2-oxobut-3-enoate 1d (1.3 g, 6.15 mmol, 1.00 equiv.), ethanol (20 mL), and hydrogen chloride (0.05 mL). The resulting mixture was stirred at room temperature for 4 h and then heated at 85° C. for 18 h. After cooling to room temperature, the mixture was diluted with H₂O (100 mL), and extracted with ethyl acetate (200 mL×2). The combined organic extracts were washed with brine (200 mL×2), dried over anhydrous sodium sulfate, and concentrated under vacuum. The residue was purified by silica gel column chromatography eluting with ethyl acetate/petroleum ether (1:3) to provide ethyl 1-(2-chloro-6-methylphenyl)-4-cyclopropyl-1H-pyrazole-5-carboxylate 8c (0.9 g, 48%) as a yellow oil.

Step 3. To a 100 mL round-bottom flask was added ethyl 1-(2-chloro-6-methylphenyl)-4-cyclopropyl-1H-pyrazole-5-carboxylate 8c (900 mg, 2.95 mmol, 1.00 equiv.), tetrahydrofuran (10 g, 138.68 mmol, 46.96 equiv), and DIBAL-H (10 mL, 1M in toluene). The resulting mixture was stirred at room temperature overnight. The reaction was quenched by the addition of 10 mL of H₂O, 30 mL of a 1M sodium hydroxide aqueous solution, and 10 mL of H₂O successively. The aqueous mixture was extracted with ethyl acetate (200 mL×2), and the combined organic extracts were washed with brine (200 mL×2), dried over anhydrous sodium sulfate, and concentrated. The residue was purified by silica gel column chromatography eluting with ethyl acetate/petroleum ether (1:2) to afford [1-(2-chloro-6-methylphenyl)-4-cyclopropyl-1H-pyrazol-5-yl]methanol 8d (0.6 g, 77%) as a yellow oil.

Step 4. To a 250 mL round-bottom flask was added 1H-1,2,3-benzotriazole (270 mg, 2.27 mmol, 1.00 equiv.) and dichloromethane (50 mL). The solution was cooled to 0° C., and added with thionyl chloride (0.54 g, 2.0 equiv.) dropwise with stirring. [1-(2-chloro-6-methylphenyl)-4-cyclopropyl-1H-pyrazol-5-yl]methanol 8d (600 mg, 2.28 mmol, 1.00 equiv.) was added. The resulting mixture was stirred at room temperature for 2 h. 200 mL of H₂O was added, the aqueous mixture was extracted with dichloromethane (200 mL×2). The combined organic extracts were washed with brine (200 mL×2), dried over anhydrous sodium sulfate and concentrated. The residue was purified by silica gel column chromatography eluting with ethyl acetate/petroleum ether (1:3) to give 1-(2-chloro-6-methylphenyl)-5-(chloromethyl)-4-cyclopropyl-1H-pyrazole 8e (0.56 g, 87%) as a yellow oil.

Step 5. To a 50 mL round-bottom flask was added 1-(2-chloro-6-methylphenyl)-5-(chloromethyl)-4-cyclopropyl-1H-pyrazole 8e (560 mg, 1.99 mmol, 1.00 equiv.), benzyl (1S,4S,5R)-5-hydroxy-2-azabicyclo[2.2.1]heptane-2-carboxylate C-1 (590 mg, 2.39 mmol, 1.20 equiv.), sodium hydride (100 mg, 60% dispersion in mineral oil, 4.17 mmol, 2.00 equiv.), and N,N-dimethylformamide (10 mL). The resulting mixture was stirred at room temperature overnight, and quenched by the addition of water/ice. The aqueous mixture was extracted with ethyl acetate (100 mL×2), and the combined organic extracts were washed with brine (100 mL), dried over anhydrous sodium sulfate and concentrated under vacuum. The residue was purified by silica gel column chromatography eluting with ethyl acetate/petroleum ether (1:1) to give benzyl (1S,4S,5R)-5-[[1-(2-chloro-6-meth- Step 1. To a 1000 mL 3-necked round-bottom flask was added 2-chloro-6-methylaniline 8a (10 g, 70.62 mmol, 1.00 equiv.), a 4M hydrogen chloride aqueous solution (60 mL), and water (45 mL). The mixture was cooled to 0° C., and added slowly with NaNO₂ (4.9 g, 71.01 mmol, 1.00 equiv.), followed by SnCl₂ (19 g, 100.20 mmol, 1.40 equiv.). The resulting mixture was stirred at room temperature for 6 h. Solids were collected by filtration. The crude product was purified by Flash-Prep-HPLC using the following conditions ylphenyl)-4-cyclopropyl-1H-pyrazol-5-yl]methoxy]-2-azabicyclo[2.2.1]heptane-2-carboxylate 8f (0.54 g, 55%) as a yellow oil.

Step 6. To a 25 mL round-bottom flask was added benzyl (1S,4S,5R)-5-[[1-(2-chloro-6-methylphenyl)-4-cyclopropyl-1H-pyrazol-5-yl]methoxy]-2-azabicyclo[2.2.1]heptane-2-carboxylate 8f (540 mg, 1.10 mmol, 1.00 equiv.), dichloromethane (8 mL), and TMSI (0.44 g, 2.00 equiv). The resulting mixture was stirred at room temperature for 0.5 h, and quenched by the addition of a 1M hydrogen chloride aqueous solution. The aqueous mixture was extracted dichloromethane (100 mL×2), and the combined organic extracts were washed with brine (50 mL×2), dried over anhydrous sodium sulfate and concentrated under vacuum. The residue was purified by silica gel column chromatography eluting with ethyl acetate/petroleum ether (1:2) to afford (1S,4S,5R)-5-[[1-(2-chloro-6-methylphenyl)-4-cyclopropyl-1H-pyrazol-5-yl]methoxy]-2-azabicyclo[2.2.1]heptane 8g (0.22 g, 56%) as a red oil.

Step 7. To a 8 mL sealed tube was added (1S,4S,5R)-5-[[1-(2-chloro-6-methylphenyl)-4-cyclopropyl-1H-pyrazol-5-yl]methoxy]-2-azabicyclo[2.2.1]heptane 8 g (100 mg, 0.28 mmol, 1.00 equiv.), methyl 2,4-difluorobenzoate (72 mg, 0.42 mmol, 1.50 equiv.), CsF (0.134 g, 3.00 equiv.), and 1-Ethyl-3-methylimidazolium dimethyl phosphate (1 mL). The resulting mixture was heated at 90° C. overnight. After cooling to room temperature, the mixture was diluted with 20 mL of H$_2$O, and extracted with ethyl acetate (100 mL×2). The combined organic extracts were washed with brine (100 mL×2), dried over anhydrous sodium sulfate and concentrated under vacuum. The residue was purified by silica gel column chromatography eluting with ethyl acetate/petroleum ether (1:2) to afford methyl 4-[(1S,4S,5R)-5-[[1-(2-chloro-6-methylphenyl)-4-cyclopropyl-1H-pyrazol-5-yl]methoxy]-2-azabicyclo[2.2.1]heptan-2-yl]-2-fluorobenzoate 8 h (91 mg, 64%) as a red oil.

Step 8. To a 25 mL round-bottom flask was added methyl 4-[(1S,4S,5R)-5-[[1-(2-chloro-6-methylphenyl)-4-cyclopropyl-1H-pyrazol-5-yl]methoxy]-2-azabicyclo[2.2.1]heptan-2-yl]-2-fluorobenzoate 8 h (91 mg, 0.18 mmol, 1.00 equiv.), methanol (3 mL), water (0.5 mL), and LiOH (75 mg, 3.13 mmol, 10.00 equiv.). The resulting mixture was heated at 50° C. for 3 h. The mixture was diluted with 10 mL of H$_2$O after cooling to room temperature, the pH value of the solution was adjusted to 3 with a 1M aqueous hydrogen chloride solution. The aqueous mixture was extracted with ethyl acetate (100 mL×2), and the combined organic extracts were washed with brine (100 mL×2), dried over anhydrous sodium sulfate and concentrated under vacuum. The crude product was purified by Prep-HPLC using the following conditions Column, XBridge Shield RP18 OBD Column, 5 um, 19*150 mm; mobile phase, Water (0.05% TFA) and ACN (50.0% ACN up to 68.0% in 8 min); Detector, uv 254/220 nm. After purification 4-[(1S,4S,5R)-5-[[1-(2-chloro-6-methylphenyl)-4-cyclopropyl-1H-pyrazol-5-yl]methoxy]-2-azabicyclo[2.2.1]heptan-2-yl]-2-fluorobenzoic acid (54.4 mg, 61%) was obtained as a white solid, $^1$H NMR (300 MHz, CD$_3$OD): δ 7.74 (t, J=8.8 Hz, 1H), 7.51-7.32 (m, 4H), 6.34 (d, J=9.3 Hz, 1H), 6.21 (d, J=14.9 Hz, 1H), 4.54 (dd, J=11.9, 4.4 Hz, 1H), 4.28 (dd, J=21.9, 11.9 Hz, 1H), 4.16 (d, J=10.0 Hz, 1H), 3.53 (d, J=12.8 Hz, 2H), 2.63 (t, J=8.1 Hz, 1H), 2.05 (d, J=1.5 Hz, 3H), 1.83 (d, J=6.3 Hz, 1H), 1.63 (s, 1H), 1.53 (s, 1H), 1.01-0.92 (m, 2H), 0.68 (s, 2H). MS (ES, m/z): [M+1]=496.

Example 14: 4-[(1S,4S,5R)-5-{[1-(2-chloro-6-fluorophenyl)-4-cyclopropyl-1H-pyrazol-5-yl]methoxy}-2-azabicyclo[2.2.1]heptan-2-yl]-2-fluorobenzoic acid (I-9)

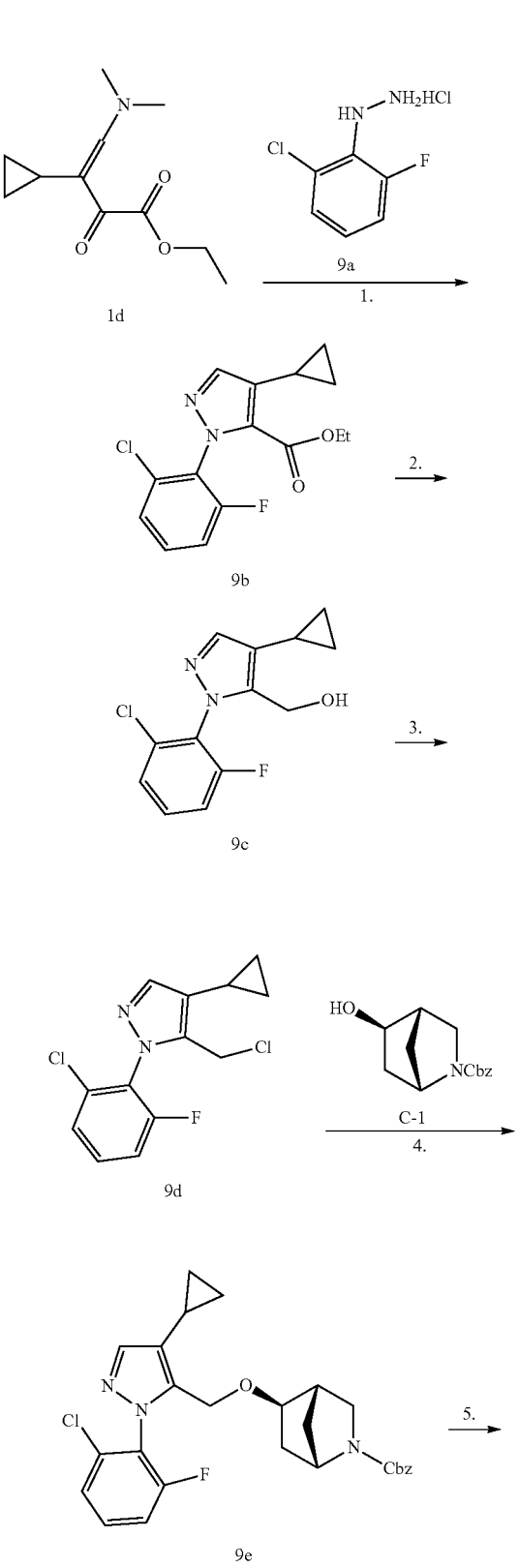

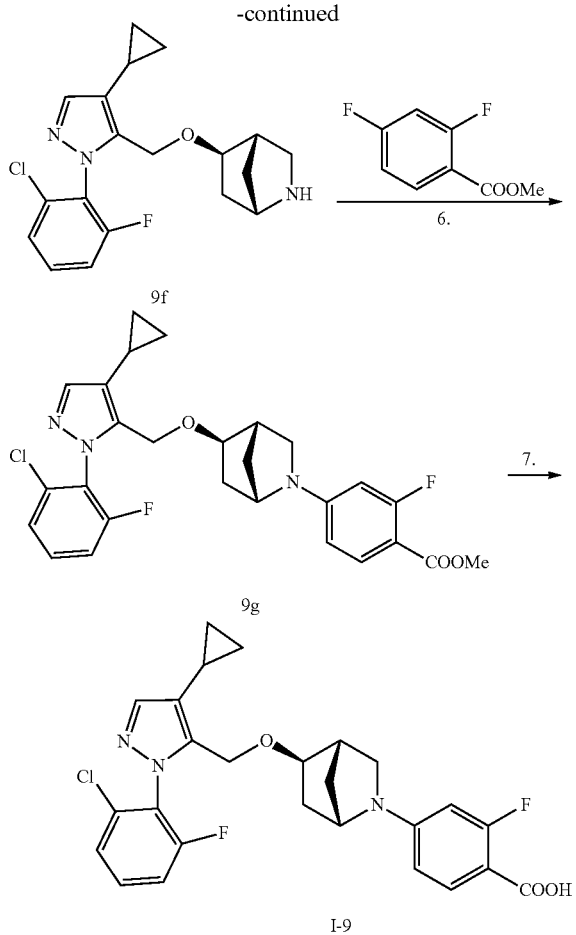

Step 1. To a 250 mL round-bottom flask purged and maintained under an inert atmosphere of nitrogen was added ethyl 3-cyclopropyl-4-(dimethylamino)-2-oxobut-3-enoate 1d (2 g, 9.47 mmol, 1.00 equiv.), ethanol (30 mL), (2-chloro-6-fluorophenyl)hydrazine hydrochloride 9a (1.7 g, 8.63 mmol, 1.10 equiv.), and hydrogen chloride (0.14 mL). The resulting mixture was stirred at 25° C. for 4 h and then heated at 85° C. for 18 h. After cooling to room temperature, the mixture was diluted with H$_2$O (75 mL), extracted with ethyl acetate (150 mL×3). The combined organic extracts were washed with brine (100 mL×2), dried over anhydrous sodium sulfate and concentrated under vacuum. The residue was purified by silica gel column chromatography eluting with ethyl acetate in petroleum ether (15%) to give ethyl 1-(2-chloro-6-fluorophenyl)-4-cyclopropyl-1H-pyrazole-5-carboxylate 9b (1.25 g, 43%) as a light yellow oil.

Step 2. To a 100 mL round-bottom flask was added ethyl 1-(2-chloro-6-fluorophenyl)-4-cyclopropyl-1H-pyrazole-5-carboxylate 9b (1.25 g, 4.05 mmol, 1.00 equiv.), tetrahydrofuran (12 mL), and a 1.5M solution of DIBAL in toluene (5.4 mL, 2.00 equiv.). The resulting mixture was stirred at room temperature for 18 h, and quenched by the addition of water (5 mL), a 1M aqueous NaOH solution (15 mL), and water (5 mL) successively. The aqueous mixture was extracted with ethyl acetate (100 mL×3), and the combined organic extracts were washed with brine (50 mL×2), dried over anhydrous sodium sulfate and concentrated under vacuum. The residue was purified by silica gel column chromatography eluting with ethyl acetate/petroleum ether (1/2) to afford [1-(2-chloro-6-fluorophenyl)-4-cyclopropyl-1H-pyrazol-5-yl]methanol 9c (900 mg, 84%) as a light yellow oil.

Step 3. To a 100 mL round-bottom flask was added 1H-1,2,3-benzotriazole (399 mg, 3.35 mmol, 1.00 equiv.) and dichloromethane (10 mL). The solution was cooled to 0° C., thionyl chloride (600 mg, 1.50 equiv.) was added, and the mixture was stirred for 0.5 at this temperature. A solution of [1-(2-chloro-6-fluorophenyl)-4-cyclopropyl-1H-pyrazol-5-yl]methanol 9c (900 mg, 3.37 mmol, 1.00 equiv.) in dichloromethane (5 mL) was added. The mixture was stirred at room temperature for 1 h, diluted with 50 mL of EA, and quenched by the addition of 10 mL of water. The aqueous mixture was extracted with ethyl acetate (100 mL×3), and the combined organic extracts were washed with brine (50 mL×2), dried and concentrated. The residue was purified by silica gel column chromatography eluting with ethyl acetate/petroleum ether (1/1) to afford 1-(2-chloro-6-fluorophenyl)-5-(chloromethyl)-4-cyclopropyl-1H-pyrazole 9d (560 mg, 58%) as a light yellow oil.

Step 4. To a 100 mL round-bottom flask purged and maintained under an inert atmosphere of nitrogen was added 1-(2-chloro-6-fluorophenyl)-5-(chloromethyl)-4-cyclopropyl-1H-pyrazole 9d (560 mg, 1.96 mmol, 1.00 equiv.), benzyl (1S,4S,5R)-5-hydroxy-2-azabicyclo[2.2.1]heptane-2-carboxylate C-1 (584 mg, 2.36 mmol, 1.20 equiv.) and N,N-dimethylformamide (7 mL). Sodium hydride (158 mg, 60% dispersion in mineral oil, 6.58 mmol, 2.00 equiv.) was added while the temperature was maintained at 0° C. The resulting mixture was stirred at room temperature overnight, diluted with 50 mL of EA, and quenched by the addition of 20 mL of water. The aqueous mixture was extracted with ethyl acetate (100 mL×2), and the combined organic layers were washed with brine (50 mL×3), dried over anhydrous sodium sulfate and concentrated under vacuum. The residue was purified by silica gel column chromatography eluting with ethyl acetate/petroleum ether (1/5) to give benzyl (1S,4S,5R)-5-[[1-(2-chloro-6-fluorophenyl)-4-cyclopropyl-1H-pyrazol-5-yl]methoxy]-2-azabicyclo[2.2.1]heptane-2-carboxylate 9e (540 mg, 53%) as a light yellow oil.

Step 5. To a 100 mL round-bottom flask was added benzyl (1S,4S,5R)-[[1-(2-chloro-6-fluorophenyl)-4-cyclopropyl-1H-pyrazol-5-yl]methoxy]-2-azabicyclo[2.2.1]heptane-2-carboxylate 9e (430 mg, 0.87 mmol, 1.00 equiv.), dichloromethane (6 mL), and TMSI (348 mg, 1.74 mmol, 2.00 equiv.). The resulting mixture was stirred at room temperature for 30 min, and quenched by the addition of a 10% of hydrogen chloride aqueous solution. The aqueous mixture was extracted with dichloromethane (10 mL×2), and the combined organic extracts were washed with brine, dried over anhydrous Na$_2$SO$_4$ and concentrated under vacuum to afford (1S,4S,5R)-5-[[1-(2-chloro-6-fluorophenyl)-4-cyclopropyl-1H-pyrazol-5-yl]methoxy]-2-azabicyclo[2.2.1]heptane 9f (260 mg, 83%) as a red solid.

Step 6. To a 50 mL round-bottom flask purged and maintained under an inert atmosphere of nitrogen was added (1S,4S,5R)-5-[[1-(2-chloro-6-fluorophenyl)-4-cyclopropyl-1H-pyrazol-5-yl]methoxy]-2-azabicyclo[2.2.1]heptane 9f (120 mg, 0.33 mmol, 1.00 equiv.), methyl 2,4-difluorobenzoate (114 mg, 0.66 mmol, 2.00 equiv.), CsF (152 mg, 1.00 mmol, 3.00 equiv.), and 1-Ethyl-3-methylimidazolium dimethyl phosphate (2 mL). The resulting mixture was heated at 90° C. overnight. After cooling to room temperature, H$_2$O (100 mL) was added, and the mixture was extracted with ethyl acetate (100 mL×3). The combined organic extracts were washed with brine (50 mL×3), dried over anhydrous sodium sulfate and concentrated under vacuum. The residue was purified by silica gel column chromatography eluting with ethyl acetate/petroleum ether (1/3) to afford methyl 4-[(1S,4S,5R)-5-[[1-(2-chloro-6-fluorophenyl)-4-cyclopropyl-1H-pyrazol-5-yl]methoxy]-2-azabicyclo[2.2.1]heptan-2-yl]-2-fluorobenzoate 9g (100 mg, 65%) as a light yellow solid.

Step 7. To a 25 mL round-bottom flask was added methyl 4-[(1S,4S,5R)-5-[[1-(2-chloro-6-fluorophenyl)-4-cyclopropyl-1H-pyrazol-5-yl]methoxy]-2-azabicyclo[2.2.1]heptan-2-yl]-2-fluorobenzoate 9g (110 mg, 0.21 mmol, 1.00 equiv.), LiOH—H$_2$O (90 mg, 2.10 mmol, 10.0 equiv), methanol (2 mL), and water (0.2 mL). The resulting mixture was stirred at 50° C. for 2 h. After cooling to room temperature, the mixture was diluted with 20 mL of water, extracted with ethyl acetate (100 mL×2), and the combined organic extracts were washed with brine (50 mL×2), dried over anhydrous sodium sulfate and concentrated under vacuum. The crude product was purified by Prep-HPLC using the following conditions: Column, XBridge Shield RP18 OBD Column 5 um, 19*150 mm; mobile phase, Water (0.05% TFA) and ACN (52.0% ACN up to 55.0% in 10 min); Detector, uv 254/220 nm. 37.5 mg product was obtained. After purification 4-[(1S,4S,5R)-5-[[1-(2-chloro-6-fluorophenyl)-4-cyclopropyl-1H-pyrazol-5-yl]methoxy]-2-azabicyclo[2.2.1]heptan-2-yl]-2-fluorobenzoic acid I-9 (37.5 mg, 25%) was obtained as an off-white solid. $^1$H NMR (300 MHz, CD$_3$OD): δ 7.74 (t, J=8.8 Hz, 1H), 7.68-7.54 (m, 1H), 7.55-7.44 (m, 2H), 7.38 (t, J=8.2 Hz, 1H), 6.34 (d, J=7.8 Hz, 1H), 6.22 (d, J=15.1 Hz, 1H), 4.55 (dd, J=12.6, 5.2 Hz, 1H), 4.52-4.38 (m, 1H), 4.17 (s, 1H), 3.53 (d, J=6.6 Hz, 1H), 2.62 (d, J=9.4 Hz, 1H), 2.54 (s, 1H), 1.88-1.76 (m, 1H), 1.61 (s, 2H), 1.32 (t, J=12.7 Hz, 1H), 1.04-0.92 (m, 2H), 0.68 (d, J=5.2 Hz, 2H). MS (ES, m/z): [M+1]=500.10.

Example 15: 4-[(1S,4S,5R)-5-{[4-cyclopropyl-1-(2,6-difluorophenyl)-1H-pyrazol-5-yl]methoxy}-2-azabicyclo[2.2.1]heptan-2-yl]-2-fluorobenzoic acid (I-10)

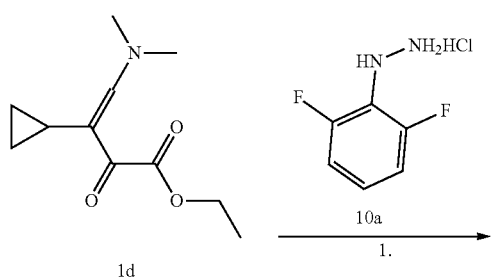

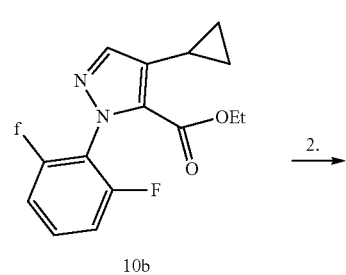

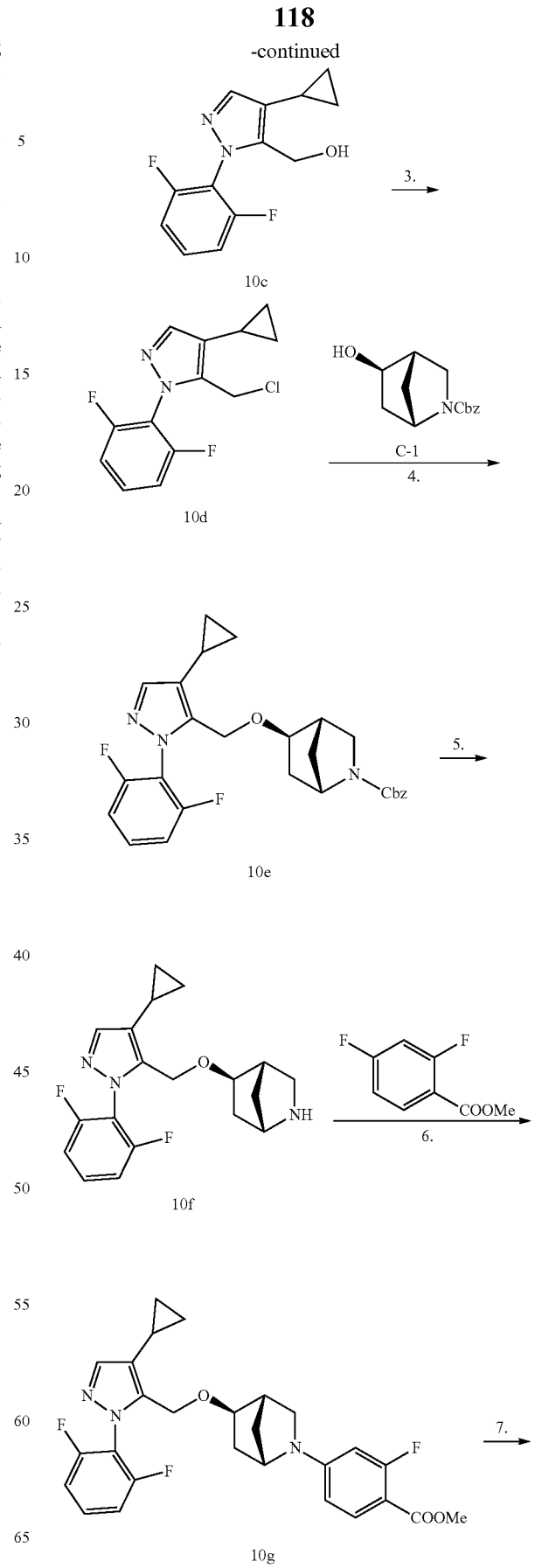

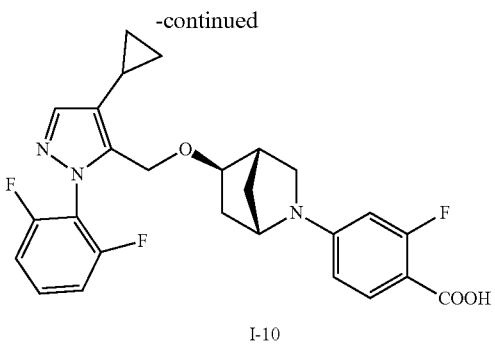

I-10

Step 1. To a 100 mL round-bottom flask was added ethyl 3-cyclopropyl-4-(dimethylamino)-2-oxobut-3-enoate 1d (1.3 g, 6.15 mmol, 1.00 equiv.), ethanol (23 mL), hydrogen chloride (cat.) (0.09 mL), and (2, 6-difluorophenyl)hydrazine hydrochloride 10a (1.33 g, 7.37 mmol, 1.10 equiv.). The resulting mixture was stirred at room temperature for 4 h and then heated at 85° C. overnight. After cooling to room temperature, water (100 mL) was added, and the mixture was extracted with ethyl acetate (250 mL×2). The combined organic extracts were washed with brine (200 mL×3), dried over anhydrous sodium sulfate and concentrated under vacuum. The crude product was purified by Flash-Prep-HPLC using the following conditions (IntelFlash-1): Column, silica gel; mobile phase, EA:PE increasing to EA:PE=15 within 20 min; Detector, UV 254 nm. After purification ethyl 4-cyclopropyl-1-(2,6-difluorophenyl)-1H-pyrazole-5-carboxylate 10b (640 mg, 36%) was obtained as a yellow oil.

Step 2. To a 25 mL round-bottom flask was added ethyl 4-cyclopropyl-1-(2,6-difluorophenyl)-1H-pyrazole-5-carboxylate 10b (620 mg, 2.12 mmol, 1.00 equiv.), tetrahydrofuran (10 mL), and a 1.5M DIBAL-H solution in Toluene (3.4 mL, 2.40 equiv.). The resulting mixture was stirred at room temperature overnight, then quenched by the addition of 1 mL of 1M NaOH aqueous solution. The mixture was further diluted with water (20 mL), and extracted with ethyl acetate (100 mL×2). The combined organic extracts were washed with brine (100 mL×2), dried over anhydrous sodium sulfate and concentrated under vacuum. The residue was purified by silica gel column chromatography eluting with ethyl acetate/petroleum ether (1:3) to give [4-cyclopropyl-1-(2,6-difluorophenyl)-1H-pyrazol-5-yl]methanol 10c (450 mg, 85%) as a light yellow oil.

Step 3. To a 25 mL round-bottom flask was added [4-cyclopropyl-1-(2,6-difluorophenyl)-1H-pyrazol-5-yl]methanol 10c (450 mg, 1.80 mmol, 1.00 equiv.), benzotriazole (1 eq) (428.4 mg, 2.00 equiv.), dichloromethane (5 mL), and thionyl chloride (424.8 mg, 2.00 equiv.). The resulting mixture was stirred at room temperature for 1 h, quenched with water (20 mL), and extracted with dichloromethane (100 mL×2). The combined organic extracts were washed with brine (100 mL×2), dried over anhydrous sodium sulfate and concentrated under vacuum. The residue was purified by silica gel column chromatography eluting with ethyl acetate/petroleum ether (1:5) to give 5-(chloromethyl)-4-cyclopropyl-1-(2,6-difluorophenyl)-1H-pyrazole 10d (270 mg, 56%) as a light yellow oil.

Step 4. To a 50 mL round-bottom flask was added benzyl (1S,4S,5R)-5-hydroxy-2-azabicyclo[2.2.1]heptane-2-carboxylate C-1 (250 mg, 1.01 mmol, 1.20 equiv.), 5-(chloromethyl)-4-cyclopropyl-1-(2,6-difluorophenyl)-1H-pyrazole 10d (225 mg, 0.84 mmol, 1.00 equiv.), and N,N-dimethylformamide (17 mL). The mixture was cooled to 0° C., and sodium hydride (70 mg, 60% dispersion in mineral oil, 1.75 mmol, 2.00 equiv.) was added in portions. The resulting mixture was stirred at room temperature overnight. The resulting mixture was diluted with EA (100 mL), quenched by the addition of H$_2$O (50 mL), and extracted with ethyl acetate (100 mL×2). The combined organic extracts were washed with brine (150 mL×2), dried over sodium sulfate and concentrated under vacuum to provide benzyl (1S,4S,5R)-5-[[4-cyclopropyl-1-(2,6-difluorophenyl)-1H-pyrazol-5-yl]methoxy]-2-azabicyclo [2.2.1]heptane-2-carboxylate 10e (490 mg, 73%) as a yellow oil.

Step 5. To a 25 mL round-bottom flask was added benzyl (1S,4S,5R)-5 [[4-cyclopropyl-1-(2,6-difluorophenyl)-1H-pyrazol-5-yl]methoxy]-2-azabicyclo[2.2.1]heptane-2-carboxylate 10e (490 mg, 1.02 mmol, 1.00 equiv.) and dichloromethane (8.2 mL). TMSI (412 mg, 2.00 equiv.) was added dropwise with stirring. The resulting mixture was stirred at room temperature for 30 min, and quenched by the addition of a 1M HCl aqueous solution (3 mL). The aqueous mixture was extracted with ethyl acetate (150 mL×2), and the combined organic extracts were washed with brine (100 mL×2), dried over anhydrous sodium sulfate and concentrated under vacuum. The residue was purified by silica gel column chromatography eluting with dichloromethane/methanol (15:1) to afford (1S,4S,5R)-5-[[4-cyclopropyl-1-(2,6-difluorophenyl)-1H-pyrazol-5-yl]methoxy]-2-azabicyclo[2.2.1]heptane 10f (100 mg, 28%) as a light yellow foam.

Step 6. To a 8 mL sealed tube was added (1S,4S,5R)-[[4-cyclopropyl-1-(2,6-difluorophenyl)-1H-pyrazol-5-yl]methoxy]-2-azabicyclo[2.2.1]heptane 10f (110 mg, 0.32 mmol, 1.00 equiv.), tert-butyl 4-bromo-2-fluorobenzoate (132 mg, 0.48 mmol, 1.50 equiv.), Pd(OAc)$_2$ (7.3 mg, 0.10 equiv.), Xantphos (37 mg, 0.06 mmol, 0.20 equiv.), dioxane (1.6 mL), and Cs$_2$CO$_3$ (315 mg, 0.97 mmol, 3.00 equiv.). The resulting mixture was heated at 90° C. overnight. After cooling to room temperature, water was added, the mixture was extracted with ethyl acetate (100 mL×2), and the combined organic extracts were washed with brine (100 mL×2), dried over anhydrous sodium sulfate and concentrated under vacuum. The residue was purified by silica gel column chromatography eluting with ethyl acetate/petroleum ether (1:3) to afford tert-butyl 4-[(1S,4S,5R)-[[4-cyclopropyl-1-(2,6-difluorophenyl)-1H-pyrazol-5-yl]methoxy]-2-azabicyclo[2.2.1]heptan-2-yl]-2-fluorobenzoate 10g (54 mg, 31%) as a yellow foam.

Step 7. To a 25 mL round-bottom flask was added tert-butyl 4-[(1S,4S,5R)-5-[[4-cyclopropyl-1-(2,6-difluorophenyl)-1H-pyrazol-5-yl]methoxy]-2-azabicyclo[2.2.1]heptan-2-yl]-2-fluorobenzoate 10g (54 mg, 0.10 mmol, 1.00 equiv.), dichloromethane (2 mL), and trifluoroacetic acid (1 mL). The resulting mixture was stirred at room temperature for 1 h, quenched with water. The aqueous mixture was extracted with dichloromethane (100 mL×2), and the combined organic extracts were washed with brine (100 mL×2), dried over sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (48.0% ACN up to 57.0% in 10 min); Detector, uv 254/220 nm. After purification 4-[(1S,4S,5R)-5-[[4-cyclopropyl-1-(2,6-difluorophenyl)-1H-pyrazol-5-yl]methoxy]-2-azabicyclo[2.2.1]heptan-2-yl]-2-fluorobenzoic acid I-10 (11.5 mg, 24%) was obtained as a white solid. $^1$H NMR (300 MHz, CD$_3$OD): δ 7.74 (t, J=8.8 Hz, 1H), 7.63 (tt, J=8.6, 6.2 Hz, 1H), 7.48 (s, 1H), 7.24 (q, J=8.5 Hz, 2H), 6.34 (dd, J=8.9, 2.2 Hz, 1H), 6.22 (dd, J=14.6, 2.2

Hz, 1H), 4.53 (d, J=2.7 Hz, 2H), 4.17 (s, 1H), 3.57-3.48 (m, 1H), 3.39 (d, J=4.2 Hz, 1H), 2.64 (s, 1H), 2.57 (d, J=19.8 Hz, 1H), 1.94-1.74 (m, 2H), 1.60 (s, 2H), 1.33 (d, J=13.2 Hz, 1H), 1.03-0.90 (m, 2H), 0.74-0.62 (m, 2H). MS (ES, m/z): [M+1]=484.

Example 16: 4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]benzoic acid (I-11)

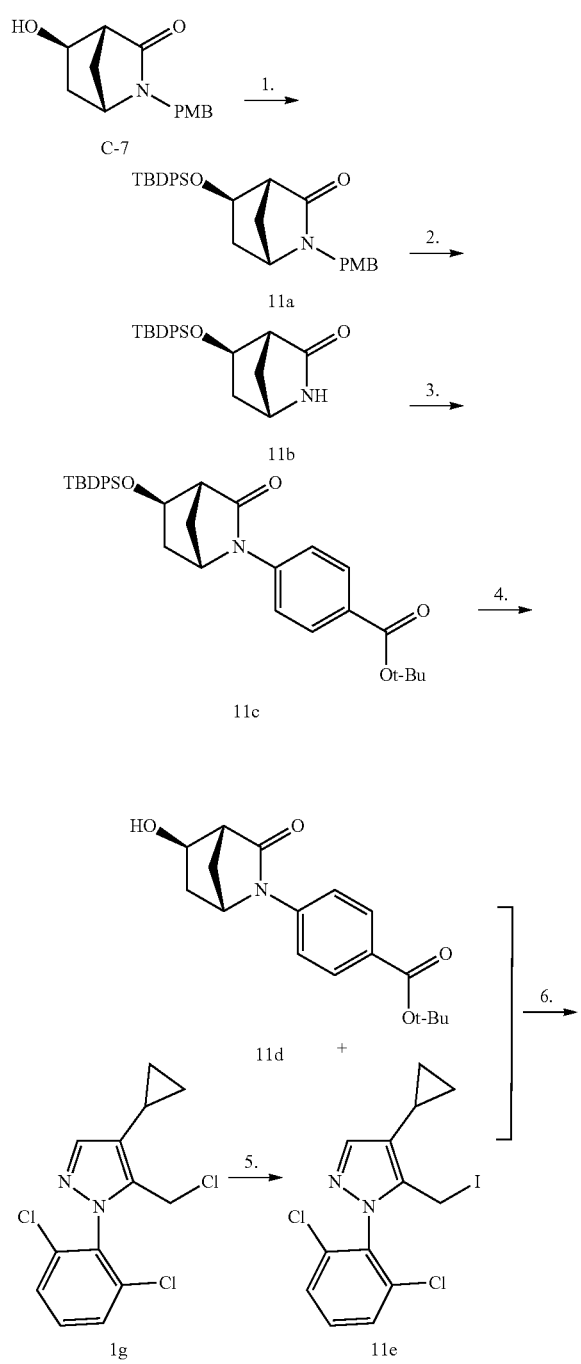

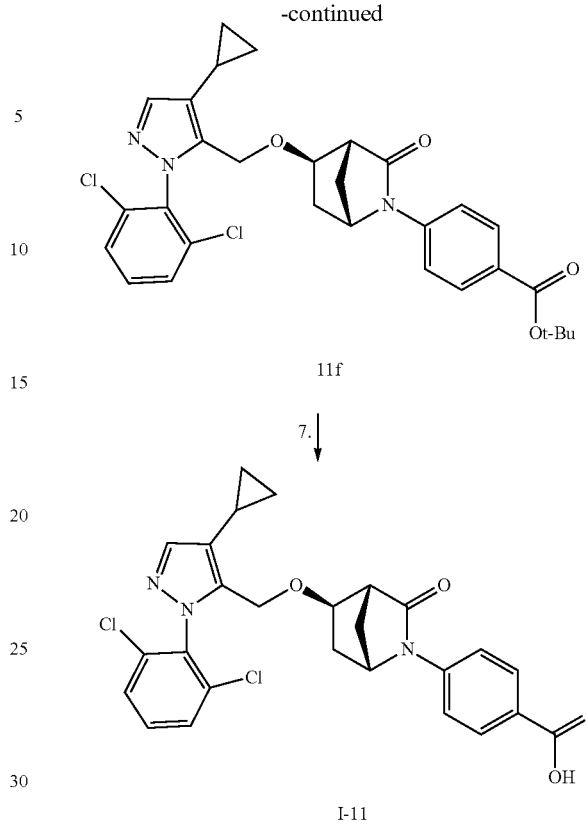

Step 1. To a 250 mL round-bottom flask was added (1S,4R,5R)-5-hydroxy-2-[(4-methoxyphenyl)methyl]-2-azabicyclo[2.2.1]heptan-3-one C-7 (4 g, 16.18 mmol, 1.00 equiv.), N,N-dimethylformamide (50 mL), TBDPSCl (4.1 g, 1.30 equiv), and imidazole (1.93 g, 2.50 equiv.). The resulting mixture was stirred at 40° C. for 4 h. After cooling, the mixture was quenched with water, and extracted with ethyl acetate (200 mL×2). The combined organic extracts were washed with brine (200 mL×2), dried over anhydrous sodium sulfate and concentrated under vacuum. The crude product was purified by Flash-Prep-HPLC using the following conditions (IntelFlash-1): Column, silica gel; mobile phase, EA/PE=0:100 increasing to EA/PE=30:70 within 20 min; Detector, UV 254 nm. Removal of solvents gave (1S,4R,5R)-5-[(tert-butyldiphenylsilyl)oxy]-2-[(4-methoxyphenyl)methyl]-2-azabicyclo[2.2.1]heptan-3-one 11a (2.95 g, 38%) as a light yellow solid.

Step 2. To a 250 mL round-bottom flask was added a solution of (1S,4R,5R)-5-[(tert-butyldiphenylsilyl)oxy]-2-[(4-methoxyphenyl)methyl]-2-azabicyclo[2.2.1]heptan-3-one 11a (1.65 g, 3.40 mmol, 1.00 equiv.) in MeCN (40 mL) and a solution of CAN (7.46 g, 4.00 equiv.) in water (17 mL). The resulting mixture was stirred at room temperature for 30 min. The aqueous mixture was extracted with ethyl acetate (100 mL×2), and the combined organic extracts were washed with brine (100 mL×2), dried over anhydrous sodium sulfate and concentrated under vacuum. The residue was purified by silica gel column chromatography eluting with ethyl acetate/petroleum ether (1:5) to afford (1S,4R,5R)-5-[(tert-butyldiphenylsilyl)oxy]-2-azabicyclo[2.2.1]heptan-3-one 11b (1.1 g, 89%) as a light yellow solid.

Step 3. To a 50 mL round-bottom flask was added (1S,4R,5R)-5-[(tert-butyldiphenylsilyl)oxy]-2-azabicyclo[2.2.1]heptan-3-one 11b (500 mg, 1.37 mmol, 1.00 equiv.), 1,4-dioxane (10 mL), Pd$_2$(dba)$_3$ (65 mg, 0.07 mmol, 0.05 equiv.), XantPhos (120 mg, 0.15 equiv), Cs$_2$CO$_3$ (670 mg, 2.06 mmol, 1.50 equiv.), and tert-butyl 4-bromobenzoate (421 mg, 1.64 mmol, 1.20 equiv.). The resulting mixture was heated at 105° C. overnight. Upon cooling to room temperature, water (100 mL) was added, the mixture was extracted with ethyl acetate (100 mL×2), and the combined organic extracts were washed with brine (100 mL×2), dried over anhydrous sodium sulfate and concentrated under vacuum. The residue was purified by silica gel column chromatography eluting with ethyl acetate/petroleum ether (1:5) to afford tert-butyl 4-[(1S,4R,5R)-5-[(tert-butyldiphenylsilyl)oxy]-3-oxo-2-azabicyclo[2.2.1]heptan-2-yl]benzoate 11c (700 mg, 94%) as a light yellow oil.

Step 4. To a 50 mL round-bottom flask was added a solution of tert-butyl 4-[(1S,4R,5R)-5-[(tert-butyldiphenylsilyl)oxy]-3-oxo-2-azabicyclo[2.2.1]heptan-2-yl]benzoate 11c (700 mg, 1.29 mmol, 1.00 equiv.) in tetrahydrofuran (1 mL) and TBAF (2 mL, 2.00 equiv). The resulting mixture was stirred at room temperature for 1 h, quenched with the addition of water (50 mL). The aqueous mixture was extracted with ethyl acetate (100 mL×2), and the combined organic extracts were washed with brine (100 mL), dried over anhydrous sodium sulfate and concentrated under vacuum. The residue was purified by silica gel column chromatography eluting with ethyl acetate to afford tert-butyl 4-[(1S,4R,5R)-5-hydroxy-3-oxo-2-azabicyclo[2.2.1]heptan-2-yl]benzoate 11d (200 mg, 51%) as an off-white solid.

Step 5. To a 250 mL round-bottom flask was added 5-(chloromethyl)-4-cyclopropyl-1-(2,6-dichlorophenyl)-1H-pyrazole 1g (1.3 g, 4.31 mmol, 1.00 equiv.), acetone (34 mL), NaI (1.3 g, 8.67 mmol, 2.00 equiv.), and TBAI (400 mg, 1.08 mmol, 0.25 equiv.). The resulting mixture was heated at 62° C. for 2 h. After cooling to room temperature, the mixture was quenched with 30 mL of water. The aqueous mixture was extracted with ethyl acetate (100 mL×2), and the combined organic extracts were washed with brine (100 mL×2), dried over anhydrous sodium sulfate and concentrated under vacuum. The crude product was purified by Flash-Prep-HPLC using the following conditions: Column, silica gel; mobile phase, EA:PE=0:100 increasing to EA:PE=15:85 within 20 min; Detector, UV 254 nm. Removal of solvents afforded 4-cyclopropyl-1-(2,6-dichlorophenyl)-5-(iodomethyl)-1H-pyrazole 11e (1.35 g, 80%) as a light yellow crude solid.

Step 6. To a 50 mL round-bottom flask was added tert-butyl 4-[(1S,4R,5R)-5-hydroxy-3-oxo-2-azabicyclo[2.2.1]heptan-2-yl]benzoate 11d (86 mg, 0.28 mmol, 1.00 equiv.), AgOTf (435 mg, 2.00 equiv.), 4 A MS (160 mg, 2 w/w), 2,6-di-tert-butylpyridine (310 mg, 6.00 equiv.), dichloromethane (9 mL), and 4-cyclopropyl-1-(2,6-dichlorophenyl)-5-(iodomethyl)-1H-pyrazole 11e (220 mg, 0.56 mmol, 2.0 equiv.). The resulting mixture was stirred at room temperature overnight. The solids were filtered out. The pH value of the solution was adjusted to 6 using a 1M HCl aqueous solution, and the mixture was extracted with dichloromethane (100 mL×2). The combined organic extracts were washed with brine, dried over anhydrous sodium sulfate and concentrated under vacuum. The residue was purified by silica gel column chromatography eluting with ethyl acetate/petroleum ether (1:1) to give tert-butyl 4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]benzoate 11f (100 mg, 62%) as a light yellow solid.

Step 7. To a 25 mL round-bottom flask was added tert-butyl 4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]benzoate 11f (120 mg, 0.21 mmol, 1.00 equiv.), dichloromethane (2 mL), and trifluoroacetic acid (1 mL). The resulting mixture was stirred at room temperature for 1 h, and quenched with water. The aqueous mixture was extracted with ethyl acetate (50 mL×2), and the combined organic extracts were washed with brine (50 mL×2), dried over anhydrous sodium sulfate and concentrated under vacuum. The crude product was purified by Prep-HPLC using the following conditions: Column, XBridge Shield RP18 OBD Column 5 um, 19*150 mm; mobile phase, Water (0.1% FA) and ACN (36% ACN up to 40% in 18 min); Detector, UV 254 nm. After purification of 4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]benzoic acid I-11 (45.4 mg, 42%) was obtained as a white solid. $^1$H NMR (300 MHz, CD$_3$OD): δ 8.06-7.95 (m, 2H), 7.69-7.50 (m, 5H), 7.47 (s, 1H), 4.56 (dd, J=15.0, 2.6 Hz, 3H), 3.87 (d, J=6.6 Hz, 1H), 2.87 (d, J=1.7 Hz, 1H), 2.21 (ddd, J=13.4, 6.9, 2.5 Hz, 1H), 2.01 (d, J=10.1 Hz, 1H), 1.83 (td, J=9.3, 8.8, 4.4 Hz, 2H), 1.68-1.56 (m, 1H), 1.07-0.90 (m, 2H), 0.68 (qd, J=4.7, 1.8 Hz, 2H). MS (ES, m/z): [M+1]=512.

Example 17: 4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-2-fluorobenzoic acid (I-12)

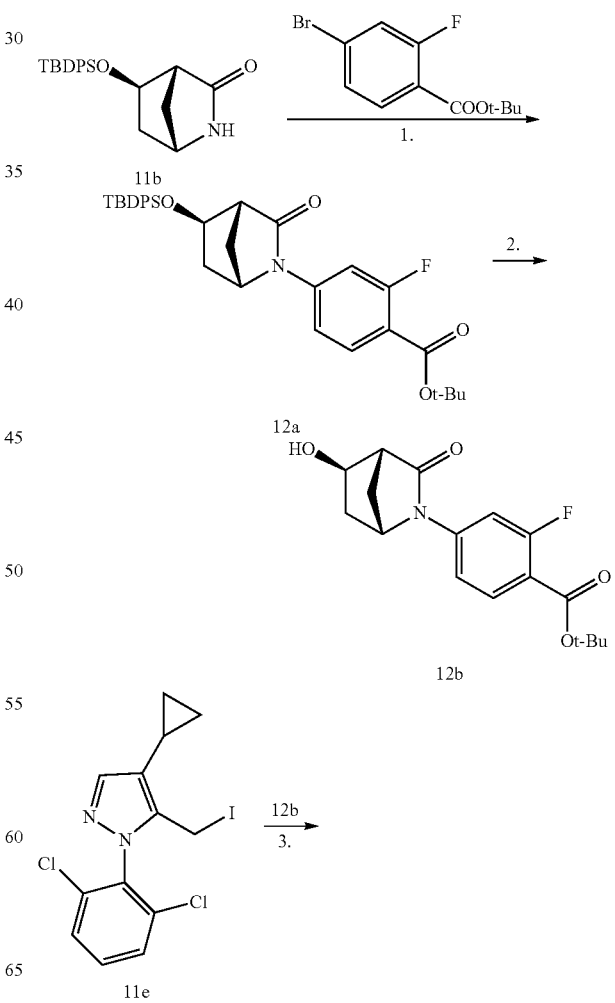

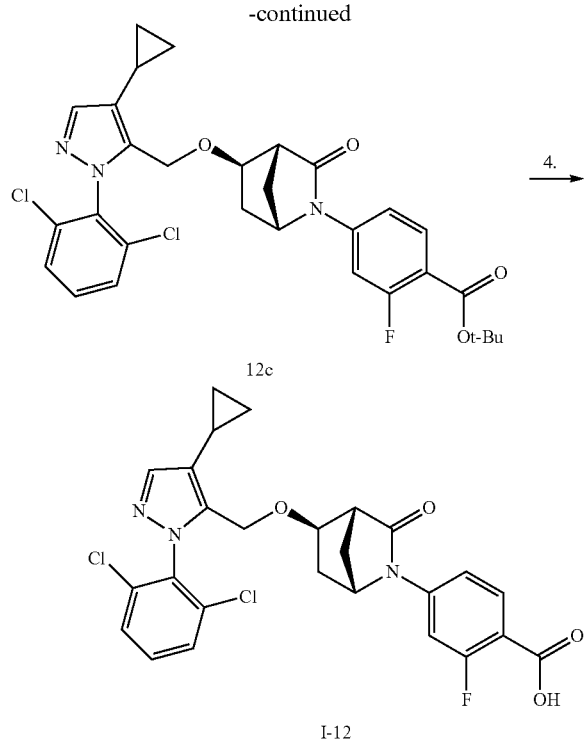

Step 1. To a 100 mL round-bottom flask was added a solution of (1S,4R,5R)-5-[(tert-butyldiphenylsilyl)oxy]-2-azabicyclo[2.2.1]heptan-3-one 11b (570 mg, 1.56 mmol, 1.00 equiv.) in 1,4-dioxane (12 mL), Pd$_2$(dba)$_3$ (71 mg, 0.08 mmol, 0.05 equiv.), XantPhos (135 mg, 0.23 mmol, 0.15 equiv.), Cs$_2$CO$_3$ (762 mg, 2.34 mmol, 1.50 equiv.), and tert-butyl 4-bromo-2-fluorobenzoate (513 mg, 1.86 mmol, 1.20 equiv.). The resulting mixture was heated at 105° C. overnight. After cooling to room temperature, water was added, the mixture was extracted with ethyl acetate (100 mL×2), and the combined organic extracts were washed with brine (100 mL×2), dried over anhydrous sodium sulfate and concentrated under vacuum. The residue was purified by silica gel column chromatography eluting with ethyl acetate/petroleum ether (1:5) to give tert-butyl 4-[(1S,4R,5R)-5-[(tert-butyldiphenylsilyl)oxy]-3-oxo-2-azabicyclo[2.2.1]heptan-2-yl]-2-fluorobenzoate 12a (710 mg, 81%) as a light yellow oil.

Step 2. To a 50 mL round-bottom flask was added tert-butyl 4-[(1S,4R,5R)-5-[(tert-butyldiphenylsilyl)oxy]-3-oxo-2-azabicyclo[2.2.1]heptan-2-yl]-2-fluorobenzoate 12a (710 mg, 1.27 mmol, 1.00 equiv.), tetrahydrofuran (2.5 mL), and TBAF (662 mg, 2.53 mmol, 2.00 equiv.). The resulting mixture was stirred at room temperature for 1 h, quenched with water. The aqueous mixture was extracted with ethyl acetate (50 mL×2), and the combined organic extracts were washed with brine (50 mL), dried over anhydrous sodium sulfate and concentrated under vacuum. The residue was purified by silica gel column chromatography eluting with ethyl acetate to afford tert-butyl 2-fluoro-4-[(1S,4R,5R)-5-hydroxy-3-oxo-2-azabicyclo[2.2.1]heptan-2-yl]benzoate 12b (210 mg, 52%) as a light yellow solid.

Step 3. To a 100 mL round-bottom flask was added tert-butyl 2-fluoro-4-[(1S,4R,5R)-5-hydroxy-3-oxo-2-azabicyclo[2.2.1]heptan-2-yl]benzoate 12b (150 mg, 0.47 mmol, 1.00 equiv.), AgOTf (249 mg, 2.00 equiv.), 4 A MS (300 mg, 2 w/w), 2,6-di-tert-butyl pyridine (558 mg, 6.00 equiv.), dichloromethane (15 mL), and 4-cyclopropyl-1-(2,6-dichlorophenyl)-5-(iodomethyl)-1H-pyrazole 11e (376 mg, 0.96 mmol, 2.00 equiv.). The resulting mixture was stirred at room temperature overnight. The solids were filtered out. The filtrate was diluted with water, and extracted with dichloromethane (100 mL×2). The combined organic extracts were washed with brine (100 mL×2), dried over anhydrous sodium sulfate and concentrated under vacuum. The residue was purified by silica gel column chromatography eluting with ethyl acetate/petroleum ether (1:2) to give tert-butyl 4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]benzoate 12c (190 mg, 72%) as a light yellow solid.

Step 4. To a 50 mL round-bottom flask was added tert-butyl 4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]-2-fluorobenzoate 12c (90 mg, 0.15 mmol, 1.00 equiv.), dichloromethane (2 mL), and trifluoroacetic acid (1 mL). The resulting mixture was stirred at room temperature for 1 h. The reaction was quenched by the addition of 10 mL of a saturated sodium bicarbonate aqueous solution. The aqueous mixture was extracted with ethyl acetate (50 mL×2), and the combined organic extracts were washed with brine (50 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (38.0% ACN up to 57.0% in 8 min); Detector, UV 254/220 nm. After purification 4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]-2-fluorobenzoic acid I-12 (46.5 mg, 57%) was obtained as a light yellow solid. $^1$H NMR (300 MHz, CD$_3$OD): δ 7.93 (t, J=8.6 Hz, 1H), 7.69-7.44 (m, 4H), 7.32 (dd, J=8.6, 2.1 Hz, 1H), 4.64-4.45 (m, 3H), 3.87 (d, J=6.8 Hz, 1H), 2.87 (s, 1H), 2.18 (ddd, J=13.6, 6.9, 2.5 Hz, 1H), 2.02 (d, J=21.7 Hz, 2H), 1.92-1.76 (m, 2H), 1.62 (d, J=13.5 Hz, 1H), 1.07-0.87 (m, 2H), 0.67 (qd, J=4.6, 1.6 Hz, 2H). MS (ES, m/z): [M+1]=530.

Example 18: 4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-3-fluorobenzoic acid (I-13)

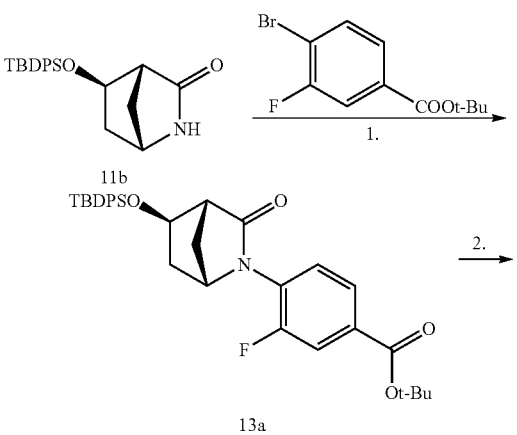

-continued

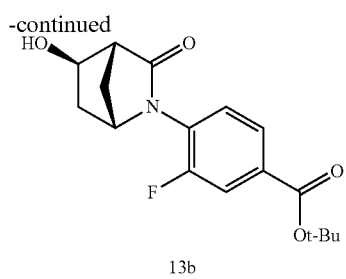

13b

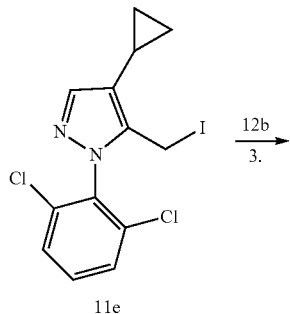

11e

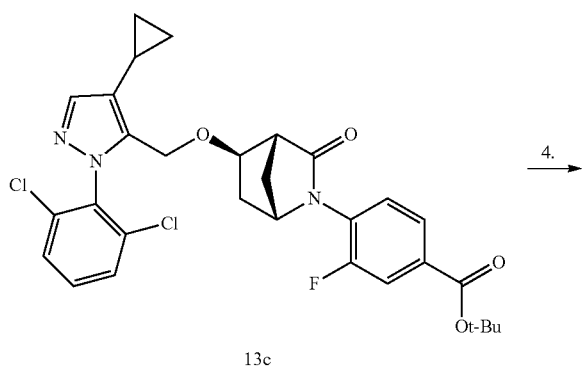

13c

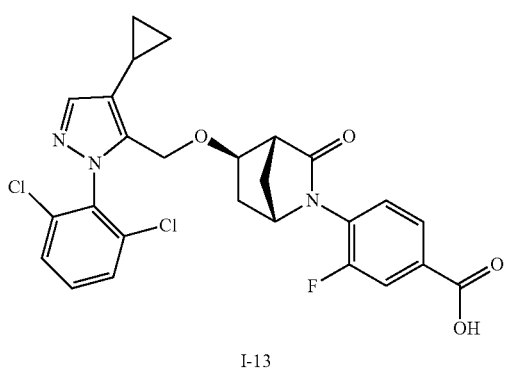

I-13

Step 1. To a 50 mL round-bottom flask was added (1S,4R,5R)-5-[(tert-butyldiphenylsilyl)oxy]-2-azabicyclo[2.2.1]heptan-3-one 11b (300 mg, 0.82 mmol, 1.00 equiv.), Pd₂(dba)₃ (39 mg, 0.04 mmol, 0.05 equiv.), XantPhos (75 mg, 0.15 equiv.), Cs₂CO₃ (411 mg, 1.26 mmol, 1.50 equiv.), 1,4-dioxane (8 mL), and tert-butyl 4-bromo-3-fluorobenzoate (240 mg, 0.87 mmol, 1.20 equiv.). The resulting mixture was heated at 105° C. overnight and concentrated under vacuum. The residue was purified by silica gel column chromatography eluting with ethyl acetate/petroleum ether (1:5) to give tert-butyl 4-[(1S,4R,5R)-5-[(tert-butyldiphenylsilyl)oxy]-3-oxo-2-azabicyclo[2.2.1]heptan-2-yl]-3-fluorobenzoate 13a (400 mg, 87%) as a light yellow solid.

Step 2. To a 50 mL round-bottom flask was added tert-butyl 4-[(1S,4R,5R)-5-[(tert-butyldiphenylsilyl)oxy]-3-oxo-2-azabicyclo[2.2.1]heptan-2-yl]-3-fluorobenzoate 13a (400 mg, 0.71 mmol, 1.00 equiv.), and a solution of TBAF (400 mg, 12.19 mmol, 2.00 equiv.) in tetrahydrofuran (2 mL). The resulting mixture was stirred at room temperature for 1 h, and quenched with water. The aqueous mixture was extracted with ethyl acetate (50 mL×2), and the combined organic extracts were washed with brine (50 mL×2), dried over anhydrous sodium sulfate and concentrated under vacuum. The residue was purified by silica gel column chromatography eluting with ethyl acetate/petroleum ether (1:5) to afford tert-butyl 3-fluoro-4-[(1S,4R,5R)-5-hydroxy-3-oxo-2-azabicyclo[2.2.1]heptan-2-yl]benzoate 13b (200 mg, 87%) as a light yellow solid.

Step 3. To a 250 mL round-bottom flask was added tert-butyl 3-fluoro-4-[(1S,4R,5R)-5-hydroxy-3-oxo-2-azabicyclo[2.2.1]heptan-2-yl]benzoate 13b (200 mg, 0.62 mmol, 1.00 equiv.), AgOTf (308 mg, 2.00 equiv.), 4 A MS (400 mg, 2.00 equiv.), 2,6-di-tert-butyl pyridine (688 mg, 6.00 equiv.), dichloromethane (20 mL), and 4-cyclopropyl-1-(2,6-dichlorophenyl)-5-(iodomethyl)-1H-pyrazole 11e (488 mg, 1.24 mmol, 2.00 equiv.). The resulting mixture was stirred at room temperature overnight. The solids were filtered out. The filtrate was diluted with water and extracted with dichloromethane (50 mL×2). The combined organic extracts were washed with brine (50 mL×2), dried over anhydrous sodium sulfate and concentrated under vacuum. The residue was purified by silica gel column chromatography eluting with ethyl acetate/petroleum ether (1:1) to afford tert-butyl 4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]-3-fluorobenzoate 13c (218 mg, 60%) as a light yellow solid.

Step 4. To a 50 mL round-bottom flask was added tert-butyl 4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]-3-fluorobenzoate 13c (170 mg, 0.29 mmol, 1.00 equiv.), dichloromethane (2 mL), and trifluoroacetic acid (1 mL). The resulting mixture was stirred at room temperature for 1 h. The reaction was quenched by the addition of 10 mL of a saturated sodium bicarbonate aqueous solution. The aqueous mixture was extracted with ethyl acetate (100 mL×2), and the combined organic extracts were washed with brine (100 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (5.0% ACN up to 48.0% in 1 min, up to 61.0% in 7 min); Detector, UV 254/220 nm. After purification 4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]-3-fluorobenzoic acid I-13 (89.6 mg, 58%) was obtained as a white solid. ¹H NMR (300 MHz, CD₃OD): δ 7.90-7.74 (m, 2H), 7.70-7.46 (m, 5H), 4.56 (d, J=2.2 Hz, 2H), 4.37 (s, 1H), 3.97 (d, J=6.6 Hz, 1H), 2.88 (d, J=1.9 Hz, 1H), 2.30 (dd, J=14.1, 7.3 Hz, 1H), 2.14 (d, J=10.0 Hz, 1H), 1.87 (td, J=9.4, 8.9, 4.7 Hz, 2H), 1.57 (d, J=13.5 Hz, 1H), 1.00 (dt, J=9.5, 3.2 Hz, 2H), 0.76-0.64 (m, 2H). MS (ES, m/z): [M+1]=530.

Example 19: 4-[(1S,3R,4S,5R)-5-{[4-cyclopropyl-1-(2,6-dichlorophenyl)-1H-pyrazol-5-yl]methoxy}-3-methyl-2-azabicyclo[2.2.1]heptan-2-yl]benzoic acid (I-14)
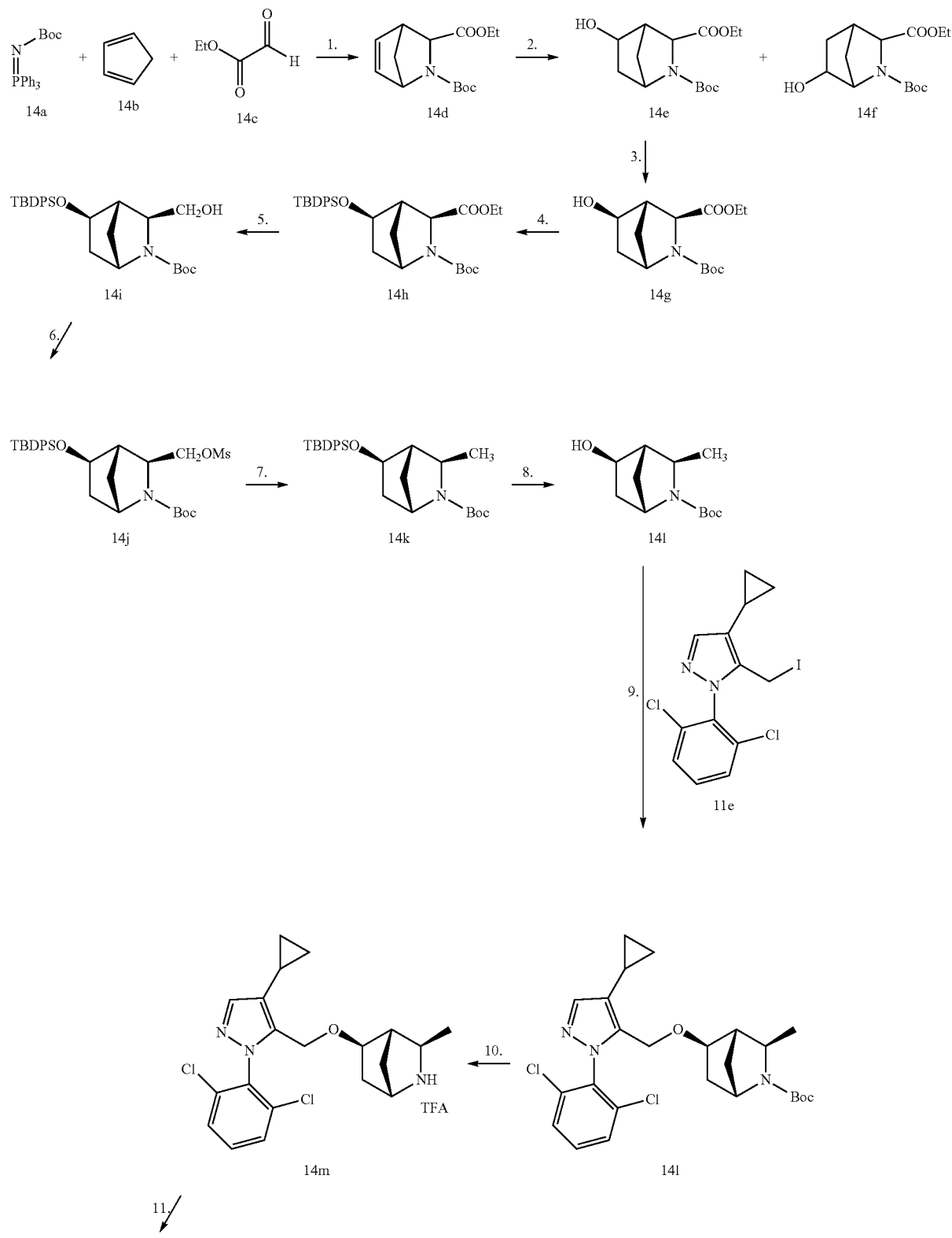

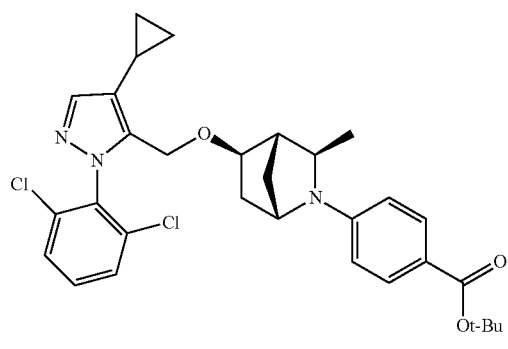 14n

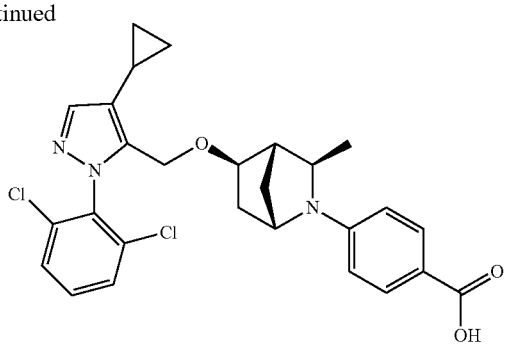 I-14

Step 1. Ethyl 2-oxoacetate 14c was predistilled at 120 to 130° C. Cyclopenta-1,3-diene 14b was freshly cracked at 175° C. To a 2000 mL round-bottom flask was added tert-butyl N-(triphenyl-[5]-phosphanylidene)carbamate 14a (56.6 g, 149.97 mmol, 1.00 equiv.), toluene (500 mL), cyclopenta-1,3-diene 14b (19.8 g, 299.54 mmol, 2.00 equiv.), and ethyl 2-oxoacetate 14c (30.6 g, 299.74 mmol, 2.00 equiv.). The resulting mixture was stirred at room temperature for 2 days and concentrated under vacuum. The residue was purified by Flash-Prep-HPLC using the following conditions (IntelFlash-1): Column, C18 silica gel; mobile phase, MeCN/H$_2$O=0:1 increasing to MeCN/H$_2$O=1:0 within 60 min; Detector, UV 220 nm. Removal of solvents afforded 2-tert-butyl 3-ethyl 2-azabicyclo[2.2.1]hept-5-ene-2,3-dicarboxylate 14d (32 g, 80%) as a light yellow oil.

Step 2. To a 2000 mL 3-necked round-bottom flask purged with and maintained under an inert atmosphere of nitrogen was added 2-tert-butyl 3-ethyl 2-azabicyclo[2.2.1]hept-5-ene-2,3-dicarboxylate 14d (26.7 g, 99.88 mmol, 1.00 equiv.) and tetrahydrofuran (400 mL, 1.00 equiv.). A 1M solution of BH$_3$ in THF (110 mL, 1.10 equiv.) was added dropwise with stirring at −78° C., and the mixture was stirred at this temperature for 15 min. The mixture was then allowed to warm to room temperature and stirred for 1 more hour. A 2M sodium hydroxide aqueous solution (175 mL, 3.50 equiv.) was added dropwise followed by the addition of a 30% H$_2$O$_2$ aqueous solution (50 mL, 5.00 equiv.) dropwise with stirring at 0° C. The resulting mixture was stirred for 30 min at room temperature. The mixture was cooled in an ice/water bath, carefully quenched by the addition of 100 mL of a sat. NaHCO$_3$ aqueous solution, and further diluted with 400 mL of brine. The aqueous mixture was extracted with ethyl acetate (300 mL×4). The combined organic extracts were washed with brine (400 mL×2), dried over anhydrous sodium sulfate and concentrated under vacuum. The crude product was purified by Flash-Prep-HPLC using the following conditions (High pressure IntelFlash-1,20 MPa): Column, C18 silica gel; mobile phase, MeCN/H$_2$O with 0.05% NH$_4$HCO$_3$=15%:85% increasing to MeCN/H$_2$O with 0.05% NH$_4$HCO$_3$=45%:55% within 30 min; Detector, UV 210 nm. Removal of solvents afforded 2-tert-butyl 3-ethyl 5-hydroxy-2-azabicyclo[2.2.1]heptane-2,3-dicarboxylate 14e (9.4g, 33%) as a light yellow oil.

Step 3. 2-tert-butyl 3-ethyl 5-hydroxy-2-azabicyclo[2.2.1]heptane-2,3-dicarboxylate 14e (5 g, 17.52 mmol, 1.00 equiv.) was resolved by Chiral HPLC using the following condition: Column, Chiralpak IC, 2*25 cm, 5 um; mobile phase, Hex- and ethanol- (hold 5.0% ethanol-in 13 min); Detector, UV 220/254 nm. After separation 2-tert-butyl 3-ethyl (1S,3S,4S,5R)-5-hydroxy-2-azabicyclo[2.2.1]heptane-2,3-dicarboxylate 14g (2 g, 40%) was obtained as a light yellow oil.

Step 4. To a 100 mL round-bottom flask was added 2-tert-butyl 3-ethyl (1S,3S,4S,5R)-5-hydroxy-2-azabicyclo[2.2.1]heptane-2,3-dicarboxylate 14g (2.2 g, 7.71 mmol, 1.00 equiv.), N,N-dimethylformamide (20 mL), imidazole (2.1 g, 4.00 equiv), and TBDPSCl (4.2 g, 2.00 equiv). The resulting mixture was stirred at 40° C. overnight. The mixture was diluted with 50 mL of brine, and extracted with ethyl acetate (250 mL×3). The combined organic extracts were washed with brine (250 mL×4), dried over anhydrous sodium sulfate, and concentrated under vacuum. The residue was purified by silica gel column chromatography eluting with ethyl acetate/petroleum ether (1:5) to give 2-tert-butyl 3-ethyl (1S,3S,4S,5R)-5-[(tert-butyldiphenylsilyl)oxy]-2-azabicyclo[2.2.1]heptane-2,3-dicarboxylate 14h (3.8g, 94%) as a light yellow solid.

Step 5. To a 250 mL round-bottom flask was added 2-tert-butyl 3-ethyl (1S,3S,4S,5R)-5-[(tert-butyldiphenylsilyl)oxy]-2-azabicyclo[2.2.1]heptane-2,3-dicarboxylate 14h (3.73 g, 7.12 mmol, 1.00 equiv.), tetrahydrofuran (26 mL), and LiBH$_4$ (389 mg, 2.00 equiv). The resulting mixture was stirred at room temperature overnight, diluted with 50 mL of EA, and then quenched by the addition of 100 mL of a saturated NH$_4$Cl aqueous solution. The aqueous mixture was extracted with ethyl acetate (200 mL×2). The combined organic extracts were washed with brine (250 mL×2), dried over anhydrous sodium sulfate, and concentrated under vacuum. The crude product was purified by Flash-Prep-HPLC using the following conditions: Column, silica gel; mobile phase, EA:PE increasing to EA:PE=15% within 15 min; Detector, UV 254 nm. Removal of solvents afforded tert-butyl (1S,3S,4S,5R)-5-[(tert-butyldiphenylsilyl)oxy]-3-(hydroxymethyl)-2-azabicyclo[2.2.1]heptane-2-carboxylate 14i (3.31 g, 96%) as a light yellow oil.

Step 6. To a 100 mL round-bottom flask was added tert-butyl (1S,3S,4S,5R)-5-[(tert-butyldiphenylsilyl)oxy]-3-(hydroxymethyl)-2-azabicyclo[2.2.1]heptane-2-carboxylate 14i (3.31 g, 6.87 mmol, 1.00 equiv.), tetrahydrofuran (42 mL), TEA (3.1 mL, 3.00 equiv.), and methanesulfonyl chloride (1.6 g, 13.97 mmol, 2.00 equiv.). The resulting mixture was stirred for 1 h at room temperature, and quenched with water. The aqueous mixture was extracted with ethyl acetate (200 mL×2), and the combined organic extracts were washed with brine (250 mL×3), dried over anhydrous sodium sulfate and concentrated under vacuum. The crude product was purified by Flash-Prep-HPLC using the following conditions: Column, silica gel; mobile phase, EA:PE increasing to EA:PE=50% within 30 min; Detector, UV 254 nm. Removal of solvents afforded tert-butyl (1S, 3S,4S,5R)-5-[(tert-butyldiphenylsi-lyl)oxy]-3-[(methanesulfonyloxy)methyl]-2-azabicyclo[2.2.1]heptane-2-carboxylate 14j (3.44 g, 89%) as a white foam.

Step 7. To a 100 mL round-bottom flask was added tert-butyl (1S,3S,4S,5R)-5-[(tert-butyldiphenylsilyl)oxy]-3-[(methanesulfonyloxy)methyl]-2-azabicyclo[2.2.1]heptane-2-carboxylate 14j (3.44 g, 6.15 mmol, 1.00 equiv.), tetrahydrofuran (28 mL), and LiBH$_4$ (1.1 g, 8.00 equiv.). The resulting mixture was heated at 60° C. overnight. After cooling to room temperature, the mixture was diluted with 100 mL of EA, and quenched with 150 mL of a sat. NH$_4$Cl aqueous solution. The aqueous mixture was extracted with ethyl acetate (150 mL×2), and the combined organic extracts were washed with brine (250 mL×2), dried over anhydrous sodium sulfate and concentrated under vacuum. The crude product was purified by Flash-Prep-HPLC with the following conditions: Column, silica gel; mobile phase, EA:PE increasing to EA:PE=10% within 10 min; Detector, UV 254 nm. Removal of solvents afforded tert-butyl (1S,3R,4S,5R)-5-[(tert-butyldiphenyl silyl)oxy]-3-methyl-2-azabicyclo[2.2.1]heptane-2-carboxylate 14k (2.39g, 84%) as a colorless oil.

Step 8. To a 100 mL round-bottom flask was added tert-butyl (1S,3R,4S,5R)-5-[(tert-butyldiphenylsilyl)oxy]-3-methyl-2-azabicyclo[2.2.1]heptane-2-carboxylate 14k (2.39 g, 5.13 mmol, 1.00 equiv.), tetrahydrofuran (14 mL), and TBAF (10.3 mL, 2.00 equiv.). The resulting mixture was stirred at room temperature overnight, and diluted with water. The aqueous mixture was extracted with ethyl acetate (200 mL×2); and the combined organic extracts were washed with brine (250 mL×3), dried over anhydrous sodium sulfate and concentrated under vacuum to give tert-butyl (1S,3R,4S,5R)-5-hydroxy-3-methyl-2-azabicyclo[2.2.1]heptane-2-carboxylate 14l (3.21 g, 99%) as a light yellow oil.

Step 9. To a 25 mL round-bottom flask was added 4-cyclopropyl-1-(2,6-dichlorophenyl)-5-(iodomethyl)-1H-pyrazole 11e (500 mg, 1.27 mmol, 1.50 equiv.), tert-butyl (1S,3R,4S,5R)-5-hydroxy-3-methyl-2-azabicyclo[2.2.1]heptane-2-carboxylate 14l (600 mg, 0.95 mmol, 1.00 equiv.), N,N-dimethylformamide (1.5 mL), and sodium hydride (69 mg, 60% dispersion in mineral oil, 1.73 mmol, 2.00 equiv). The resulting mixture was stirred at room temperature overnight. The aqueous mixture was diluted with EA (100 mL), and quenched with water. The aqueous mixture was extracted with ethyl acetate (100 mL×2). The combined organic extracts were washed with brine (150 mL×2), dried over anhydrous sodium sulfate and concentrated under vacuum. The residue was purified by silica gel column chromatography eluting with ethyl acetate/petroleum ether (1:3) to afford tert-butyl (1S,3R,4S,5R)-5-[[4-cyclopropyl-1-(2,6-dichlorophenyl)-1H-pyrazol-5-yl]methoxy]-3-methyl-2-azabicyclo[2.2.1]heptane-2-carboxylate 14m (250 mg, 53%) as a yellow oil.

Step 10. To a 50 mL round-bottom flask was added tert-butyl (1S,3R,4S,5R)-5-[[4-cyclopropyl-1-(2,6-dichlorophenyl)-1H-pyrazol-5-yl]methoxy]-3-methyl-2-azabicyclo[2.2.1]heptane-2-carboxylate 14m (550 mg, 0.67 mmol, 1.00 equiv.), dichloromethane (11 mL), and trifluoroacetic acid (5.5 mL). The resulting mixture was stirred at room temperature for 1 h and concentrated under vacuum. The crude product was purified by Flash-Prep-HPLC using the following conditions (IntelFlash-1): Column, silica gel; mobile phase, EA:PE increasing to EA:PE=100 within 5 min; Detector, UV 254 nm. Removal of solvents afforded (1S,3R,4S,5R)-5-[[4-cyclopropyl-1-(2,6-dichlorophenyl)-1H-pyrazol-5-yl]methoxy]-3-methyl-2-azabicyclo[2.2.1]heptane 14n (100 mg, 29%), a trifluoroacetic acid salt, as a light yellow oil.

Step 11. To a 5 mL sealed tube was added (1S,3R,4S,5R)-5-[[4-cyclopropyl-1-(2,6-dichlorophenyl)-1H-pyrazol-5-yl]methoxy]-3-methyl-2-azabicyclo[2.2.1]heptane, trifluoroacetic acid salt, 14n (70 mg, 0.14 mmol, 1.00 equiv.), tert-butyl 4-bromobenzoate (54 mg, 0.21 mmol, 1.50 equiv.), Ruphos precatalyst (24 mg, 0.20 equiv.), Ruphos (13 mg, 0.20 equiv.), Cs$_2$CO$_3$ (136 mg, 0.42 mmol, 3.00 equiv), and tol (1 mL). The resulting mixture was heated at 110° C. overnight. After cooling to room temperature, water was added, the mixture was extracted with ethyl acetate (100 mL×2). The combined organic extracts were washed with brine (150 mL×2), dried over anhydrous sodium sulfate and concentrated under vacuum. The residue was purified by silica gel column chromatography eluting with ethyl acetate/petroleum ether (1:1) to provide tert-butyl 4-[(1S,3R,4S,5R)-5-[[4-cyclopropyl-1-(2,6-dichlorophenyl)-1H-pyrazol-5-yl]methoxy]-3-methyl-2-azabicyclo[2.2.1]heptan-2-yl]benzoate 14o (40 mg, 51%) as a light yellow oil.

Step 12. To a 25 mL round-bottom flask was added tert-butyl 4-[(1S,3R,4S,5R)-5-[[4-cyclopropyl-1-(2,6-dichlorophenyl)-1H-pyrazol-5-yl]methoxy]-3-methyl-2-azabicyclo[2.2.1]heptan-2-yl]benzoate 14o (40 mg, 0.07 mmol, 1.00 equiv.), dichloromethane (1 mL), and trifluoroacetic acid (0.5 mL). The resulting mixture was stirred for 1 h at room temperature and quenched with a saturated sodium bicarbonate aqueous solution. The aqueous mixture was extracted with ethyl acetate (100 mL×2), and the combined organic extracts were washed with brine (150 mL×3), dried over anhydrous sodium sulfate and concentrated under vacuum. The crude product was purified by Prep-HPLC using the following conditions: Column, XBridge Shield RP18 OBD Column 5 um, 19*150 mm; mobile phase, Water (0.05% TFA) and ACN (52.0% ACN up to 70.0% in 8 min); Detector, UV 254/220 nm. After purification 4-[(1S,3R,4S,5R)-5-[[4-cyclopropyl-1-(2,6-dichlorophenyl)-1H-pyrazol-5-yl]methoxy]-3-methyl-2-azabicyclo[2.2.1]heptan-2-yl] benzoic acid I-14 (21 mg, 58%) was obtained as a white solid. $^1$H NMR (300 MHz, CD$_3$OD): δ 7.81 (d, J=8.9 Hz, 2H), 7.68-7.32 (m, 4H), 6.59 (d, J=8.9 Hz, 2H), 4.48 (d, J=1.3 Hz, 2H), 3.97 (s, 1H), 3.29 (s, 1H), 3.06 (t, J=6.2 Hz, 1H), 2.19 (d, J=4.3 Hz, 1H), 1.81 (dd, J=9.1, 3.8 Hz, 2H), 1.66-1.53 (m, 2H), 1.33-1.17 (m, 4H), 0.93 (dd, J=8.5, 4.7 Hz, 2H), 0.63 (p, J=4.8 Hz, 2H). MS (ES, m/z): [M+1] =512.14.

Example 20: 4-[(1S,3R,4S,5R)-5-{[4-cyclopropyl-1-(2,6-dichlorophenyl)-1H-pyrazol-5-yl]methoxy}-3-methyl-2-azabicyclo[2.2.1]heptan-2-yl]-2-fluorobenzoic acid (I-15)

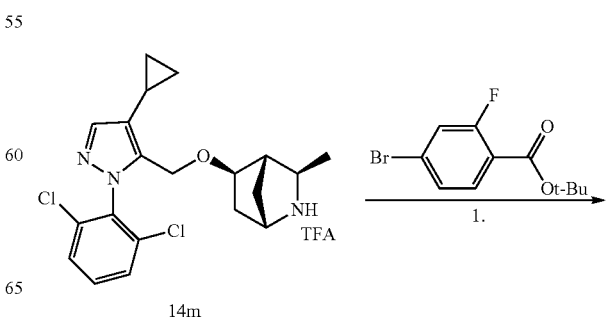

14m

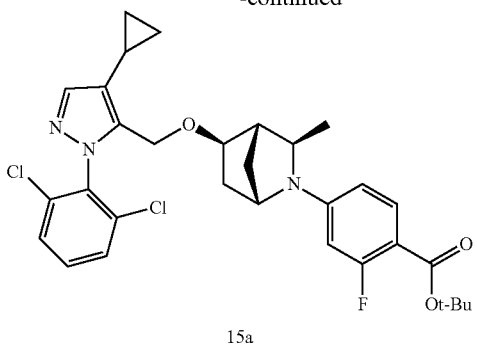

15a

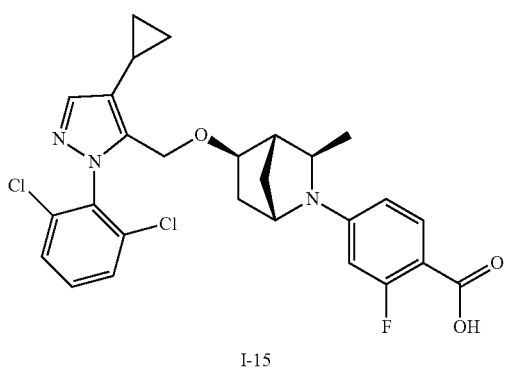

I-15

Step 1. To an 8 mL sealed tube was added tert-butyl 4-bromo-2-fluorobenzoate (156 mg, 0.57 mmol, 1.50 equiv.), (1S,3R,4S,5R)-5-[[4-cyclopropyl-1-(2,6-dichlorophenyl)-1H-pyrazol-5-yl]methoxy]-3-methyl-2-azabicyclo[2.2.1]heptane, trifluoroacetic acid salt 14m (150 mg, 0.30 mmol, 1.00 equiv.), Ruphos precatalyst (63 mg, 0.20 equiv.), Ruphos (36 mg, 0.20 equiv.), Cs$_2$CO$_3$ (367 mg, 1.13 mmol, 3.00 equiv.), and toluene (2.5 mL). The resulting mixture was heated at 110° C. overnight. After cooling to room temperature, water was added, the aqueous mixture was extracted with ethyl acetate (150 mL×2), and the combined organic extracts were washed with brine (200 mL×2), dried over anhydrous sodium sulfate and concentrated under vacuum. The residue was purified by silica gel column chromatography eluting with ethyl acetate/petroleum ether (1:1) to give tert-butyl 4-[(1S,3R,4S,5R)-5-[[4-cyclopropyl-1-(2,6-dichlorophenyl)-1H-pyrazol-5-yl]methoxy]-3-methyl-2-azabicyclo[2.2.1]heptan-2-yl]-2-fluorobenzoate 15a (130 mg, 75%) as a light yellow oil.

Step 2. To a 25 mL round-bottom flask was added tert-butyl 4-[(1S,3R,4S,5R)-5-[[4-cyclopropyl-1-(2,6-dichlorophenyl)-1H-pyrazol-5-yl]methoxy]-3-methyl-2-azabicyclo[2.2.1]heptan-2-yl]-2-fluorobenzoate 15a (130 mg, 0.22 mmol, 1.00 equiv.), dichloromethane (3 mL), and trifluoroacetic acid (1.5 mL). The resulting mixture was stirred at room temperature for 1 h and quenched with the addition of a saturated sodium bicarbonate aqueous solution. The aqueous mixture was extracted with ethyl acetate (100 mL×2). The combined organic extracts were washed with brine (100 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (52.0% ACN up to 70.0% in 8 min); Detector, UV 254/220 nm. After purification 4-[(1S,3R,4S,5R)-5-[[4-cyclopropyl-1-(2,6-dichlorophenyl)-1H-pyrazol-5-yl]methoxy]-3-methyl-2-azabicyclo[2.2.1]heptan-2-yl]-2-fluorobenzoic acid I-15 (25.2 mg, 21%) was obtained as a light red solid. $^1$H NMR (300 MHz, CD$_3$OD): δ 7.74 (t, J=8.8 Hz, 1H), 7.66-7.49 (m, 3H), 7.44 (s, 1H), 6.41 (d, J=10.0 Hz, 1H), 6.28 (d, J=14.7 Hz, 1H), 4.49 (s, 2H), 3.95 (s, 1H), 3.08 (d, J=6.5 Hz, 1H), 2.21 (s, 1H), 1.88-1.77 (m, 2H), 1.55 (dd, J=30.3, 8.9 Hz, 2H), 1.35-1.16 (m, 4H), 0.99-0.88 (m, 2H), 0.69-0.59 (m, 2H). MS (ES, m/z): [M+1]=530.13.

Example 21: 4-[(1S,3R,4S,5R)-5-{[4-cyclopropyl-1-(2,6-dichlorophenyl)-1H-pyrazol-5-yl]methoxy}-3-ethyl-2-azabicyclo[2.2.1]heptan-2-yl]benzoic acid (I-16) and 4-[(1R,3S,4R,5S)-5-{[4-cyclopropyl-1-(2,6-dichlorophenyl)-1H-pyrazol-5-yl]methoxy}-3-ethyl-2-azabicyclo[2.2.1]heptan-2-yl]benzoic acid (I-17)

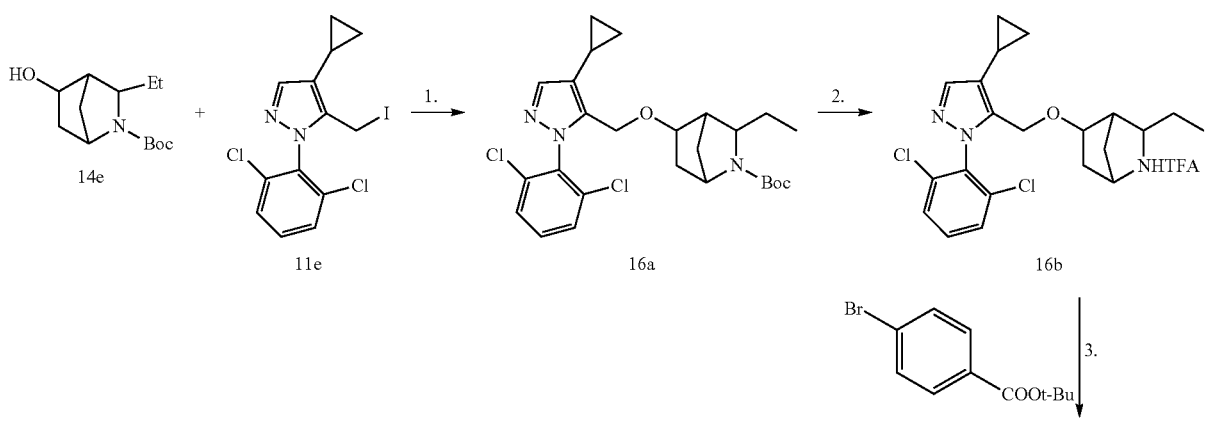

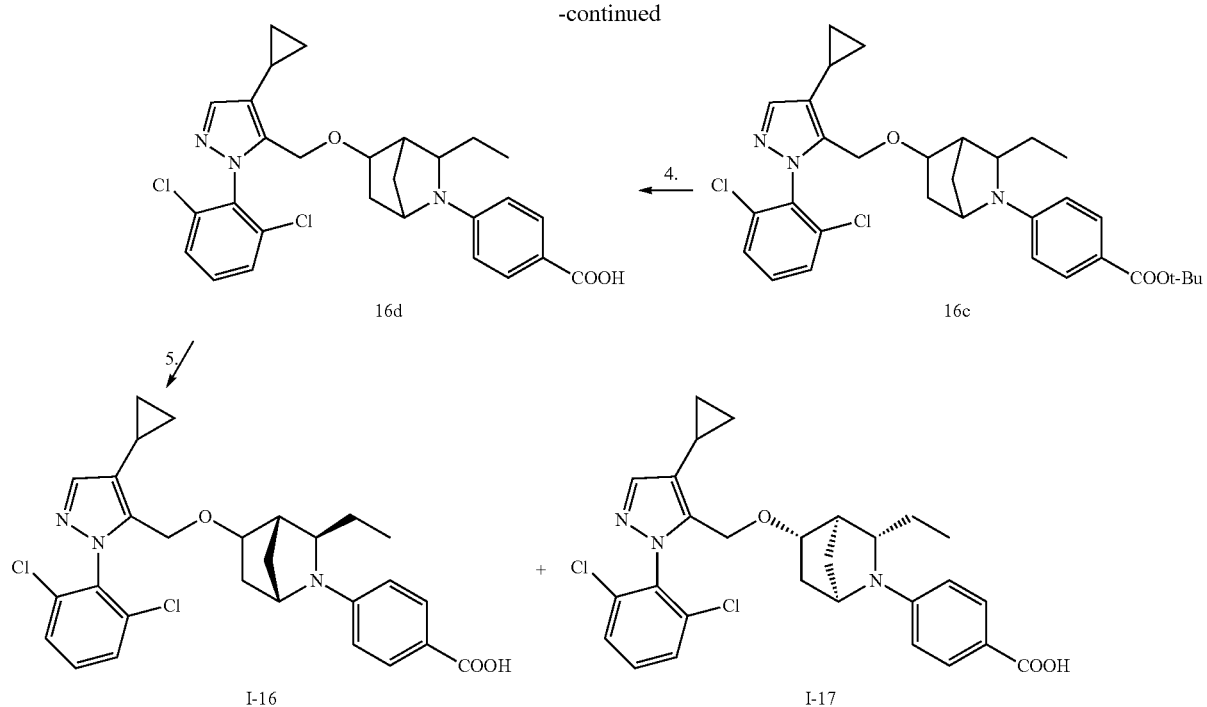

Step 1. To a 50 mL round-bottom flask purged and maintained under an inert atmosphere of nitrogen was added tert-butyl 3-ethyl-5-hydroxy-2-azabicyclo[2.2.1]heptane-2-carboxylate 14e (185 mg, 0.77 mmol, 1.00 equiv.), 4-cyclopropyl-1-(2,6-dichlorophenyl)-5-(iodomethyl)-1H-pyrazole11e (600 mg, 1.53 mmol, 2.00 equiv.), N,N-dimethylformamide (4 mL), and sodium hydride (70 mg, 60% dispersion in mineral oil, 1.67 mmol, 2.00 equiv.). The resulting mixture was stirred at room temperature for 4 h. The mixture was diluted with EA (20 mL), then quenched by the addition of water (10 mL), and extracted with ethyl acetate (100 mL×2). The combined organic extracts were washed with brine (50 mL×4), dried over anhydrous sodium sulfate and concentrated under vacuum. The residue was purified by silica gel column chromatography eluting with ethyl acetate/petroleum ether (1/3) to give tert-butyl 5-[[4-cyclopropyl-1-(2,6-dichlorophenyl)-1H-pyrazol-5-yl]methoxy]-3-ethyl-2-azabicyclo[2.2.1]heptane-2-carboxylate 16a (200 mg, 52%) as a light yellow oil.

Step 2. To a 100 mL round-bottom flask was added tert-butyl 5-[[4-cyclopropyl-1-(2,6-dichlorophenyl)-1H-pyrazol-5-yl]methoxy]-3-ethyl-2-azabicyclo[2.2.1]heptane-2-carboxylate 16a (200 mg, 0.39 mmol, 1.00 equiv.), dichloromethane (2 mL), and trifluoroacetic acid (1 mL). The resulting mixture was stirred for 1 h at room temperature and concentrated under vacuum. The residue was purified by silica gel column chromatography eluting with dichloromethane/methanol (10/1) to afford 5-[[4-cyclopropyl-1-(2,6-dichlorophenyl)-1H-pyrazol-5-yl]methoxy]-3-ethyl-2-azabicyclo[2.2.1]heptane 16b (160 mg, 81%) as a light yellow oil.

Step 3. To a 25 mL round-bottom flask purged and maintained under an inert atmosphere of nitrogen was added 5-[[4-cyclopropyl-1-(2,6-dichlorophenyl)-1H-pyrazol-5-yl]methoxy]-3-ethyl-2-azabicyclo[2.2.1]heptane 16b (120 mg, 0.30 mmol, 1.00 equiv.), tert-butyl 4-bromobenzoate (118 mg, 0.46 mmol, 1.50 equiv), Ruphos (27 mg, 0.06 mmol, 0.20 equiv), Cs₂CO₃ (287 mg, 0.88 mmol, 3.00 equiv.), toluene (2.5 mL), and Ruphos-precatalyst (50 mg, 0.06 mmol, 0.20 equiv.). The resulting mixture was heated at 110° C. overnight and concentrated under vacuum. The residue was purified by silica gel column chromatography eluting with ethyl acetate/petroleum ether (1/3) to afford tert-butyl 4-(5-[[4-cyclopropyl-1-(2,6-dichlorophenyl)-1H-pyrazol-5-yl]methoxy]-3-ethyl-2-azabicyclo[2.2.1]heptan-2-yl)benzoate 16c (130 mg, 76%) as a light yellow oil.

Step 4. To a 25 mL round-bottom flask was added tert-butyl 4-(5-[[4-cyclopropyl-1-(2,6-dichlorophenyl)-1H-pyrazol-5-yl]methoxy]-3-ethyl-2-azabicyclo[2.2.1]heptan-2-yl)benzoate 16c (130 mg, 0.22 mmol, 1.00 equiv.), dichloromethane (1 mL), and trifluoroacetic acid (0.5 mL). The resulting mixture was stirred at room temperature for 1 h and concentrated under vacuum. The crude product was purified by Flash-Prep-HPLC using the following conditions (IntelFlash-1): Column, C18 silica gel; mobile phase, ACN/H2O=5% increasing to ACN/H2O=65% within 30 min; Detector, UV 254 nm. Removal of solvents afforded 4-(5-[[4-cyclopropyl-1-(2,6-dichlorophenyl)-1H-pyrazol-5-yl]methoxy]-3-ethyl-2-azabicyclo[2.2.1]heptan-2-yl)benzoic acid 16d (70 mg, 60%) as a light yellow solid.

Step 5. The racemic mixture of acids 16d was separated by Chiral-Prep-HPLC using the following conditions (Prep-HPLC-004): Column, CHIRALPAK IC, 2*25 cm, 5 um; mobile phase, Hex (0.1% FA)- and ethanol- (hold 20.0% ethanol-in 16 min); Detector, UV 220/254 nm. After separation, 4-[(1S,3R,4S,5R)-5-[[4-cyclopropyl-1-(2,6-dichlorophenyl)-1H-pyrazol-5-yl]methoxy]-3-ethyl-2-azabicyclo[2.2.1]heptan-2-yl]benzoic acid I-16 (21.0 mg, 30%) was obtained as a light yellow solid, having the longer retention time on chiral HPLC, and also obtained was 4-[(1R,3S,4R,5S)-5-[[4-cyclopropyl-1-(2,6-dichlorophenyl)-1H-pyrazol-5-yl]methoxy]-3-ethyl-2-azabicyclo[2.2.1]heptan-2-yl]benzoic acid I-17 (18.9 mg, 27%) as a light yellow solid with shorter retention time on chiral HPLC.

I-16: [α]_D=+37.7° (CHCl₃, 26.6° C.); retention time in Chiral HPLC=3.494 min; ¹H NMR (300 MHz, CDCl₃): δ 7.97-7.87 (m, 2H), 7.53-7.34 (m, 4H), 6.48 (d, J=8.9 Hz, 2H), 5.32 (s, 1H), 4.50-4.34 (m, 2H), 3.88 (s, 1H), 3.32 (d, J=6.3 Hz, 1H), 2.71 (d, J=9.5 Hz, 1H), 2.35 (d, J=4.2 Hz, 1H), 1.75 (tt, J=9.3, 5.7 Hz, 3H), 1.62-1.37 (m, 2H), 1.37-1.19 (m, 3H), 1.03-0.80 (m, 5H), 0.73-0.58 (m, 2H). MS (ES, m/z): [M+1]=526.20.

I-17: [α]_D=−54.8° (CHCl₃, 26.4° C.); retention time in Chiral HPLC=2.892 min; ¹H NMR (300 MHz, CDCl₃): δ 7.97-7.87 (m, 2H), 7.53-7.34 (m, 4H), 6.48 (d, J=8.9 Hz, 2H), 5.32 (s, 1H), 4.50-4.34 (m, 2H), 3.88 (s, 1H), 3.32 (d, J=6.3 Hz, 1H), 2.71 (d, J=9.5 Hz, 1H), 2.35 (d, J=4.2 Hz, 1H), 1.75 (tt, J=9.3, 5.7 Hz, 3H), 1.62-1.37 (m, 2H), 1.37-1.19 (m, 3H), 1.03-0.80 (m, 5H), 0.73-0.58 (m, 2H). MS (ES, m/z): [M+1]=526.20.

Example 22: 4-[(1S,3R,4S,5R)-5-{[4-cyclopropyl-1-(2,6-dichlorophenyl)-1H-pyrazol-5-yl]methoxy}-3-ethyl-2-azabicyclo[2.2.1]heptan-2-yl]-2-fluorobenzoic acid (I-18) and 4-[(1R,3S,4R,5S)-5-{[4-cyclopropyl-1-(2,6-dichlorophenyl)-1H-pyrazol-5-yl]methoxy}-3-ethyl-2-azabicyclo[2.2.1]heptan-2-yl]-2-fluorobenzoic acid (I-19)

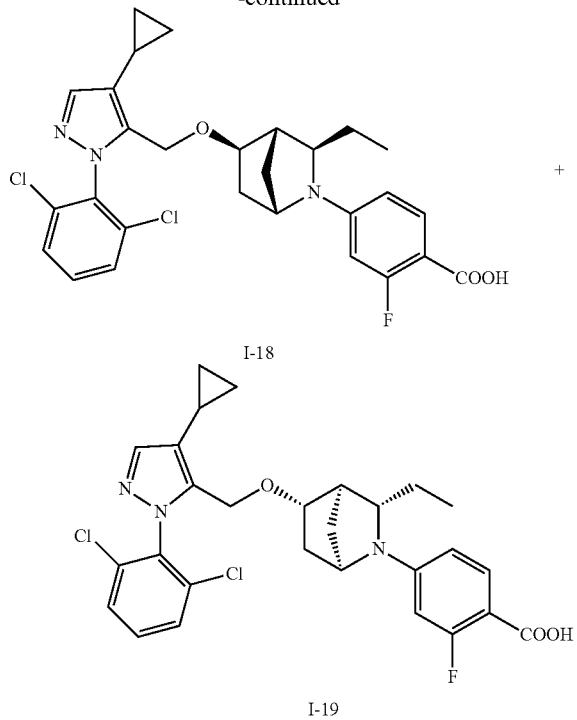

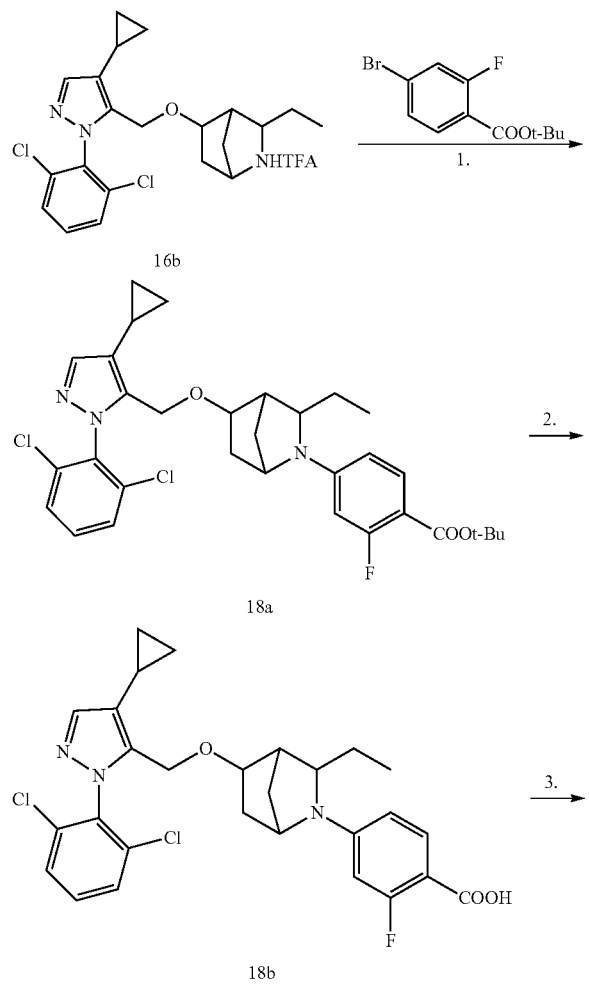

Step 1. To a 50 mL round-bottom flask was added Cs₂CO₃ (480 mg, 1.47 mmol, 3.00 equiv.), toluene (4 mL), tert-butyl 4-bromo-2-fluorobenzoate (162 mg, 0.59 mmol, 1.20 equiv.), 5-[[4-cyclopropyl-1-(2,6-dichlorophenyl)-1H-pyrazol-5-yl]methoxy]-3-ethyl-2-azabicyclo[2.2.1]heptane trifluoro acid acid salt 16b (200 mg, 0.49 mmol, 1.00 equiv.), Ruphos (82.3 mg, 0.20 equiv.), and Rupos preacatalyst (46 mg, 0.20 equiv.). The resulting mixture was heated at 110° C. overnight. After cooling to room temperature, the mixture was diluted with H₂O (50 mL), extracted with ethyl acetate (100 mL×2), and the combined organic extracts were washed with brine, dried over anhydrous sodium sulfate, and concentrated under vacuum. The residue was purified by silica gel column chromatography eluting with ethyl acetate/hexane (1/3) to afford tert-butyl 4-(5-[[4-cyclopropyl-1-(2,6-dichlorophenyl)-1H-pyrazol-5-yl]methoxy]-3-ethyl-2-azabicyclo[2.2.1]heptan-2-yl)-2-fluorobenzoate 18a (180 mg, 61%) as a yellow oil.

Step 2. To a 50 mL round-bottom flask was added tert-butyl 4-(5-[[4-cyclopropyl-1-(2,6-dichlorophenyl)-1H-pyrazol-5-yl]methoxy]-3-ethyl-2-azabicyclo[2.2.1]heptan-2-yl)-2-fluorobenzoate 18a (180 mg, 0.30 mmol, 1.00 equiv.), trifluoroacetic acid (2 mL), and dichloromethane (4 mL). The resulting mixture was stirred at room temperature for 1 h. The mixture was diluted with H₂O (50 mL), extracted with ethyl acetate (100 mL×2), and the combined organic extracts were washed with brine, dried over anhydrous sodium sulfate and concentrated under vacuum. The residue was purified by silica gel column chromatography eluting with ethyl acetate/hexane (1:1) to provide 4-(5-[[4-cyclopropyl-1-(2,6-dichlorophenyl)-1H-pyrazol-5-yl]methoxy]-3-ethyl-2-azabicyclo[2.2.1]heptan-2-yl)-2-fluorobenzoic acid 18b (150 mg, 92%) as a yellow oil.

Step 3. The racemic acid mixture 18b was separated by Chiral-Prep-HPLC using the following conditions: Column, CHIRALPAK IE, 2*25 cm, 5 um; mobile phase, Hex:DCM=5:1(0.1% TFA)- and ethanol-(hold 50.0% ethanol-in 20 min); Detector, UV 220/254 nm. After separation, 4-[(1S, 3R,4S,5R)-5-[[4-cyclopropyl-1-(2,6-dichlorophenyl)-1H-pyrazol-5-yl]methoxy]-3-ethyl-2-azabicyclo[2.2.1]heptan-2-yl]-2-fluorobenzoic acid I-18 (20.6 mg, 14%) was obtained as a yellow oil, with shorter retention time on chiral HPLC, also obtained was 4-[(1S,3R,4S,5R)-5-[[4-cyclopropyl-1-(2,6-dichlorophenyl)-1H-pyrazol-5-yl]methoxy]-3-ethyl-2-azabicyclo[2.2.1]heptan-2-yl]-2-fluorobenzoic acid I-19 (20.6 mg, 14%), with longer retention time on chiral HPLC, as a yellow oil.

I-18: d (+), $[\alpha]_D$=+51.47° (CHCl$_3$, 26.1° C.); $^1$H NMR (300 MHz, CD$_3$OD): δ 7.74 (t, J=8.8 Hz, 1H), 7.66-7.45 (m, 3H), 7.43 (s, 1H), 6.36 (dd, J=8.9, 2.3 Hz, 1H), 6.23 (d, J=14.6 Hz, 1H), 4.47 (d, J=1.3 Hz, 2H), 3.92 (s, 1H), 3.33-3.24 (m, 1H), 2.74 (dd, J=10.6, 2.6 Hz, 1H), 2.38 (d, J=4.3 Hz, 1H), 1.88-1.68 (m, 3H), 1.72-1.63 (m, OH), 1.56 (ddd, J=13.3, 7.0, 2.2 Hz, 1H), 1.47 (d, J=10.4 Hz, 1H), 1.41-1.13 (m, 2H), 1.12-1.00 (m, OH), 1.03-0.82 (m, 5H), 0.73-0.53 (m, 2H). MS (ES, m/z): [M+1]=544.

I-19: l (−), $[\alpha]_D$=−49.2° (CHCl$_3$, 26.3° C.); $^1$H NMR (400 MHz, CD$_3$OD): δ 7.73 (t, J=8.8 Hz, 1H), 7.59 (ddd, J=8.3, 5.3, 1.6 Hz, 2H), 7.57-7.48 (m, 1H), 7.43 (s, 1H), 6.35 (dd, J=8.9, 2.3 Hz, 1H), 6.22 (d, J=14.4 Hz, 1H), 4.46 (d, J=2.2 Hz, 2H), 3.92 (s, 1H), 3.32-3.25 (m, 1H), 2.73 (dd, J=10.6, 2.6 Hz, 1H), 2.37 (d, J=4.3 Hz, 1H), 1.86-1.64 (m, 3H), 1.55 (ddd, J=13.4, 7.0, 2.4 Hz, 1H), 1.47 (d, J=10.4 Hz, 1H), 1.29 (dqd, J=17.5, 7.5, 3.6 Hz, 2H), 1.17 (d, J=6.1 Hz, OH), 1.01-0.83 (m, 5H), 0.62 (dddd, J=12.6, 11.5, 6.6, 2.9 Hz, 2H). MS (ES, m/z): [M+1]=544.

Example 23: 4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-N-(oxane-4-sulfonyl)benzamide (I-20)

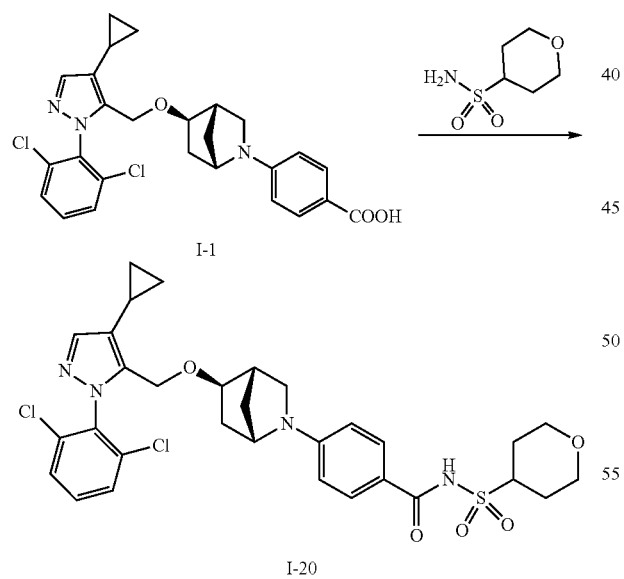

mixture was stirred at room temperature overnight. The mixture was diluted with EA (20 mL), and quenched with 20 mL of water. The aqueous mixture was extracted with ethyl acetate (100 mL), and the organic extract was washed with a 1M hydrogen chloride aqueous solution (20 mL×2) followed by brine (20 mL×2). The organic layer was dried over anhydrous sodium sulfate and concentrated under vacuum. The residue was dissolved in 3 mL of DMF and purified by Prep-HPLC using the following conditions: Column, XBridge Shield RP18 OBD Column, 5 um, 19*150 mm; mobile phase, Water (0.05% TFA) and ACN (48.0% ACN up to 56.0% in 10 min); Detector, uv 254 nm. After purification 4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-N-(oxane-4-sulfonyl)benzamide I-20 (49.1 mg, 30%) was obtained as a yellow solid. $^1$H NMR (400 MHz, CD$_3$OD): δ 7.78-7.71 (m, 2H), 7.66-7.50 (m, 3H), 7.46 (s, 1H), 6.58-6.50 (m, 2H), 4.53-4.41 (m, 2H), 4.21 (d, J=2.2 Hz, 1H), 4.07 (ddd, J=11.9, 4.7, 2.0 Hz, 2H), 3.95 (tt, J=11.6, 4.3 Hz, 1H), 3.56-3.34 (m, 5H), 2.64 (d, J=9.6 Hz, 1H), 2.55 (d, J=3.7 Hz, 1H), 2.08-1.75 (m, 6H), 1.61 (q, J=9.8 Hz, 2H), 1.32 (dt, J=12.8, 2.9 Hz, 2H), 1.02-0.88 (m, 2H), 0.66 (qd, J=4.7, 1.8 Hz, 2H). MS (ES, m/z): [M+1]=645.20.

Example 24: 4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-N-[(2,2-dimethyloxan-4-yl)sulfonyl]benzamide (I-21)

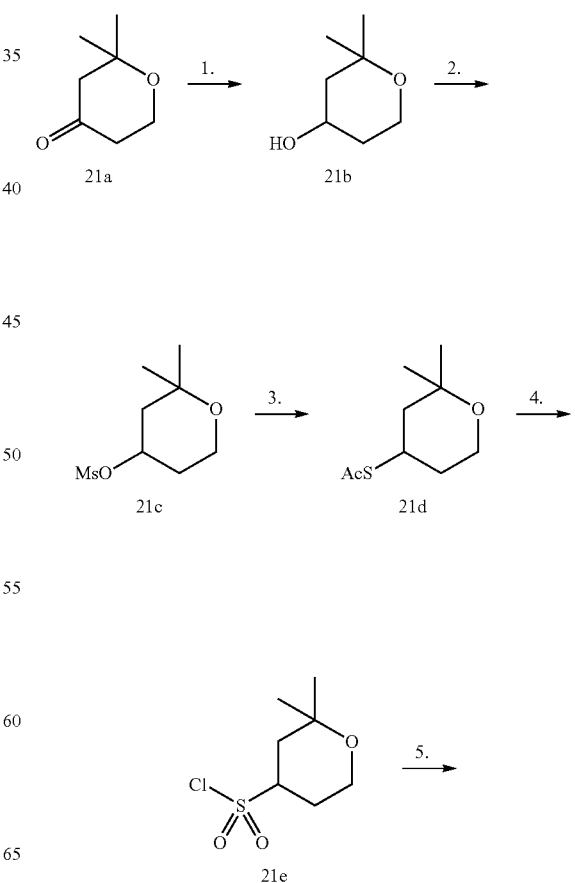

To a 3 mL round-bottom flask was added 4-[(1S,4S,5R)-5-[[4-cyclopropyl-1-(2,6-dichlorophenyl)-1H-pyrazol-5-yl]methoxy]-2-azabicyclo[2.2.1]heptan-2-yl]benzoic acid I-1 (125 mg, 0.25 mmol, 1.00 equiv.), dichloromethane (3 mL), 4-dimethylaminopyridine (92 mg, 0.75 mmol, 3.00 equiv.), EDCI (73 mg, 0.38 mmol, 1.50 equiv.), oxane-4-sulfonamide (124 mg, 0.75 mmol, 2.00 equiv.). The resulting

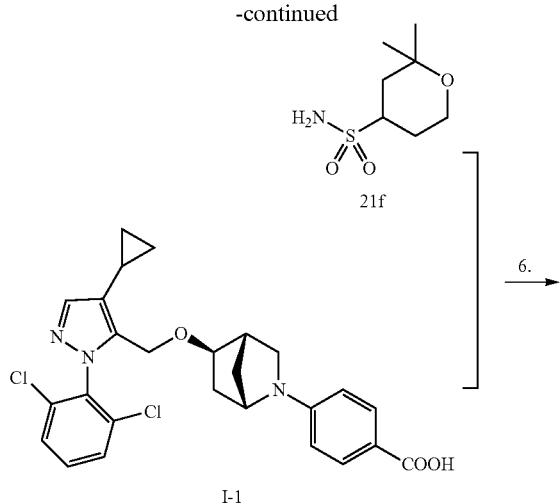

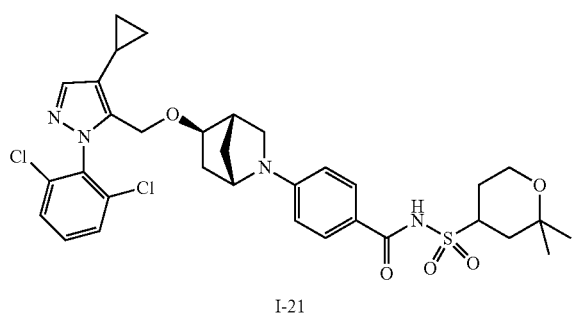

Step 1. To a 500 mL round-bottom flask was added 2,2-dimethyloxan-4-one 21a (10 g, 78.02 mmol, 1.00 equiv.) and methanol (100 mL). NaBH$_4$ (5.9 g, 155.96 mmol, 2.00 equiv.) was added in several batches at 0° C. The resulting mixture was stirred at room temperature for 3 h, then diluted with 200 mL of EA, washed with brine (100 mL×2), dried over anhydrous sodium sulfate, and concentrated under vacuum. The residue was purified by silica gel column chromatography eluting with ethyl acetate in petroleum ether (0% to 100%) to give 2,2-dimethyloxan-4-ol 21b (9 g, 89%) as a light yellow oil.

Step 2. To a 500 mL round-bottom flask purged with and maintained under an inert atmosphere of nitrogen was added a solution of 2,2-dimethyloxan-4-ol 21b (9 g, 69.13 mmol, 1.00 equiv.) in dichloromethane (200 mL) followed by TEA (7.69 g, 76.00 mmol, 1.10 equiv.). The mixture was cooled to 0° C., MSCl (8.68 g, 76.14 mmol, 1.10 equiv.) was added dropwise with stirring. The resulting mixture was stirred at room temperature for 2 h. The mixture was diluted with DCM (200 mL), washed with brine (100 mL×2), dried over anhydrous sodium sulfate, and concentrated under vacuum. The residue was purified by silica gel column chromatography eluting with ethyl acetate in petroleum ether (0% to 30%) to give 2,2-dimethyloxan-4-yl methanesulfonate 21c (14g, 97%) as a white solid.

Step 3. To a 250 mL round-bottom flask purged with and maintained under an inert atmosphere of nitrogen was added 2,2-dimethyloxan-4-yl methanesulfonate 21c (2 g, 9.60 mmol, 1.00 equiv.), N,N-dimethylformamide (50 mL), and AcSK (3.4 g, 3.00 equiv.). The resulting mixture was heated at 80° C. for 2 h. After cooling to room temperature, the mixture was diluted with EA (200 mL), washed with brine (50 mL×5), dried over anhydrous sodium sulfate, and concentrated under vacuum. The residue was purified by silica gel column chromatography eluting with ethyl acetate/petroleum ether (1/5) to afford 1-[(2,2-dimethyloxan-4-yl)sulfanyl]ethan-1-one 21d (1 g, 55%) as a red crude oil.

Step 4. To a 250 mL round-bottom flask was added a solution of NCS (2.8 g, 20.97 mmol, 4.00 equiv.) in MeCN (21 mL) followed by the addition of a 12M hydrogen chloride solution (5.3 mL, 63.6 mmol, 12.0 eq.). The mixture was cooled at 0° C. for 10 min, a solution of 1-[(2,2-dimethyloxan-4-yl)sulfanyl]ethan-1-one 21d (1 g, 5.31 mmol, 1.00 equiv.) in MeCN (5.3 mL) was added dropwise with stirring. The resulting mixture was stirred for 10 min at 0° C., and diluted with EA (200 mL). The organic mixture was washed with brine (50 mL×3), dried over anhydrous sodium sulfate and concentrated under vacuum. The residue was purified by silica gel column chromatography eluting with ethyl acetate/petroleum ether (5/1) to afford 2,2-dimethyloxane-4-sulfonyl chloride 21e (600 mg, 53%) as a crude red solid.

Step 5. To a 100 mL round-bottom flask was added 2,2-dimethyloxane-4-sulfonyl chloride 21e (700 mg, 3.29 mmol, 1.00 equiv.) and a saturated solution of NH$_3$ in tetrahydrofuran (20 mL). The resulting mixture was stirred at 0° C. for 2h and concentrated under vacuum. The residue was diluted with 30 mL of ether. The precipitated solids were filtered out. The filtrate was concentrated under vacuum to give 2,2-dimethyloxane-4-sulfonamide 21f (530 mg, 83%) as a light yellow crude solid, which was used in the next step without further purification.

Step 6. To a 25 mL round-bottom flask was added 4-[(1S,4S,5R)-5-[[4-cyclopropyl-1-(2,6-dichlorophenyl)-1H-pyrazol-5-yl]methoxy]-2-azabicyclo[2.2.1]heptan-2-yl] benzoic acid I-1 (100 mg, 0.20 mmol, 1.00 equiv.), 2,2-dimethyloxane-4-sulfonamide 21f (58 mg, 0.30 mmol, 1.50 equiv), 4-dimethylaminopyridine (73 mg, 0.60 mmol, 3.00 equiv), dichloromethane (2 mL), EDCI (58 mg, 0.30 mmol, 1.50 equiv.). The resulting mixture was stirred at room temperature overnight. The mixture was diluted with 150 mL of EA, and then treated with a 10% aqueous hydrogen chloride solution until pH value of the mixture reaching 6. The mixture was washed with brine (50 mL×3), dried over anhydrous sodium sulfate, and concentrated under vacuum. The crude product was purified by Prep-HPLC using the following conditions: Column, XBridge Shield RP18 OBD Column, 5 um, 19*150 mm; mobile phase, Water (0.05% TFA) and ACN (5.0% ACN up to 56.0% in 1 min, up to 70.0% in 7 min); Detector, uv 254 nm. 50.1 mg product was obtained. After purification 4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-N-(2,2-dimethyloxane-4-sulfonyl)benzamide I-21 (50.1 mg, 37%) was obtained as an off-white solid. $^1$H NMR (300 MHz, DMSO-d6): δ 11.44 (s, 1H), 7.79-7.62 (m, 4H), 7.64-7.52 (m, 1H), 7.41 (s, 1H), 6.50 (d, J=8.7 Hz, 2H), 4.36 (s, 2H), 4.21 (s, 1H), 3.97 (d, J=12.5 Hz, 2H), 3.77-3.66 (m, 1H), 3.59 (t, J=11.6 Hz, 1H), 3.44 (d, J=6.3 Hz, 1H), 3.31 (dd, J=9.6, 4.0 Hz, 1H), 2.55 (s, 1H), 1.88-1.72 (m, 3H), 1.77-1.57 (m, 1H), 1.62-1.37 (m, 3H), 1.16 (d, J=15.4 Hz, 7H), 0.93-0.83 (m, 2H), 0.65-0.54 (m, 2H). MS (ES, m/z): [M+1]=673.30.

Example 25: Synthesis of I-22 to I-24

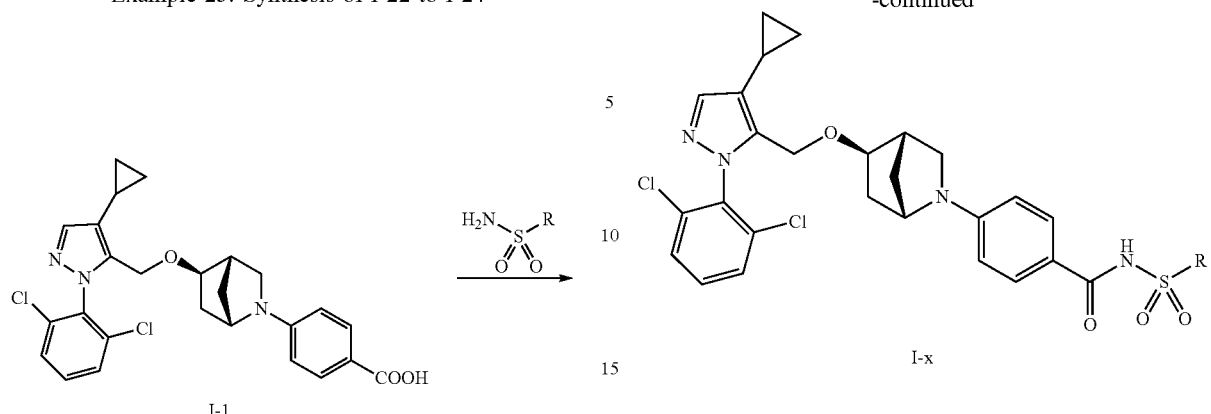

Acyl-sulfonamides I-22 to I-24 were prepared from acid I-1 and the corresponding sulfonamide $RSO_2NH_2$ following the procedure described in Preparative Example 23. The data for compounds I-22 to I-24 is summarized in Table 1.

TABLE 1

| $RSO_2NH_2$ | Cmpd Structure | Cmpd No. | MS/$^1$H NMR |
|---|---|---|---|
| ![H2N-SO2-cyclopropyl] | ![structure I-22] | I-22 | MS (ES, m/z): [M + 1] = 601.14.<br>$^1$H NMR (300 MHz, CD$_3$OD) δ: 7.75 (d, J = 8.9 Hz, 2H), 7.68-7.50 (m, 3H), 7.47 (s, 1H), 6.56 (d, J = 8.8 Hz, 2H), 4.48 (d, J = 2.1 Hz, 2H), 4.22 (s, 1H), 3.53 (d, J = 6.5 Hz, 1H), 3.41 (dd, J = 9.6, 4.1 Hz, 2H), 3.23-3.10 (m, 1H), 2.64 (d, J = 9.6 Hz, 1H), 2.57 (s, 1H), 1.95-1.74 (m, 2H), 1.62 (q, J = 10.0 Hz, 2H), 1.39-1.24 (m, 3H), 1.19-1.06 (m, 2H), 1.03-0.91 (m, 2H), 0.67 (dt, J = 6.0, 3.0 Hz, 2H). |
| ![H2N-SO2-tetrahydrofuran] | ![structure I-23] | I-23 | MS (ES, m/z): [M + 1] = 631.2.<br>$^1$H NMR (400 MHz, CD$_3$OD) δ: 7.74 (d, J = 8.9 Hz, 2H), 7.66-7.50 (m, 3H), 7.46 (s, 1H), 6.55 (d, J = 8.9 Hz, 2H), 4.61-4.41 (m, 3H), 4.28-4.19 (m, 2H), 4.09-3.93 (m, 2H), 3.82 (q, J = 7.2 Hz, 1H), 3.53 (d, J = 6.6 Hz, 1H), 3.40 (dd, J = 9.5, 4.0 Hz, 1H), 2.64 (d, J = 9.6 Hz, 1H), 2.55 (s, 1H), 2.50-2.26 (m, 2H), 1.92-1.75 (m, 2H), 1.68-1.55 (m, 2H), 1.33 (d, J = 13.5 Hz, 1H), 1.01-0.92 (m, 2H), 0.71-0.62 (m, 2H). |

TABLE 1-continued

| RSO₂NH₂ | Cmpd Structure | Cmpd No. | MS/¹H NMR |
|---|---|---|---|
| (structure) | (structure) | I-24 | MS (ES, m/z): [M + 1] = 645. ¹H NMR (400 MHz, CD₃OD) δ: 7.75 (d, J = 9.0 Hz, 2H), 7.61 (ddd, J = 9.3, 7.9, 1.7 Hz, 2H), 7.59-7.50 (m, 1H), 7.46 (s, 1H), 6.55 (d, J = 8.9 Hz, 2H), 4.54-4.41 (m, 2H), 4.21 (s, 1H), 4.01 (dd, J = 8.7, 7.2 Hz, 1H), 3.87 (td, J = 8.4, 4.8 Hz, 1H), 3.82-3.67 (m, 2H), 3.66-3.49 (m, 3H), 3.40 (dd, J = 9.5, 4.1 Hz, 1H), 2.74 (dq, J = 14.8, 7.4 Hz, 1H), 2.68-2.60 (m, 1H), 2.56 (s, 1H), 2.24 (dtd, J = 12.5, 7.7, 4.8 Hz, 1H), 1.92-1.71 (m, 3H), 1.68-1.55 (m, 2H), 1.33 (d, J = 13.3 Hz, 1H), 0.96 (dtd, J = 9.1, 4.5, 4.1, 2.2 Hz, 2H), 0.66 (qd, J = 4.7, 1.9 Hz, 2H). |

Example 26: Synthesis of I-25 to I-28

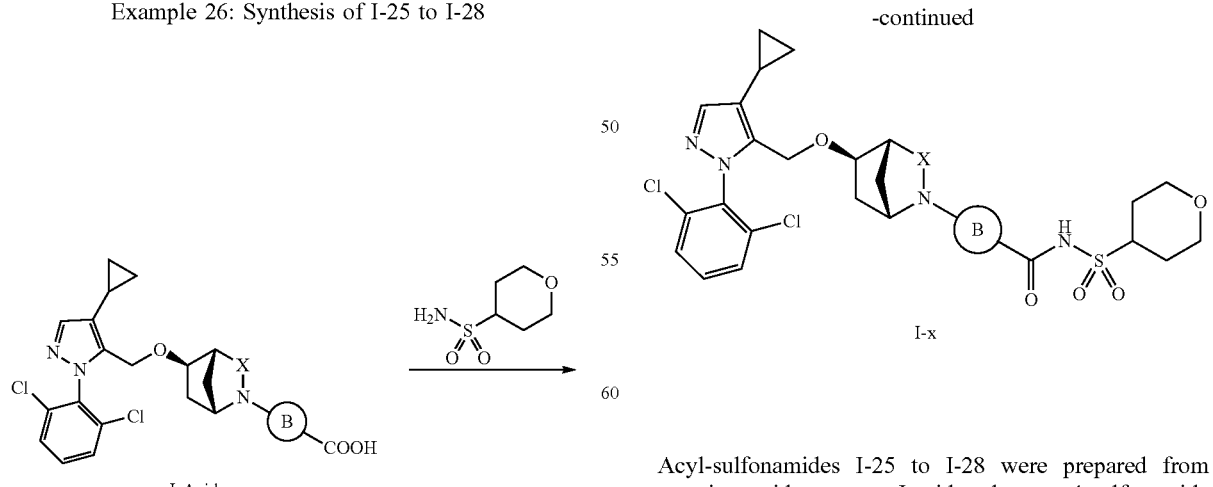

Acyl-sulfonamides I-25 to I-28 were prepared from appropriate acid precursor I-acid and oxane-4-sulfonamide following the procedure described in Preparative Example 23. The data for compounds I-25 to I-28 is summarized in Table 2.

TABLE 2

| I-Acid | Cmpd Structure | Cmpd No. | MS/¹H NMR |
|---|---|---|---|
| I-5 | | I-25 | MS (ES, m/z): [M + 1] = 646.16. ¹H NMR (300 MHz, CD$_3$OD) δ: 7.98-7.89 (m, 2H), 7.69-7.50 (m, 3H), 7.47 (s, 1H), 6.99 (dd, J = 8.9, 2.8 Hz, 1H), 4.49 (d, J = 2.1 Hz, 2H), 4.31 (s, 1H), 4.13-4.01 (m, 2H), 3.95-3.79 (m, 1H), 3.57 (d, J = 6.2 Hz, 1H), 3.45 (td, J = 11.2, 2.6 Hz, 3H), 2.72 (d, J = 9.7 Hz, 1H), 2.61 (s, 1H), 2.08-1.75 (m, 6H), 1.65 (q, J = 10.0 Hz, 2H), 1.37 (d, J = 13.5 Hz, 1H), 0.97 (dt, J = 8.6, 3.1 Hz, 2H), 0.67 (dt, J = 6.1, 3.1 Hz, 2H). |
| I-11 | | I-26 | MS (ES, m/z): [M + 1] = 659. ¹H NMR (300 MHz, CD$_3$OD) δ: 7.97-7.86 (m, 2H), 7.70-7.50 (m, 5H), 7.47 (s, 1H), 4.65-4.46 (m, 3H), 4.07 (d, J = 11.2 Hz, 2H), 4.03-3.83 (m, 2H), 3.46 (td, J = 11.4, 2.7 Hz, 2H), 2.88 (s, 1H), 2.20 (dd, J = 15.4, 7.2 Hz, 1H), 2.00-1.83 (m, 7H), 1.83 (q, J = 5.3 Hz, 2H), 1.63 (d, J = 13.4 Hz, 1H), 0.99 (dd, J = 8.5, 2.3 Hz, 2H), 0.67 (dd, J = 5.0, 1.9 Hz, 2H). |
| I-12 | | I-27 | MS (ES, m/z): [M + 1] = 677. ¹H NMR (300 MHz, CD$_3$OD) δ: 7.78-7.50 (m, 5H), 7.47 (s, 1H), 7.37 (dd, J = 8.6, 2.1 Hz, 1H), 4.65-4.45 (m, 3H), 4.08 (dd, J = 12.0, 3.7 Hz, 2H), 4.00-3.82 (m, 2H), 3.47 (td, J = 11.7, 2.5 Hz, 2H), 2.89 (s, 1H), 2.23-2.10 (m, 1H), 2.09-1.77 (m, 7H), 1.62 (d, J = 13.5 Hz, 1H), 1.05-0.91 (m, 2H), 0.67 (qd, J = 4.6, 1.6 Hz, 2H). |
| I-15 | | I-28 | MS (ES, m/z): [M + 1] = 677.17 ¹H NMR (400 MHz, CD$_3$OD) δ: 7.80-7.49 (m, 4H), 7.44 (s, 1H), 6.46 (dd, J = 8.9, 2.3 Hz, 1H), 6.31 (dd, J = 15.0, 2.3 Hz, 1H), 4.47 (s, 2H), 4.13-4.03 (m, 2H), 3.99-3.87 (m, 2H), 3.47 (td, J = 11.7, 2.3 Hz, 2H), 3.29 (d, J = 6.4 Hz, 1H), 3.09 (q, J = 6.3 Hz, 1H), 2.21 (d, J = 4.2 Hz, 1H), 2.07-1.96 (m, 2H), 1.96-1.86 (m, 2H), 1.85-1.75 (m, 2H), 1.66-1.55 (m, 1H), 1.49 (d, J = 10.4 Hz, 1H), 1.33-1.22 (m, 1H), 1.19 (d, J = 6.2 Hz, 3H), 0.93 (dddd, J = 8.5, 6.6, 5.0, 3.3 Hz, 2H), 0.71-0.56 (m, 2H). |

Example 27: N-(cyclopropanesulfonyl)-4-[(1S,3R,4S,5R)-5-{[4-cyclopropyl-1-(2,6-dichlorophenyl)-1H-pyrazol-5-yl]methoxy}-3-methyl-2-azabicyclo[2.2.1]heptan-2-yl]-2-fluorobenzamide (I-29)

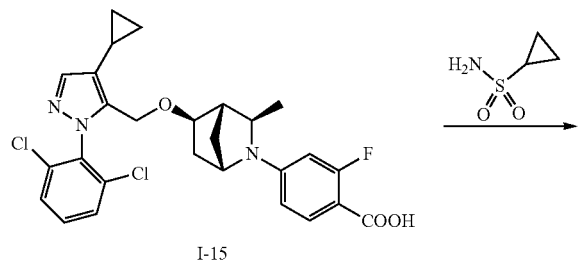

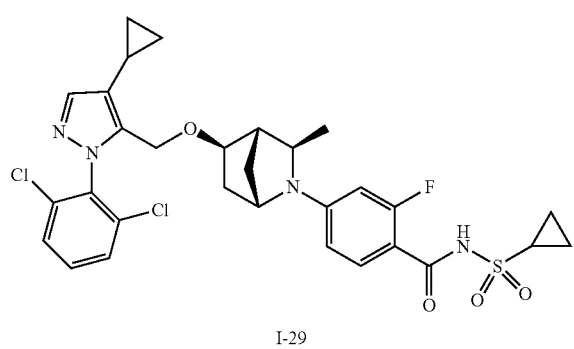

To a 25 mL round-bottom flask was added 4-[(1S,3R,4S,5R)-[[4-cyclopropyl-1-(2,6-dichlorophenyl)-1H-pyrazol-5-yl]methoxy]-3-methyl-2-azabicyclo[2.2.1]heptan-2-yl]-2-fluorobenzoic acid I-15 (65 mg, 0.12 mmol, 1.00 equiv.), cyclopropanesulfonamide (30 mg, 0.25 mmol, 2.00 equiv.), EDCI (36 mg, 0.19 mmol, 1.50 equiv.), 4-dimethylaminopyridine (45 mg, 0.37 mmol, 3.00 equiv.), and dichloromethane (1.5 mL). The resulting mixture was stirred at room temperature overnight. The resulting solution diluted with ethyl acetate (10 mL) and quenched with water (10 mL). The aqueous mixture was extracted with ethyl acetate (50 mL). The organic extract was washed with brine (50 mL), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (5.0% ACN up to 60.0% in 1 min, up to 72.0% in 7 min); Detector, UV 254/220 nm. After purification N-(cyclopropanesulfonyl)-4-[(1S,3R,4S,5R)-5-[[4-cyclopropyl-1-(2,6-dichlorophenyl)-1H-pyrazol-5-yl]methoxy]-3-methyl-2-azabicyclo[2.2.1]heptan-2-yl]-2-fluorobenzamide I-29 (26.2 mg, 34%) was obtained as a white solid. $^1$H NMR (300 MHz, CD$_3$OD): δ 7.68-7.49 (m, 4H), 7.45 (s, 1H), 6.48 (dd, J=8.9, 2.3 Hz, 1H), 6.32 (dd, J=15.1, 2.3 Hz, 1H), 4.49 (s, 2H), 3.98 (s, 1H), 3.30 (s, 1H), 3.22-3.04 (m, 2H), 2.22 (s, 1H), 1.94-1.75 (m, 2H), 1.62 (dd, J=13.8, 6.3 Hz, 1H), 1.50 (d, J=10.2 Hz, 1H), 1.34-1.11 (m, 8H), 1.04-0.86 (m, 2H), 0.65 (hept, J=4.8 Hz, 2H). MS (ES, m/z): [M+1]=633.14.

Example 28: 2-[(1S,4S,5R)-5-{[4-cyclopropyl-1-(2,6-dichlorophenyl)-1H-pyrazol-5-yl]methoxy}-2-azabicyclo[2.2.1]heptan-2-yl]-4-fluoro-1,3-benzothiazole-6-carboxylic acid (I-30)

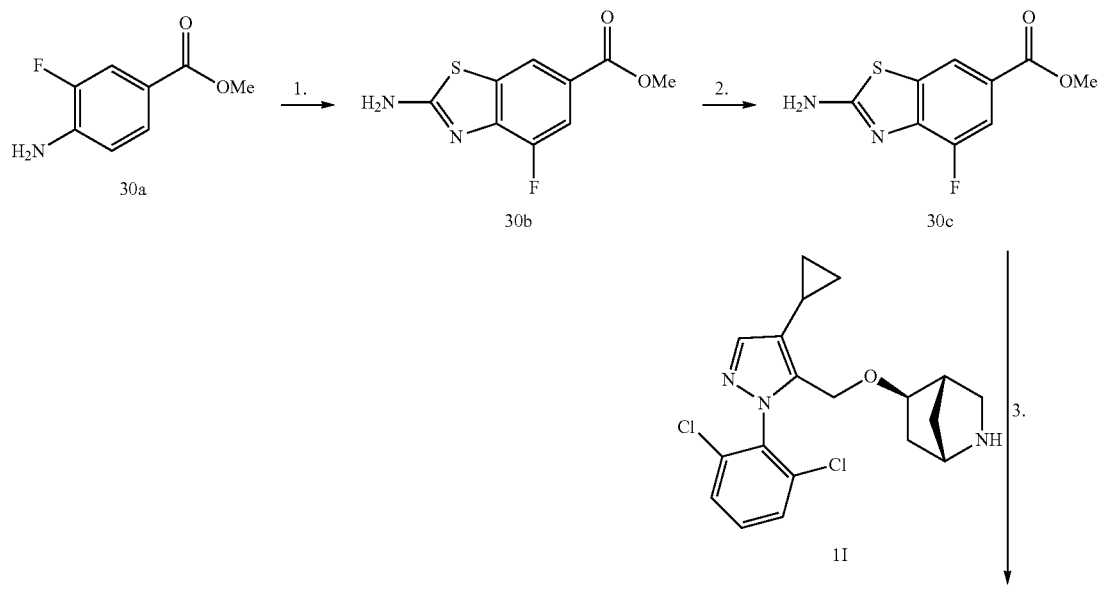

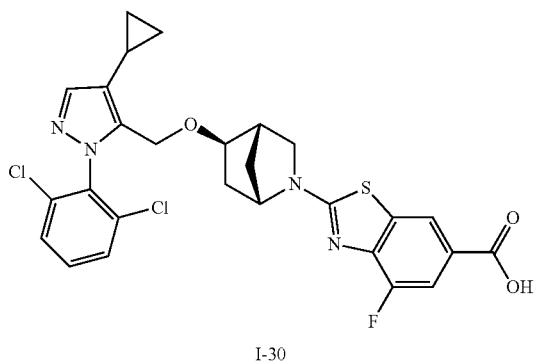

I-30

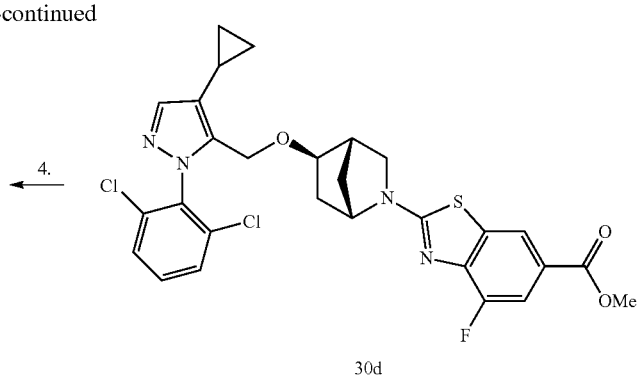

30d

Step 1. To a 1 L round-bottom flask was added methyl 4-amino-3-fluorobenzoate 30a (20 g, 118.24 mmol, 1.0 equiv.), AcOH (400 mL), and NaSCN (38.34 g, 473.33 mmol, 4.0 equiv.). The mixture was cooled at 0° C., and bromine (18.7 g, 117.01 mmol, 1.0 equiv) was added dropwise with stirring. The reaction mixture was stirred at 0° C. for 2 hours, then at 30° C. for 3 days. 400 mL of water was added, the pH value of the solution was adjusted to 9 using sodium hydroxide. Solids were collected by filtration and dried in an oven under reduced pressure, to give 28 g (crude) of methyl 2-amino-4-fluoro-1,3-benzothiazole-6-carboxylate 30b as a yellow solid. The crude product was carried onto the next step without further purification.

Step 2. To a 250 mL round-bottom flask was added CuBr$_2$ (2.96 g, 1.50 equiv.) and MeCN (100 mL). The resulting mixture was cooled at 0° C., and t-BuONO (2.4 mL) was added dropwise followed by the batchwise addition of ethyl 2-amino-4-fluoro-1,3-benzothiazole-6-carboxylate 30b (2 g, 8.84 mmol, 1.0 equiv.) at 0° C. The reaction mixture was stirred overnight at 30° C. and then concentrated under reduced pressure. The crude product was purified by Flash-Prep-HPLC, using the following conditions: Column, silica gel; mobile phase, eluting with PE:EA, 100:0 to 90:10 over 10 min; Detector, UV 254 nm, to afford 507.9 mg (20%) of methyl 2-bromo-4-fluoro-1,3-benzothiazole-6-carboxylate 30c as a light yellow solid. $^1$H NMR (300 MHz, DMSO-d$_6$) δ: 8.67 (d, J=1.4 Hz, 1H), 7.84 (dt, J=11.1, 1.2 Hz, 1H), 3.92 (s, 3H). MS (ES, m/z): [M+1]=290.

Step 3. To a 50 mL round-bottom flask was added (1S,4S,5R)-5-[[4-cyclopropyl-1-(2,6-dichlorophenyl)-1H-pyrazol-5-yl]methoxy]-2-azabicyclo[2.2.1]heptane 11 (80 mg, 0.21 mmol, 1.00 equiv.), DMA (2 mL), methyl 2-bromo-4-fluoro-1,3-benzothiazole-6-carboxylate 30c (74 mg, 0.26 mmol, 1.00 equiv.), and Cs$_2$CO$_3$ (205 mg, 0.63 mmol, 2.00 equiv.). The resulting mixture was heated at 60° C. overnight. After cooling to room temperature, water was added, the mixture was extracted with ethyl acetate (100 mL×2), and the combined organic extracts were washed with brine (50 mL×2), dried over anhydrous sodium sulfate and concentrated under vacuum. The residue was purified by silica gel column chromatography eluting with ethyl acetate/petroleum ether (1:5) to give methyl 2-[(1S,4S,5R)-5-[[4-cyclopropyl-1-(2,6-dichlorophenyl)-1H-pyrazol-5-yl]methoxy]-2-azabicyclo[2.2.1]heptan-2-yl]-4-fluoro-1,3-benzothiazole-6-carboxylate 30d (100 mg, 80%) as an off-white solid.

Step 4. To a 50 mL round-bottom flask was added methyl 2-[(1S,4S,5R)-5-[[4-cyclopropyl-1-(2,6-dichlorophenyl)-1H-pyrazol-5-yl]methoxy]-2-azabicyclo[2.2.1]heptan-2-yl]-4-fluoro-1,3-benzothiazole-6-carboxylate 30d (100 mg, 0.17 mmol, 1.00 equiv.), methanol (1.5 mL), LiOH (68 mg, 2.84 mmol, 10.00 equiv.), and water (0.2 mL). The resulting mixture was stirred at 35° C. overnight, diluted with 10 mL of ethyl acetate, and added with a 1M HCl aqueous solution to adjust the pH value to 6. The aqueous mixture was extracted with ethyl acetate (100 mL×2), and the combined organic extracts were washed with brine (30 mL×2), dried over anhydrous sodium sulfate and concentrated under vacuum. The crude product was purified by Prep-HPLC with the following conditions: Column, XBridge Prep OBD C18 Column, 19*250 mm, 5 um; mobile phase, Water (0.05% TFA) and ACN (53.0% ACN up to 73.0% in 8 min); Detector, UV 220 nm. After purification 2-[(1S,4S,5R)-5-[[4-cyclopropyl-1-(2,6-dichlorophenyl)-1H-pyrazol-5-yl]methoxy]-2-azabicyclo[2.2.1]heptan-2-yl]-4-fluoro-1,3-benzothiazole-6-carboxylic acid I-30 (44.4 mg, 45%) was obtained as an off-white solid. $^1$H NMR (400 MHz, CD$_3$OD): δ 8.15 (d, J=1.5 Hz, 1H), 7.69 (dd, J=11.5, 1.5 Hz, 1H), 7.63 (ddd, J=8.2, 6.1, 1.6 Hz, 2H), 7.60-7.51 (m, 1H), 7.47 (s, 1H), 4.57-4.30 (m, 2H), 3.68 (dd, J=6.9, 2.4 Hz, 1H), 3.54 (dd, J=10.0, 4.0 Hz, 1H), 3.06 (s, 1H), 2.69-2.63 (m, 1H), 2.06 (q, J=7.8, 7.2 Hz, 1H), 1.83 (tt, J=8.5, 5.1 Hz, 1H), 1.71 (s, 2H), 1.42 (d, J=13.6 Hz, 1H), 1.02-0.89 (m, 2H), 0.68 (td, J=5.8, 4.0 Hz, 2H)). MS (ES, m/z): [M+1]=573.

Example 29: 4-cyclopropoxy-2-[(1S,4S,5R)-5-{[4-cyclopropyl-1-(2,6-dichlorophenyl)-1H-pyrazol-5-yl]methoxy}-2-azabicyclo[2.2.1]heptan-2-yl]-1,3-benzothiazole-6-carboxylic acid (I-31)

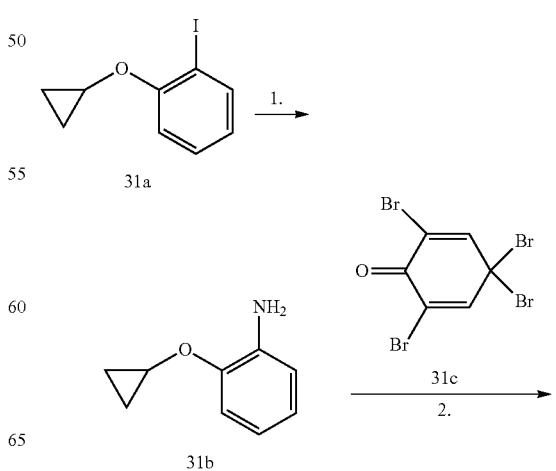

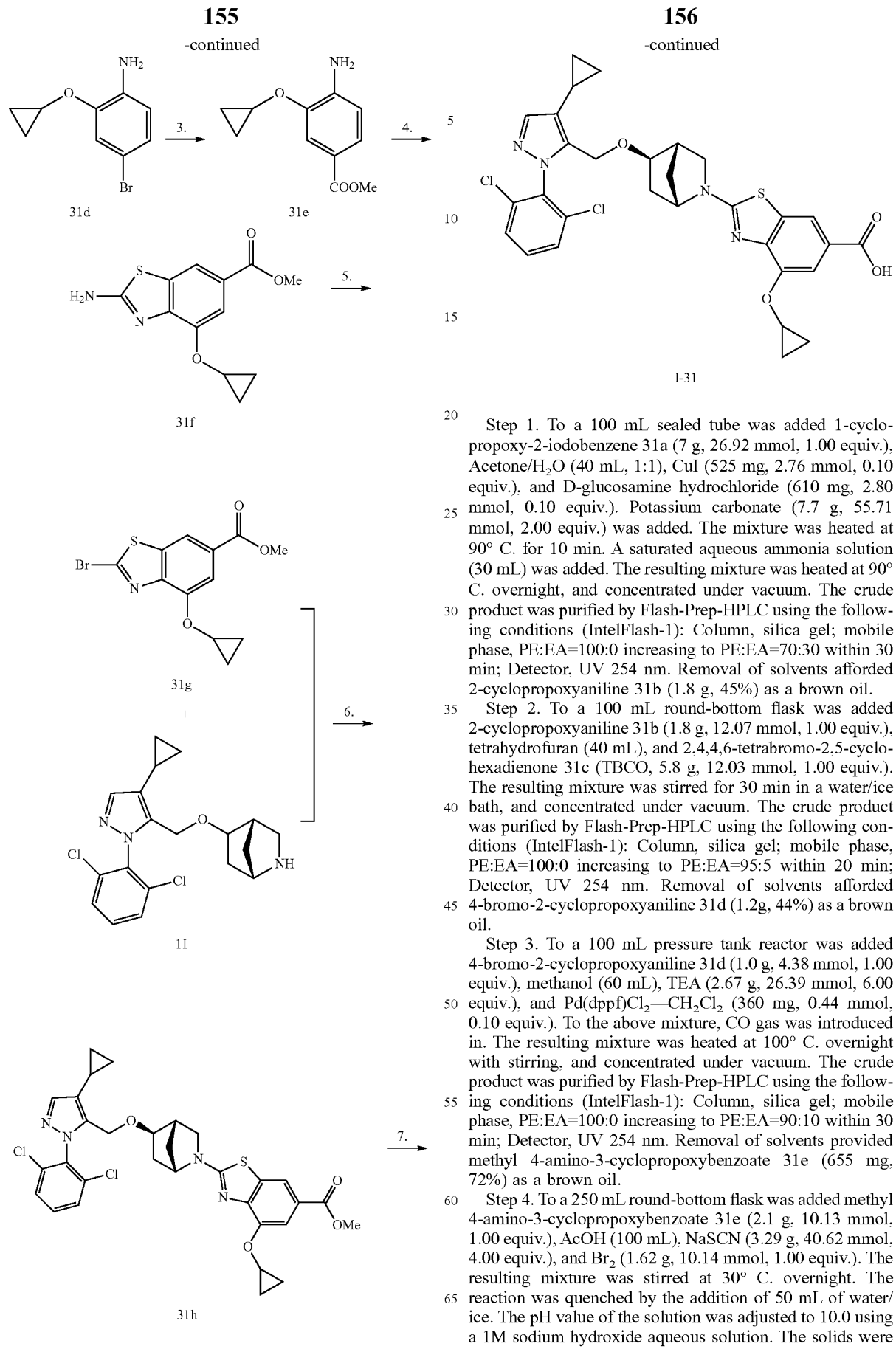

Step 1. To a 100 mL sealed tube was added 1-cyclopropoxy-2-iodobenzene 31a (7 g, 26.92 mmol, 1.00 equiv.), Acetone/H$_2$O (40 mL, 1:1), CuI (525 mg, 2.76 mmol, 0.10 equiv.), and D-glucosamine hydrochloride (610 mg, 2.80 mmol, 0.10 equiv.). Potassium carbonate (7.7 g, 55.71 mmol, 2.00 equiv.) was added. The mixture was heated at 90° C. for 10 min. A saturated aqueous ammonia solution (30 mL) was added. The resulting mixture was heated at 90° C. overnight, and concentrated under vacuum. The crude product was purified by Flash-Prep-HPLC using the following conditions (IntelFlash-1): Column, silica gel; mobile phase, PE:EA=100:0 increasing to PE:EA=70:30 within 30 min; Detector, UV 254 nm. Removal of solvents afforded 2-cyclopropoxyaniline 31b (1.8 g, 45%) as a brown oil.

Step 2. To a 100 mL round-bottom flask was added 2-cyclopropoxyaniline 31b (1.8 g, 12.07 mmol, 1.00 equiv.), tetrahydrofuran (40 mL), and 2,4,4,6-tetrabromo-2,5-cyclohexadienone 31c (TBCO, 5.8 g, 12.03 mmol, 1.00 equiv.). The resulting mixture was stirred for 30 min in a water/ice bath, and concentrated under vacuum. The crude product was purified by Flash-Prep-HPLC using the following conditions (IntelFlash-1): Column, silica gel; mobile phase, PE:EA=100:0 increasing to PE:EA=95:5 within 20 min; Detector, UV 254 nm. Removal of solvents afforded 4-bromo-2-cyclopropoxyaniline 31d (1.2g, 44%) as a brown oil.

Step 3. To a 100 mL pressure tank reactor was added 4-bromo-2-cyclopropoxyaniline 31d (1.0 g, 4.38 mmol, 1.00 equiv.), methanol (60 mL), TEA (2.67 g, 26.39 mmol, 6.00 equiv.), and Pd(dppf)Cl$_2$—CH$_2$Cl$_2$ (360 mg, 0.44 mmol, 0.10 equiv.). To the above mixture, CO gas was introduced in. The resulting mixture was heated at 100° C. overnight with stirring, and concentrated under vacuum. The crude product was purified by Flash-Prep-HPLC using the following conditions (IntelFlash-1): Column, silica gel; mobile phase, PE:EA=100:0 increasing to PE:EA=90:10 within 30 min; Detector, UV 254 nm. Removal of solvents provided methyl 4-amino-3-cyclopropoxybenzoate 31e (655 mg, 72%) as a brown oil.

Step 4. To a 250 mL round-bottom flask was added methyl 4-amino-3-cyclopropoxybenzoate 31e (2.1 g, 10.13 mmol, 1.00 equiv.), AcOH (100 mL), NaSCN (3.29 g, 40.62 mmol, 4.00 equiv.), and Br$_2$ (1.62 g, 10.14 mmol, 1.00 equiv.). The resulting mixture was stirred at 30° C. overnight. The reaction was quenched by the addition of 50 mL of water/ice. The pH value of the solution was adjusted to 10.0 using a 1M sodium hydroxide aqueous solution. The solids were collected by filtration to give methyl 2-amino-4-cyclopropoxy-1,3-benzothiazole-6-carboxylate 31f (2.0g, 75%) as a reddish solid.

Step 5. To a 250 mL round-bottom flask was added methyl 2-amino-4-cyclopropoxy-1,3-benzothiazole-6-carboxylate 31f (2.0 g, 7.57 mmol, 1.00 equiv.), t-BuONO (1.76 g, 17.09 mmol, 2.26 equiv.), CuBr$_2$ (2.53 g, 11.35 mmol, 1.50 equiv.), and MeCN (60 mL). The resulting mixture was stirred at 30° C. overnight, and concentrated under vacuum. The crude product was purified by Flash-Prep-HPLC using the following conditions (IntelFlash-1): Column, silica gel; mobile phase, PE:EA=100:0 increasing to PE:EA=95:5 within 25 min; Detector, UV 254 nm. Removal of solvent gave methyl 2-bromo-4-cyclopropoxy-1,3-benzothiazole-6-carboxylate 31g (2.1 g, 85%) as a gray solid.

Step 6. To a 100 mL round-bottom flask was added (1S,4S,5R)-5-[[4-cyclopropyl-1-(2,6-dichlorophenyl)-1H-pyrazol-5-yl]methoxy]-2-azabicyclo[2.2.1]heptane 1I (46 mg, 0.12 mmol, 1.00 equiv.), DMA (1.5 mL), methyl 2-bromo-4-cyclopropoxy-1,3-benzothiazole-6-carboxylate 31g (40 mg, 0.12 mmol, 1.00 equiv.), and Cs$_2$CO$_3$ (78 mg, 0.24 mmol, 2.00 equiv.). The resulting mixture was heated at 60° C. overnight. After cooling to room temperature, water was added, the aqueous mixture was extracted with ethyl acetate (100 mL×2), and the combined organic extracts were washed with brine (50 mL×2), dried over anhydrous sodium sulfate and concentrated under vacuum. The residue was purified by silica gel column chromatography eluting with ethyl acetate/petroleum ether (1:3) to give methyl 4-cyclopropoxy-2-[(1S,4S,5R)-5-[[4-cyclopropyl-1-(2,6-dichlorophenyl)-1H-pyrazol-5-yl]methoxy]-2-azabicyclo[2.2.1]heptan-2-yl]-1,3-benzothiazole-6-carboxylate 31h (45 mg, 59%) as a light yellow solid.

Step 7. To a 50 mL round-bottom flask was added methyl 4-cyclopropoxy-2-[(1S,4S,5R)-5-[[4-cyclopropyl-1-(2,6-dichlorophenyl)-1H-pyrazol-5-yl]methoxy]-2-azabicyclo[2.2.1]heptan-2-yl]-1,3-benzothiazole-6-carboxylate 31h (45 mg, 0.07 mmol, 1.00 equiv.), methanol (1 mL), LiOH (30 mg, 1.25 mmol, 10.00 equiv), and water (0.2 mL). The resulting mixture was stirred at 50° C. for 2 h. After cooling to room temperature, the mixture was diluted with 20 mL of ethyl acetate and treated with a 1M hydrogen chloride aqueous solution to adjust the pH value to 6. The aqueous mixture was extracted with ethyl acetate (100 mL×2), and the combined organic extracts were washed with brine (30 mL×3), dried over anhydrous sodium sulfate and concentrated under vacuum. The crude product was purified by Prep-HPLC using the following conditions: Column, XBridge Prep OBD C18 Column, 19*250 mm, 5 um; mobile phase, Water (0.05% NH3H2O) and ACN (51.0% ACN up to 59.0% in 10 min); Detector, UV 220 nm. After purification 4-cyclopropoxy-2-[(1S,4S,5R)-5-[[4-cyclopropyl-1-(2,6-dichlorophenyl)-1H-pyrazol-5-yl]methoxy]-2-azabicyclo[2.2.1]heptan-2-yl]-1,3-benzothiazole-6-carboxylic acid I-31 (24.9 mg, 57%) was obtained as an off-white solid. $^1$H NMR (400 MHz, CD$_3$OD): δ 8.03 (d, J=1.5 Hz, 1H), 7.93 (d, J=1.5 Hz, 1H), 7.67-7.60 (m, 2H), 7.60-7.51 (m, 1H), 7.47 (s, 1H), 4.57-4.45 (m, 2H), 4.03 (tt, J=6.4, 3.1 Hz, 1H), 3.73-3.66 (m, 1H), 3.57 (dd, J=10.3, 4.0 Hz, 1H), 3.09 (d, J=10.0 Hz, 1H), 2.69 (s, 1H), 2.07 (dd, J=13.8, 6.8 Hz, 1H), 1.83 (tt, J=8.5, 5.1 Hz, 1H), 1.73 (s, 2H), 1.42 (d, J=13.9 Hz, 1H), 1.02-0.83 (m, 6H), 0.72-0.64 (m, 2H). MS (ES, m/z): [M+1]=611.

Example 30: 2-[(1S,4S,5R)-5-{[4-cyclopropyl-1-(2,6-dichlorophenyl)-1H-pyrazol-5-yl]methoxy}-2-azabicyclo[2.2.1]heptan-2-yl]-4-(oxan-4-yl)-1,3-benzothiazole-6-carboxylic acid (I-32)

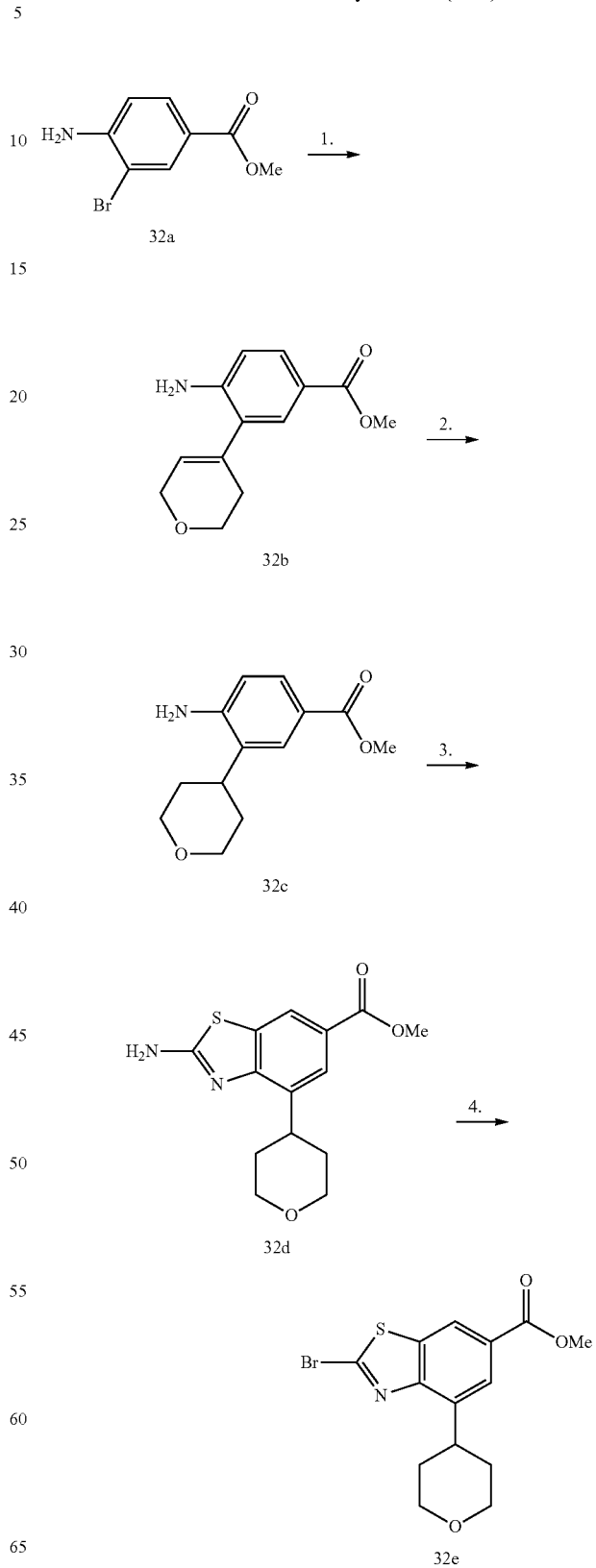

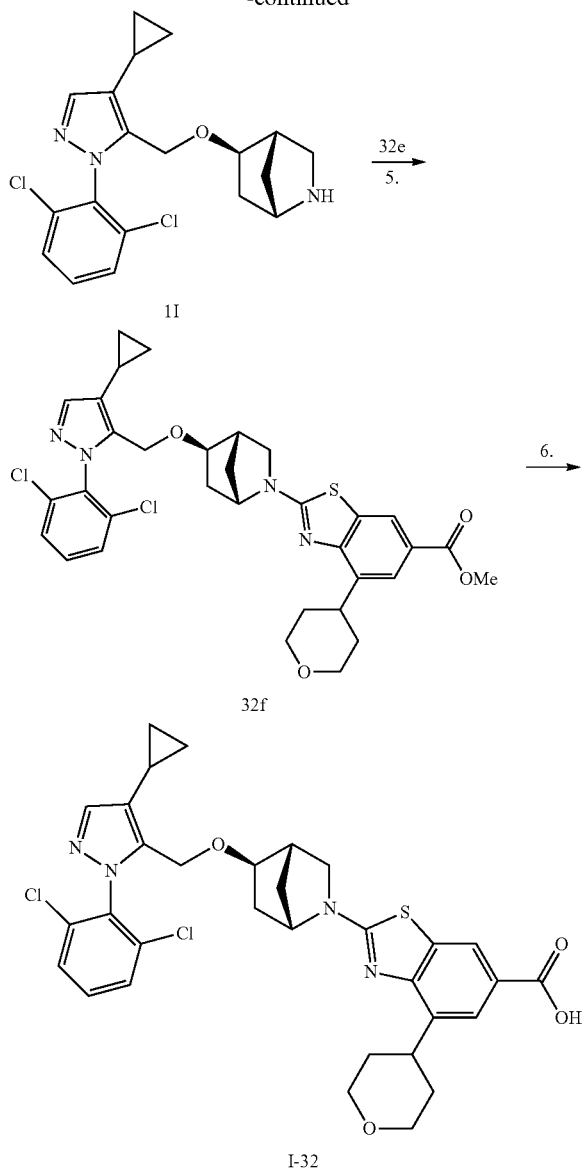

Step 1. To a 250 mL round-bottom flask was added methyl 4-amino-3-bromobenzoate 32a (2.4 g, 10.43 mmol, 1.00 equiv.), 2-(3,6-dihydro-2H-pyran-4-yl)-4,4,5,5-tetramethyl-1,3,2-dioxaborolane (2.6 g, 12.38 mmol, 1.20 equiv.), dioxane (100 mL), aq. sodium bicarbonate (37 mL, 3.50 equiv, 1M), and Pd(PPh$_3$)$_4$ (1.21 g, 1.05 mmol, 0.10 equiv.). The resulting mixture was heated at 100° C. overnight. After cooling to room temperature, the mixture was diluted with 300 mL of EA and washed with brine (200 mL×2). The organic phase was dried over anhydrous sodium sulfate and concentrated under vacuum. The crude product was purified by Flash-Prep-HPLC using the following conditions (Intel-Flash-1): Column, silica gel; mobile phase, PE:EA=100:0 increasing to PE:EA=50:50 within 30 min; Detector, UV 254 nm. Removal of solvents afforded methyl 4-amino-3-(3,6-dihydro-2H-pyran-4-yl)benzoate 32b (2.4 g, 99% as a white solid.

Step 2. To a 50 mL round-bottom flask was added methyl 4-amino-3-(3,6-dihydro-2H-pyran-4-yl)benzoate 32b (1.2 g, 5.14 mmol, 1.00 equiv.), methanol (24 mL), and Palladium on carbon (1.2 g, 10 wt %). Hydrogen gas was introduced in. The resulting mixture was stirred at room temperature under an atmosphere of hydrogen. The solids were filtered out, and the filtrate was concentrated under vacuum to give methyl 4-amino-3-(oxan-4-yl)benzoate 32d (1.14 g, 94%) as a white solid.

Step 3. To a 50 mL round bottom flask was added methyl 4-amino-3-(oxan-4-yl)benzoate 32c (1.14 g, 4.85 mmol, 1.00 equiv.), AcOH (10 mL), NaSCN (1.58 g, 19.51 mmol, 4.00 equiv.), and Br$_2$ (772 mg, 4.83 mmol, 1.00 equiv.). The resulting mixture was stirred at 30° C. overnight. The mixture was quenched by the addition of 200 mL of water/ice. The pH value of the solution was adjusted to 10 using sodium hydroxide pellets. The solids were filtered out. The resulting mixture was concentrated under vacuum to give methyl 2-amino-4-(oxan-4-yl)-1,3-benzothiazole-6-carboxylate 32d (1.15 g, 81%) as an orange color solid.

Step 4. To a 50 mL round-bottom flask was added methyl 2-amino-4-(oxan-4-yl)-1,3-benzothiazole-6-carboxylate 32d (1.15 g, 3.93 mmol, 1.00 equiv.), MeCN (20 mL), t-BuONO (920 mg, 9.02 mmol, 2.26 equi.v), and CuBr$_2$ (1.32 g, 5.92 mmol, 1.50 equiv.). The resulting mixture was stirred at 30° C. overnight, and then concentrated under vacuum. The crude product was purified by Flash-Prep-HPLC using the following conditions (IntelFlash-1): Column, silica gel; mobile phase, EA:PE=0:100 increasing to EA:PE=5:95 within 30 min; Detector, UV 254 nm. Removal of solvents afforded methyl 2-bromo-4-(oxan-4-yl)-1,3-benzothiazole-6-carboxylate 32e (1.08 g, 77%) as a yellow solid.

Step 5. To a 100 mL round-bottom flask purged and maintained under an inert atmosphere of nitrogen was added (1S,4S,5R)-5-[[4-cyclopropyl-1-(2,6-dichlorophenyl)-1H-pyrazol-5-yl]methoxy]-2-azabicyclo[2.2.1]heptane 1I (100 mg, 0.26 mmol, 1.00 equiv.), DMA (3 mL), Cs$_2$CO$_3$ (173 mg, 0.53 mmol, 2.00 equiv.), and methyl 2-bromo-4-(oxan-4-yl)-1,3-benzothiazole-6-carboxylate 32e (112 mg, 0.31 mmol, 1.20 equiv.). The resulting mixture was heated at 60° C. overnight and concentrated under vacuum. The residue was purified by silica gel column chromatography eluting with ethyl acetate/petroleum ether (1:3) to give methyl 2-[(1S,4S,5R)-5-[[4-cyclopropyl-1-(2,6-dichlorophenyl)-1H-pyrazol-5-yl]methoxy]-2-azabicyclo[2.2.1]heptan-2-yl]-4-(oxan-4-yl)-1,3-benzothiazole-6-carboxylate 32f (125 mg, 72%) as a light yellow solid.

Step 6. To a 50 mL round-bottom flask was added methyl 2-[(1S,4S,5R)-5-[[4-cyclopropyl-1-(2,6-dichlorophenyl)-1H-pyrazol-5-yl]methoxy]-2-azabicyclo[2.2.1]heptan-2-yl]-4-(oxan-4-yl)-1,3-benzothiazole-6-carboxylate 32f (125 mg, 0.19 mmol, 1.00 equiv.), methanol (2 mL), LiOH (77 mg, 1.93 mmol, 10.00 equiv.), and water (0.2 mL). The resulting mixture was heated at 50° C. for 2 h. After cooling to room temperature, the mixture was diluted with 10 mL of ethyl acetate, and treated with a 1M HCl aqueous solution to adjust the pH value of the mixture to 6. The aqueous mixture was extracted with ethyl acetate (100 mL×2), and the combined organic extracts were washed with (30 mL×2), dried over anhydrous sodium sulfate and concentrated under vacuum. The crude product was purified by Prep-HPLC using the following conditions: Column, XBridge Shield RP18 OBD Column 5 um, 19*150 mm; mobile phase, Water (0.05% TFA) and ACN (53.0% ACN up to 70.0% in 8 min); Detector, uv 254 nm. After purification 2-[(1S,4S,5R)-5-[[4-cyclopropyl-1-(2,6-dichlorophenyl)-1H-pyrazol-5-yl]methoxy]-2-azabicyclo[2.2.1]heptan-2-yl]-4-(oxan-4-yl)-1,3-benzothiazole-6-carboxylic acid I-32 (71.1 mg, 58%) was obtained as an off-white solid. $^1$H NMR (400 MHz, CD₃OD): δ 8.19 (d, J=1.7 Hz, 1H), 7.87 (d, J=1.7 Hz, 1H), 7.63 (td, J=7.9, 1.7 Hz, 2H), 7.59-7.51 (m, 1H), 7.47 (s, 1H), 4.57-4.44 (m, 2H), 4.38 (s, 1H), 4.14-4.05 (m, 2H), 3.71-3.59 (m, 3H), 3.59-3.46 (m, 2H), 3.06 (d, J=10.0 Hz, 1H), 2.66 (d, J=3.7 Hz, 1H), 2.11-2.01 (m, 1H), 1.96 (dd, J=12.7, 4.3 Hz, 2H), 1.89-1.77 (m, 3H), 1.70 (s, 2H), 1.47-1.28 (m, 1H), 1.02-0.89 (m, 2H), 0.72-0.63 (m, 2H). MS (ES, m/z): [M+1]=639.

Example 31: 3-{4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-3-fluorophenyl}propanoic acid (I-33)

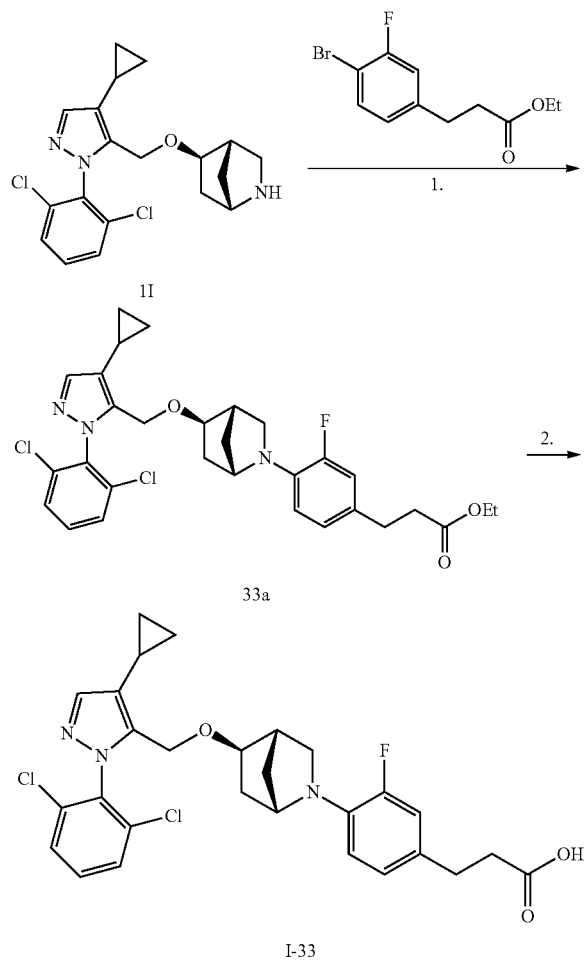

Step 1. To a 50 mL round-bottom flask was added a solution of (1S,4S,5R)-5-[[4-cyclopropyl-1-(2,6-dichlorophenyl)-1H-pyrazol-5-yl]methoxy]-2-azabicyclo[2.2.1]heptane 1I (120 mg, 0.32 mmol, 1.00 equiv.) in toluene (3 ml), ethyl 3-(4-bromo-3-fluorophenyl)propanoate (105 mg, 0.38 mmol, 1.10 equiv.), Ru-phos precatalyst (54 mg, 0.20 equiv), Ruphos (28 mg, 0.20 equiv.), and Cs₂CO₃ (311 g, 954.51 mmol, 3.00 equiv.). The resulting mixture was heated at 110° C. overnight and concentrated under vacuum. The residue was purified by silica gel column chromatography eluting with ethyl acetate/petroleum ether (1:3) to give ethyl 3-[4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-3-fluorophenyl]propanoate 33a (78 mg, 43%) as an off-white solid.

Step 2. To a 50 mL round-bottom flask was added ethyl 3-[4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-3-fluorophenyl]propanoate 33a (78 mg, 0.14 mmol, 1.00 equiv.), ethanol (2 mL), LiOH (51 mg, 1.28 mmol, 10.00 equiv.), water (0.2 mL). The resulting mixture was stirred at 50° C. for 2 h. After cooling to room temperature, the mixture was diluted with 20 mL of ethyl acetate. A 1M HCl aqueous solution was added to adjust the pH value to 6. The aqueous mixture was extracted with ethyl acetate (100 mL×2), and the combined organic extracts were washed with brine (30 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (50.0% ACN up to 66.0% in 8 min); Detector, UV 254 nm. After purification 3-[4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-3-fluorophenyl]propanoic acid I-33 (18.7 mg, 25%) was obtained as an off-white solid. ¹H NMR (400 MHz, CD₃OD): δ 7.69-7.51 (m, 4H), 7.46 (s, 1H), 7.02-6.91 (m, 2H), 6.83 (t, J=8.9 Hz, 1H), 4.53-4.41 (m, 2H), 4.17-4.11 (m, 1H), 3.59-3.49 (m, 2H), 2.85 (t, J=7.5 Hz, 2H), 2.77 (dd, J=10.3, 2.7 Hz, 1H), 2.57 (t, J=7.5 Hz, 2H), 2.54-2.47 (m, 1H), 2.08-1.98 (m, 1H), 1.81 (tt, J=8.4, 5.1 Hz, 1H), 1.65 (s, 2H), 1.30 (dt, J=14.1, 2.8 Hz, 1H), 1.02-0.84 (m, 2H), 0.71-0.60 (m, 2H). MS (ES, m/z): [M+1]=544.

Example 32: 3-{4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-2-fluorophenyl}propanoic acid (I-34)

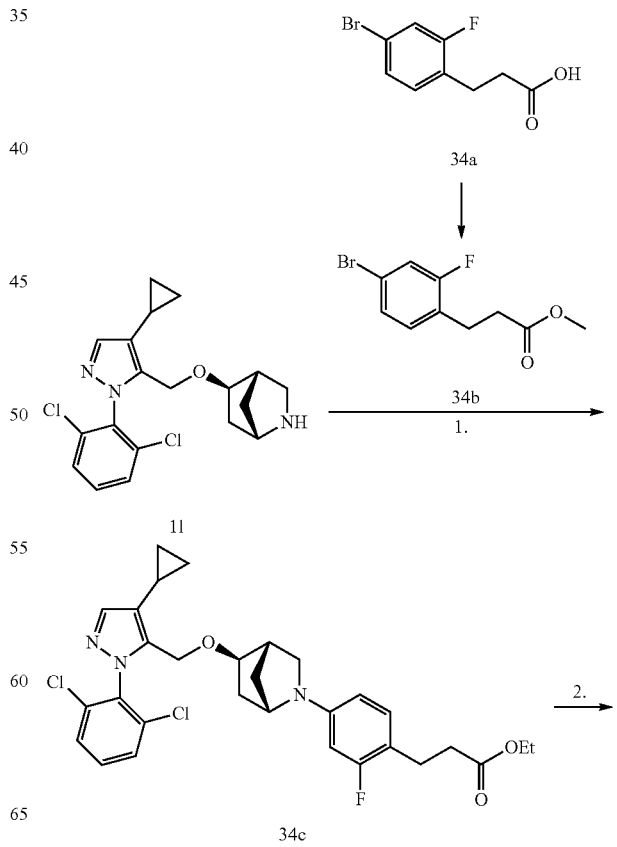

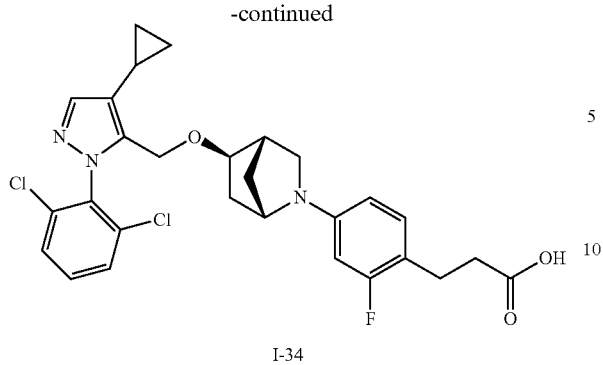

I-34

Step 1. To a 100 mL round-bottom flask was added 3-(4-bromo-2-fluorophenyl)propanoic acid 34a (100 mg, 0.40 mmol, 1.00 equiv.), methanol (2 mL), and thionyl chloride (138 mg, 3.00 equiv.). The resulting mixture was stirred at 70° C. overnight. After cooling to room temperature, the mixture was diluted with 20 mL of ethyl acetate and then quenched with 20 mL of water/ice. The aqueous mixture was extracted with ethyl acetate (100 mL×2), and the combined organic extracts were washed with brine (30 mL×2), dried over anhydrous sodium sulfate and concentrated under vacuum. The residue was purified by silica gel column chromatography eluting with ethyl acetate/petroleum ether (1:5) to give methyl 3-(4-bromo-2-fluorophenyl)propanoate 34b (110 mg) as a light yellow crude solid.

Step 2. To a 50 mL round-bottom flask was added a solution of (1S,4S,5R)-5-[[4-cyclopropyl-1-(2,6-dichlorophenyl)-1H-pyrazol-5-yl]methoxy]-2-azabicyclo[2.2.1]heptane 11 (110 mg, 0.29 mmol, 1.00 equiv) in toluene (3 mL), Ru-phos precatalyst (0.2 mg, 0.20 equiv.), Ruphos (0.2 mg, 0.20 equiv.), Cs$_2$CO$_3$ (311 mg, 0.95 mmol, 3.00 equiv.), and methyl 3-(4-bromo-2-fluorophenyl)propanoate 34b (96 mg, 0.37 mmol, 1.00 equiv.). The resulting mixture was heated at 110° C. overnight. The mixture was concentrated under vacuum. The residue was purified by silica gel column chromatography eluting with ethyl acetate/petroleum ether (1:3) to afford methyl 3-[4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-2-fluorophenyl]propanoate 34c (45 mg, 28%) as a light yellow solid.

Step 3. To a 50 mL round-bottom flask was added methyl 3-[4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-2-fluorophenyl]propanoate 34c (45 mg, 0.08 mmol, 1.00 equiv.), methanol (1.5 mL), LiOH (34 mg, 1.42 mmol, 10.00 equiv.), and water (0.2 mL). The resulting mixture was stirred at 50° C. for 2 h. After cooling to room temperature, the mixture was diluted with 20 mL of ethyl acetate, and the pH value of the solution was adjusted to 6 using a 1M hydrogen chloride aqueous solution. The aqueous mixture was extracted with ethyl acetate (100 mL×2), and the combined organic extracts were washed with brine (30 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (51.0% ACN up to 68.0% in 8 min); Detector, uv 254 nm. After purification 3-[4-[(1S,4S,5R)-5-[[4-cyclopropyl-1-(2,6-dichlorophenyl)-1H-pyrazol-5-yl]methoxy]-2-azabicyclo [2.2.1]heptan-2-yl]-2-fluorophenyl]propanoic acid I-34 (14 mg, 32%) was obtained as an off-white solid. $^1$H NMR (400 MHz, CD$_3$OD): δ 7.65-7.49 (m, 3H), 7.45 (s, 1H), 7.05 (t, J=8.6 Hz, 1H), 6.37-6.24 (m, 2H), 4.46 (d, J=2.4 Hz, 2H), 4.02 (d, J=2.5 Hz, 1H), 3.46 (dd, J=7.0, 2.3 Hz, 1H), 3.41-3.34 (m, 1H), 2.82 (t, J=7.7 Hz, 2H), 2.58-2.46 (m, 4H), 1.94-1.74 (m, 2H), 1.60 (s, 2H), 1.26 (dt, J=13.4, 2.6 Hz, 1H), 1.02-0.89 (m, 2H), 0.66 (qd, J=4.8, 2.3 Hz, 2H). MS (ES, m/z): [M+1]=544.

Example 33: 3-{4-[(1S,4S,5R)-5-{[4-cyclopropyl-1-(2,6-difluorophenyl)-1H-pyrazol-5-yl]methoxy}-2-azabicyclo[2.2.1]heptan-2-yl]-3-fluorophenyl}propanoic acid (I-35)

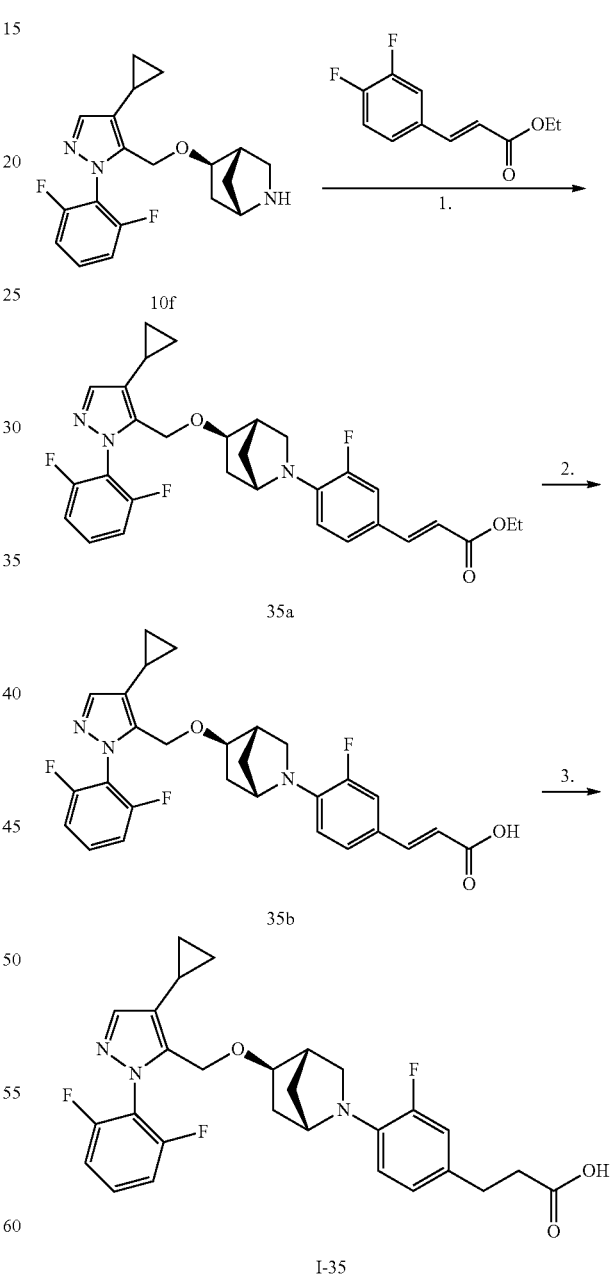

Step 1. To a 5 mL sealed tube was added (1S,4S,5R)-5-[[4-cyclopropyl-1-(2,6-difluorophenyl)-1H-pyrazol-5-yl]methoxy]-2-azabicyclo[2.2.1]heptane 10f (120 mg, 0.35 mmol, 1.00 equiv.), ethyl (2E)-3-(3,4-difluorophenyl)prop- 2-enoate (148 mg, 0.70 mmol, 2.00 equiv.), 1-Ethyl-3-methylimidazolium dimethyl phosphate (2 mL), CsF (106 mg, 2.00 equiv). The resulting solution was heated at 90° C. overnight. After cooling to room temperature, water was added and the mixture was extracted with ethyl acetate (100 mL×2). The combined organic extracts were washed with brine (100 mL×2), dried over anhydrous sodium sulfate and concentrated under vacuum. The residue was purified by silica gel column chromatography eluting with PE:EA (3:1) to give ethyl (2E)-3-[4-[(1S,4S,5R)-5-[[4-cyclopropyl-1-(2,6-difluorophenyl)-1H-pyrazol-5-yl]methoxy]-2-azabicyclo[2.2.1]heptan-2-yl]-3-fluorophenyl]prop-2-enoate 35a (80 mg, 43%) as a yellow oil.

Step 2. To a 25 mL round-bottom flask was added ethyl (2E)-3-[4-[(1S,4S,5R)-5-[[4-cyclopropyl-1-(2,6-difluorophenyl)-1H-pyrazol-5-yl]methoxy]-2-azabicyclo[2.2.1]heptan-2-yl]-3-fluorophenyl]prop-2-enoate 35a (80 mg, 0.15 mmol, 1.00 equiv.), ethanol (1 mL), water (0.5 mL), and lithium hydroxide monohydrate (62.6 mg, 1.49 mmol, 10.00 equiv.). The resulting mixture was stirred at 60° C. for 1.5 h. The pH value of the solution was adjusted to 4 using a 1M HCl aqueous solution. The aqueous mixture was extracted with ethyl acetate (150 mL×2), and the combined organic extracts were washed with brine (150 mL), dried over anhydrous sodium sulfate and concentrated under vacuum to afford (2E)-3-[4-[(1S,4S,5R)-5-[[4-cyclopropyl-1-(2,6-difluorophenyl)-1H-pyrazol-5-yl]methoxy]-2-azabicyclo[2.2.1]heptan-2-yl]-3-fluorophenyl]prop-2-enoic acid 35b (70 mg, 92%) as a light yellow oil.

Step 3. To a 50 mL round-bottom flask was added (2E)-3-[4-[(1S,4S,5R)-5-[[4-cyclopropyl-1-(2,6-difluorophenyl)-1H-pyrazol-5-yl]methoxy]-2-azabicyclo[2.2.1]heptan-2-yl]-3-fluorophenyl]prop-2-enoic acid 35b (70 mg, 0.14 mmol, 1.00 equiv.), ethanol (12 mL), and hydrazine monohydrate (52.2 mg, 1.06 mmol, 8.00 equiv.). The resulting mixture was heated at 80° C. overnight. After cooling to room temperature, the mixture was diluted with 100 mL of EA, and treated with a 1M HCl aqueous solution to adjust the pH value of the solution to 6. The aqueous mixture was extracted with ethyl acetate (100 mL×2), and the combined organic extracts were washed with brine (150 mL×3), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (48.0% ACN up to 64.0% in 8 min); Detector, uv 254/220 nm. After purification 3-[4-[(1S,4S,5R)-5-[[4-cyclopropyl-1-(2,6-difluorophenyl)-1H-pyrazol-5-yl]methoxy]-2-azabicyclo[2.2.1]heptan-2-yl]-3-fluorophenyl]propanoic acid I-35 (23.1 mg, 33%) was obtained as a light yellow foam. $^1$H NMR (400 MHz, CDCl$_3$): δ 7.52-7.40 (m, 2H), 7.08 (q, J=8.3 Hz, 2H), 6.92-6.81 (m, 2H), 6.63 (t, J=8.7 Hz, 1H), 4.49 (d, J=2.0 Hz, 2H), 4.11 (s, 1H), 3.62-3.54 (m, 1H), 3.46 (d, J=6.6 Hz, 1H), 2.87 (t, J=7.6 Hz, 2H), 2.73-2.60 (m, 3H), 2.44 (d, J=3.5 Hz, 1H), 2.13-2.01 (m, 1H), 1.94-1.57 (m, 3H), 1.36-1.25 (m, 2H), 1.00-0.88 (m, 2H), 0.71-0.62 (m, 2H). MS (ES, m/z): [M+1]=512.

Example 34: 3-{4-[(1S,4S,5R)-5-{[4-cyclopropyl-1-(2,6-dimethylphenyl)-1H-pyrazol-5-yl]methoxy}-2-azabicyclo[2.2.1]heptan-2-yl]-3-fluorophenyl}propanoic acid (I-36)

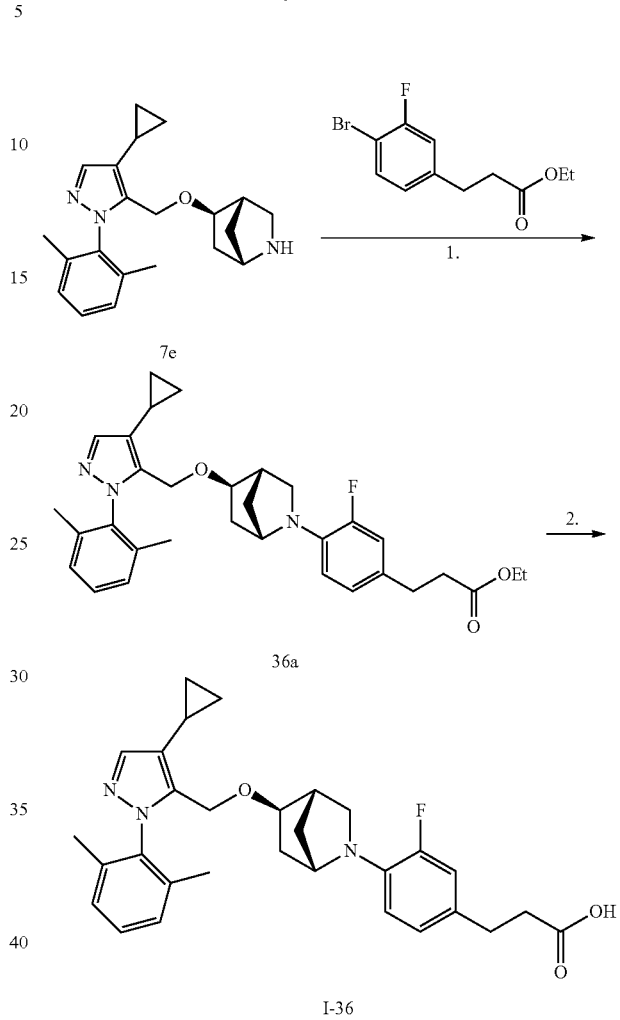

Step 1. To an 8 mL sealed tube was added (1S,4S,5R)-5-((4-cyclopropyl-1-(2,6-dimethylphenyl)-1H-pyrazol-5-yl)methoxy)-2-aza-bicyclo[2.2.1]heptane 7e (100 mg, 0.28 mmol, 1.00 equiv.), ethyl 3-(4-bromo-3-fluorophenyl)propanoate (81 mg, 0.28 mmol, 1.00 equiv.), Pd(OAc)$_2$ (13 mg, 0.056 mmol, 0.2 equiv.), XantPhos (46 mg, 0.056 mmol, 0.2 equiv), Cs$_2$CO$_3$ (270 mg, 0.84 mmol, 3.00 equiv.), and dioxane (2 ml). The resulting mixture was heated at 90° C. overnight. After cooling to room temperature, the mixture was diluted with 20 mL of H2O, extracted with ethyl acetate (100 mL×2), and the combined organic extracts were washed with brine (100 mL×2), dried over anhydrous sodium sulfate and concentrated under vacuum. The residue was purified by silica gel column chromatography eluting with ethyl acetate/petroleum ether (1:2) to afford ethyl 3-(4-((1S,4S,5R)-5-((4-cyclopropyl-1-(2,6-dimethylphenyl)-1H-pyrazol-5-yl)methoxy)-2-aza-bicyclo[2.2.1]heptan-2-yl)-3-fluorophenyl)propanoate 36a (80 mg, 51%) as a red oil.

Step 2. To a 50 mL round-bottom flask was added ethyl 3-[4-[(1S,4S,5R)-5-[[4-cyclopropyl-1-(2,6-dimethylphenyl)-1H-pyrazol-5-yl]methoxy]-2-azabicyclo[2.2.1]heptan-2-yl]-3-fluorophenyl]propanoate 36a (80 mg, 0.15 mmol, 1.00 equiv.), LiOH (62 mg, 2.59 mmol, 10.00 equiv.), ethanol (2 mL), and water (0.2 mL). The resulting mixture was heated at 50° C. for 2 h. After cooling to room temperature, the mixture was diluted with 50 mL of H$_2$O, and extracted with ethyl acetate (50 mL×2). The combined organic extracts were washed with brine (10 mL×2), dried over anhydrous sodium sulfate and concentrated under vacuum. The crude product was purified by Prep-HPLC using the following conditions: Column, XBridge Shield RP18 OBD Column 5 um, 19*150 mm; mobile phase, Water (0.05% TFA) and ACN (5.0% ACN up to 58.0% in 1 min, up to 70.0% in 7 min); Detector, uv 254/220 nm. After purification 3-[4-[(1S,4S,5R)-5-[[4-cyclopropyl-1-(2,6-dimethylphenyl)-1H-pyrazol-5-yl]methoxy]-2-azabicyclo[2.2.1]heptan-2-yl]-3-fluorophenyl]propanoic acid I-36 (9.7 mg, 13%) was obtained as a black solid. $^1$H NMR (300 MHz, CD$_3$OD): δ 7.45-7.27 (m, 2H), 7.21 (d, J=7.6 Hz, 2H), 6.97-6.84 (m, 2H), 6.71 (t, J=8.9 Hz, 1H), 4.44-4.21 (m, 2H), 4.08 (s, 1H), 3.58-3.40 (m, 2H), 2.82 (t, J=7.5 Hz, 2H), 2.66 (dd, J=10.0, 3.0 Hz, 1H), 2.56 (t, J=7.5 Hz, 2H), 2.44 (d, J=4.1 Hz, 1H), 1.96 (d, J=1.5 Hz, 7H), 1.81 (tt, J=8.3, 5.1 Hz, 1H), 1.60 (s, 2H), 1.21 (d, J=13.9 Hz, 1H), 1.01-0.86 (m, 2H), 0.75 0.60 (m, 2H). MS (ES, m/z): [M+1]=504.

Example 35: 3-{4-[(1S,4S,5R)-5-{[1-(2-chloro-6-methylphenyl)-4-cyclopropyl-1H-pyrazol-5-yl]methoxy}-2-azabicyclo[2.2.1]heptan-2-yl]-3-fluorophenyl}propanoic acid (I-37)

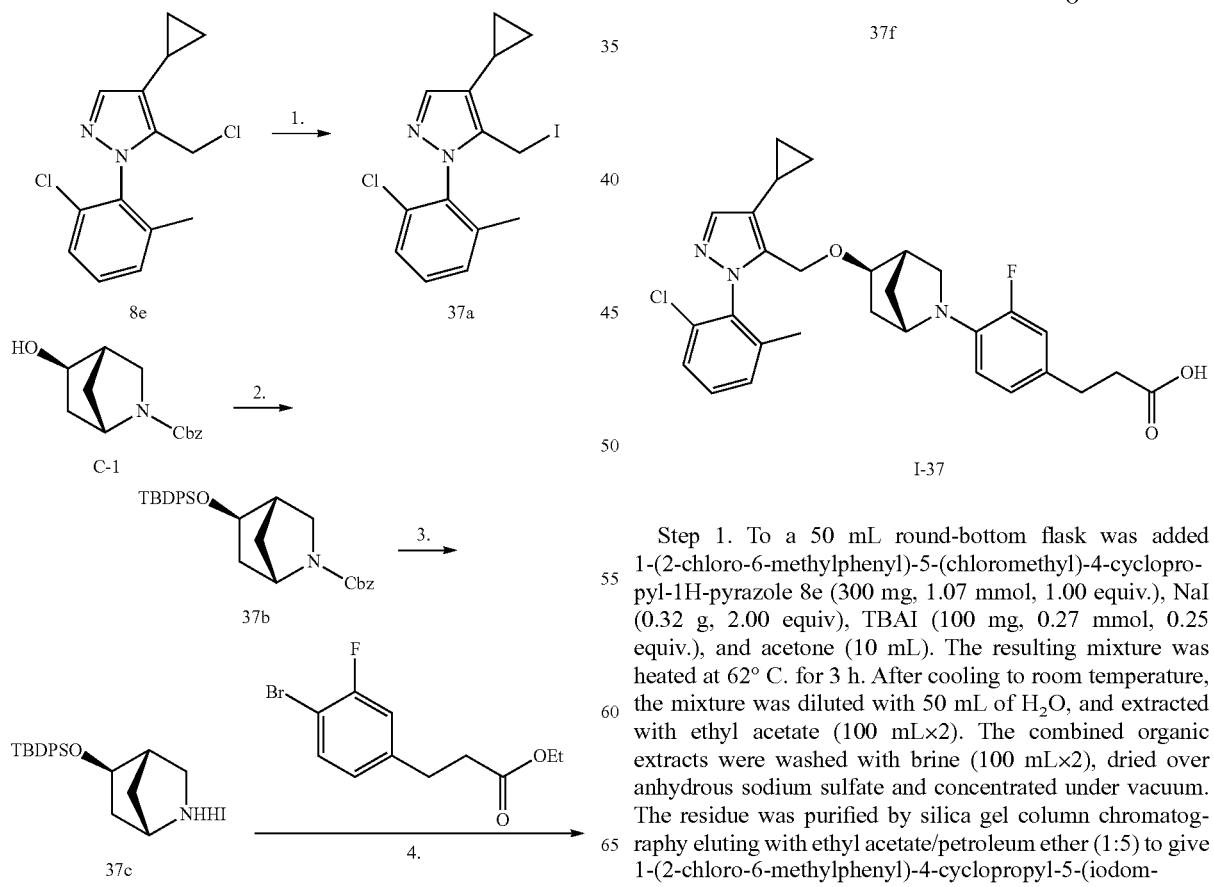

Step 1. To a 50 mL round-bottom flask was added 1-(2-chloro-6-methylphenyl)-5-(chloromethyl)-4-cyclopropyl-1H-pyrazole 8e (300 mg, 1.07 mmol, 1.00 equiv.), NaI (0.32 g, 2.00 equiv), TBAI (100 mg, 0.27 mmol, 0.25 equiv.), and acetone (10 mL). The resulting mixture was heated at 62° C. for 3 h. After cooling to room temperature, the mixture was diluted with 50 mL of H$_2$O, and extracted with ethyl acetate (100 mL×2). The combined organic extracts were washed with brine (100 mL×2), dried over anhydrous sodium sulfate and concentrated under vacuum. The residue was purified by silica gel column chromatography eluting with ethyl acetate/petroleum ether (1:5) to give 1-(2-chloro-6-methylphenyl)-4-cyclopropyl-5-(iodomethyl)-1H-pyrazole 37a (240 mg, 60%) as a red oil.

Step 2. To a 50 mL round bottom flask was added (1S,4S,5R)-5-hydroxy-2-azabicyclo[2.2.1]heptane-2-carboxylate C-1 (100 mg, 0.40 mmol, 1.00 equiv.), TBDPSCl (222 mg, 2.00 equiv), Imidazole (110 mg, 4.00 equiv), and N,N-dimethylformamide (1 mL). The resulting mixture was stirred at room temperature overnight. The mixture was diluted with 100 mL of $H_2O$, and extracted with ethyl acetate (100 mL×2). The combined organic extracts were washed with brine, dried over anhydrous sodium sulfate, and concentrated. The residue was purified by silica gel column chromatography eluting with ethyl acetate/hexane (1:4) to give benzyl (1S,4S)-5-(tert-butyldiphenylsilyl)-2-azabicyclo[2.2.1]heptane-2-carboxylate 37b (180 mg, 95%) as a yellow oil.

Step 3. To a 50 mL round-bottom flask was added benzyl (1S,4S)-5-(tert-butyldiphenylsilyl)-2-azabicyclo[2.2.1]heptane-2-carboxylate 37b (200 mg, 0.43 mmol, 1.00 equiv.), dichloromethane (1 mL), and TMSI (165 mg, 2.00 equiv). The resulting mixture was stirred at room temperature for 1 h, and quenched by the addition of 3 mL of a 1M hydrogen chloride aqueous solution. The aqueous mixture was extracted with dichloromethane (30 mL×2), and the combined organic extracts were washed with brine, dried over anhydrous sodium sulfate, and concentrated. The residue was purified by C18 column with ACN/$H_2O$ (0% to 10%, 30 min). Removal of solvents afforded (1S,4S)-5-(tert-butyldiphenylsilyl)-2-azabicyclo[2.2.1]heptane 37c (140 mg, 98%) as a yellow oil.

Step 4. To a 100 mL round-bottom flask was added (1S,4S)-5-(tert-butyldiphenylsilyl)-2-azabicyclo[2.2.1]heptane 37c (1 g, 2.98 mmol, 1.00 equiv.), ethyl 3-(4-bromo-3-fluorophenyl)propanoate (1.17 g, 4.25 mmol, 1.50 equiv.), Ruphos (0.48 g, 0.20 equiv.), Ruphos precatalyst (0.27 g, 0.20 equiv.), toluene (25 mL), and $Cs_2CO_3$ (2.79 g, 8.56 mmol, 3.00 equiv.). The resulting mixture was heated for at 110° C. overnight. After cooling to room temperature, the mixture was diluted with 50 mL of $H_2O$, and extracted with ethyl acetate (100 mL×2). The combined organic extracts were washed with brine (100 mL×2), dried and concentrated. The residue was purified by silica gel column chromatography eluting with ethyl acetate/hexane (1:3) to afford ethyl 3-[4-[(1S,4S)-5-(tert-butyldiphenylsilyl)-2-azabicyclo[2.2.1]heptan-2-yl]-3-fluorophenyl]propanoate 37d (1.5 g, 95%) as a yellow oil.

Step 5. To a 50 mL round-bottom flask was added ethyl 3-[4-[(1S,4S)-5-(tert-butyldiphenylsilyl)-2-azabicyclo[2.2.1]heptan-2-yl]-3-fluorophenyl]propanoate 37d (2.18 g, 4 mmol, 1.00 equiv.) and a 1M solution of TBAF in THF (8 ml, 8 mmol, 2 equiv.). The mixture was stirred at room temperature for 1 hour. The resulting solution was diluted with 50 mL of $H_2O$, and extracted with ethyl acetate (50 mL×2). The combined organic extracts were washed with brine (100 mL), dried over anhydrous sodium sulfate and concentrated under vacuum. The residue was purified by silica gel column chromatography eluting with ethyl acetate/petroleum ether (2:1) to provide 3-3-fluoro-4-[(1S,4S,5R)-5-hydroxy-2-azabicyclo[2.2.1]heptan-2-yl]phenylpropanoate 37e (614 mg, 50%) as a yellow oil.

Step 6. To a 50 mL round-bottom flask was added ethyl 3-3-fluoro-4-[(1S,4S,5R)-5-hydroxy-2-azabicyclo[2.2.1]heptan-2-yl]phenylpropanoate 37e (150 mg, 0.49 mmol, 1.00 equiv.), dichloromethane (5 mL), 4A molecular sieves (0.3 g), 2,6-di-tert-butylpyridine (560 mg, 2.93 mmol, 6.00 equiv.), and AgOTf (250 mg, 0.98 mmol, 2.00 equiv.). 1-(2-Chloro-6-methylphenyl)-4-cyclopropyl-5-(iodomethyl)-1H-pyrazole 37a (270 mg, 0.72 mmol, 1.50 equiv.) was added slowly with stirring at room temperature. The reaction mixture was stirred at room temperature overnight. Water (50 mL) was added, the mixture was extracted with ethyl acetate (100 mL×2), and the combined organic extracts were washed with brine (100 mL×2), dried over anhydrous sodium sulfate and concentrated under vacuum. The residue was purified by silica gel column chromatography eluting with ethyl acetate/petroleum ether (1:2) to give ethyl 3-[4-[(1S,4S,5R)-5-[[1-(2-chloro-6-methylphenyl)-4-cyclopropyl-1H-pyrazol-5-yl]methoxy]-2-azabicyclo[2.2.1]heptan-2-yl]-3-fluorophenyl]propanoate 37f (90 mg, 33%) as a yellow oil.

Step 7. To a 25 mL round-bottom flask was added ethyl 3-[4-[(1S,4S,5R)-5-[[1-(2-chloro-6-methylphenyl)-4-cyclopropyl-1H-pyrazol-5-yl]methoxy]-2-azabicyclo[2.2.1]heptan-2-yl]-3-fluorophenyl]propanoate 37f (90 mg, 0.16 mmol, 1.00 equiv.), ethanol (3 mL), water (0.5 mL), and LiOH—$H_2O$ (69 mg, 2.88 mmol, 10.00 equiv.). The resulting mixture was stirred at 50° C. for 2h. Upon cooling to room temperature, the mixture was diluted with 20 mL of $H_2O$, the pH value of the solution was adjusted to 3 using a 1M hydrogen chloride aqueous solution. The aqueous mixture was extracted with ethyl acetate (100 mL×2), and the combined organic extracts were washed with brine (100 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (50.0% ACN up to 72.0% in 8 min); Detector, UV 254/220 nm. After purification 3-[4-[(1S,4S,5R)-5-[[1-(2-chloro-6-methylphenyl)-4-cyclopropyl-1H-pyrazol-5-yl]methoxy]-2-azabicyclo[2.2.1]heptan-2-yl]-3-fluorophenyl]propanoic acid I-37 (51 mg, 60%) was obtained as a gray solid. $^1$H NMR (300 MHz, $CD_3OD$): δ 7.52-7.43 (m, 3H), 7.43-7.32 (m, 1H), 6.96-6.85 (m, 2H), 6.69 (s, 1H), 4.52 (dd, J=12.0, 5.0 Hz, 1H), 4.27 (dd, J=21.8, 11.9 Hz, 1H), 4.08 (d, J=11.0 Hz, 1H), 3.47 (dd, J=23.3, 8.0 Hz, 2H), 2.83 (t, J=7.5 Hz, 2H), 2.58 (q, J=10.6, 7.6 Hz, 4H), 2.04 (d, J=2.4 Hz, 4H), 1.96 (dd, J=13.7, 6.8 Hz, 1H), 1.90-1.74 (m, 1H), 1.62 (s, 1H), 1.52 (q, J=10.5, 10.0 Hz, 1H), 1.34 (d, J=13.5 Hz, 1H), 1.10 (d, J=13.8 Hz, 1H), 0.96 (dq, J=8.3, 1.4 Hz, 2H), 0.67 (dd, J=6.8, 5.0 Hz, 2H). MS (ES, m/z): [M+1]=524.

Example 36: 3-{4-[(1S,4S,5R)-5-{[1-(2-chloro-6-fluorophenyl)-4-cyclopropyl-1H-pyrazol-5-yl]methoxy}-2-azabicyclo[2.2.1]heptan-2-yl]-3-fluorophenyl}propanoic acid (I-38)

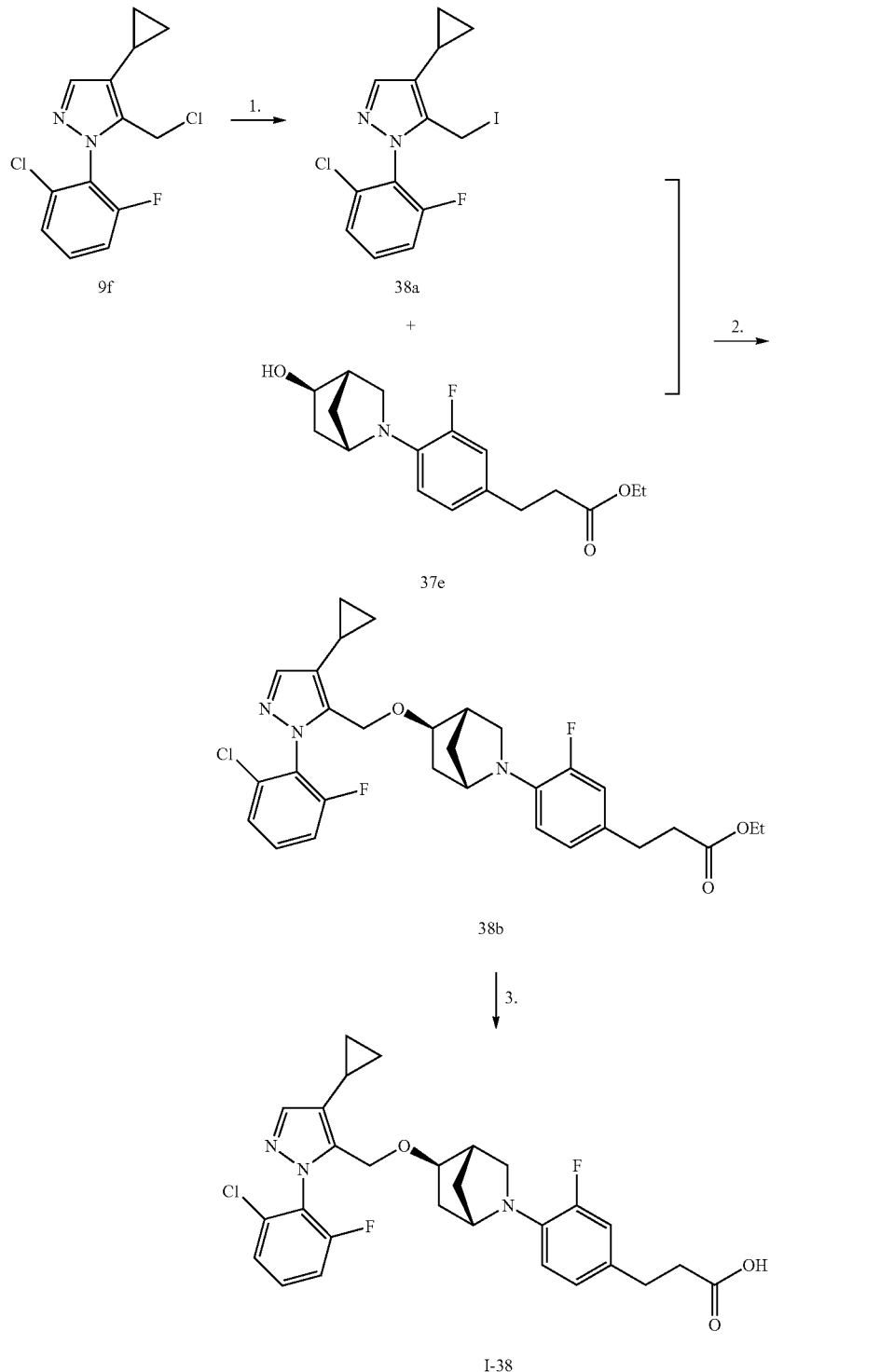

Step 1. To a 50 mL round-bottom flask was added 1-(2-chloro-6-fluorophenyl)-5-(chloromethyl)-4-cyclopropyl-1H-pyrazole 9f (160 mg, 0.56 mmol, 1.00 equiv.), NaI (0.17 g, 2.00 equiv), TBAI (52 mg, 0.14 mmol, 0.25 equiv.), and acetone (5 mL). The resulting mixture was heated at 62° C. for 3 h. After cooling to room temperature, the mixture was diluted with 50 mL of H₂O, and extracted with ethyl acetate (100 mL×2). The combined organic extracts were washed with brine (100 mL×2), dried over anhydrous sodium sulfate and concentrated under vacuum. The residue was purified by silica gel column chromatography eluting with ethyl acetate/petroleum ether (1:5) to give 1-(2-chloro-6-fluorophenyl)-4-cyclopropyl-5-(iodomethyl)-1H-pyrazole 38a (0.19 g, 90%) as a red oil.

Step 2. To a 50-mL round-bottom flask was added ethyl 3-3-fluoro-4-[(1S,4S,5R)-5-hydroxy-2-azabicyclo[2.2.1]heptan-2-yl]phenylpropanoate 37e (120 mg, 0.39 mmol, 1.00 equiv.), dichloromethane (5 mL), 4A MS (0.24 g), AgOTf (0.2 g, 2.00 equiv.), and 2,6-di-tert-butylpyridine (448 mg, 2.35 mmol, 6.00 equiv.). 1-(2-chloro-6-fluorophenyl)-4-cyclopropyl-5-(iodomethyl)-1H-pyrazole 38a (220 mg, 0.58 mmol, 1.50 equiv.) was added dropwise with stirring at room temperature. The resulting mixture was stirred at room temperature overnight, diluted with 50 mL of H₂O, and extracted with ethyl acetate (100 mL×2). The combined organic extracts were washed with brine (100 mL×2), dried over anhydrous sodium sulfate and concentrated under vacuum. The residue was purified by silica gel column chromatography eluting with ethyl acetate/petroleum ether (1:2) to provide ethyl 3-[4-[(1S,4S,5R)-5-[[1-(2-chloro-6-fluorophenyl)-4-cyclopropyl-1H-pyrazol-5-yl]methoxy]-2-azabicyclo[2.2.1]heptan-2-yl]-3-fluorophenyl]propanoate 38b (134 mg, 62%) as a red oil.

Step 3. To a 25 mL round-bottom flask was added ethyl 3-[4-[(1S,4S,5R)-5-[[1-(2-chloro-6-fluorophenyl)-4-cyclopropyl-1H-pyrazol-5-yl]methoxy]-2-azabicyclo[2.2.1]heptan-2-yl]-3-fluorophenyl]propanoate 38b (134 mg, 0.24 mmol, 1.00 equiv.), ethanol (2 mL), water (0.5 mL), and LiOH—H₂O (100 mg, 4.18 mmol, 10.00 equiv.). The resulting mixture was stirred at 50° C. for 2 h. Upon cooling to room temperature, 20 mL of H₂O was added to the mixture, and the pH value of the solution was adjusted to 3 using a 1M hydrogen chloride aqueous solution. The aqueous mixture was extracted with ethyl acetate (100 mL×2), and the combined organic extracts were washed with brine (100 mL×2), dried over anhydrous sodium sulfate and concentrated under vacuum. The crude product was purified by Prep-HPLC using the following conditions Column, XBridge Shield RP18 OBD Column 5 um, 19*150 mm; mobile phase, Water (0.05% TFA) and ACN (48.0% ACN up to 68.0% in 8 min); Detector, UV 254/220 nm. After purification 3-[4-[(1S,4S,5R)-5-[[1-(2-chloro-6-fluorophenyl)-4-cyclopropyl-1H-pyrazol-5-yl]methoxy]-2-azabicyclo[2.2.1]heptan-2-yl]-3-fluorophenyl]propanoic acid I-38 (37.4 mg, 29%) was obtained as a gray solid. ¹H NMR (300 MHz, CD₃OD): δ 7.60 (td, J=8.3, 5.6 Hz, 1H), 7.53-7.43 (m, 2H), 7.43-7.26 (m, 1H), 6.96-6.84 (m, 2H), 6.68 (t, J=8.8 Hz, 1H), 4.53 (dd, J=12.6, 3.5 Hz, 1H), 4.43 (dd, J=12.6, 7.4 Hz, 1H), 4.08 (s, 1H), 3.58-3.41 (m, 2H), 2.83 (t, J=7.5 Hz, 2H), 2.67-2.51 (m, 3H), 2.45 (s, 1H), 2.05-1.94 (m, 1H), 1.89-1.73 (m, 1H), 1.59 (s, 2H), 1.26 (t, J=13.0 Hz, 1H), 0.96 (dt, J=8.5, 3.1 Hz, 2H), 0.73-0.61 (m, 2H). MS (ES, m/z): [M+1]=528.

Example 37: 3-{4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-3-fluorophenyl}propanoic acid (I-39)

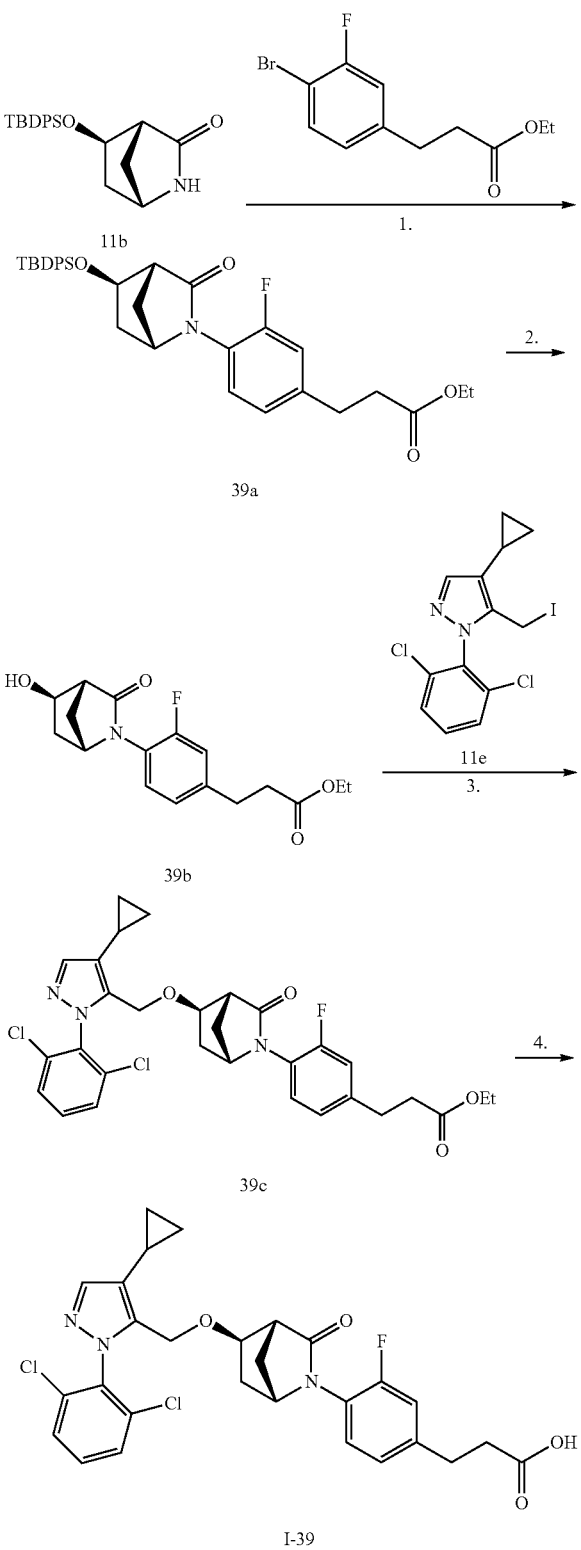

Step 1. To a 50 mL round-bottom flask was added a solution of (1S,4R,5R)-5-[(tert-butyldiphenylsilyl)oxy]-2-azabicyclo[2.2.1]heptan-3-one 11b (340 mg, 0.93 mmol, 1.00 equiv.) in 1,4-dioxane (7 mL). Ethyl 3-(4-bromo-3-fluorophenyl)propanoate (306 mg, 1.11 mmol, 1.20 equiv.), Cs$_2$CO$_3$ (455 mg, 1.40 mmol, 1.50 equiv.), XantPhos (81 mg, 0.15 equiv.), and Pd$_2$(dba)$_3$ (43 mg, 0.05 mmol, 0.05 equiv.) were added. The resulting mixture was heated at 105° C. overnight. After cooling to room temperature, water was added, the mixture was extracted with ethyl acetate (50 mL×2), and the combined organic extracts were washed with brine (50 mL×2), dried over anhydrous sodium sulfate and concentrated under vacuum. The residue was purified by silica gel column chromatography eluting with ethyl acetate/petroleum ether (1:3) to afford ethyl 3-[4-[(1S,4R,5R)-5-[(tert-butyldiphenylsilyl)oxy]-3-oxo-2-azabicyclo[2.2.1]heptan-2-yl]-3-fluorophenyl]propanoate 39a (450 mg, 86%) as a light yellow crude solid.

Step 2. To a 25 mL round-bottom flask was added a solution of ethyl 3-[4-[(1S,4R,5R)-5-[(tert-butyldiphenylsilyl)oxy]-3-oxo-2-azabicyclo[2.2.1]heptan-2-yl]-3-fluorophenyl]propanoate 39a (450 mg, 0.80 mmol, 1.00 equiv.) in tetrahydrofuran (2 mL) followed by TBAF (210 mg, 0.80 mmol, 2.00 equiv.). The resulting mixture was stirred for 1 h at room temperature, quenched with water, and extracted with ethyl acetate (50 mL×2). The combined organic extracts were washed with brine (50 mL×2), dried over anhydrous sodium sulfate and concentrated under vacuum. The residue was purified by silica gel column chromatography eluting with ethyl acetate to give ethyl 3-[3-fluoro-4-[(1S,4R,5R)-5-hydroxy-3-oxo-2-azabicyclo[2.2.1]heptan-2-yl]phenyl]propanoate 39b (240 mg, 93%) as a light yellow oil.

Step 3. To a 100 mL round-bottom flask was added ethyl 3-[3-fluoro-4-[(1S,4R,5R)-5-hydroxy-3-oxo-2-azabicyclo[2.2.1]heptan-2-yl]phenyl]propanoate 39b (120 mg, 0.37 mmol, 1.00 equiv.), AgOTf (192 mg, 2.00 equiv), 4 AMS (240 mg, 2 w/w), 2,6-di-tert-butyl pyridine (424 mg, 6.00 equiv), dichloromethane (12 mL), and 4-cyclopropyl-1-(2,6-dichlorophenyl)-5-(iodomethyl)-1H-pyrazole 11e (293 mg, 0.75 mmol, 2.00 equiv.). The resulting mixture was stirred at room temperature overnight. The solids were filtered out, the filtrate was quenched with water and extracted with dichloromethane (100 mL×2). The combined organic extracts were washed with brine (100 mL), dried over anhydrous sodium sulfate and concentrated under vacuum. The residue was purified by silica gel column chromatography eluting with ethyl acetate/petroleum ether (1:2) to provide ethyl 3-[4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]-3-fluorophenyl]propanoate 39c (160 mg, 73%) as a light yellow solid.

Step 4. To a 50 mL round-bottom flask was added ethyl 3-[4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]-3-fluorophenyl]propanoate 39c (160 mg, 0.27 mmol, 1.00 equiv.), ethanol (5 mL), LiOH (110 mg, 4.59 mmol, 10.00 equiv), and water (0.5 mL). The resulting mixture was stirred for 2 h at 60° C. After cooling to room temperature, the mixture was treated with a 1M HCl aqueous solution to adjust the pH value to 6. The aqueous mixture was extracted with ethyl acetate (100 mL×2), and the combined organic extracts were washed with brine (100 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (5.0% ACN up to 46.0% in 1 min, up to 60.0% in 7 min); Detector, uv 254/220 nm. After purification 3-[4-[(1S,4R,5R)-5-[[4-cyclopropyl-1-(2,6-dichlorophenyl)-1H-pyrazol-5-yl]methoxy]-3-oxo-2-azabicyclo[2.2.1]heptan-2-yl]-3-fluorophenyl]propanoic acid I-39 (38.2 mg, 25%) was obtained as a white solid. $^1$H NMR (300 MHz, CD$_3$OD): δ 7.69-7.50 (m, 3H), 7.49 (s, 1H), 7.22 (t, J=8.2 Hz, 1H), 7.16-7.03 (m, 2H), 4.55 (d, J=1.6 Hz, 2H), 4.18 (s, 1H), 3.96 (d, J=6.6 Hz, 1H), 2.93 (t, J=7.4 Hz, 2H), 2.82 (d, J=1.7 Hz, 1H), 2.62 (t, J=7.4 Hz, 2H), 2.23 (dd, J=13.6, 7.0 Hz, 1H), 2.12 (d, J=9.9 Hz, 1H), 1.94-1.75 (m, 2H), 1.50 (d, J=13.5 Hz, 1H), 1.09-0.91 (m, 2H), 0.69 (qd, J=4.5, 1.5 Hz, 2H). MS (ES, m/z): [M+1]=558.

Example 38: 3-{4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-3-fluorophenyl}cyclobutane-1-carboxylic acid (I-40)

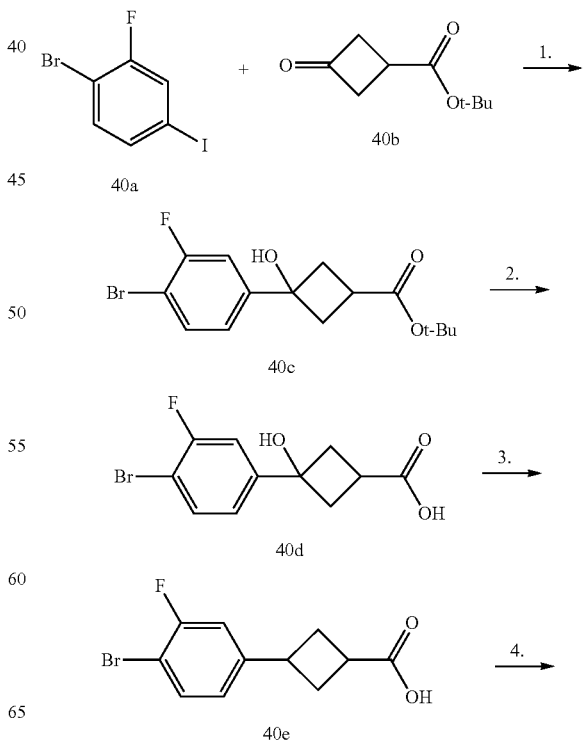

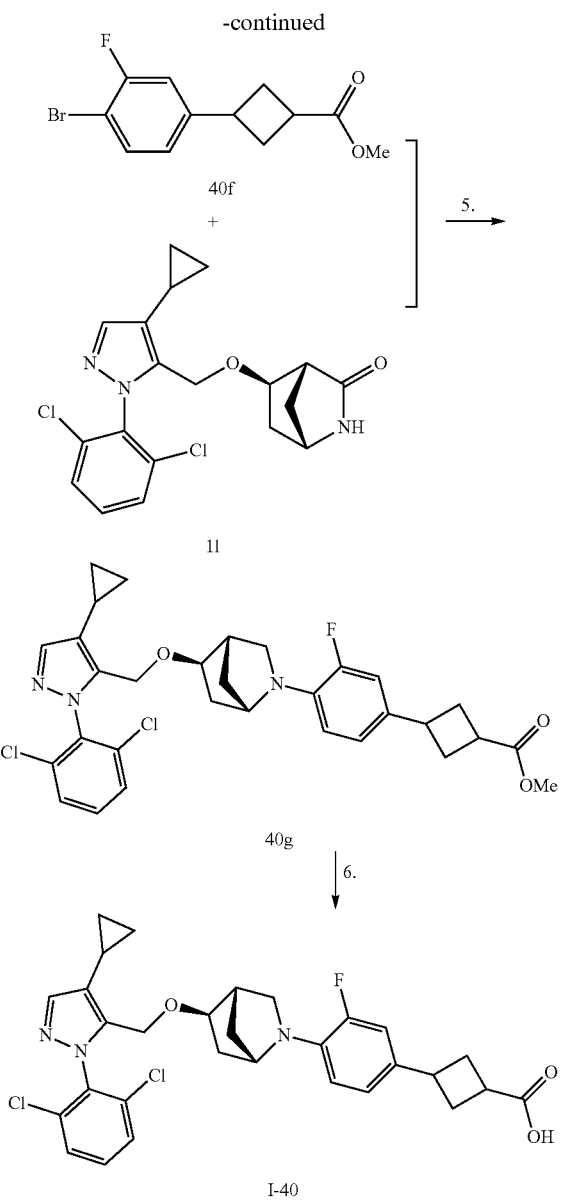

tane-1-carboxylate 40c (620 mg, 1.80 mmol, 1.00 equiv.), methanol (3 mL), and a 40% sodium hydroxide aqueous solution (3 mL, 17.00 equiv.). The resulting mixture was stirred at room temperature for 3 h. The pH value of the solution was adjusted to 4 using a 1M HCl aqueous solution. The aqueous mixture was extracted with ethyl acetate (250 mL×2), and the combined organic extracts were washed with brine, dried over anhydrous sodium sulfate and concentrated under vacuum to provide 3-(4-bromo-3-fluorophenyl)-3-hydroxycyclobutane-1-carboxylic acid 40d (570 mg) as a light yellow crude oil.

Step 3. To a 25 mL round-bottom flask was added 3-(4-bromo-3-fluorophenyl)-3-hydroxycyclobutane-1-carboxylic acid 40d (570 mg, 1.97 mmol, 1.00 equiv.), trifluoroacetic acid (5.7 mL), and triethylsilane (458 mg, 3.94 mmol, 2.00 equiv.). The resulting mixture was stirred at room temperature for 4 h. The mixture was diluted with 100 mL of EA, and washed with a 10% $Na_2SO_3$ aqueous solution (150 mL×3). The pH value of the aqueous washings were adjusted to 4 using a 1M HCl aqueous solution, and the aqueous mixture was extracted with ethyl acetate (150 mL×2). All organic extracts were combined, dried over anhydrous sodium sulfate and concentrated under vacuum. The residue was purified by silica gel column chromatography eluting with ethyl acetate/petroleum ether (1:3) to afford 3-(4-bromo-3-fluorophenyl)cyclobutane-1-carboxylic acid 40e (350 mg, 65%) as a light yellow powder.

Step 4. To a 25 mL round-bottom flask was added 3-(4-bromo-3-fluorophenyl)cyclobutane-1-carboxylic acid 40e (350 mg, 1.28 mmol, 1.00 equiv.) and methanol (2.6 mL, 3.00 equiv). Thionyl chloride (303.7 mg, 2.55 mmol, 2.00 equiv.) was added dropwise with stirring at 0° C. The resulting mixture was heated at 70° C. for 1 h. After cooling to room temperature, the mixture was quenched with water/ice. The aqueous mixture was extracted with ethyl acetate (150 mL×2), and the combined organic extracts were washed with brine, dried over anhydrous sodium sulfate and concentrated under vacuum. The residue was purified by silica gel column chromatography eluting with ethyl acetate/petroleum ether (1:10) to give methyl 3-(4-bromo-3-fluorophenyl)cyclobutane-1-carboxylate 40f (280 mg, 76%) as a light yellow oil.

Step 5. To a 25 mL round-bottom flask was added (1S,4S,5R)-5-[4-cyclopropyl-1-(2,6-dichlorophenyl)-1H-pyrazol-5-yl]methoxy-2-azabicyclo[2.2.1]heptane 1I (80 mg, 0.21 mmol, 1.00 equiv.), methyl 3-(4-bromo-3-fluorophenyl)cyclobutane-1-carboxylate 40f (92 mg, 0.32 mmol, 1.50 equiv.), Ru-phos-precatalyst (36.8 mg, 0.20 equiv.), Ru-phos (20 mg, 0.20 equiv.), $Cs_2CO_3$ (208 mg, 0.64 mmol, 3.00 equiv.), and toluene (8 mL). The resulting mixture was heated at 110° C. overnight. After cooling to room temperature, water was added, the mixture was extracted with ethyl acetate (100 mL×2). The combined organic extracts were washed with brine (100 mL×3), dried over sodium sulfate and concentrated under vacuum. The residue was purified by silica gel column chromatography eluting with EA:PE (1:3) to give This methyl 3-[4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-3-fluorophenyl]cyclobutane-1-carboxylate 40g (60 mg, 49%) as a light yellow oil.

Step 6. To a 25 mL round-bottom flask was added methyl 3-[4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-3-fluorophenyl]cyclobutane-1-carboxylate 40g (60 mg, 0.10 mmol, 1.00 equiv.), methanol (1 mL), water (0.5 mL), and LiOH (44 mg, 1.84 mmol, 10.00 equiv.). The resulting mixture was heated at 60° C. for 1 h. After cooling Step 1. To a 100 mL 3-necked round-bottom flask was added a solution of 1-bromo-2-fluoro-4-iodobenzene 40a (1 g, 3.32 mmol, 1.00 equiv.) in tetrahydrofuran (10.4 mL). A 2M solution of i-PrMgCl in THF (1.7 mL, 1.00 equiv) was added dropwise with stirring at 0° C. during a 30 min period. The reaction mixture was stirred for another 3 h at 0° C., then cooled to −70° C., and added with tert-Butyl 3-oxocyclobutane-1-carboxylate 40b (570 mg, 3.35 mmol, 1.00 equiv.) dropwise in 10 min. The resulting mixture was stirred at −78° C. for 1 h, and continued at room temperature overnight. Water was added, the mixture was extracted with ethyl acetate (250 mL×2), and the combined organic extracts were washed with a saturated $NH_4Cl$ aqueous solution (250 mL×3), dried over anhydrous sodium sulfate and concentrated under vacuum. The residue was purified by silica gel column chromatography eluting with ethyl acetate/petroleum ether (1:15) to afford tert-butyl 3-(4-bromo-3-fluorophenyl)-3-hydroxycyclobutane-1-carboxylate 40c (620 mg, 54%) as a light yellow oil.

Step 2. To a 25 mL round-bottom flask was added tert-butyl 3-(4-bromo-3-fluorophenyl)-3-hydroxycyclobuto room temperature, the mixture was diluted with ethyl acetate (20 mL), and the pH value of the solution was adjusted to 4 using a 1M HCl aqueous solution. The aqueous mixture was extracted with ethyl acetate (100 mL×2), and the combined organic extracts were washed with brine (100 mL×3), dried over anhydrous sodium sulfate and concentrated under vacuum. The crude product was purified by Prep-HPLC using the following conditions: Column, XBridge Shield RP18 OBD Column 5 um, 19*150 mm; mobile phase, Water (0.05% TFA) and ACN (5.0% ACN up to 64.0% in 1 min, up to 66.0% in 7 min); Detector, uv 254/220 nm. After purification 3-[4-[(1S,4S,5R)-5-[[4-cyclopropyl-1-(2,6-dichlorophenyl)-1H-pyrazol-5-yl]methoxy]-2-azabicyclo[2.2.1]heptan-2-yl]-3-fluorophenyl]cyclobutane-1-carboxylic acid I-40 (28.8 mg, 49%) was obtained as an off-white solid. $^1$H NMR (300 MHz, CD$_3$OD): δ 7.66-7.43 (m, 3H), 7.44 (s, 1H), 6.97-6.82 (m, 2H), 6.64 (td, J=8.5, 3.1 Hz, 1H), 4.44 (d, J=2.4 Hz, 2H), 4.06 (s, 1H), 3.71-3.34 (m, 3H), 3.17-2.98 (m, 1H), 2.66-2.50 (m, 3H), 2.42 (d, J=10.9 Hz, 1H), 2.44-2.16 (m, 2H), 2.07-1.91 (m, 1H), 1.79 (tt, J=8.3, 5.1 Hz, 1H), 1.56 (s, 2H), 1.24 (d, J=13.6 Hz, 1H), 1.05-0.83 (m, 2H), 0.71-0.59 (m, 2H). MS (ES, m/z): [M+1]=570.

Example 39: 4-[(1S,4S,5R)-5-{[1-cyclopropyl-4-(2,6-dichlorophenyl)-1H-pyrazol-5-yl]methoxy}-2-azabicyclo[2.2.1]heptan-2-yl]benzoic acid (I-41)

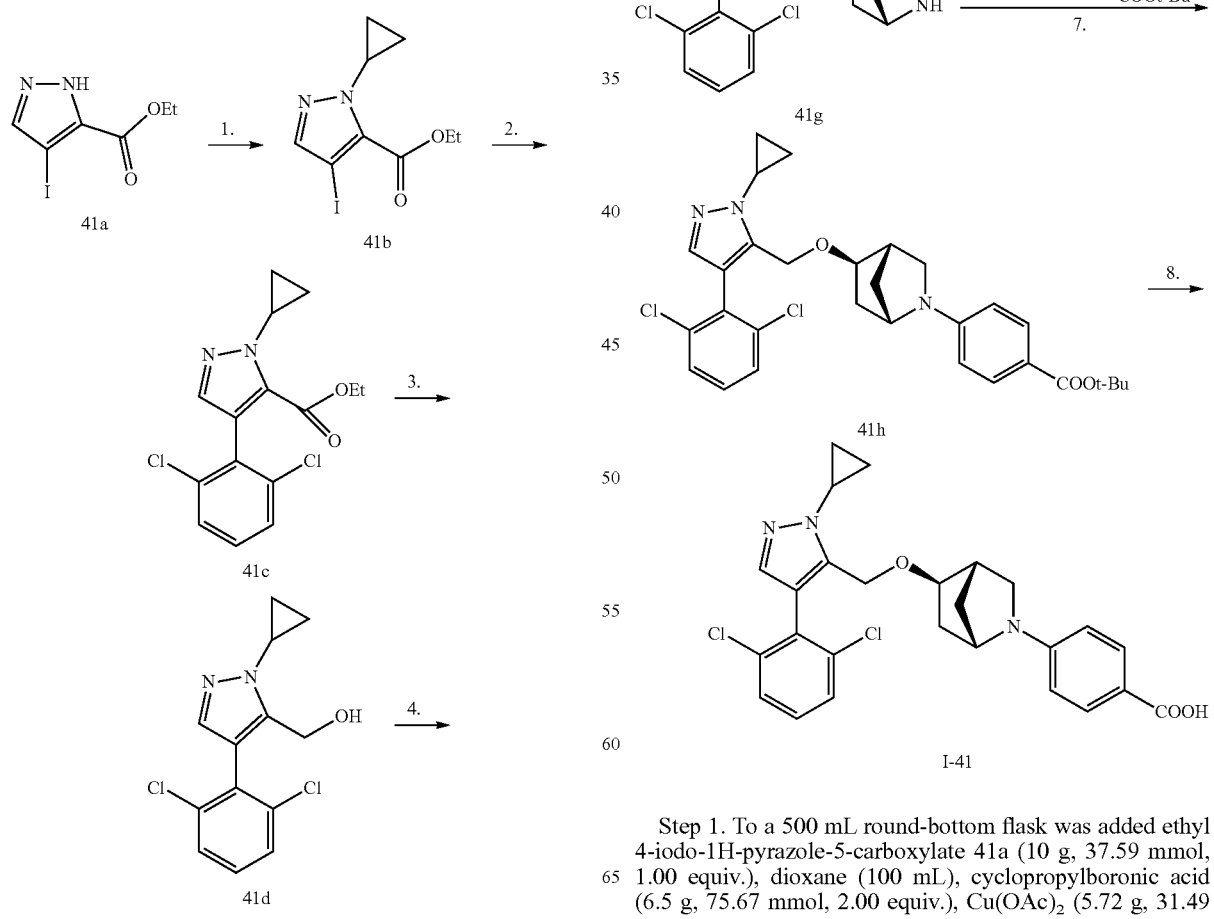

Step 1. To a 500 mL round-bottom flask was added ethyl 4-iodo-1H-pyrazole-5-carboxylate 41a (10 g, 37.59 mmol, 1.00 equiv.), dioxane (100 mL), cyclopropylboronic acid (6.5 g, 75.67 mmol, 2.00 equiv.), Cu(OAc)$_2$ (5.72 g, 31.49 mmol, 0.84 equiv.), Cs$_2$CO$_3$ (30.6 g, 93.92 mmol, 2.50 equiv.), and 4-dimethylaminopyridine (18.3 g, 149.79 mmol, 4.00 equiv.). The resulting mixture was stirred at 50° C. for 12 h under an atmosphere of oxygen. After cooling to room temperature, the mixture was diluted with 300 mL of EA, washed with brine (100 mL×3), dried and concentrated. The residue was purified by silica gel column chromatography eluting with ethyl acetate/petroleum ether (0% to 10%) to give ethyl 1-cyclopropyl-4-iodo-1H-pyrazole-5-carboxylate 41b (4.37 g, 38%) as a colorless oil.

Step 2. To a 250 mL round-bottom flask was added ethyl 1-cyclopropyl-4-iodo-1H-pyrazole-5-carboxylate 41b (2.0 g, 6.53 mmol, 1.00 equiv.), toluene (100 mL), (2,6-dichlorophenyl)boronic acid (2.5 g, 13.10 mmol, 2.00 equiv.), $Pd_2(dba)_3$ (340 mg, 0.37 mmol, 0.05 equiv.), $K_3PO_4$ (4.2 g, 19.79 mmol, 3.00 equiv.), and Sphos (540 mg, 1.32 mmol, 0.20 equiv.). The resulting mixture was heated at 100° C. overnight. Upon cooling to room temperature, the mixture was diluted with EA (500 mL), washed with brine (300 mL×3), dried over sodium sulfate and concentrated under vacuum. The residue was purified by silica gel column chromatography eluting with ethyl acetate/petroleum ether (0% to 10%) to afford ethyl 1-cyclopropyl-4-(2,6-dichlorophenyl)-1H-pyrazole-5-carboxylate 41c (1.8 g, 85%) as a colorless oil.

Step 3. To a 250 mL round-bottom flask was added ethyl 1-cyclopropyl-4-(2,6-dichlorophenyl)-1H-pyrazole-5-carboxylate 41c (1.913 g, 5.88 mmol, 1.00 equiv.), tetrahydrofuran (20 mL), and $LiAlH_4$ (449 mg, 11.83 mmol, 2.00 equiv.). The resulting mixture was stirred at room temperature for 2 h. The mixture was diluted with ethyl acetate, and quenched with the addition of a 1M hydrogen chloride aqueous solution slowly. The aqueous mixture was extracted with ethyl acetate (250 mL×2), and the combined organic extracts were washed with brine (100 mL×2), dried over anhydrous sodium sulfate and concentrated under vacuum to provide [1-cyclopropyl-4-(2,6-dichlorophenyl)-1H-pyrazol-5-yl]methanol 41d (650 mg, 39%) as a colorless oil.

Step 4. To a 100 mL round-bottom flask was added benzotriazole (210 mg, 1.00 equiv.) and dichloromethane (5 mL). The solution was cooled at 0° C., thionyl chloride (418 mg, 2.00 equiv.) was added dropwise with stirring. Reaction continued for 30 min. A solution of [1-cyclopropyl-4-(2,6-dichlorophenyl)-1H-pyrazol-5-yl]methanol 41d (500 mg, 1.77 mmol, 1.00 equiv.) in dichloromethane (5 mL) was added slowly at 0° C. The resulting mixture was then stirred at room temperature overnight. The mixture was diluted with of ethyl acetate, quenched by the addition of water/ice. The aqueous mixture was extracted with ethyl acetate (150 mL), and the organic extract was washed with brine (30 mL×3), dried over anhydrous sodium sulfate and concentrated under vacuum. The residue was purified by silica gel column chromatography eluting with ethyl acetate/petroleum ether (1:5) to afford 5-(chloromethyl)-1-cyclopropyl-4-(2,6-dichlorophenyl)-1H-pyrazole 41e (334 mg, 63%) as a light yellow oil.

Step 5. To a 50 mL round-bottom flask was added 5-(chloromethyl)-1-cyclopropyl-4-(2,6-dichlorophenyl)-1H-pyrazole 41e (280 mg, 0.93 mmol, 1.00 equiv.), N,N-dimethylformamide (3 mL), and benzyl (1S,4S,5R)-5-hydroxy-2-azabicyclo[2.2.1]heptane-2-carboxylate C-1 (231 mg, 0.93 mmol, 1.00 equiv.). The mixture was cooled to 0° C., and sodium hydride (75 mg, 60% dispersed in mineral oil, 3.12 mmol, 2.00 equiv.) was added in portions. The resulting mixture was stirred at room temperature overnight, diluted with ethyl acetate, and then quenched by the addition of water/ice. The aqueous mixture was extracted with 100 mL of ethyl acetate. The organic extract was washed with brine (30 mL×3), dried over anhydrous sodium sulfate and concentrated under vacuum to give benzyl (1S,4S,5R)-5-[[1-cyclopropyl-4-(2,6-dichlorophenyl)-1H-pyrazol-5-yl]methoxy]-2-azabicyclo[2.2.1]heptane-2-carboxylate 41f (460 mg, 97%) as a light yellow crude oil.

Step 6. To a 50 mL round-bottom flask was added benzyl (1S,4S,5R)-5-[[1-cyclopropyl-4-(2,6-dichlorophenyl)-1H-pyrazol-5-yl]methoxy]-2-azabicyclo[2.2.1]heptane-2-carboxylate 41f (460 mg, 0.90 mmol, 1.00 equiv.) and dichloromethane (8 mL). TMSI (373 mg, 2.00 equiv.) was added dropwise with stirring. The resulting mixture was stirred at room temperature for 30 min, then diluted with dichloromethane. The reaction was quenched by the addition of a 1M hydrogen chloride aqueous solution. The resulting mixture was extracted with dichloromethane (50 mL×2). The combined organic extracts were washed with brine, dried over anhydrous sodium sulfate and concentrated under vacuum. The residue was purified by silica gel column chromatography eluting with dichloromethane/methanol (10:1) to afford (1S,4S,5R)-5-[[1-cyclopropyl-4-(2,6-dichlorophenyl)-1H-pyrazol-5-yl]methoxy]-2-azabicyclo[2.2.1]heptane 41g (170 mg, 50%) as a light yellow solid.

Step 7. To a 50 mL round-bottom flask purged and maintained under an inert atmosphere of nitrogen was added (1S,4S,5R)-5-[[1-cyclopropyl-4-(2,6-dichlorophenyl)-1H-pyrazol-5-yl]methoxy]-2-azabicyclo[2.2.1]heptane 41g (120 mg, 0.32 mmol, 1.00 equiv.), toluene (5 mL), $Pd_2(dba)_3$ (43 mg, 0.05 mmol, 0.10 equiv.), BINAP (58 mg, 0.09 mmol, 0.20 equiv.), $Cs_2CO_3$ (460 mg, 1.41 mmol, 3.00 equiv.), and tert-butyl 4-bromobenzoate (256 mg, 1.00 mmol, 1.00 equiv.). The resulting mixture was heated at 110° C. overnight and concentrated under vacuum. The residue was purified by silica gel column chromatography eluting with ethyl acetate/petroleum ether (1:5) to afford tert-butyl 4-[(1S,4S,5R)-5-[[1-cyclopropyl-4-(2,6-dichlorophenyl)-1H-pyrazol-5-yl]methoxy]-2-azabicyclo[2.2.1]heptan-2-yl]benzoate 41h (80 mg, 45%) as a light yellow solid.

Step 8. To a 50 mL round-bottom flask was added tert-butyl 4-[(1S,4S,5R)-5-[[1-cyclopropyl-4-(2,6-dichlorophenyl)-1H-pyrazol-5-yl]methoxy]-2-azabicyclo[2.2.1]heptan-2-yl]benzoate 41h (80 mg, 0.14 mmol, 1.00 equiv.), dichloromethane (2 mL), and trifluoroacetic acid (1 mL). The resulting mixture was stirred for 1 h at room temperature, and quenched with water. The aqueous mixture was extracted with ethyl acetate (200 mL), and the organic extract was washed with brine (30 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (50.0% ACN up to 65.0% in 8 min); Detector, uv 254 nm. After purification 4-[(1S,4S,5R)-5-[[1-cyclopropyl-4-(2,6-dichlorophenyl)-1H-pyrazol-5-yl]methoxy]-2-azabicyclo[2.2.1]heptan-2-yl]benzoic acid I-41 (23.1 mg, 32%) was obtained as an off-white solid. $^1$H NMR (300 MHz, $CD_3OD$): δ 7.81-7.72 (m, 2H), 7.44 (dd, J=7.4, 1.9 Hz, 1H), 7.36-7.20 (m, 3H), 6.44 (d, J=8.9 Hz, 2H), 4.61-4.44 (m, 2H), 4.14 (s, 1H), 3.68-3.52 (m, 1H), 3.46 (d, J=6.3 Hz, 1H), 3.37-3.27 (m, 1H), 2.54 (d, J=9.4 Hz, 1H), 2.45 (s, 1H), 1.70 (d, J=9.7 Hz, 3H), 1.58 (d, J=10.2 Hz, 1H), 1.40-1.04 (m, 5H). MS (ES, m/z): [M+1]=498.

Example 40: 4-[(1S,4S,5R)-5-{[1-cyclopropyl-4-(2,6-dichlorophenyl)-1H-pyrazol-5-yl]methoxy}-2-azabicyclo[2.2.1]heptan-2-yl]-2-fluorobenzoic acid (I-42)

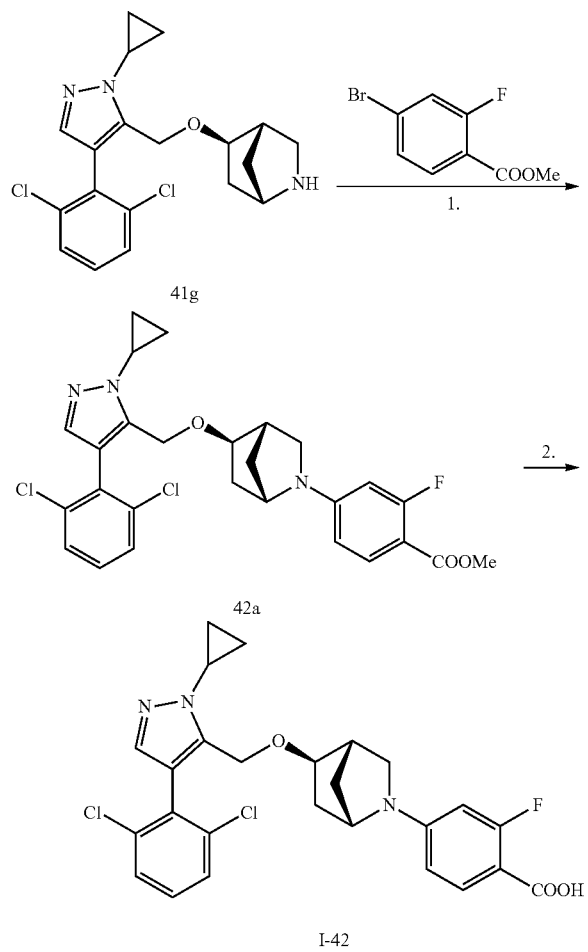

Step 1. To a 50 mL round-bottom flask purged and maintained under an inert atmosphere of nitrogen was added a solution of (1S,4S,5R)-5-[[1-cyclopropyl-4-(2,6-dichlorophenyl)-1H-pyrazol-5-yl]methoxy]-2-azabicyclo[2.2.1]heptane 41g (650 mg, 1.72 mmol, 1.00 equiv.) in toluene (10 mL), methyl 4-bromo-2-fluorobenzoate (440 mg, 1.89 mmol, 1.10 equiv.), Xantphos (77.6 mg, 0.13 mmol, 0.20 equiv.), Pd(OAc)$_2$ (200 mg, 0.89 mmol, 0.20 equiv.), and Cs$_2$CO$_3$ (1.68 mg, 0.01 mmol, 3.00 equiv.). The resulting mixture was heated at 90° C. overnight. After cooling to room temperature, the mixture was diluted with water (10 mL), and extracted with ethyl acetate (50 mL×2). The combined organic extracts were washed with brine (50 mL×2), dried over anhydrous sodium sulfate and concentrated under vacuum. The residue was purified by silica gel column chromatography eluting with ethyl acetate/petroleum ether (1:3) to give methyl 4-[(1S,4S,5R)-5-[[1-cyclopropyl-4-(2,6-dichlorophenyl)-1H-pyrazol-5-yl]methoxy]-2-azabicyclo[2.2.1]heptan-2-yl]-2-fluorobenzoate 42a (210 mg, 23%) as a yellow oil.

Step 2. To a 25 mL round-bottom flask was added a solution of methyl 4-[(1S,4S,5R)-5-[[1-cyclopropyl-4-(2,6-dichlorophenyl)-1H-pyrazol-5-yl]methoxy]-2-azabicyclo[2.2.1]heptan-2-yl]-2-fluorobenzoate 42a (210 mg, 0.40 mmol, 1.00 equiv.) in methanol (3 mL), and a solution of LiOH (167 mg, 6.97 mmol, 10.00 equiv.) in water (0.3 mL). The resulting mixture was stirred at 35° C. overnight. The mixture was diluted with EA, and a 1M HCl aqueous solution was added to adjust the pH value of the solution to 3. The aqueous mixture was extracted with ethyl acetate (100 mL), and the organic extract was washed with brine (100 mL), dried over anhydrous sodium sulfate and concentrated under vacuum. The crude product was purified by Prep-HPLC using the following conditions (Column, XBridge Shield RP18 OBD Column 5 um, 19*150 mm; mobile phase, Water (0.05% TFA) and ACN (48.0% ACN up to 66.0% in 8 min); Detector, UV 254 nm. After purification 4-[(1S,4S,5R)-5-[[1-cyclopropyl-4-(2,6-dichlorophenyl)-1H-pyrazol-5-yl]methoxy]-2-azabicyclo[2.2.1]heptan-2-yl]-2-fluorobenzoic acid I-42 (160 mg, 78%) was obtained as a white solid. $^1$H NMR (300 MHz, CD$_3$OD): δ 7.74 (t, J=8.8 Hz, 1H), 7.50 (dd, J=7.7, 1.6 Hz, 1H), 7.43-7.26 (m, 3H), 6.31 (dd, J=8.9, 2.3 Hz, 1H), 6.19 (dd, J=14.6, 2.3 Hz, 1H), 4.66-4.49 (m, 2H), 4.17 (d, J=2.2 Hz, 1H), 3.68 (tt, J=7.3, 3.8 Hz, 1H), 3.53 (d, J=6.4 Hz, 1H), 3.35 (s, 1H), 3.31 (s, 1H), 2.64-2.47 (m, 2H), 1.81-1.58 (m, 3H), 1.47-1.05 (m, 5H). MS (ES, m/z): [M+1]=516.15.

Example 41: 3-{4-[(1S,4S,5R)-5-{[1-cyclopropyl-4-(2,6-dichlorophenyl)-1H-pyrazol-5-yl]methoxy}-2-azabicyclo[2.2.1]heptan-2-yl]phenyl}propanoic acid (I-43)

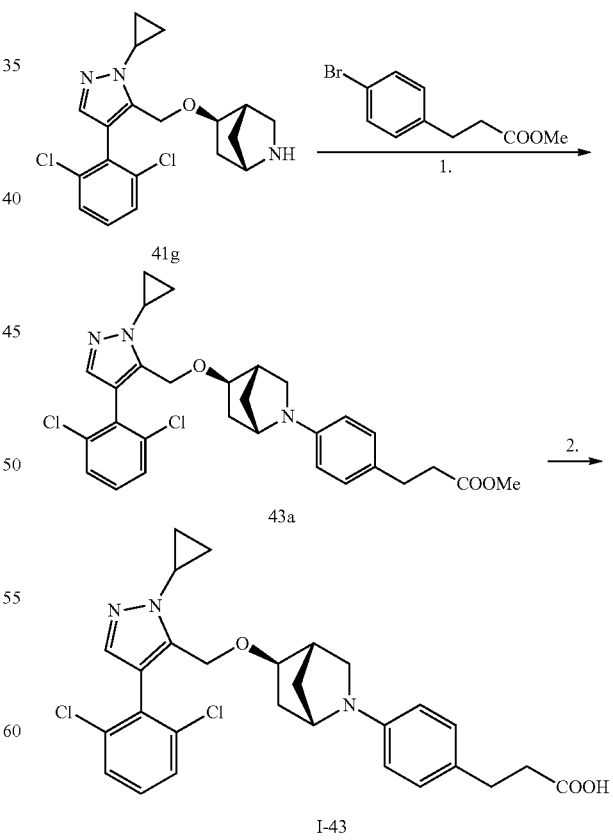

Step 1. To a 8 mL sealed tube was added (1S,4S,5R)-5-[[1-cyclopropyl-4-(2,6-dichlorophenyl)-1H-pyrazol-5-yl]

methoxy]-2-azabicyclo[2.2.1]heptane 41g (150 mg, 0.40 mmol, 1.00 equiv.), a solution of methyl 3-(4-bromophenyl)propanoate (116 mg, 0.48 mmol, 1.20 equiv.) in toluene (3 mL), Ru-phos (38 mg, 0.08 mmol, 0.20 equiv.), Ru-phos-precatalyst (68 mg, 0.08 mmol, 0.20 equiv.), and $Cs_2CO_3$ (260 mg, 0.80 mmol, 2.00 equiv.). The resulting mixture was heated at 110° C. overnight. Upon cooling to room temperature, the mixture was diluted with EA (50 mL), washed successively with $H_2O$ (50 mL) and brine (50 mL), dried over anhydrous sodium sulfate and concentrated under vacuum. The residue was purified by silica gel column chromatography eluting with ethyl acetate/petroleum ether (1:3) to give methyl 3-[4-[(1S,4S,5R)-5-[[1-cyclopropyl-4-(2,6-dichlorophenyl)-1H-pyrazol-5-yl]methoxy]-2-azabicyclo[2.2.1]heptan-2-yl]phenyl]propanoate 43a (108 mg, 50%) as a colorless oil.

Step 2. To a 100 mL round-bottom flask was added methyl 3-[4-[(1S,4S,5R)-5-[[1-cyclopropyl-4-(2,6-dichlorophenyl)-1H-pyrazol-5-yl]methoxy]-2-azabicyclo[2.2.1]heptan-2-yl]phenyl]propanoate 43a (108 mg, 0.20 mmol, 1.00 equiv.), methanol (5 mL), water (0.5 mL), and LiOH (84 mg, 3.51 mmol, 10.00 equiv.). The resulting mixture was heated at 60° C. for 2 h. After cooling to room temperature, the mixture was diluted with EA (50 mL), the pH value of the solution was adjusted to 2 using a 1M HCl aqueous solution, and the mixture was washed with brine (30 mL×2). The organic solution was dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (5.0% ACN up to 47.0% in 1 min, up to 60.0% in 7 min); Detector, uv 254 nm. After purification 3-[4-[(1S,4S,5R)-5-[[1-cyclopropyl-4-(2,6-dichlorophenyl)-1H-pyrazol-5-yl]methoxy]-2-azabicyclo[2.2.1]heptan-2-yl]phenyl]propanoic acid I-43 (32.6 mg, 31%) was obtained as a white solid. $^1$H NMR (300 MHz, $CD_3OD$): δ 7.54-7.45 (m, 1H), 7.44-7.17 (m, 5H), 6.82 (s, 2H), 4.68-4.51 (m, 2H), 4.17 (s, 1H), 3.68 (tt, J=7.5, 3.9 Hz, 1H), 3.55 (d, J=6.8 Hz, 1H), 3.46 (s, 1H), 2.89 (t, J=7.5 Hz, 2H), 2.78 (s, 1H), 2.66-2.52 (m, 3H), 1.82 (d, J=8.2 Hz, 3H), 1.46-1.08 (m, 6H)). MS (ES, m/z): [M+1]=526.25.

Example 42: 3-{4-[(1S,4S,5R)-5-{[1-cyclopropyl-4-(2,6-dichlorophenyl)-1H-pyrazol-5-yl]methoxy}-2-azabicyclo[2.2.1]heptan-2-yl]-3-fluorophenyl}propanoic acid (I-44)

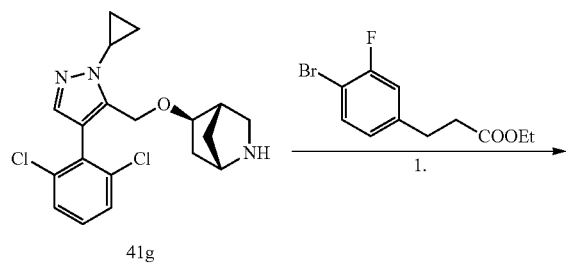

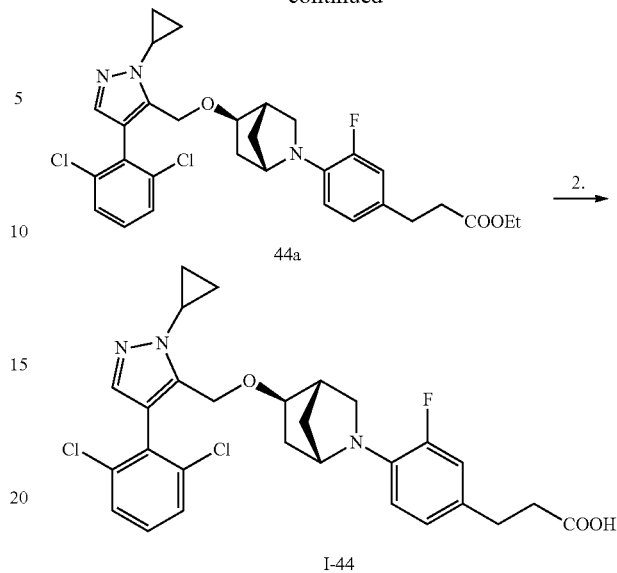

Step 1. To a 8 mL sealed tube was added (1S,4S,5R)-5-[[1-cyclopropyl-4-(2,6-dichlorophenyl)-1H-pyrazol-5-yl]methoxy]-2-azabicyclo[2.2.1]heptane 41g (140 mg, 0.37 mmol, 1.00 equiv.), a solution of ethyl 3-(4-bromo-3-fluorophenyl)propanoate (123 mg, 0.45 mmol, 1.20 equiv) in toluene (3 mL), Ru-phos (35 mg, 0.07 mmol, 0.20 equiv.), Ru-phos-precatalyst (64 mg, 0.08 mmol, 0.20 equiv.), and Cesium carbonate (243 mg, 0.74 mmol, 2.00 equiv.). The resulting mixture was heated at 110° C. overnight. After cooling to room temperature, the mixture was diluted with EA (50 mL), washed successively with $H_2O$ (50 mL) and brine (50 mL), dried over anhydrous sodium sulfate and concentrated under vacuum. The residue was purified by silica gel column chromatography eluting with ethyl acetate/petroleum ether (1:3) to give ethyl 3-[4-[(1S,4S,5R)-5-[[1-cyclopropyl-4-(2,6-dichlorophenyl)-1H-pyrazol-5-yl]methoxy]-2-azabicyclo[2.2.1]heptan-2-yl]-3-fluorophenyl]propanoate 44a (50 mg, 24%) as a colorless oil.

Step 2. To a 100 mL round-bottom flask was added ethyl 3-[4-[(1S,4S,5R)-5-[[1-cyclopropyl-4-(2,6-dichlorophenyl)-1H-pyrazol-5-yl]methoxy]-2-azabicyclo[2.2.1]heptan-2-yl]-3-fluorophenyl]propanoate 44a (50 mg, 0.09 mmol, 1.00 equiv.) and ethanol (5 mL). Water (0.5 mL) was added followed by LiOH (40 mg, 1.67 mmol, 10.00 equiv.). The resulting mixture was stirred at 60° C. for 2 h. The mixture was diluted with EA (50 mL) after cooling to room temperature. The pH value of the solution was adjusted to 2 using a 1M HCl aqueous solution. The mixture was washed with brine (30 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (54.0% ACN up to 60.0% in 8 min); Detector, uv 254 nm. After purification 3-[4-[(1S,4S,5R)-5-[[1-cyclopropyl-4-(2,6-dichlorophenyl)-1H-pyrazol-5-yl]methoxy]-2-azabicyclo[2.2.1]heptan-2-yl]-3-fluorophenyl]propanoic acid I-44 (29.3 mg, 62%) was obtained as a brown solid. $^1$H NMR (300 MHz, $CD_3OD$): δ 7.49 (dd, J=7.1, 2.3 Hz, 1H), 7.42-7.29 (m, 3H), 6.93 (d, J=15.4 Hz, 2H), 6.68 (s, 1H), 4.66-4.49 (m, 2H), 4.11 (s, 1H), 3.49 (t, J=6.9 Hz, 2H), 2.85 (t, J=7.4 Hz, 2H), 2.59 (t, J=7.5 Hz, 2H), 2.43 (s, 1H), 1.69

(d, J=13.6 Hz, 1H), 1.42-1.21 (m, 5H), 1.14 (d, J=7.5 Hz, 2H), 0.13 (s, 2H). MS (ES, m/z): [M+1]=544.10.

Example 43: 4-[(1S,4S,5R)-5-{[1-cyclopropyl-4-(2, 6-dichlorophenyl)-1H-pyrazol-5-yl]methoxy}-2-azabicyclo[2.2.1]heptan-2-yl]-2-fluoro-N-(2-methanesulfonylethyl)benzamide (I-45)

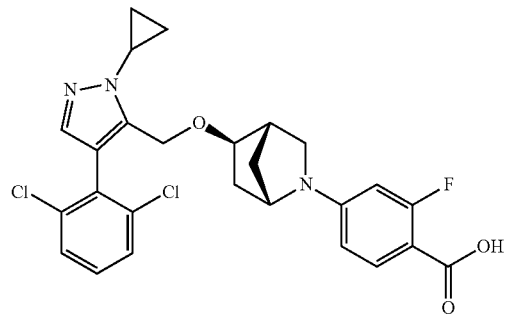

I-42

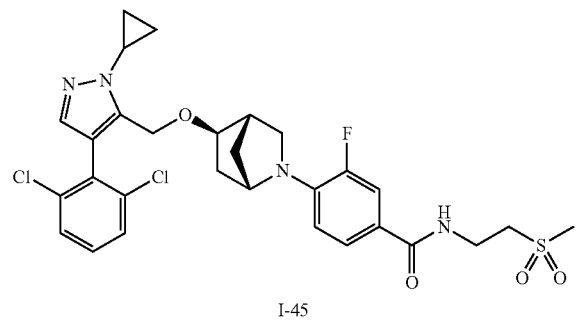

I-45

To a 25 mL round-bottom flask purged and maintained under an inert atmosphere of nitrogen was added a solution of 4-[(1S,4S,5R)-5-[[1-cyclopropyl-4-(2,6-dichlorophenyl)-1H-pyrazol-5-yl]methoxy]-2-azabicyclo[2.2.1]heptan-2-yl]-2-fluorobenzoic acid I-42 (120 mg, 0.23 mmol, 1.00 equiv.) in N,N-dimethylformamide (2.5 mL), 2-methanesulfonylethan-1-amine hydrochloride (48 mg, 0.30 mmol, 1.30 equiv.), HATU (133 mg, 0.35 mmol, 1.50 equiv.), and DIEA (120 mg, 0.93 mmol, 4.00 equiv.). The resulting mixture was stirred for 2 h at room temperature. The solids were filtered out. The crude product was purified by Prep-HPLC using the following conditions (mobile phase, Water (0.05% TFA) and ACN (42.0% ACN up to 60.0% in 8 min); Detector, UV 254 nm. After purification 4-[(1S,4S,5R)-5-[[1-cyclopropyl-4-(2,6-dichlorophenyl)-1H-pyrazol-5-yl]methoxy]-2-azabicyclo[2.2.1]heptan-2-yl]-2-fluoro-N-(2-methanesulfonylethyl)benzamide I-45 (63.4 mg, 44%) was obtained as a white solid. $^1$H NMR (300 MHz, CD$_3$OD): δ 7.69 (t, J=9.0 Hz, 1H), 7.49 (dd, J=7.5, 1.8 Hz, 1H), 7.42-7.26 (m, 3H), 6.36 (dd, J=8.9, 2.3 Hz, 1H), 6.22 (dd, J=15.6, 2.3 Hz, 1H), 4.66-4.48 (m, 2H), 4.15 (s, 1H), 3.93-3.81 (m, 2H), 3.67 (tt, J=7.3, 3.8 Hz, 1H), 3.56-3.37 (m, 3H), 3.04 (d, J=0.7 Hz, 3H), 2.62-2.46 (m, 2H), 1.79-1.57 (m, 3H), 1.46-1.05 (m, 5H). MS (ES, m/z): [M+1]=621.20.

Example 44: 4-[(1S,4S,5R)-5-{[1-cyclopropyl-4-(2, 6-dichlorophenyl)-1H-pyrazol-5-yl]methoxy}-2-azabicyclo[2.2.1]heptan-2-yl]-N-(oxane-4-sulfonyl)benzamide (I-46)

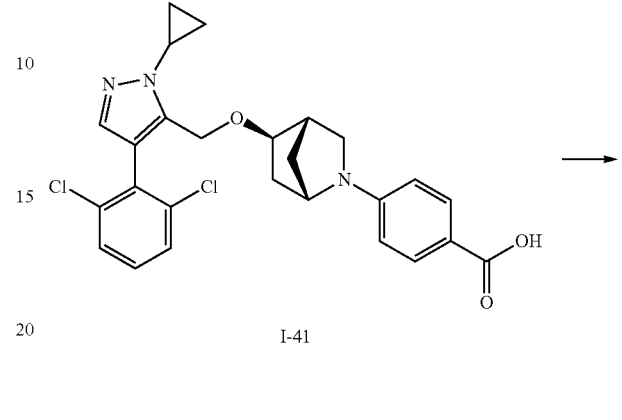

I-41

I-46

To a 8 mL sealed tube was added 4-[(1S,4S,5R)-5-[[1-cyclopropyl-4-(2,6-dichlorophenyl)-1H-pyrazol-5-yl]methoxy]-2-azabicyclo[2.2.1]heptan-2-yl]benzoic acid I-41 (150 mg, 0.30 mmol, 1.00 equiv), a solution of oxane-4-sulfonamide (100 mg, 0.61 mmol, 2.00 equiv.) in dichloromethane (2 mL), 4-dimethylaminopyridine (110 mg, 0.90 mmol, 3.00 equiv), and EDCI (87 mg, 0.45 mmol, 1.50 equiv.). The resulting mixture was stirred overnight at room temperature. The mixture was diluted with 30 mL of DCM, and washed with brine (30 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (45.0% ACN up to 64.0% in 8 min); Detector, UV 254 nm. After purification 4-[(1S,4S,5R)-5-[[1-cyclopropyl-4-(2,6-dichlorophenyl)-1H-pyrazol-5-yl]methoxy]-2-azabicyclo[2.2.1]heptan-2-yl]-N-(oxane-4-sulfonyl)benzamide I-46 (92.7 mg, 48%) as an off-white solid. $^1$H NMR (300 MHz, CD$_3$OD): δ 7.76 (d, J=8.7 Hz, 2H), 7.50 (dd, J=7.6, 1.5 Hz, 1H), 7.43-7.26 (m, 3H), 6.54 (d, J=8.8 Hz, 2H), 4.67-4.50 (m, 2H), 4.23 (s, 1H), 4.08 (d, J=12.3 Hz, 2H), 4.02-3.90 (m, 1H), 3.69 (dt, J=7.4, 3.6 Hz, 1H), 3.57-3.33 (m, 4H), 2.62 (d, J=9.7 Hz, 1H), 2.53 (s, 1H), 2.04-1.88 (m, 4H), 1.82-1.62 (m, 3H), 1.42 (d, J=13.1 Hz, 1H), 1.31-1.09 (m, 4H). MS (ES, m/z): [M+1]=645.25.

Example 45: 2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-fluoro-1,3-benzothiazole-6-carboxylic acid (I-47)

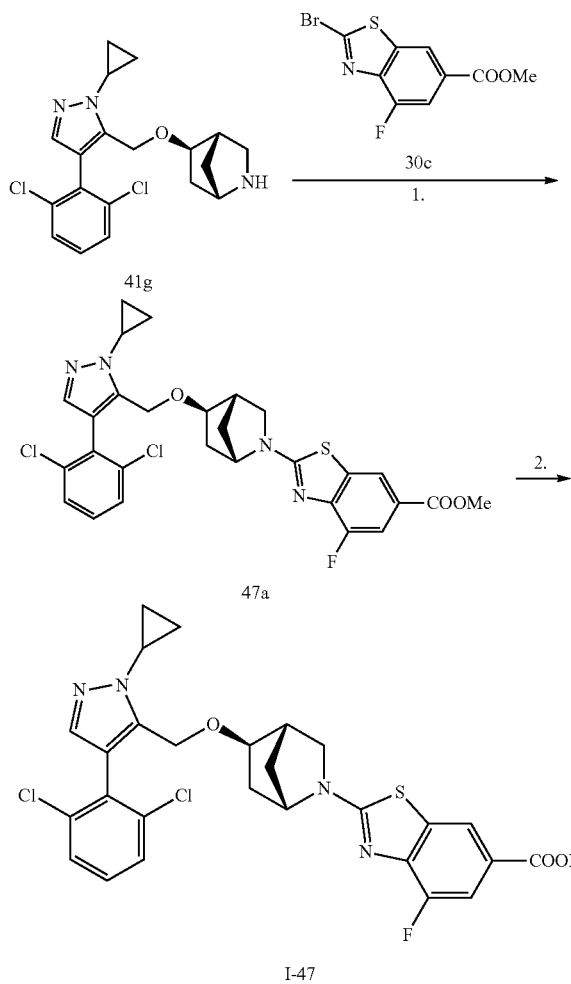

Step 1. To a 50 mL round-bottom flask purged and maintained under an inert atmosphere of nitrogen was added (1S,4S,5R)-5-[[1-cyclopropyl-4-(2,6-dichlorophenyl)-1H-pyrazol-5-yl]methoxy]-2-azabicyclo [2.2.1]heptane 41g (80 mg, 0.21 mmol, 1.00 equiv.), DMA (2 mL), methyl 2-bromo-4-fluoro-1,3-benzothiazole-6-carboxylate 30c (74 mg, 0.26 mmol, 2.00 equiv.), and $Cs_2CO_3$ (137 mg, 0.42 mmol, 2.00 equiv.). The resulting mixture was heated at 60° C. overnight. Upon cooling to room temperature, the mixture was diluted with water (50 mL), extracted with ethyl acetate (50 mL×3), and the combined organic extracts were washed with brine (30 mL×3), dried over anhydrous sodium sulfate and concentrated under vacuum. The residue was purified by silica gel column chromatography eluting with ethyl acetate/petroleum ether (1:5) to afford methyl 2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-4-fluoro-1,3-benzothiazole-6-carboxylate 47a (50 mg, 40%) as an off-white solid.

Step 2. To a 50 mL round-bottom flask was added methyl 2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-4-fluoro-1,3-benzothiazole-6-carboxylate 47a (50 mg, 0.09 mmol, 1.00 equiv), methanol (2 mL), LiOH (40 mg, 1.67 mmol, 10.00 equiv), and water (0.2 mL). The resulting mixture was stirred overnight at 35° C. The mixture was diluted with ethyl acetate (10 mL), and the pH value of the solution was adjusted to 6 using a 1M hydrogen chloride aqueous solution. The aqueous mixture was extracted with ethyl acetate (100 mL×2), and the combined organic extracts were washed with brine (50 mL×2), dried over anhydrous sodium sulfate and concentrated under vacuum. The crude product was purified by Prep-HPLC using the following conditions: Column, XBridge Prep C18 OBD Column, 5 um, 19*150 mm; mobile phase, Water (0.05% TFA) and ACN (50.0% ACN up to 62.0% in 8 min); Detector, uv 254 nm. After purification 2-[(1S,4S,5R)-5-[[1-cyclopropyl-(2,6-dichlorophenyl)-1H-pyrazol-5-yl]methoxy]-2-azabicyclo[2.2.1]heptan-2-yl]-4-fluoro-1,3-benzothiazole-6-carboxylic acid I-47 (33.1 mg, 68%) was obtained as an off-white solid. $^1$H NMR (300 MHz, $CD_3OD$): δ 8.11 (d, J=1.5 Hz, 1H), 7.70-7.59 (m, 1H), 7.46 (dd, J=7.9, 1.4 Hz, 1H), 7.44-7.22 (m, 3H), 4.56 (s, 2H), 4.40-4.21 (m, 1H), 3.70-3.58 (m, 2H), 3.46 (d, J=6.3 Hz, 1H), 2.97 (s, 1H), 2.57 (s, 1H), 1.89 (d, J=8.4 Hz, 1H), 1.83-1.64 (m, 2H), 1.47 (d, J=13.7 Hz, 1H), 1.26 (s, 1H), 1.23-1.17 (m, 2H), 1.17-1.04 (m, 2H). MS (ES, m/z): [M+1]=573.

Example 46: 4-cyclopropoxy-2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-1,3-benzothiazole-6-carboxylic acid (I-48)

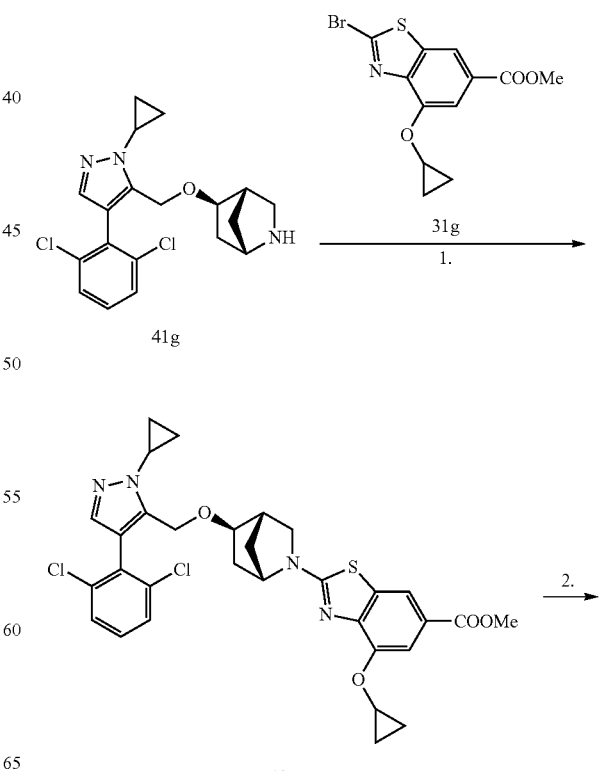

-continued

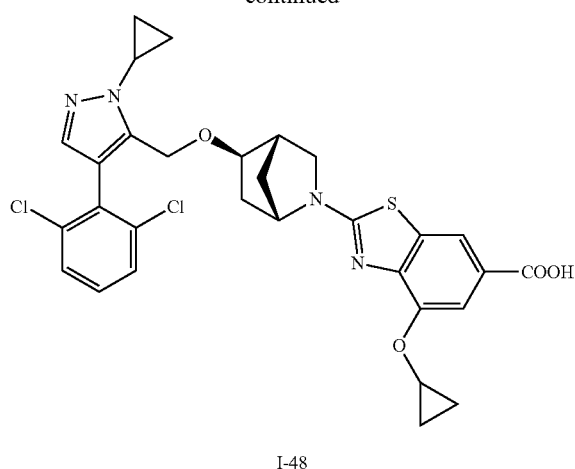

I-48

Step 1. To a 50 mL round-bottom flask was added methyl 2-bromo-4-cyclopropoxy-1,3-benzothiazole-6-carboxylate 31g (80 mg, 0.24 mmol, 1.00 equiv.), Cs$_2$CO$_3$ (160 mg, 0.49 mmol, 2.00 equiv.), DMA (3 mL), and (1S,4S,5R)-5-[1-cyclopropyl-4-(2,6-dichlorophenyl)-1H-pyrazol-5-yl]methoxy-2-azabicyclo[2.2.1]heptane 41g (110 mg, 0.29 mmol, 1.20 equiv.). The resulting mixture was heated at 60° C. overnight. After cooling to room temperature, the mixture was diluted with 20 mL of H$_2$O, and extracted with ethyl acetate (50 mL×2). The combined organic extracts were washed with brine (50 mL×2), dried over anhydrous sodium sulfate and concentrated under vacuum to give methyl 4-cyclopropoxy-2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-1,3-benzothiazole-6-carboxylate 48a (130 mg, 85%) as a yellow oil.

Step 2. To a 50 mL round-bottom flask was added methyl 4-cyclopropoxy-2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-1,3-benzothiazole-6-carboxylate 48a (130 mg, 0.21 mmol, 1.00 equiv.), LiOH—H$_2$O (87 mg, 2.1 mmol, 10.00 equiv.), methanol (3 mL), and water (0.6 mL). The resulting mixture was heated for 1 h at 50° C. The mixture was diluted with 20 mL of H$_2$O upon cooling to room temperature, and extracted with ethyl acetate (50 mL×2). The combined organic extracts were washed with brine (50 mL), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (48% ACN up to 66% in 8 min); Detector, UV 254 nm. 58 mg product was obtained. After purification 4-cyclopropoxy-2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-1,3-benzothiazole-6-carboxylic acid I-48 (57.6 mg, 45%) was obtained as a white solid. $^1$H NMR (300 MHz, CD$_3$OD): δ 8.05 (d, J=1.5 Hz, 1H), 7.95 (d, J=1.5 Hz, 1H), 7.52 (dd, J=8.0, 1.4 Hz, 1H), 7.45-7.38 (m, 1H), 7.34 (t, J=8.0 Hz, 2H), 4.62 (s, 2H), 4.47 (s, 1H), 4.04 (dq, J=6.2, 3.0 Hz, 1H), 3.70 (dq, J=7.0, 3.8 Hz, 2H), 3.35 (s, 1H), 3.08 (s, 1H), 2.66 (s, 1H), 2.00 (dd, J=13.7, 6.5 Hz, 1H), 1.91-1.72 (m, 2H), 1.54 (d, J=13.7 Hz, 1H), 1.32-1.21 (m, 2H), 1.20-1.09 (m, 2H), 0.98-0.86 (m, 4H). MS (ES, m/z): [M+1]=611.2.

Example 47: 2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-(oxan-4-yl)-1,3-benzothiazole-6-carboxylic acid (I-49)

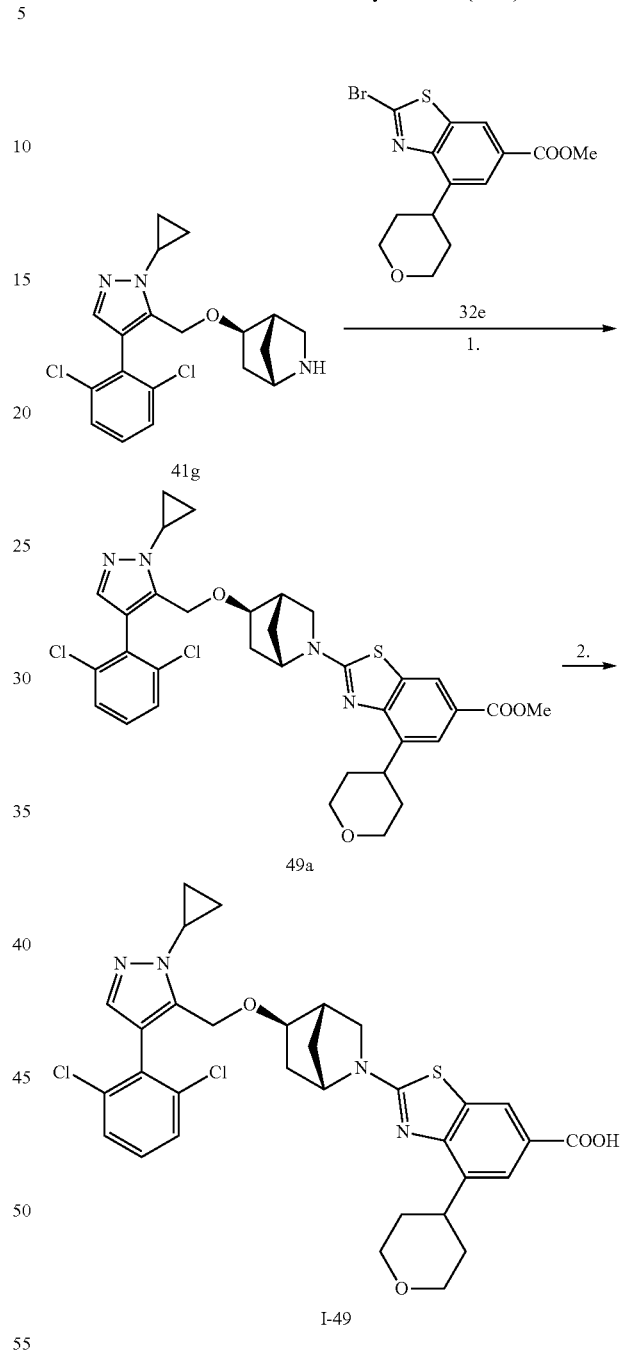

Step 1. To a 50 mL round-bottom flask was added (1S,4S,5R)-5-[[1-cyclopropyl-4-(2,6-dichlorophenyl)-1H-pyrazol-5-yl]methoxy]-2-azabicyclo[2.2.1]heptane 41g (64 mg, 0.17 mmol, 1.00 equiv.), DMA (1.5 mL), methyl 2-bromo-4-(oxan-4-yl)-1,3-benzothiazole-6-carboxylate 32e (60 mg, 0.17 mmol, 1.00 equiv.), and Cs$_2$CO$_3$ (110 mg, 0.34 mmol, 2.00 equiv.). The resulting mixture was heated at 60° C. overnight. After cooling to room temperature, the mixture was diluted with water (20 mL), and extracted with ethyl acetate (50 mL×2). The combined organic extracts were washed with brine (50 mL×2), dried over anhydrous sodium sulfate and concentrated under vacuum. The residue was purified by silica gel column chromatography eluting with ethyl acetate/petroleum ether (1:2) to give methyl 2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-4-(oxan-4-yl)-1,3-benzothiazole-6-carboxylate 49a (100 mg, 90%) as a light yellow solid.

Step 2. To a 50 mL round-bottom flask was added methyl 2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-4-(oxan-4-yl)-1,3-benzothiazole-6-carboxylate 49a (85 mg, 0.13 mmol, 1.00 equiv.), methanol (2 mL), LiOH (55 mg, 2.30 mmol, 10.00 equiv.), and water (0.2 mL). The resulting mixture was stirred overnight at 35° C. and diluted with 10 mL of EA. The pH value of the solution was adjusted to 6 using a 1M hydrogen chloride aqueous solution. The aqueous mixture was extracted with ethyl acetate (50 mL). The organic extract was washed with brine (20 mL×2), dried over anhydrous sodium sulfate and concentrated under vacuum. The residue was dissolved in 2 mL of DMF and purified by Prep-HPLC using the following conditions: Column, XBridge Shield RP18 OBD Column, 5 um, 19*150 mm; mobile phase, Water (0.05% TFA) and ACN (55.0% ACN up to 71.0% in 8 min); Detector, UV 254 nm. After purification 2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-4-(oxan-4-yl)-1,3-benzothiazole-6-carboxylic acid I-49 (47.3 mg, 57%) was obtained as an off-white solid. $^1$H NMR (300 MHz, DMSO-d6): δ 12.62 (s, 1H), 8.21 (d, J=1.7 Hz, 1H), 7.71 (d, J=1.7 Hz, 1H), 7.63-7.32 (m, 4H), 4.53 (s, 2H), 4.05-3.94 (m, 2H), 3.80-3.59 (m, 2H), 3.57-3.31 (m, 4H), 2.96 (s, 1H), 2.60-2.52 (m, 2H), 1.95-1.64 (m, 7H), 1.43 (d, J=13.3 Hz, 1H), 1.29-0.98 (m, 4H). MS (ES, m/z): [M+1]=639.

Example 48: 2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-[(3S)-oxolan-3-yl]-1,3-benzothiazole-6-carboxylic acid (I-50)

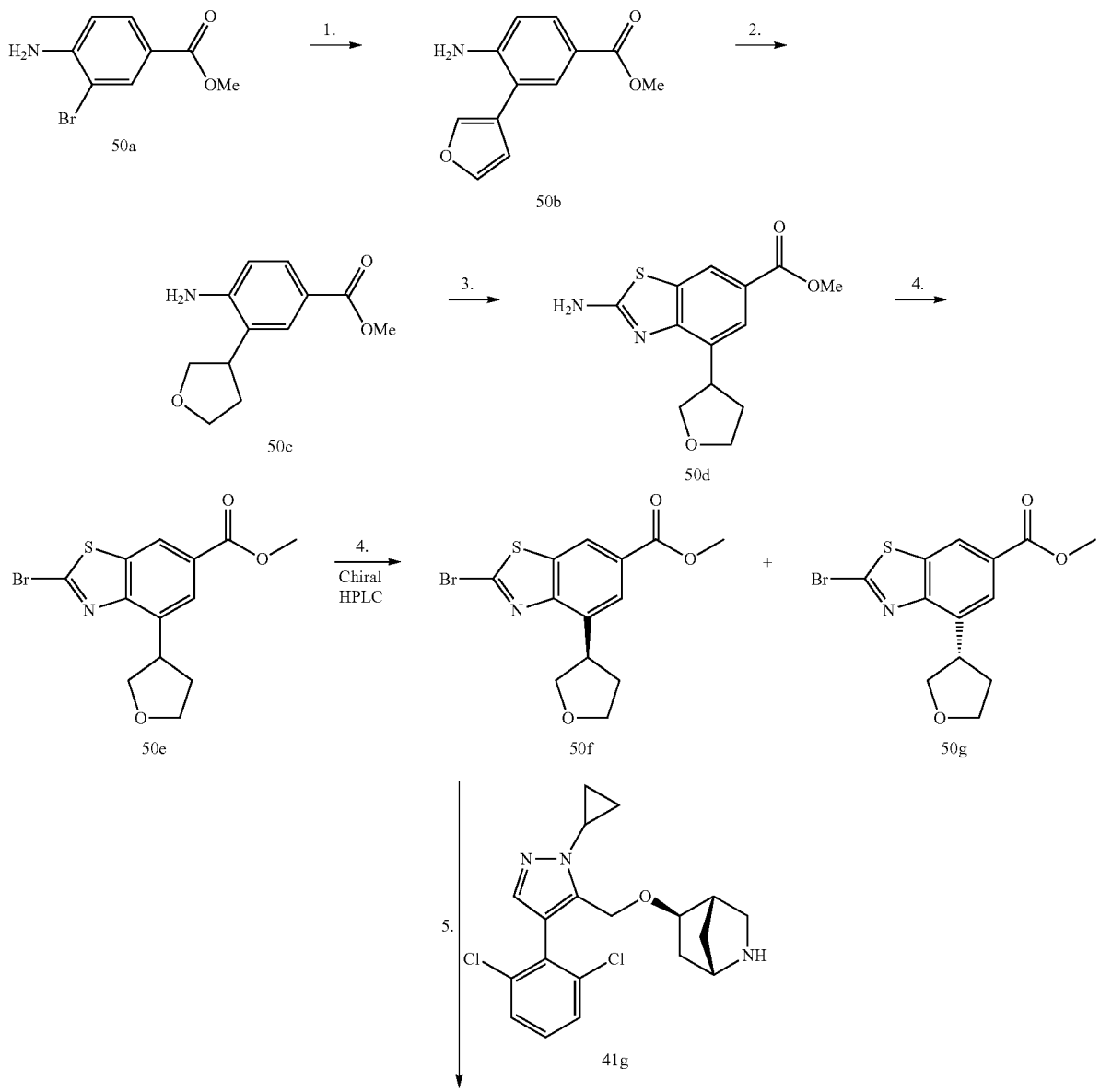

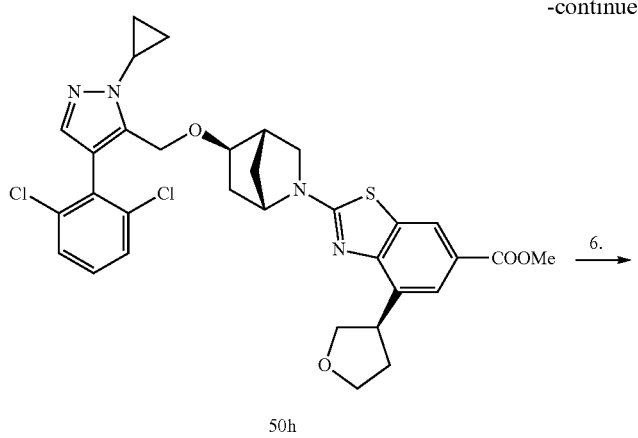

50h

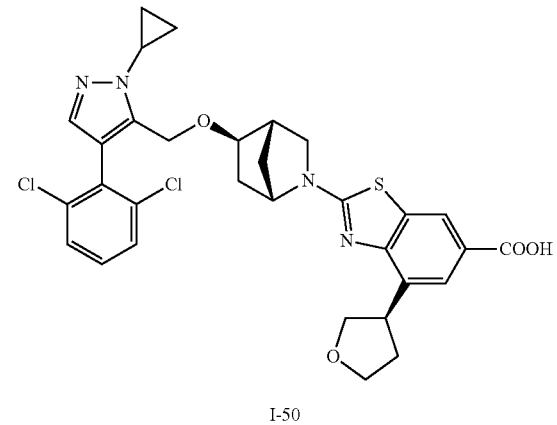

I-50

Step 1. To a 1 L round-bottom flask purged with and maintained under an inert atmosphere of nitrogen was added methyl 4-amino-3-bromobenzoate 50a (13.6 g, 59.12 mmol, 1.00 equiv.), (furan-3-yl)boronic acid (10 g, 89.37 mmol, 1.50 equiv.), 1,4-dioxane (500 mL), 1M aq. $NaHCO_3$ (17.5 g, 3.50 equiv.), and tetrakis(triphenylphosphine) palladium (6.86 g, 5.94 mmol, 0.10 equiv.). The resulting mixture was heated at 110° C. overnight with stirring. After cooling to room temperature, the mixture was diluted with 200 mL of water, and extracted with ethyl acetate (500 mL×2). The combined organic extracts were washed successively with $H_2O$ (500 mL) and brine (500 mL×2), dried over anhydrous sodium sulfate, and concentrated under vacuum. The crude product was purified by Flash-Prep-HPLC using the following conditions (IntelFlash-1): Column, silica gel; mobile phase: EA:PE=0:100 increasing to EA:PE=50:50 within 20 min; Detector, UV 254 nm. Removal of solvents gave methyl 4-amino-3-(furan-3-yl)benzoate 50b (8.345 g, 65%) as a yellow oil.

Step 2. To a 25 mL round-bottom flask was added methyl 4-amino-3-(furan-3-yl) benzoate 50b (7.1 g, 32.69 mmol, 1.00 equiv.), Palladium on carbon (3 g, 10 wt %), tetrahydrofuran (30 mL), and methanol (30 mL). Hydrogen gas was introduced via a gas balloon. The resulting mixture was stirred at 30° C. overnight. The solids were filtered out. The filtrate was concentrated under vacuum to give methyl 4-amino-3-(oxolan-3-yl)benzoate 50c (6.9 g, 95%) as a white solid.

Step 3. To a 500 mL round-bottom flask was added methyl 4-amino-3-(oxolan-3-yl) benzoate 50c (11.7 g, 52.88 mmol, 1.00 equiv.), AcOH (150 mL), NaSCN (17.2 g, 212.35 mmol, 4.00 equiv.), and $Br_2$ (8.5 g, 53.19 mmol, 1.00 equiv.). The resulting mixture was stirred at 30° C. overnight. The reaction was quenched by the addition of 100 mL of water/ice. The pH value of the solution was adjusted to 10 using sodium hydroxide. The solids were collected by filtration and dried to afford methyl 2-amino-4-(oxolan-3-yl)-1,3-benzothiazole-6-carboxylate 50d (12.4 g, 84%) as a yellow solid.

Step 4. To a 50 mL round-bottom flask was added methyl 2-amino-4-(oxolan-3-yl)-1,3-benzothiazole-6-carboxylate 50d (600 mg, 2.16 mmol, 1.00 equiv.), MeCN (10 mL), t-BuONO (502 mg, 4.87 mmol, 2.26 equiv.), $CuBr_2$ (722 mg, 3.24 mmol, 1.50 equiv.). The resulting mixture was stirred at 30° C. overnight and concentrated under vacuum. The residue was purified by silica gel column chromatography eluting with ethyl acetate in hexanes (0% to 5%) to give a racemic mixture 50e (500 mg). This racemic mixture was separated by chiral HPLC under following conditions: Column, CHIRALPAK IF, 2*25 cm, 5 um; mobile phase, Hex- and ethanol-(hold 30.0% ethanol-in 14 min); Detector, UV 254/220 nm. After separation, methyl 2-bromo-4-[(3R)-oxolan-3-yl]-1,3-benzothiazole-6-carboxylate 50f (201.8 mg, 27%) and methyl 2-bromo-4-[(3S)-oxolan-3-yl]-1,3-benzothiazole-6-carboxylate 50g (202.3 mg, 27%) were obtained, both are light yellow solids; the absolute stereo-configuration of 50f and 50g was arbitrarily assigned. 50f: $^1$HNMR (300 MHz, $CDCl_3$): δ 2.124 (1H, m), 2.496 (1H, m), 3.862 (1H, m), 4.032 (4H, m), 4.128 (1H, m), 4.328 (2H, m), 8.060 (1H, s), 8.400 (1H, s); MS (ES, m/z): [M+1]=343; 50g: $^1$HNMR (300 MHz, $CDCl_3$): δ 2.124 (1H, m), 2.496 (1H, m), 3.862 (1H, m), 4.032 (4H, m), 4.128 (1H, m), 4.328 (2H, m), 8.060 (1H, s), 8.400 (1H, s); MS (ES, m/z): [M+1]=343.

Step 5. To a 50 mL round-bottom flask was added (1S,4S,5R)-5-[[1-cyclopropyl-4-(2,6-dichlorophenyl)-1H-pyrazol-5-yl]methoxy]-2-azabicyclo[2.2.1]heptane 41g (66 mg, 0.17 mmol, 1.00 equiv.), DMA (1.5 mL), methyl 2-bromo-4-[(3S)-oxolan-3-yl]-1,3-benzothiazole-6-carboxylate 50f (60 mg, 0.18 mmol, 1.00 equiv), and $Cs_2CO_3$ (115 mg, 0.35 mmol, 2.00 equiv.). The resulting mixture was heated at 60° C. overnight. After cooling to room temperature, the mixture was diluted with water (50 mL), extracted with ethyl acetate (100 mL×2), and the combined organic extracts were washed with brine (50 mL×2), dried over anhydrous sodium sulfate and concentrated under vacuum. The residue was purified by silica gel column chromatography eluting with ethyl acetate/petroleum ether (1:2) to afford methyl 2-[(1S,4S,5R)-5-[[1-cyclopropyl-4-(2,6-dichlorophenyl)-1H-pyrazol-5-yl]methoxy]-2-azabicyclo [2.2.1]heptan-2-yl]-4-[(3S)-oxolan-3-yl]-1,3-benzothiazole-6-carboxylate 50h (90 mg, 81%) as a light yellow solid.

Step 6. To a 50 mL round-bottom flask was added methyl 2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-4-[(3 S)-oxolan-3-yl]-1,3-benzothiazole-6-carboxylate 50h (90 mg, 0.14 mmol, 1.00 equiv.), methanol (1 mL), LiOH (56 mg, 2.34 mmol, 10.00 equiv.), and water (0.2 mL). The resulting mixture was stirred at room temperature overnight. The mixture was diluted with 20 mL of ethyl acetate. The pH value of the solution was adjusted to 6 using a 1M hydrogen chloride aqueous solution. The aqueous mixture was extracted with ethyl acetate (100 mL×2). The combined organic extracts were washed with brine (50 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (60.0% ACN up to 75.0% in 8 min); Detector, UV 254 nm. After purification 2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-4-[(3S)-oxolan-3-yl]-1,3-benzothiazole-6-carboxylic acid I-50 (57.1 mg, 65%) was obtained as an off-white solid. $^1$H NMR (400 MHz, CD$_3$OD): δ 8.23 (d, J=1.6 Hz, 1H), 7.93 (d, J=1.6 Hz, 1H), 7.51 (dd, J=8.0, 1.3 Hz, 1H), 7.42-7.36 (m, 2H), 7.31 (t, J=8.0 Hz, 1H), 4.61 (d, J=2.5 Hz, 2H), 4.38 (s, 1H), 4.26-4.10 (m, 2H), 4.00 (dq, J=15.6, 7.6 Hz, 2H), 3.87 (t, J=7.6 Hz, 1H), 3.69 (ddd, J=12.4, 7.9, 4.5 Hz, 2H), 3.51 (dd, J=10.1, 4.0 Hz, 1H), 3.03 (d, J=10.2 Hz, 1H), 2.61 (s, 1H), 2.51-2.38 (m, 1H), 2.22 (dq, J=12.4, 7.7 Hz, 1H), 1.99-1.89 (m, 1H), 1.84 (d, J=10.3 Hz, 1H), 1.75 (d, J=10.3 Hz, 1H), 1.56-1.46 (m, 1H), 1.33-1.21 (m, 2H), 1.21-1.08 (m, 2H). MS (ES, m/z): [M+1]=625.

Example 49: 2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-[(3R)-oxolan-3-yl]-1,3-benzothiazole-6-carboxylic acid (I-51)

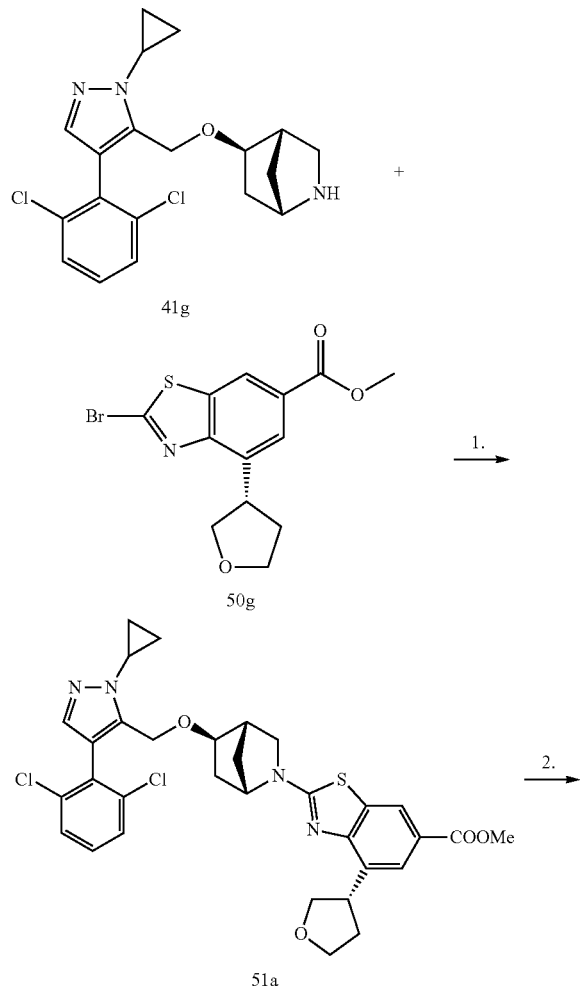

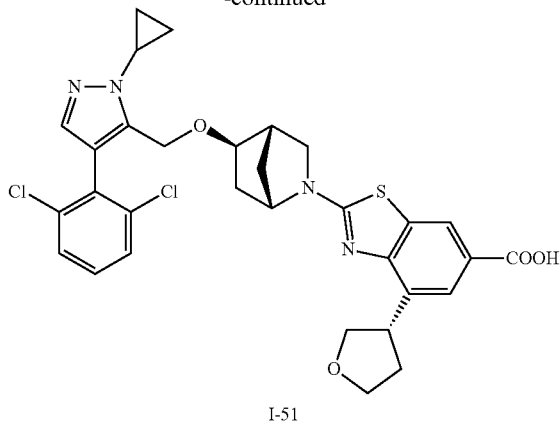

Step 1. To a 50 mL round-bottom flask was added (1S,4S,5R)-5-[[1-cyclopropyl-4-(2,6-dichlorophenyl)-1H-pyrazol-5-yl]methoxy]-2-azabicyclo[2.2.1]heptane 41g (66 mg, 0.17 mmol, 1.00 equiv.), DMA (1.5 mL), methyl 2-bromo-4-[(3R)-oxolan-3-yl]-1,3-benzothiazole-6-carboxylate 50g (60 mg, 0.18 mmol, 1.00 equiv.), and Cs$_2$CO$_3$ (115 mg, 0.35 mmol, 2.00 equiv.). The resulting mixture was heated at 60° C. overnight. After cooling to room temperature, the mixture was diluted with 50 mL of water, extracted with ethyl acetate (100 mL×2), and the combined organic extracts were washed with brine (30 mL×2), dried over anhydrous sodium sulfate and concentrated under vacuum. The residue was purified by silica gel column chromatography eluting with ethyl acetate/petroleum ether (1:2) to provide methyl 2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-4-[(3R)-oxolan-3-yl]-1,3-benzothiazole-6-carboxylate 51a (107 mg, 96%) as a light yellow solid.

Step 2. To a 50 mL round-bottom flask was added methyl 2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-4-[(3R)-oxolan-3-yl]-1,3-benzothiazole-6-carboxylate 51a (107 mg, 0.17 mmol, 1.00 equiv.), methanol (1 mL), LiOH (67 mg, 2.80 mmol, 10.00 equiv), and water (0.2 mL). The resulting mixture was stirred at 35° C. overnight. The mixture was diluted with 20 mL of ethyl acetate. The pH value of the solution was adjusted to 6 using a 1M hydrogen chloride aqueous solution. The aqueous mixture was extracted with ethyl acetate (100 mL×2), and the combined organic extracts were washed with brine (50 mL×2), dried and concentrated. The crude product was purified by Prep-HPLC using the following conditions: Column, XBridge Shield RP18 OBD Column, 5 um, 19*150 mm; mobile phase, Water (0.05% TFA) and ACN (60.0% ACN up to 75.0% in 8 min); Detector, UV 254 nm. After purification 2-[(1S,4S,5R)-5-[[1-cyclopropyl-4-(2,6-dichlorophenyl)-1H-pyrazol-5-yl]methoxy]-2-azabicyclo[2.2.1]heptan-2-yl]-4-[(3R)-oxolan-3-yl]-1,3-benzothiazole-6-carboxylic acid I-51 (44.2 mg, 42%) was obtained as an off-white solid. $^1$H NMR (400 MHz, CD$_3$OD): δ 8.23 (d, J=1.6 Hz, 1H), 7.93 (d, J=1.6 Hz, 1H), 7.50 (dd, J=8.0, 1.3 Hz, 1H), 7.38 (d, J=6.5 Hz, 2H), 7.31 (t, J=8.0 Hz, 1H), 4.67-4.55 (m, 2H), 4.36 (s, 1H), 4.24 (t, J=7.8 Hz, 1H), 4.16 (td, J=8.2, 4.8 Hz, 1H), 4.02 (tt, J=15.5, 7.7 Hz, 2H), 3.83 (t, J=7.7 Hz, 1H), 3.68 (qd, J=7.2, 3.9 Hz, 2H), 3.50 (dd, J=10.1, 4.1 Hz, 1H), 3.03 (d, J=9.9 Hz, 1H), 2.61 (s, 1H), 2.49-2.36 (m, 1H), 2.24 (dq, J=12.4, 7.8 Hz, 1H), 1.99-1.89 (m, 1H), 1.83 (d, J=10.1

Hz, 1H), 1.75 (d, J=10.3 Hz, 1H), 1.55-1.47 (m, 1H), 1.33-1.21 (m, 2H), 1.21-1.08 (m, 2H). MS (ES, m/z): [M+1]=625.

Example 50: 4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]benzoic acid (I-52)

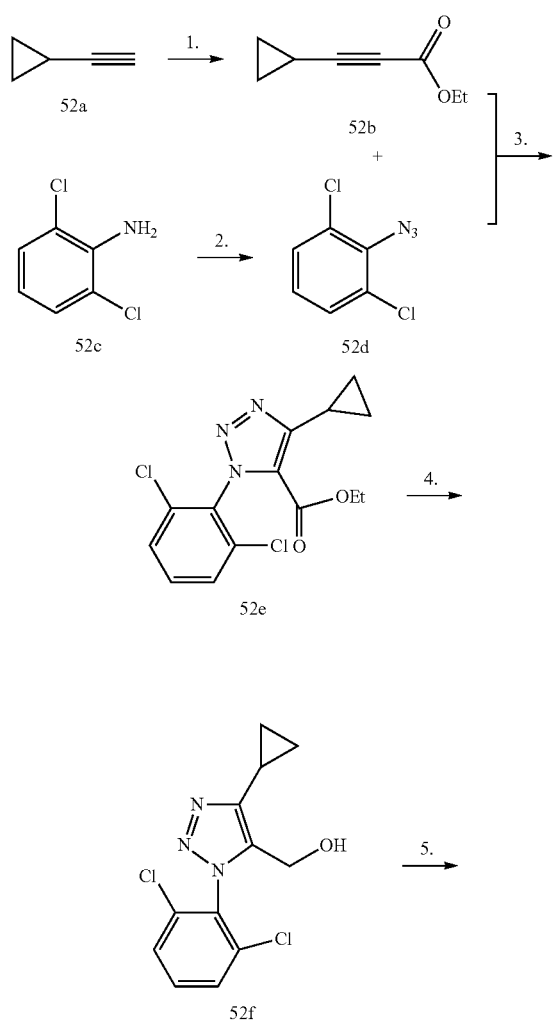

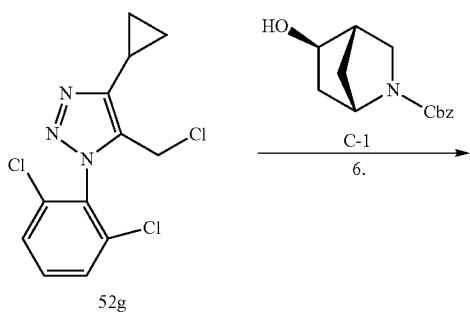

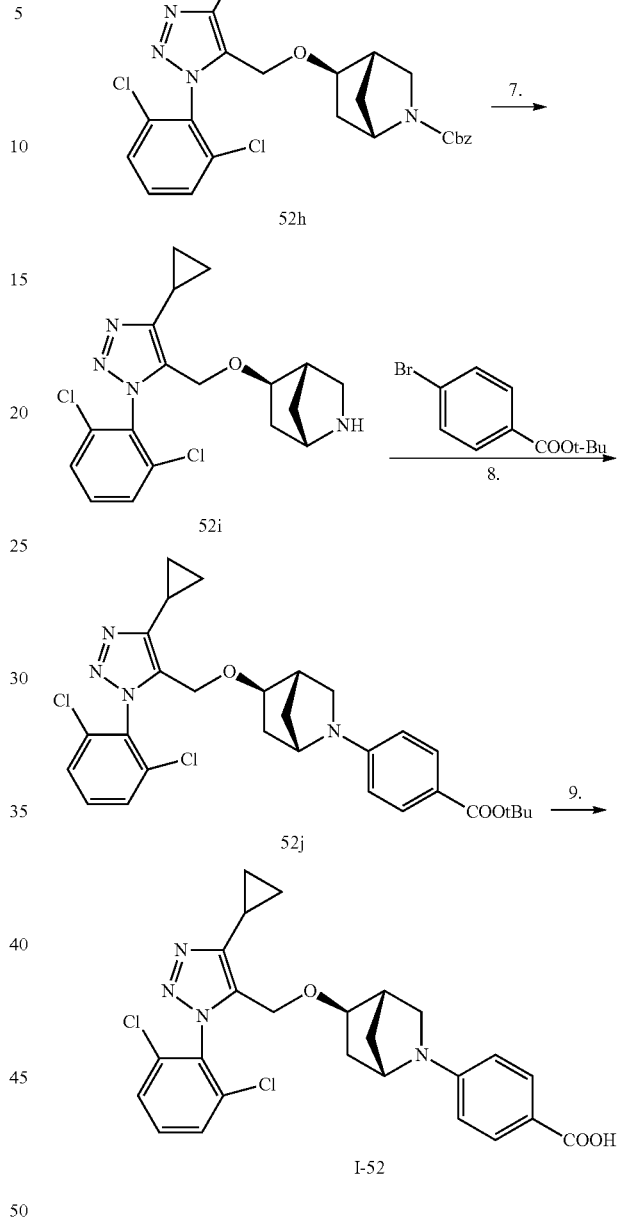

Step 1. To a 250 mL 3-neck round-bottom flask was added cyclopropylacetylene 52a (4.0 g, 60.51 mmol, 1.00 equiv.) and ether (100 mL). The solution was cooled to −78° C., and a 2.5M solution of nBuLi in THF (25.6 mL, 1.10 equiv.) was added dropwise with stirring. Ethyl chloroformate (9 mL, 1.56 equiv.) was added dropwise. Cooling bath was removed, the resulting mixture was stirred for 1 h at room temperature. The reaction was quenched by the addition of a saturated NH$_4$Cl aqueous solution. The aqueous mixture was extracted with ethyl acetate (200 mL×2), and the combined organic extracts were washed with brine (200 mL×2), dried over anhydrous sodium sulfate and concentrated under vacuum. The residue was purified by silica gel column chromatography eluting with petroleum ether to afford ethyl 3-cyclopropylprop-2-ynoate 52b (2.3 g, 28%) as a yellow oil.

Step 2. To a 250 mL round-bottom flask was added 2,6-dichloroaniline 52c (6.41 g, 39.56 mmol, 1.00 equiv.), CH$_3$CN (50 mL), t-BuNO$_2$ (6.1 g, 1.50 equiv), and TMSN$_3$ (5.45 g, 1.20 equiv.).

The resulting mixture was stirred at room temperature for 3h. Solvent was removed under vacuum. The residue was purified by silica gel column chromatography eluting with petroleum ether to give 2-azido-1,3-dichlorobenzene 52d (3.4 g, 46%) as a yellow oil.

Step 3. To a 50 mL round-bottom flask was added 2-azido-1,3-dichlorobenzene 52d (1.29 g, 6.86 mmol, 1.00 equiv.), ethyl 3-cyclopropylprop-2-ynoate 52b (2.3 g, 16.65 mmol, 2.40 equiv.), and toluene (10 mL). The resulting mixture was heated at 110° C. overnight, and concentrated under vacuum. The residue was purified by silica gel column chromatography eluting with ethyl acetate/petroleum ether (1:5) to give ethyl 4-cyclopropyl-1-(2,6-dichlorophenyl)-1H-1,2,3-triazole-5-carboxylate 52e (0.69g, 31%) as a yellow oil.

Step 4. To a 100 mL round-bottom flask was added ethyl 4-cyclopropyl-1-(2,6-dichlorophenyl)-1H-1,2,3-triazole-5-carboxylate 52e (1.2 g, 3.68 mmol, 1.00 equiv.), tetrahydrofuran (15 mL), and LAH (280 mg, 7.38 mmol, 2.00 equiv.). The resulting mixture was stirred at room temperature for 2 h, and quenched with an aqueous solution of Rochelle salt (KNaC$_4$H$_4$O$_6$). The resulting mixture was extracted with ethyl acetate (200 mL×2), and the combined organic extracts were washed with brine (200 mL×2), dried, and concentrated. The residue was purified by silica gel column chromatography eluting with ethyl acetate/petroleum ether (1:1) to give [4-cyclopropyl-1-(2,6-dichlorophenyl)-1H-1,2,3-triazol-5-yl]methanol 52f (0.6 g, 75%) as a yellow oil.

Step 5. To a 250 mL round-bottom flask was added [4-cyclopropyl-1-(2,6-dichlorophenyl)-1H-1,2,3-triazol-5-yl]methanol 52f (570 mg, 2.01 mmol, 1.00 equiv.), benzotriazole (600 mg, 2.50 equiv), thionyl chloride (475 mg, 2.00 equiv), and dichloromethane (50 mL). The resulting mixture was stirred at room temperature overnight. The mixture was diluted with 100 mL of DCM, and washed with brine (100 mL×2), dried over anhydrous sodium sulfate and concentrated under vacuum. The residue was purified by silica gel column chromatography eluting with ethyl acetate/hexane (1:3) to afford 5-(chloromethyl)-4-cyclopropyl-1-(2,6-dichlorophenyl)-1H-1,2,3-triazole 52g (500 mg, 82%) as a yellow oil.

Step 6. To a 100 mL round-bottom flask was added 5-(chloromethyl)-4-cyclopropyl-1-(2,6-dichlorophenyl)-1H-1,2,3-triazole 52g (200 mg, 0.66 mmol, 1.00 equiv.), benzyl (1S,4S,5R)-5-hydroxy-2-azabicyclo[2.2.1]heptane-2-carboxylate C-1 (246 mg, 0.99 mmol, 1.50 equiv.), and N,N-dimethylformamide (10 mL). The mixture was cooled to 0° C., sodium hydride (50 mg, 60% dispersion in mineral oil, 2.08 mmol, 2.00 equiv.) was added in several batches. The resulting mixture was stirred at room temperature overnight. The mixture was diluted with 30 mL of EA, and then quenched by the addition of water/ice. The aqueous mixture was extracted with ethyl acetate (100 mL×2), and the combined organic extracts were washed with brine (100 mL×2), dried over anhydrous sodium sulfate and concentrated under vacuum to give benzyl (1S,4S,5R)-5-[[4-cyclopropyl-1-(2,6-dichlorophenyl)-1H-1,2,3-triazol-5-yl]methoxy]-2-azabicyclo[2.2.1]heptane-2-carboxylate 52h (0.25g, 74%) as a yellow oil.

Step 7. To a 50 mL round-bottom flask was added benzyl (1S,4S,5R)-5-[[4-cyclopropyl-1-(2,6-dichlorophenyl)-1H-1,2,3-triazol-5-yl]methoxy]-2-azabicyclo[2.2.1]heptane-2-carboxylate 52h (250 mg, 0.49 mmol, 1.00 equiv.), dichloromethane (10 mL), and TMSI (0.19 g, 2.00 equiv). The resulting mixture was stirred at room temperature for 15 min, then diluted with 10 mL of DCM. A 1M hydrogen chloride aqueous solution (2 mL) was added. The aqueous mixture was extracted with dichloromethane (10 mL×3), and the combined organic extracts were washed with brine, dried over anhydrous sodium sulfate and concentrated under vacuum. The residue was purified by silica gel column chromatography eluting with dichloromethane/methanol (10:1) to afford (1S,4S,5R)-5-[[4-cyclopropyl-1-(2,6-dichlorophenyl)-1H-1,2,3-triazol-5-yl]methoxy]-2-azabicyclo[2.2.1]heptane 52i (20 mg, 11%) as a yellow oil.

Step 8. To a 250 mL round-bottom flask was added (1S,4S,5R)-5-[[4-cyclopropyl-1-(2,6-dichlorophenyl)-1H-1,2,3-triazol-5-yl]methoxy]-2-azabicyclo[2.2.1]heptane 52i (40 mg, 0.11 mmol, 1.00 equiv.), tert-butyl 4-bromobenzoate (40 mg, 0.16 mmol, 1.50 equiv.), Pd$_2$(dba)$_3$ (20 mg, 0.02 mmol, 0.20 equiv.), BINAP (26 mg, 0.04 mmol, 0.40 equiv.), Cs$_2$CO$_3$ (138 mg, 0.42 mmol, 4.00 equiv.), and toluene (5 mL). The resulting mixture was heated at 110° C. overnight. After cooling to room temperature, the mixture was diluted with H$_2$O (50 mL), and extracted with ethyl acetate (100 mL×2). The combined organic extracts were washed with brine (100 mL×2), dried over anhydrous sodium sulfate, and concentrated. The residue was purified by silica gel column chromatography eluting with ethyl acetate/hexane (1:2) to afford tert-butyl 4-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]benzoate 52j (50 mg, 85%) as a yellow oil.

Step 9. To a 250 mL round-bottom flask was added tert-butyl 4-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]benzoate 52j (50 mg, 0.09 mmol, 1.00 equiv.), trifluoroacetic acid (2 mL), and dichloromethane (0.6 mL). The resulting mixture was stirred at room temperature for 1 h. The mixture was diluted with 50 mL of H$_2$O, and extracted with ethyl acetate (100 mL×2). The combined organic extracts were washed with brine (100 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (45.0% ACN up to 64.0% in 8 min); Detector, UV 254 nm. 40 mL product was obtained. After purification 4-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]benzoic acid I-52 (8 mg, 18%) was obtained as a white crystal. $^1$H NMR (400 MHz, CD$_3$OD): δ 7.81 (d, J=8.7 Hz, 2H), 7.74-7.59 (m, 3H), 6.51 (d, J=8.7 Hz, 2H), 4.62-4.49 (m, 2H), 4.18 (d, J=2.4 Hz, 1H), 3.56-3.49 (m, 1H), 3.40 (dd, J=9.4, 4.1 Hz, 1H), 2.61 (d, J=9.4 Hz, 1H), 2.55 (d, J=3.5 Hz, 1H), 2.04 (ddd, J=12.8, 8.4, 5.0 Hz, 1H), 1.90 (dd, J=13.4, 6.9 Hz, 1H), 1.58 (s, 2H), 1.31 (d, J=13.0 Hz, 1H), 1.12-0.97 (m, 4H). MS (ES, m/z): [M+1]=499.2.

Example 51: 4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-2-fluorobenzoic acid (I-53)

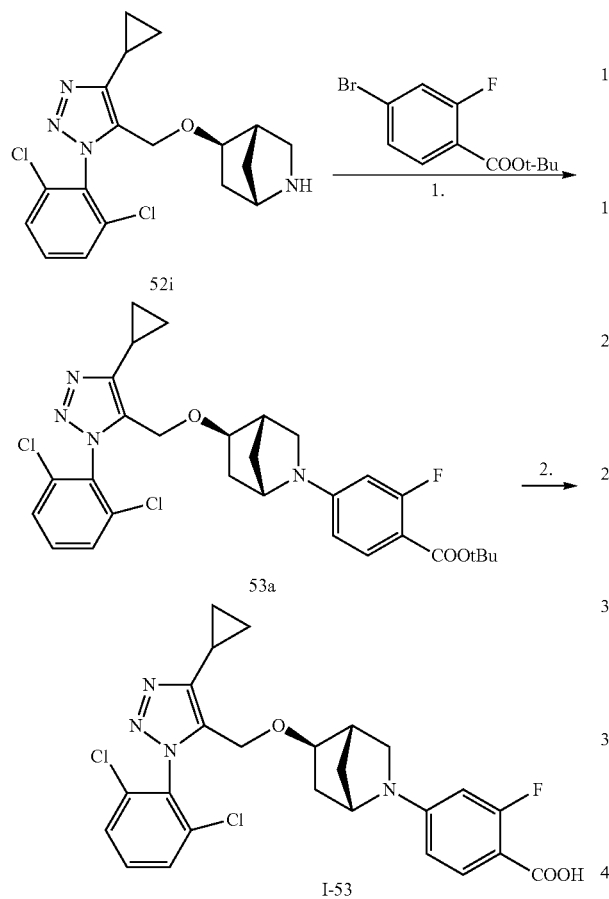

Step 1. To a 50 mL round-bottom flask purged and maintained under an inert atmosphere of nitrogen was added (1S,4S,5R)-5-[[4-cyclopropyl-1-(2,6-dichlorophenyl)-1H-1,2,3-triazol-5-yl]methoxy]-2-azabicyclo[2.2.1]heptane 52i (120 mg, 0.32 mmol, 1.00 equiv.), toluene (3 mL), Pd(OAc)$_2$ (14 mg, 0.06 mmol, 0.20 equiv.), Xantphos (36 mg, 0.06 mmol, 0.20 equiv.), Cs$_2$CO$_3$ (310 mg, 0.95 mmol, 3.00 equiv.), and tert-butyl 4-bromo-2-fluorobenzoate (96 mL, 1.10 equiv.). The resulting mixture was heated at 90° C. overnight and then concentrated under vacuum. The residue was purified by silica gel column chromatography eluting with ethyl acetate/petroleum ether (1/3). Removal of solvents afforded tert-butyl 4-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]-2-fluorobenzoate 53a (60 mg, 33%) as a light yellow oil.

Step 2. To a 50 mL round-bottom flask was added tert-butyl 4-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]-2-fluorobenzoate 53a (60 mg, 0.10 mmol, 1.00 equiv.), dichloromethane (2 mL), and trifluoroacetic acid (1 mL). The resulting mixture was stirred at room temperature for 2 h, diluted with 100 mL of EA, and washed with a saturated sodium bicarbonate aqueous solution (10 mL×2). The organic solution was dried over anhydrous sodium sulfate and concentrated under vacuum. The crude product was purified by Prep-HPLC using the following conditions: Column, XBridge Prep OBD C18 Column, 19*250 mm, 5 um; mobile phase, Water (0.05% TFA) and ACN (50.0% ACN up to 62.0% in 9 min); Detector, UV 220 nm. After purification 4-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]-2-fluorobenzoic acid I-53 (27.5 mg, 51%) was obtained as an off-white solid. $^1$H NMR (300 MHz, CD$_3$OD): δ 7.83-7.48 (m, 4H), 6.39-6.01 (m, 2H), 4.61-4.39 (m, 2H), 4.12 (s, 1H), 3.50 (dd, J=7.0, 2.4 Hz, 1H), 3.39-3.30 (m, 1H), 2.54 (dd, J=21.3, 6.8 Hz, 2H), 2.00 (tt, J=8.8, 5.1 Hz, 1H), 1.84 (dd, J=13.4, 6.8 Hz, 1H), 1.53 (s, 2H), 1.31-1.11 (m, 2H), 1.08-0.76 (m, 4H). MS (ES, m/z): [M+1]=517.2.

Example 52: 3-{4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-3-fluorophenyl}propanoic acid (I-54)

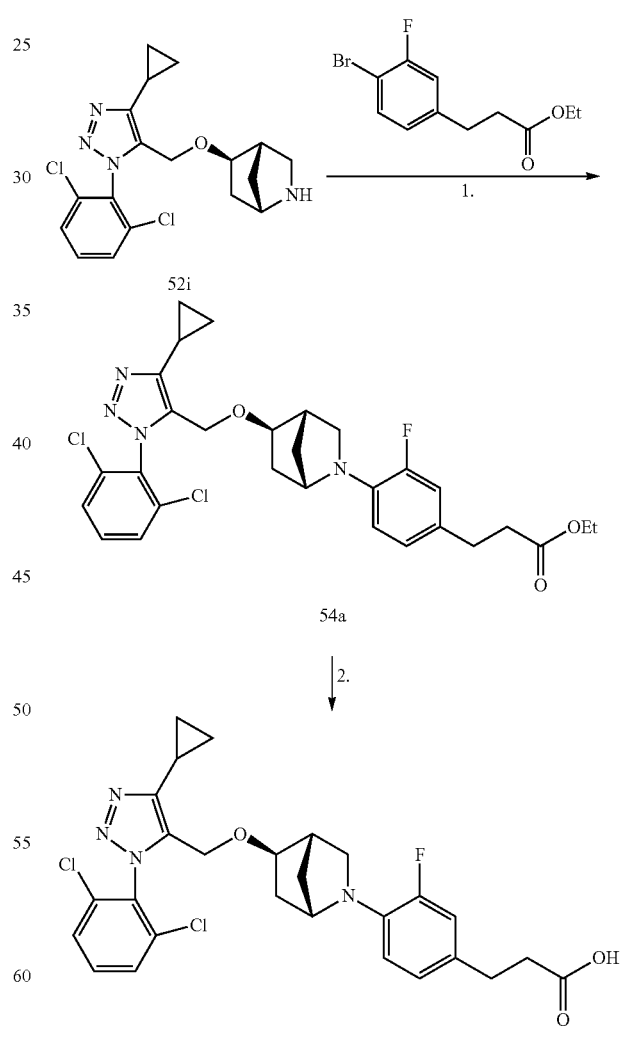

Step 1. To a 100 mL round-bottom flask was added a solution of (1S,4S,5R)-5-[[4-cyclopropyl-1-(2,6-dichlorophenyl)-1H-1,2,3-triazol-5-yl]methoxy]-2-azabicyclo [2.2.1]heptane 52i (120 mg, 0.32 mmol, 1.00 equiv.) in toluene (3 ml), ethyl 3-(4-bromo-3-fluorophenyl)propanoate (96 mg, 0.35 mmol, 1.10 equiv), Ruphos precatalyst (54 mg, 0.20 equiv.), Ruphos (29 mg, 0.20 equiv.), and $Cs_2CO_3$ (62 mg, 0.19 mmol, 3.00 equiv.). The resulting mixture was heated at 110° C. overnight and concentrated under vacuum. The residue was purified by silica gel column chromatography eluting with ethyl acetate/petroleum ether (1:3) to provide ethyl 3-[4-[(1S,4S,5R)-5-[[4-cyclopropyl-1-(2,6-dichlorophenyl)-1H-1,2,3-triazol-5-yl]methoxy]-2-azabicyclo [2.2.1]heptan-2-yl]-3-fluorophenyl]propanoate 54a (100 mg, 55%) as a light yellow solid.

Step 2. To a 50 mL round-bottom flask was added ethyl 3-[4-[(1S,4S,5R)-5-[[4-cyclopropyl-1-(2,6-dichlorophenyl)-1H-1,2,3-triazol-5-yl]methoxy]-2-azabicyclo[2.2.1] heptan-2-yl]-3-fluorophenyl]propanoate 54a (100 mg, 0.17 mmol, 1.00 equiv.), ethanol (1.5 mL), LiOH (73 mg, 1.83 mmol, 10.00 equiv), and water (0.2 mL). The resulting mixture was stirred at 50° C. for 2 h. The mixture was diluted with 20 mL of water, extracted with ethyl acetate (50 mL×2), and the combined organic extracts were washed with brine (30 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (46.0% ACN up to 64.0% in 8 min); Detector, UV 254 nm. After purification 3-[4-[(1S,4S,5R)-5-[[4-cyclopropyl-1-(2,6-dichlorophenyl)-1H-1,2,3-triazol-5-yl]methoxy]-2-azabicyclo [2.2.1]heptan-2-yl]-3-fluorophenyl]propanoic acid I-54 (14.1 mg, 15%) was obtained as an off-white solid. $^1$H NMR (400 MHz, $CD_3OD$): δ 7.73-7.59 (m, 3H), 7.00-6.88 (m, 2H), 6.79 (t, J=8.9 Hz, 1H), 4.62-4.49 (m, 2H), 4.13 (s, 1H), 3.54 (ddd, J=14.8, 7.4, 3.0 Hz, 2H), 2.84 (t, J=7.5 Hz, 2H), 2.78-2.67 (m, 1H), 2.57 (t, J=7.5 Hz, 2H), 2.54-2.48 (m, 1H), 2.04 (tdd, J=8.0, 5.1, 2.5 Hz, 2H), 1.68-1.53 (m, 2H), 1.29 (dt, J=14.1, 2.8 Hz, 1H), 1.12-0.97 (m, 4H). MS (ES, m/z): [M+1]=545.

Example 53: 3-{4-[(1S,4S,5R)-5-{[4-cyclopropyl-1-(2,6-dichlorophenyl)-1H-1,2,3-triazol-5-yl] methoxy}-2-azabicyclo[2.2.1]heptan-2-yl]-2-fluorophenyl}propanoic acid (I-55)

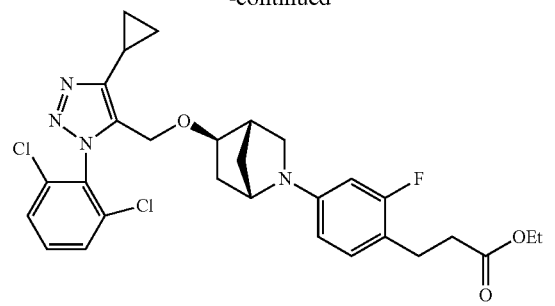

55a

2.

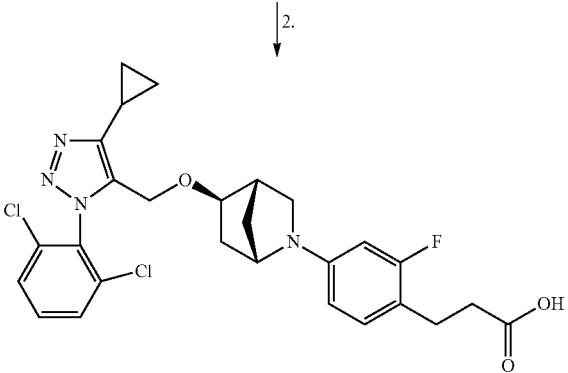

I-55

Following the two-step procedures described in Preparative Example 52, by reacting (1S,4S,5R)-5-[[4-cyclopropyl-1-(2,6-dichlorophenyl)-1H-1,2,3-triazol-5-yl]methoxy]-2-azabicyclo[2.2.1]heptane 52i with ethyl 3-(4-bromo-2-fluorophenyl)propanoate, the titled product 3-[4-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]-2-fluorophenyl]propanoic acid I-55 was obtained as a white solid. $^1$H NMR (300 MHz, $CD_3OD$): δ 7.75-7.60 (m, 3H), 7.01 (t, J=8.7 Hz, 1H), 6.26 (d, J=7.5 Hz, 2H), 4.54 (d, J=2.6 Hz, 2H), 4.00 (s, 1H), 3.45 (d, J=6.5 Hz, 2H), 2.80 (t, J=7.7 Hz, 2H), 2.58-2.01 (m, 5H), 1.87 (d, J=7.7 Hz, 1H), 1.54 (s, 2H), 1.26 (s, 1H), 1.12-0.99 (m, 4H). MS (ES, m/z): [M+1]=545.

Example 54: 4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-N-(oxane-4-sulfonyl)benzamide (I-56)

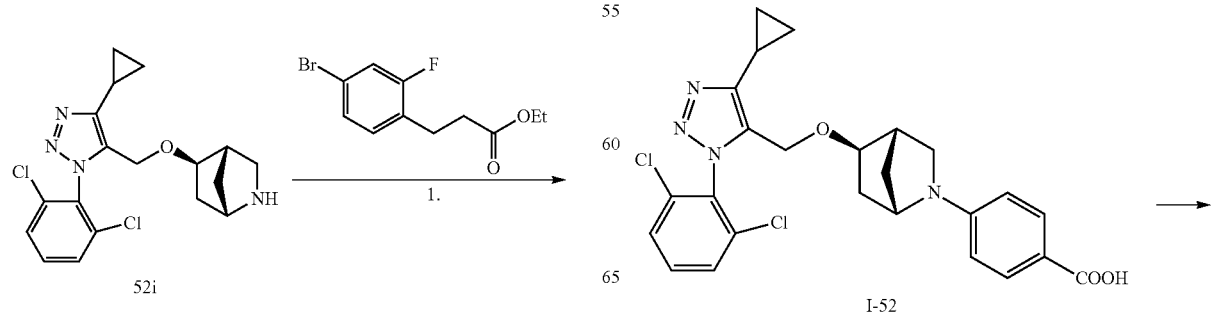

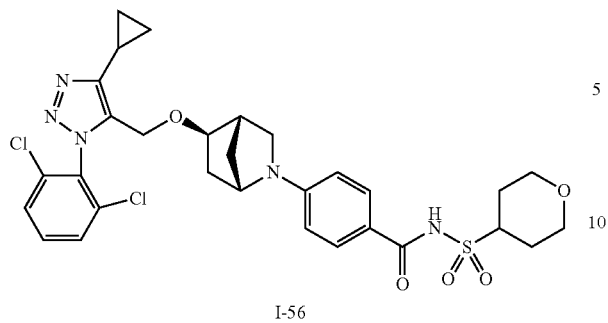

I-56

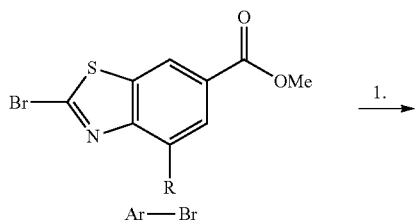

To a 100 mL round-bottom flask was added 4-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]benzoic acid I-52 (60 mg, 0.12 mmol, 1.00 equiv.), dichloromethane (2 mL), oxane-4-sulfonamide (60 mg, 0.36 mmol, 2.00 equiv.), EDCI (34 mg, 0.18 mmol, 1.50 equiv), and 4-dimethylaminopyridine (44 mg, 0.36 mmol, 3.00 equiv.). The resulting mixture was stirred at room temperature overnight. The mixture was diluted with 30 mL of ethyl acetate, washed with brine (30 mL×2), dried over anhydrous sodium sulfate and concentrated under vacuum. The crude product was purified by Prep-HPLC using the following conditions: Column, XBridge Prep OBD C18 Column, 19*250 mm, 5 um; mobile phase, Water (0.05% TFA) and ACN (53.0% ACN up to 65.0% in 8 min); Detector, UV 220 nm. After purification 4-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]-N-(oxane-4-sulfonyl)benzamide I-56 (7.2 mg, 9%) was obtained as an off-white solid. $^1$H NMR (400 MHz, CD$_3$OD): δ 7.78-7.72 (m, 2H), 7.72-7.60 (m, 3H), 6.58-6.51 (m, 2H), 4.63-4.50 (m, 2H), 4.21 (s, 1H), 4.07 (ddd, J=11.8, 4.7, 2.0 Hz, 2H), 3.95 (tt, J=11.6, 4.3 Hz, 1H), 3.57-3.33 (m, 4H), 2.64 (d, J=9.6 Hz, 1H), 2.60-2.54 (m, 1H), 2.10-1.83 (m, 6H), 1.61-1.56 (m, 2H), 1.38-1.23 (m, 2H), 1.12-0.97 (m, 4H). MS (ES, m/z): [M+1]=646.

Example 55: Synthesis of I-57 to I-60

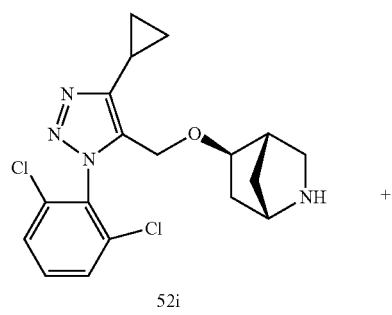

52i

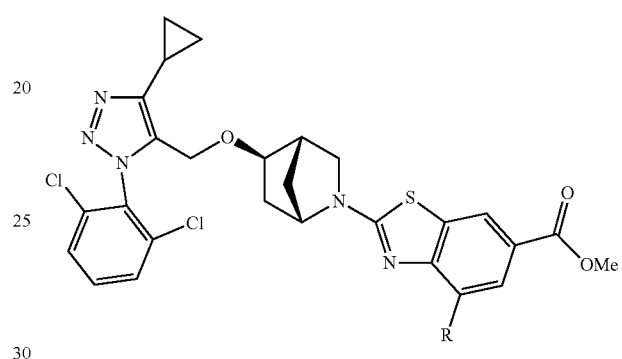

Intermediate-R

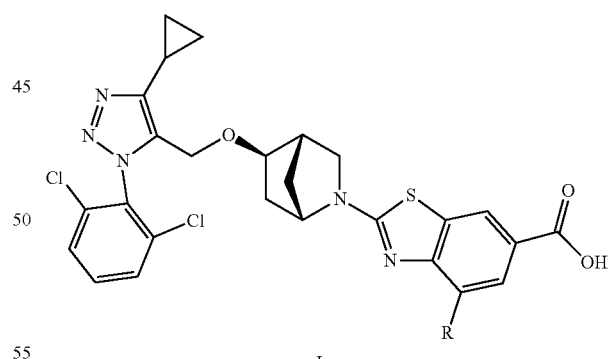

I-x

Benzothiazole carboxylic acid containing compounds I-57 to I-60 were prepared by reacting intermediate 52i with appropriately substituted aryl bromide (Ar—Br) following the two-step procedures described in Preparative Example 46. The data for compounds I-57 to I-60 is summarized in Table 3.

TABLE 3

| Ar-Br | Cmpd Structure | Cmpd No. | MS/¹H NMR |
|---|---|---|---|
| 31g | | I-57 | MS (ES, m/z): [M + 1] = 612.15.<br>¹H NMR (300 MHz, CD$_3$OD) δ: 8.04 (d, J = 1.4 Hz, 1H), 7.94 (d, J = 1.5 Hz, 1H), 7.78-7.60 (m, 3H), 4.69-4.52 (m, 2H), 4.45 (s, 1H), 4.04 (tt, J = 6.2, 3.1 Hz, 1H), 3.71 (d, J = 6.4 Hz, 1H), 3.63-3.52 (m, 1H), 3.21 (s, 1H), 3.10 (d, J = 9.1 Hz, 1H), 2.71 (s, 1H), 2.08 (tq, J = 9.2, 5.2, 4.3 Hz, 2H), 1.70 (t, J = 8.2 Hz, 2H), 1.43 (d, J = 14.1 Hz, 1H), 1.17-1.00 (m, 4H), 0.90 (td, J = 11.6, 10.1, 6.7 Hz, 4H). |
| 50f | | I-58 | MS (ES, m/z): [M + 1] = 626.<br>¹H NMR (300 MHz, CD$_3$OD) δ: 8.21 (d, J = 1.7 Hz, 1H), 7.91 (d, J = 1.7 Hz, 1H), 7.77-7.59 (m, 3H), 4.68-4.55 (m, 2H), 4.35 (s, 1H), 4.30-3.91 (m, 4H), 3.81 (t, J = 7.7 Hz, 1H), 3.68 (d, J = 6.3 Hz, 1H), 3.52 (s, 2H), 3.05 (d, J = 10.3 Hz, 1H), 2.66 (s, 1H), 2.48-2.35 (m, 1H), 2.33-2.17 (m, 1H), 2.14-1.99 (m, 2H), 1.68 (d, J = 6.9 Hz, 2H), 1.41 (d, J = 13.7 Hz, 1H), 1.15-0.99 (m, 4H). |
| 50g | | I-59 | MS (ES, m/z): [M + 1] = 626.<br>¹H NMR (300 MHz, CD$_3$OD) δ: 8.23 (d, J = 1.6 Hz, 1H), 7.93 (d, J = 1.7 Hz, 1H), 7.78-7.60 (m, 3H), 4.69-4.52 (m, 2H), 4.39 (s, 1H), 4.28-3.80 (m, 5H), 3.75-3.66 (m, 1H), 3.61-3.01 (m, 2H), 2.69 (d, J = 3.6 Hz, 1H), 2.53-2.36 (m, 1H), 2.30-1.99 (m, 3H), 1.68 (t, J = 8.5 Hz, 2H), 1.42 (d, J = 14.0 Hz, 1H), 1.07 (dtd, J = 10.5, 8.3, 5.7 Hz, 4H). |
| 32e | | I-60 | MS (ES, m/z): [M + 1] = 640.<br>¹H NMR (300 MHz, DMSO-d$_6$) δ: 12.61 (s, 1H), 8.20 (d, J = 1.6 Hz, 1H), 7.86-7.65 (m, 4H), 4.53 (d, J = 1.6 Hz, 2H), 4.26 (s, 1H), 3.99 (dd, J = 10.5, 3.3 Hz, 2H), 3.68-3.59 (m, 3H), 3.57-3.31 (m, 4H), 2.97 (d, J = 9.8 Hz, 1H), 2.60 (d, J = 3.0 Hz, 1H), 2.18-2.03 (m, 1H), 2.01-1.68 (m, 5H), 1.62 (d, J = 10.0 Hz, 1H), 1.50-1.39 (m, 1H), 1.28 (d, J = 13.7 Hz, 1H), 1.09-0.90 (m, 4H). |

211

Example 56: 2-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-4-[(3S)-oxolan-3-yloxy]-1,3-benzothiazole-6-carboxylic acid (I-61)

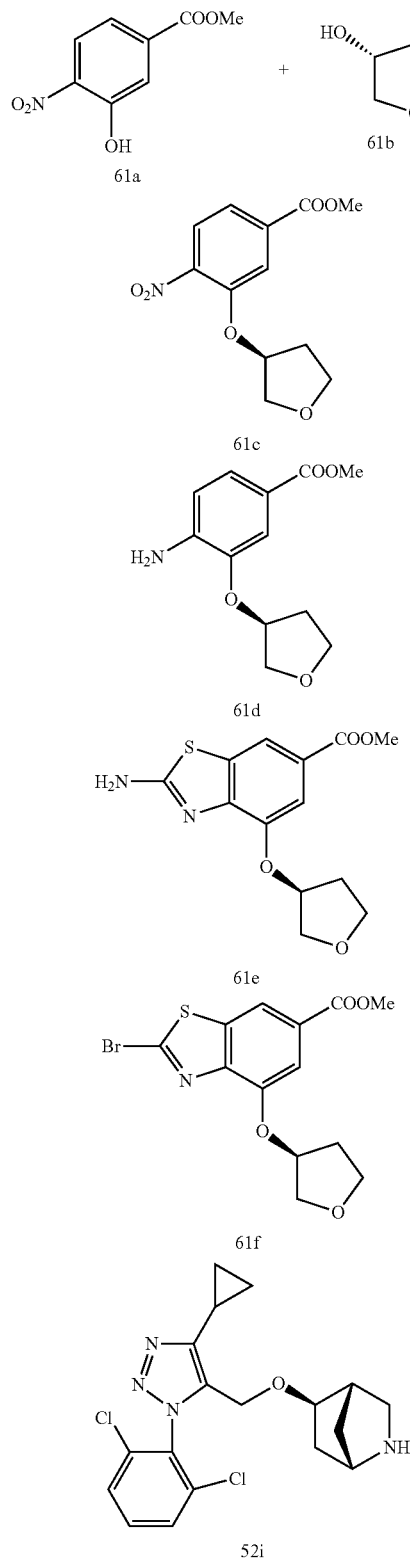

212

-continued

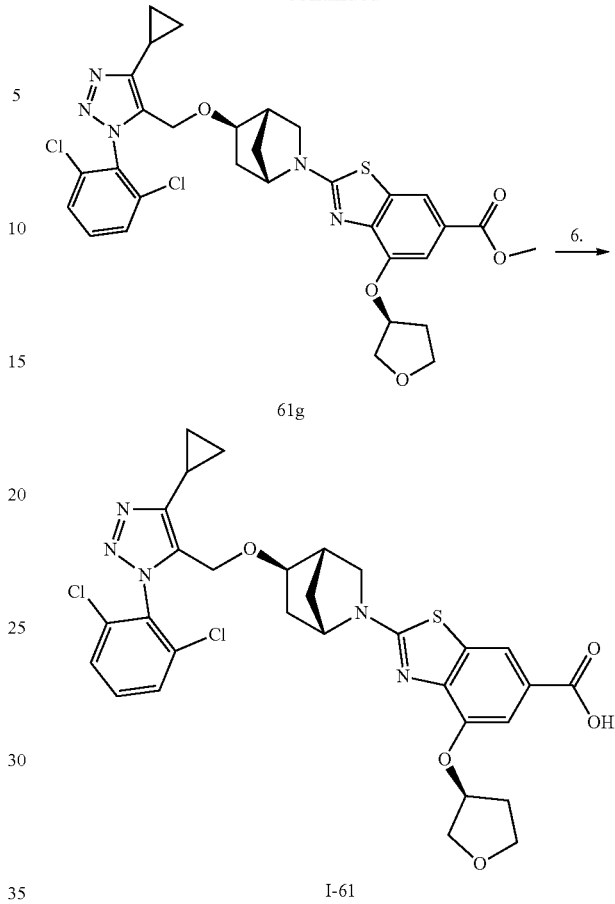

Step 1. To a 1000 mL round-bottom flask purged with and maintained under an inert atmosphere of nitrogen was added methyl 3-hydroxy-4-nitrobenzoate 61a (10 g, 50.72 mmol, 1.00 equiv.), PPh$_3$ (19.9 g, 75.87 mmol, 1.50 equiv), tetrahydrofuran (240 mL), and (3R)-oxolan-3-ol 61b (5.4 g, 61.29 mmol, 1.20 equiv.). DIAD (15.4 g, 76.16 mmol, 1.50 equiv) was added. The resulting mixture was heated at 50° C. overnight with stirring. The mixture was concentrated under vacuum and the residue was purified by silica gel column chromatography eluting with ethyl acetate in petroleum ether (0% to 20%) to give methyl 4-nitro-3-[(3S)-oxolan-3-yloxy]benzoate 61c (7.7g, 57%) as a light yellow solid.

Step 2. To a 250 mL round-bottom flask was added methyl 4-nitro-3-[(3S)-oxolan-3-yloxy]benzoate 61c (7.7 g, 28.81 mmol, 1.00 equiv.), methanol (100 mL), and Palladium on carbon (7.7 g, 10 wt %). Hydrogen gas was introduced. The reaction mixture was stirred at 30° C. for 1 h. Solids were filtered out, and the filtrate was concentrated under vacuum to afford methyl 4-amino-3-[(3S)-oxolan-3-yloxy]benzoate 61d (7.4 g, crude) as a colorless oil.

Step 3. To a 250 mL round-bottom flask was added methyl 4-amino-3-[(3S)-oxolan-3-yloxy]benzoate 61d (7.4 g, 31.19 mmol, 1.00 equiv.), AcOH (128 mL), NaSCN (10.4 g, 4.00 equiv.), and Br$_2$ (7.7 g, 48.18 mmol, 1.50 equiv.). The resulting mixture was stirred at 30° C. overnight, quenched by the addition of 50 mL of water/ice. The pH value of the solution was adjusted to 10.0 using a 1M sodium hydroxide aqueous solution. Solids were collected by filtration to afford methyl 2-amino-4-[(3S)-oxolan-3-yloxy]-1,3-benzothiazole-6-carboxylate 61e (11 g, crude) as a reddish solid.

Step 4. To a 250 mL round-bottom flask was added methyl 2-amino-4-[(3S)-oxolan-3-yloxy]-1,3-benzothiazole-6-carboxylate 61e (2.5 g, 8.49 mmol, 1.00 equiv.), CuBr$_2$ (2.8 g, 12.73 mmol, 1.50 equiv.), t-BuONO (2.2 g, 21.36 mmol, 2.50 equiv.), and MeCN (100 mL). The resulting mixture was stirred at 30° C. overnight and concentrated under vacuum. The residue was purified by silica gel column chromatography eluting with ethyl acetate in petroleum ether (0% to 20%) to produce methyl 2-bromo-4-[(3S)-oxolan-3-yloxy]-1,3-benzothiazole-6-carboxylate 61f (670 mg, 22%) as a light yellow solid.

Step 5. To a 8 mL round-bottom flask was added (1S,4S,5R)-5-[[4-cyclopropyl-1-(2,6-dichlorophenyl)-1H-1,2,3-triazol-5-yl]methoxy]-2-azabicyclo[2.2.1]heptane 52i (100 mg, 0.26 mmol, 1.00 equiv.), methyl 2-bromo-4-[(3S)-oxolan-3-yloxy]-1,3-benzothiazole-6-carboxylate 61f (100 mg, 0.28 mmol, 1.10 equiv.), Cs$_2$CO$_3$ (170 mg, 0.52 mmol, 2.00 equiv.), and DMA (2 mL). The resulting mixture was heated at 60° C. overnight. After cooling to room temperature, the mixture was diluted with 30 mL of H$_2$O, and extracted with ethyl acetate (50 mL×2). The combined organic extracts were washed with brine (50 mL×2), dried and concentrated. The residue was purified by silica gel column chromatography eluting with ethyl acetate/petroleum ether (1:4) to afford methyl 2-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]-4-[(3S)-oxolan-3-yl oxy]-1,3-benzothiazole-6-carboxylate 61g (125 mg, 72%) as a yellow oil.

Step 6. To a 250 mL round-bottom flask was added methyl 2-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]-4-[(3 S)-oxolan-3-yloxy]-1,3-benzothiazole-6-carboxylate 61g (125 mg, 0.19 mmol, 1.00 equiv.), LiOH·H$_2$O (80 mg, 1.9 mmol, 10.00 equiv.), methanol (5 mL), and water (1 mL). The resulting mixture was heated at 60° C. for 1 h. After cooling to room temperature, a 1M hydrogen chloride aqueous solution (10 mL) was added. The aqueous mixture was extracted with ethyl acetate (100 mL×2). The combined organic extracts were washed with brine (100 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (38.0% ACN up to 56.0% in 8 min); Detector, UV 254 nm. After purification 2-[(1S,4S,5R)-5-[[4-cyclopropyl-1-(2,6-dichlorophenyl)-1H-1,2,3-triazol-5-yl]methoxy]-2-azabicyclo [2.2.1]heptan-2-yl]-4-[(3S)-oxolan-3-yloxy]-1,3-benzothiazole-6-carboxylic acid I-61 (45.8 mg, 37%) was obtained as a white solid. $^1$H NMR (300 MHz, CD$_3$OD): δ 8.05 (d, J=1.4 Hz, 1H), 7.78-7.65 (m, 3H), 7.56 (d, J=1.4 Hz, 1H), 5.31 (t, J=5.4 Hz, 1H), 4.70-4.53 (m, 2H), 4.46 (s, 1H), 4.18-3.85 (m, 3H), 3.72 (d, J=6.0 Hz, 1H), 3.65-3.55 (m, 1H), 3.37 (s, 1H), 3.14 (s, 1H), 2.72 (d, J=3.8 Hz, 1H), 2.47-2.19 (m, 2H), 2.18-2.00 (m, 2H), 1.71 (t, J=8.2 Hz, 2H), 1.44 (d, J=13.7 Hz, 1H), 1.17-1.00 (m, 4H). MS (ES, m/z): [M+1]=643.8.

Example 57: 2-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-4-[(3R)-oxolan-3-yloxy]-1,3-benzothiazole-6-carboxylic acid (I-62)

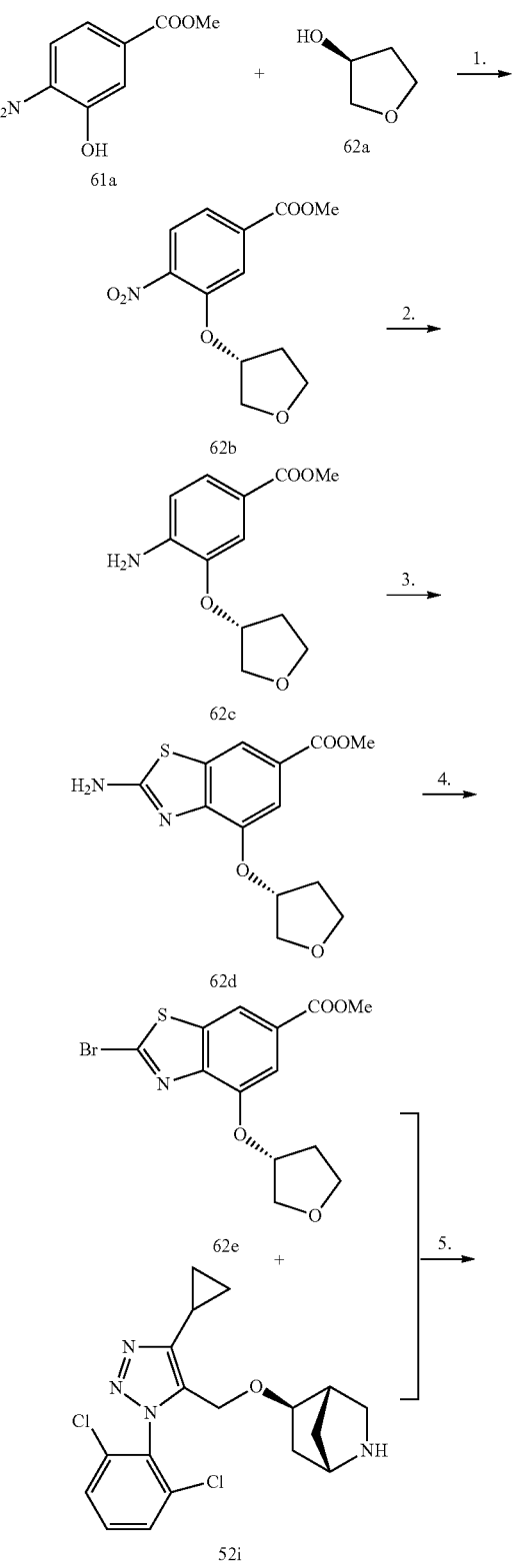

-continued

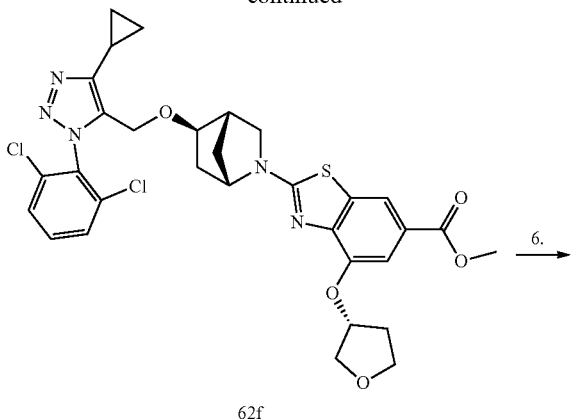

62f

↓ 6.

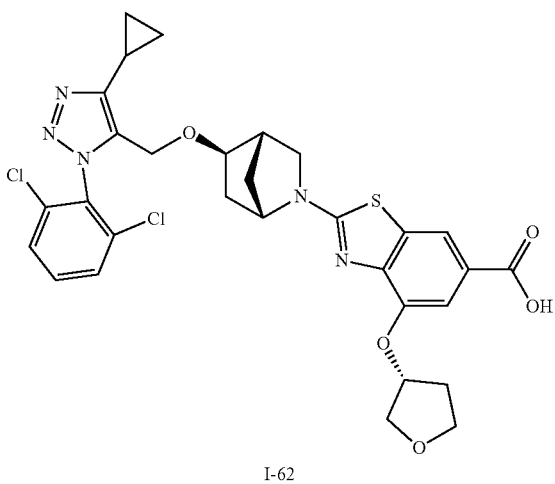

I-62

Step 1. To a 1000 mL round-bottom flask was added methyl 3-hydroxy-4-nitrobenzoate 61a (10 g, 50.72 mmol, 1.00 equiv.), tetrahydrofuran (400 mL), and PPh₃ (20 g, 76.25 mmol, 1.50 equiv.). (3S)-Oxolan-3-ol 62a (4.5 g, 51.08 mmol, 1.00 equiv.) was added. The mixture was cooled to 0° C., and added DIAD (15.4 g, 76.16 mmol, 1.50 equiv.). The reaction mixture was heated at 50° C. overnight, and concentrated under vacuum. The residue was purified by silica gel column chromatography eluting with ethyl acetate in hexanes (0% to 25%) to afford methyl 4-nitro-3-[(3R)-oxolan-3-yloxy]benzoate 62b (10 g, 80%) as a red oil.

Step 2. To a 1000 mL round-bottom flask was added methyl 4-nitro-3-[(3R)-oxolan-3-yloxy]benzoate 62b (10.9 g, 40.79 mmol, 1.00 equiv.), methanol (200 mL), tetrahydrofuran (200 mL), and Palladium on carbon (11 g, 10 wt %). Hydrogen gas was introduced in. The resulting mixture was stirred under an atmosphere of hydrogen overnight. Solids were filtered out, and the filtrate was concentrated under vacuum to give methyl 4-amino-3-[(3R)-oxolan-3-yloxy]benzoate 62c (9.5 g, 98%) as a reddish oil.

Step 3. To a 500 mL round-bottom flask was added methyl 4-amino-3-[(3R)-oxolan-3-yloxy]benzoate 62c (9.5 g, 40.04 mmol, 1.00 equiv.) AcOH (300 mL), NaSCN (13.0 g, 160.49 mmol, 4.00 equiv.), and Br₂ (6.4 g, 40.05 mmol, 1.00 equiv.). The resulting mixture was stirred at 30° C. overnight. The mixture was diluted with 500 mL of H₂O/ice. The pH value of the solution was adjusted to 10.0 using sodium hydroxide. The solids were collected by filtration, dried, to afford methyl 2-amino-4-[(3R)-oxolan-3-yloxy]-1,3-benzothiazole-6-carboxylate 62d (10.2 g, 87%) as a red solid.

Step 4. To a 250 mL round-bottom flask was added methyl 2-amino-4-[(3R)-oxolan-3-yloxy]-1,3-benzothiazole-6-carboxylate 62d (10.2 g, 34.66 mmol, 1.00 equiv.), CH₃CN (150 mL), CuBr₂ (11.6 g, 52.02 mmol, 1.50 equiv), and t-BuONO (8 g, 78.43 mmol, 2.26 equiv). The resulting mixture was stirred at 30° C. overnight. The mixture was concentrated under vacuum, and the residue was purified by silica gel column chromatography eluting with ethyl acetate in hexanes (0% to 5%). Removal of solvents afforded methyl 2-bromo-4-[(3R)-oxolan-3-yloxy]-1,3-benzothiazole-6-carboxylate 62e (3.4 g, 27%) as a light yellow solid.

Step 5. To a 8 mL sealed tube was added (1S,4S,5R)-5-[[4-cyclopropyl-1-(2,6-dichlorophenyl)-1H-1,2,3-triazol-5-yl]methoxy]-2-azabicyclo[2.2.1]heptane 52i (100 mg, 0.26 mmol, 1.00 equiv.), methyl 2-bromo-4-[(3R)-oxolan-3-yloxy]-1,3-benzothiazole-6-carboxylate 62e (100 mg, 0.28 mmol, 1.10 equiv.), Cs₂CO₃ (170 mg, 0.52 mmol, 2.00 equiv.), and DMA (2 mL). The resulting mixture was heated at 60° C. overnight. After cooling to room temperature, the mixture was diluted with 30 mL of H₂O, and extracted with ethyl acetate (50 mL×2). The combined organic extracts were washed with brine (50 mL×2), dried over anhydrous sodium sulfate and concentrated. The residue was purified by silica gel column chromatography eluting with ethyl acetate/petroleum ether (1:4) to give methyl 2-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]-4-[(3R)-oxolan-3-yloxy]-1,3-benzothiazole-6-carboxylate 62f (112 mg, 65%) as a yellow oil.

Step 6. To a 250 mL round-bottom flask was added methyl 2-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]-4-[(3R)-oxolan-3-yloxy]-1,3-benzothiazole-6-carboxylate 62f (140 mg, 0.21 mmol, 1.00 equiv.), LiOH·H₂O (90 mg, 2.1 mmol, 10.00 equiv.), methanol (5 mL), and water (1 mL). The resulting mixture was heated at 60° C. for 1 h. After cooling to room temperature, a 1M HCl aqueous solution (10 mL) was added, the aqueous mixture was extracted with ethyl acetate (100 mL×2). The combined organic extracts were washed with brine (100 mL×2), dried over anhydrous sodium sulfate and concentrated under vacuum. The crude product was purified by Prep-HPLC using the following conditions: Column, XBridge Shield RP18 OBD Column, 5 um, 19*150 mm; mobile phase, Water (0.05% TFA) and ACN (38.0% ACN up to 56.0% in 8 min); Detector, UV 254 nm. After purification 2-[(1S,4S,5R)-5-[[4-cyclopropyl-1-(2,6-dichlorophenyl)-1H-1,2,3-triazol-5-yl]methoxy]-2-azabicyclo[2.2.1]heptan-2-yl]-4-[(3R)-oxolan-3-yloxy]-1,3-benzothiazole-6-carboxylic acid I-62 (85.2 mg, 62%) was obtained as a white solid. $^1$H NMR (300 MHz, CD₃OD): δ 8.05 (s, 1H), 7.78-7.60 (m, 3H), 7.57 (s, 1H), 5.32 (d, J=5.3 Hz, 1H), 4.61 (d, J=5.0 Hz, 2H), 4.47 (s, 1H), 4.18-3.98 (m, 3H), 3.99-3.86 (m, 1H), 3.72 (d, J=6.2 Hz, 1H), 3.60 (d, J=10.7 Hz, 1H), 3.14 (s, 1H), 2.73 (d, J=2.9 Hz, 1H), 2.32 (dp, J=25.6, 6.8 Hz, 2H), 2.10 (dt, J=14.9, 7.6 Hz, 2H), 1.73 (d, J=6.0 Hz, 2H), 1.44 (d, J=13.6 Hz, 1H), 1.14-1.00 (m, 4H). MS (ES, m/z): [M+1]=642.15.

217
Example 58: 2-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]-4-(trifluoromethoxy)-1,3-benzothiazole-6-carboxylic acid (I-63)
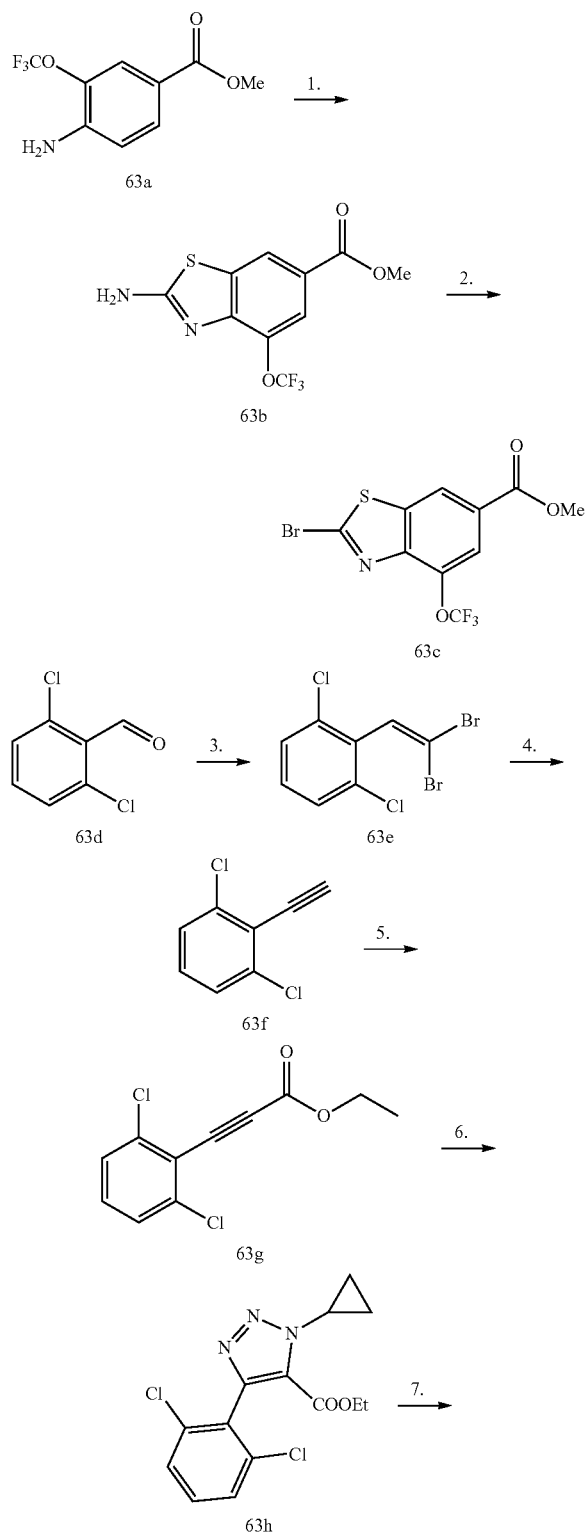
218
-continued
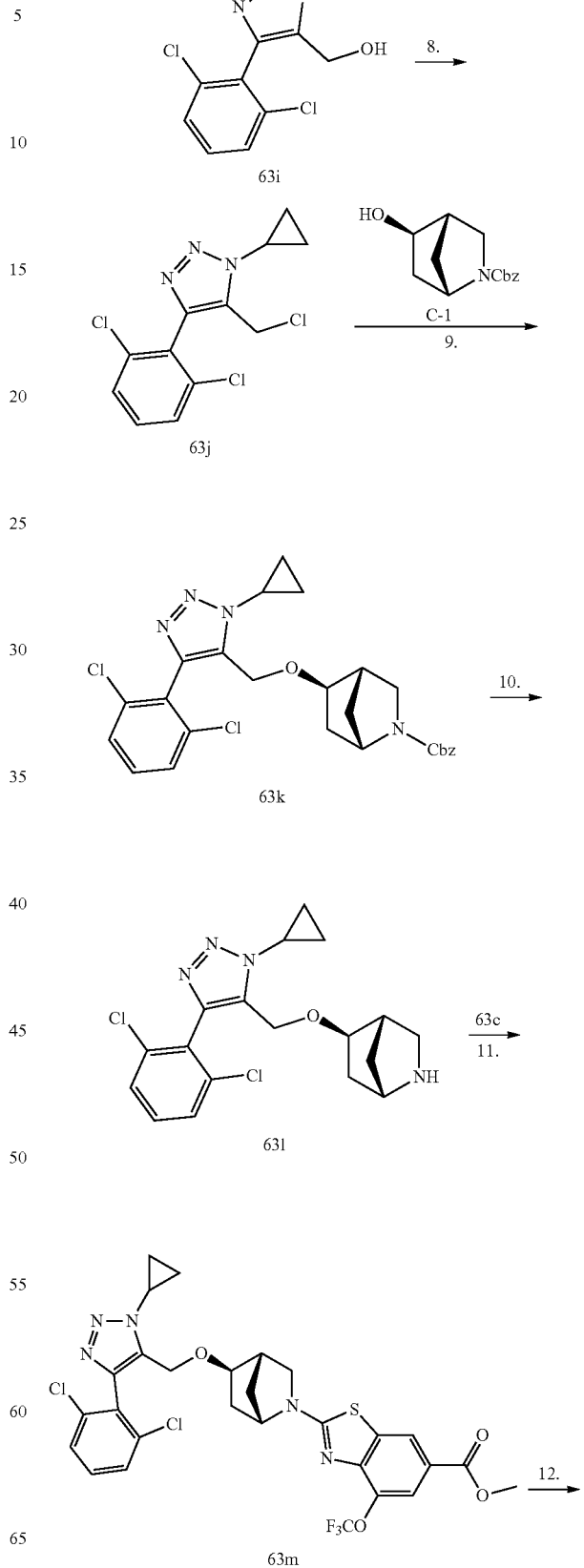

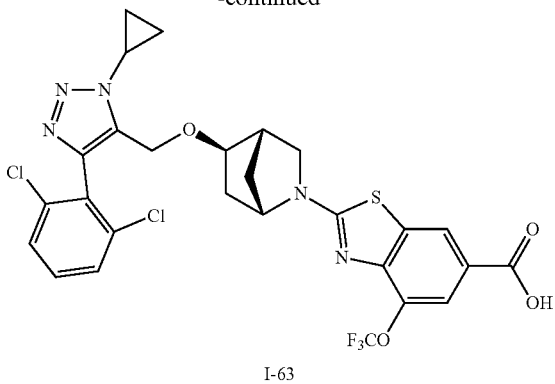

I-63

Step 1. To a 500 mL round-bottom flask was added methyl 4-amino-3-(trifluoromethoxy)benzoate 63a (7.1 g, 30.19 mmol, 1.0 equiv.), AcOH (100 mL), and NaSCN (12.1 g, 149.25 mmol, 5.0 equiv.), followed by the dropwise addition of a solution of bromine (9.6 g, 60.07 mmol, 2.0 equiv.) in AcOH (50 mL) at 0° C. over 1 hr. The mixture was stirred at 0° C. for 2 h, and then at 40° C. overnight. The reaction mixture was cooled to 0° C., and a second batch of NaSCN (12.2 g, 150.49 mmol, 5.0 equiv.) was added, followed by the dropwise addition of a solution of bromine (9.6 g, 60.07 mmol, 2.0 equiv.) in AcOH (50 mL) over 1 hr. Again, the reaction mixture was stirred at 0° C. for 2 h, and then at 40° C. for 3 days. The resulting mixture was diluted with 200 mL of water and the pH value of the aqueous solution was adjusted to 9 with sodium hydroxide. The resulting solids were collected by filtration, washed with water (20 ml×2), and dried in an oven at 60° C. for 6 h to provide of methyl 2-amino-4-(trifluoromethoxy)-1,3-benzothiazole-6-carboxylate 63b (5.4 g, 61%) as a brown solid.

Step 2. To a 250 mL round-bottom flask was added methyl 2-amino-4-(trifluoromethoxy)-1,3-benzothiazole-6-carboxylate 63b (2.9 g, 9.92 mmol, 1.0 equiv.), MeCN (100 mL), and CuBr$_2$ (3.4 g, 15.22 mmol, 1.5 equiv.), followed by the dropwise addition of t-BuONO (3.1 g, 30.06 mmol, 3.0 equiv). The resulting mixture was stirred at 30° C. overnight, and then concentrated under reduced pressure. The resulting residue was purified via silica gel column eluting with ethyl acetate/petroleum ether (1:10) to provide of methyl 2-bromo-4-(trifluoromethoxy)-1,3-benzothiazole-6-carboxylate 63c (1.8 g, 51%) as a white solid. $^1$H NMR (300 MHz, CD$_3$OD) δ: 8.681 (s, 1H), 8.020 (s, 1H), 3.955 (s, 3H). MS (ES, m/z): [M+1]=356, [M+3]=358.

Step 3. To a 2000 mL round-bottom flask was added 2,6-dichlorobenzaldehyde 63d (50 g, 285.69 mmol, 1.00 equiv.), dichloromethane (1500 mL), and CBr$_4$ (190.6 g). The mixture was cooled to 0-5° C., and PPh$_3$ (301.55 g, 1.15 mol, 4.02 equiv.) was added in several batches. The resulting mixture was stirred at 10-25° C. for 4 days and concentrated under vacuum. The residue was purified by silica gel column chromatography eluting with ethyl acetate/petroleum ether to afford 1,3-dichloro-2-(2,2-dibromoethenyl)benzene 63e (65g, 69%) as a light yellow oil.

Step 4. To a 2000 mL 3-necked round-bottom flask was added 1,3-dichloro-2-(2,2-dibromoethenyl)benzene 63e (65 g, 196.47 mmol, 1.00 equiv.) and tetrahydrofuran (1500 mL). The solution was cooled to −78° C., a 1M solution of n-BuLi in THF (198 mL) was added dropwise with stirring. The resulting mixture was stirred at −78° C. for 2 h, and then quenched with the addition of a saturated NH$_4$Cl aqueous solution (200 mL). The aqueous mixture was extracted with ethyl acetate (500 mL×3), and the combined organic extracts were washed with brine, dried, and concentrated under vacuum. The residue was purified by silica gel column chromatography eluting with ethyl acetate/petroleum ether to afford 1,3-dichloro-2-ethynylbenzene 63f (20.2 g, 60%) as a white solid.

Step 5. To a 2000 mL 3-necked round-bottom flask purged and maintained under an inert atmosphere of nitrogen was added 1,3-dichloro-2-ethynylbenzene 63f (20.2 g, 118.11 mmol, 1.00 equiv.) and tetrahydrofuran (1000 mL). The solution was cooled to −78° C., and a 1.0M solution of n-BuLi in THF (120 mL) was added dropwise with stirring. Reaction was continued for 0.5h at −78° C. Ethyl chloroformate (16.66 g, 153.51 mmol, 1.30 equiv.) was added dropwise with stirring. The resulting mixture was stirred at −78° C. for 3 h, and continued at 10-15° C. overnight. The reaction was then quenched by the addition a saturated NH$_4$Cl aqueous solution (200 mL). The aqueous mixture was extracted with ethyl acetate (500 mL×3), and the combined organic extracts were concentrated under vacuum. The residue was purified by silica gel column chromatography eluting with ethyl acetate/petroleum ether to provide ethyl 3-(2,6-dichlorophenyl)prop-2-ynoate 63g (16.5 g, 57%) as a light yellow solid.

Step 6. To a 10 mL sealed tube was added ethyl 3-(2,6-dichlorophenyl)prop-2-ynoate 63g (100 mg, 0.41 mmol, 1.00 equiv.), toluene (2 mL), and azidocyclopropane (0.5 mL). The resulting mixture was heated at 80° C. for 3 days. The mixture was concentrated under vacuum. The residue was purified by silica gel column chromatography eluting with ethyl acetate/petroleum ether (1:10 to 1:5). Removal of solvent afforded ethyl 1-cyclopropyl-4-(2,6-dichlorophenyl)-1H-1,2,3-triazole-5-carboxylate 63h (25 mg, 19%) as a light brown oil.

Step 7. To a 100 mL round-bottom flask was added ethyl 1-cyclopropyl-4-(2,6-dichlorophenyl)-1H-1,2,3-triazole-5-carboxylate 63h (150 mg, 0.46 mmol, 1.00 equiv.), tetrahydrofuran (50 mL), and LiAlH$_4$ (27 mg, 0.71 mmol, 1.55 equiv.). The resulting mixture was stirred at 10-25° C. for 1 h, and quenched by the addition of 2 mL of water/ice. The mixture was dried over anhydrous sodium sulfate. The solids were filtered out, and the filtrate was concentrated under vacuum to afford [1-cyclopropyl-4-(2,6-dichlorophenyl)-1H-1,2,3-triazol-5-yl]methanol 63i (120 mg, 92%) as a light yellow solid.

Step 8. To a 100 mL round-bottom flask was added benzotriazole (331.2 mg) and dichloromethane (20 mL), and cooled to 0-5° C. Thionyl chloride (750.5 mg) was added dropwise with stirring. The reaction mixture was stirred at 15-25° C. for 0.5 h. A solution of [1-cyclopropyl-4-(2,6-dichlorophenyl)-1H-1,2,3-triazol-5-yl]methanol 63i (790 mg, 2.78 mmol, 1.00 equiv.) in dichloromethane (5 mL) was added dropwise with stirring. The resulting mixture was stirred at 10-25° C. overnight, then quenched by the addition of water/ice (100 mL). The aqueous mixture was extracted with dichloromethane (50 mL×3), and the combined organic extracts were washed with brine, dried over anhydrous sodium sulfate, and concentrated under vacuum. The residue was purified by silica gel column chromatography eluting with ethyl acetate/petroleum ether (0:1 to 1:20). Removal of solvents afforded 5-(chloromethyl)-1-cyclopropyl-4-(2,6-dichlorophenyl)-1H-1,2,3-triazole 63j (428 mg, 51%) as a light brown oil.

Step 9. To a 100 mL round-bottom flask was added 5-(chloromethyl)-1-cyclopropyl-4-(2,6-dichlorophenyl)-1H-1,2,3-triazole 63j (428 mg, 1.41 mmol, 1.00 equiv.), N,N-dimethylformamide (20 mL), benzyl (1S,4S,5R)-5-hydroxy-2-azabicyclo[2.2.1]heptane-2-carboxylate C-1 (524.7 mg, 2.12 mmol, 1.50 equiv.), tetrabutylammonium iodide (60 mg, 0.16 mmol, 0.11 equiv.), and sodium hydride (226 mg, 60% dispersion in mineral oil, 9.42 mmol, 6.66 equiv.). The resulting mixture was stirred at 10-25° C. overnight. The mixture was diluted with 100 mL of EA, then quenched by the addition of 200 mL of water/ice. The aqueous mixture was extracted with ethyl acetate (100 mL×3), the combined organic extracts were concentrated under vacuum. The residue was purified by silica gel column chromatography eluting with ethyl acetate/petroleum ether (1:1) to afford benzyl (1S,4S,5R)-5-[[1-cyclopropyl-4-(2,6-dichlorophenyl)-1H-1,2,3-triazol-5-yl]methoxy]-2-azabicyclo[2.2.1]heptane-2-carboxylate 63k (530 mg, 73%) as a light brown oil.

Step 10. To a 100 mL round-bottom flask was added benzyl (1S,4S,5R)-5-[[1-cyclopropyl-4-(2,6-dichlorophenyl)-1H-1,2,3-triazol-5-yl]methoxy]-2-azabicyclo[2.2.1]heptane-2-carboxylate 63k (530 mg, 1.03 mmol, 1.00 equiv.), dichloromethane (5 mL), and iodotrimethylsilane (413 mg, 2.06 mmol, 2.00 equiv.). The resulting mixture was stirred at 10-25° C. overnight, and quenched by the addition of a 1M HCl aqueous solution (2 mL). The aqueous mixture was extracted with dichloromethane (50 mL×2), and the combined organic extracts were washed with brine, dried over anhydrous sodium sulfate and concentrated. The residue was purified by silica gel column chromatography eluting with ethyl acetate/petroleum ether (1:5, to 1:1, and to 1:0). Removal of solvents afforded (1S,4S,5R)-5-[[1-cyclopropyl-4-(2,6-dichlorophenyl)-1H-1,2,3-triazol-5-yl]methoxy]-2-azabicyclo[2.2.1]heptane 631 (230 mg, 59%) as a light brown oil.

Step 11. To a 50 mL round-bottom flask was added (1S,4S,5R)-5-[[1-cyclopropyl-4-(2,6-dichlorophenyl)-1H-1,2,3-triazol-5-yl]methoxy]-2-azabicyclo[2.2.1]heptane 631 (16 mg, 0.04 mmol, 1.00 equiv.), DMA (2 mL), methyl 2-bromo-4-(trifluoromethoxy)-1,3-benzothiazole-6-carboxylate 63c (22.5 mg, 0.06 mmol, 1.50 equiv.), and Cs₂CO₃ (41.26 mg, 0.13 mmol, 3.00 equiv.). The resulting mixture was heated at 60° C. overnight. After cooling to room temperature, the mixture was diluted with H₂O (50 mL), extracted with ethyl acetate (50 mL×3), and the combined organic extracts were washed with brine, dried, and concentrated under vacuum. The residue was purified by silica gel column chromatography eluting with ethyl acetate/petroleum ether (1:10 to 1:5, and to 1:3). Removal of solvents afforded methyl 2-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]-4-(trifluoromethoxy)-1,3-benzothiazole-6-carboxylate 63m (5 mg, 18%) as a light brown solid.

Step 12. To a 50 mL round-bottom flask was added methyl 2-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]-4-(trifluoromethoxy)-1,3-benzothiazole-6-carboxylate 63m (21 mg, 0.03 mmol, 1.00 equiv.), ethanol (2 mL), water (0.1 mL), and sodium hydroxide (30 mg, 0.75 mmol, 23.37 equiv.). The resulting mixture was heated at 60° C. for 2 h. After cooling to temperature, the mixture was treated with a 1M hydrogen chloride aqueous solution to adjust the pH value to 7. The aqueous mixture was concentrated under vacuum. The crude product was purified by Prep-HPLC using the following conditions Column, XBridge Shield RP18 OBD Column 5 um, 19*150 mm; mobile phase, Water (0.05% TFA) and ACN (53.0% ACN up to 71.0% in 8 min); Detector, UV 254 nm. 8.5 mg product was obtained. After purification 2-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]-4-(trifluoromethoxy)-1,3-benzothiazole-6-carboxylic acid I-63 (8.5 mg, 41%) was obtained as a white solid. ¹H NMR (400 MHz, CDCl₃): δ 8.27 (d, J=1.6 Hz, 1H), 7.99-7.93 (m, 1H), 7.50-7.30 (m, 3H), 4.61 (d, J=1.2 Hz, 2H), 3.76 (tt, J=7.5, 3.9 Hz, 1H), 3.67 (d, J=6.5 Hz, 1H), 3.42 (s, 3H), 2.63 (s, 1H), 2.06 (dd, J=14.1, 6.6 Hz, 1H), 1.88-1.73 (m, 2H), 1.63-1.46 (m, 3H), 1.31-1.23 (m, 2H). MS (ES, m/z): [M+1]=640.1.

Example 59: Synthesis of I-64 to I-67

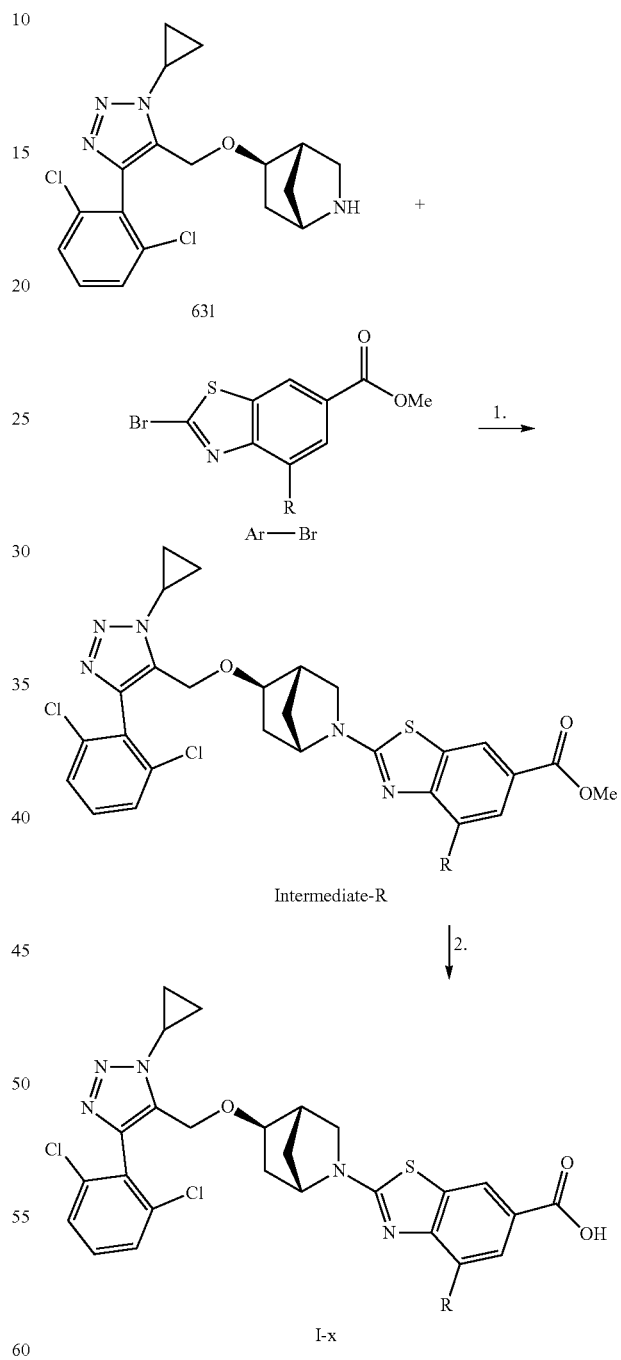

Benzothiazole carboxylic acid containing compounds I-64 to I-67 were prepared by reacting intermediate 631 with appropriately substituted aryl bromide (Ar—Br) following the two-step procedures described in Preparative Example 46. The data for compounds I-64 to I-67 is summarized in Table 4.

TABLE 4

| Ar-Br | Cmpd Structure | Cmpd No. | MS/¹H NMR |
|---|---|---|---|
| 31g | | I-64 | MS (ES, m/z): [M + 1] = 612.1.<br>¹H NMR (400 MHz, CD₃OD) δ: 8.04 (d, J = 1.5 Hz, 1H), 7.94 (d, J = 1.5 Hz, 1H), 7.60-7.42 (m, 3H), 4.78-4.59 (m, 2H), 4.48 (s, 1H), 4.04 (tt, J = 6.4, 3.0 Hz, 1H), 3.89 (tt, J = 7.4, 3.8 Hz, 1H), 3.80-3.71 (m, 1H), 3.57 (dd, J = 10.3, 4.0 Hz, 1H), 3.09 (d, J = 10.0 Hz, 1H), 2.76-2.70 (m, 1H), 2.12- 2.01 (m, 1H), 1.81 (q, J = 10.6 Hz, 2H), 1.65-1.51 (m, 1H), 1.46-1.37 (m, 2H), 1.35-1.25 (m, 3H), 0.99-0.84 (m, 4H). |
| 50f | | I-65 | MS (ES, m/z): [M + 1] = 626.1<br>¹H NMR (400 MHz, CDCl₃) δ: 8.18 (s, 1H), 8.03 (s, 1H), 7.47 (dd, J = 8.0, 1.3 Hz, 1H), 7.42 (dd, J = 8.2, 1.3 Hz, 1H), 7.35 (t, J = 8.0 Hz, 1H), 4.62 (s, 2H), 4.24 (d, J = 25.1 Hz, 4H), 4.01 (d, J = 7.5 Hz, 1H), 3.90 (s, 1H), 3.76 (td, J = 10.0, 9.0, 5.3 Hz, 3H), 3.23 (s, 1H), 2.69 (s, 1H), 2.52 (s, 1H), 2.09 (d, J = 46.7 Hz, 2H), 1.90 (d, J = 10.2 Hz, 1H), 1.81 (d, J = 10.6 Hz, 1H), 1.65 (d, J = 12.9 Hz, 1H), 1.58-1.45 (m, 2H), 1.27 (d, J = 7.2 Hz, 2H). |
| 50g | | I-66 | MS (ES, m/z): [M + 1] = 626.1<br>¹H NMR (400 MHz, CDCl₃) δ: 8.20 (d, J = 1.6 Hz, 1H), 8.01 (d, J = 1.5 Hz, 1H), 7.47 (dd, J = 7.9, 1.3 Hz, 1H), 7.40 (dd, J = 8.2, 1.3 Hz, 1H), 7.33 (t, J = 8.0 Hz, 1H), 4.61 (s, 2H), 4.28 (t, J = 7.6 Hz, 1H), 4.18 (q, J = 7.3 Hz, 2H), 4.02 (q, J = 7.6 Hz, 1H), 3.89 (t, J = 7.4 Hz, 1H), 3.76 (tt, J = 7.3, 3.8 Hz, 1H), 3.70 (s, 1H), 3.59 (s, 1H), 3.14 (s, 1H), 2.66 (s, 1H), 2.49 (q, J = 5.7, 5.1 Hz, 1H), 2.19 (dd, J = 12.8, 7.1 Hz, 1H), 2.09 (d, J = 11.9 Hz, 1H), 1.87 (d, J = 10.0 Hz, 1H), 1.79 (d, J = 10.5 Hz, 1H), 1.61 (d, J = 13.3 Hz, 1H), 1.57-1.46 (m, 2H), 1.33-1.21 (m, 2H). |
| 32e | | I-67 | MS (ES, m/z): [M + 1] = 640.1<br>¹H NMR (400 MHz, CDCl₃) δ: 8.09 (s, 1H), 7.94 (d, J = 1.4 Hz, 1H), 7.47 (dd, J = 8.0, 1.3 Hz, 1H), 7.41 (dd, J = 8.2, 1.3 Hz, 1H), 7.34 (t, J = 8.0 Hz, 1H), 4.62 (d, J = 1.9 Hz, 2H), 4.14 (dd, J = 10.7, 5.2 Hz, 2H), 3.80-3.66 (m, 6H), 3.22 (s, 1H), 2.69 (s, 1H), 2.18 (d, J = 12.0 Hz, 1H), 2.04-1.81 (m, 6H), 1.65 (d, J = 13.7 Hz, 1H), 1.58-1.44 (m, 2H), 1.33-1.21 (m, 2H). |

225

Example 60: 4-cyclobutyl-2-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]-1,3-benzothiazole-6-carboxylic acid (I-68)

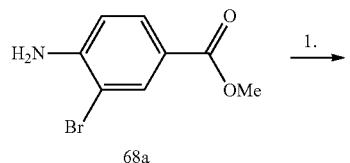
68a

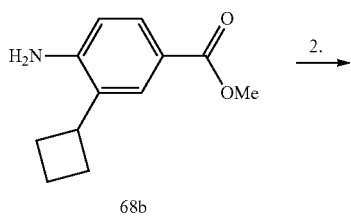
68b

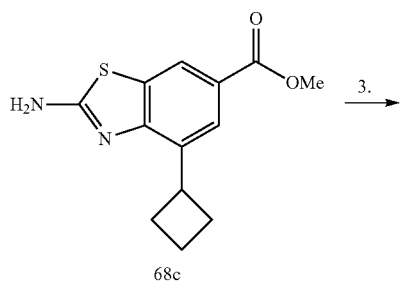
68c

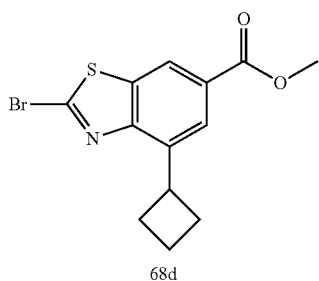
68d

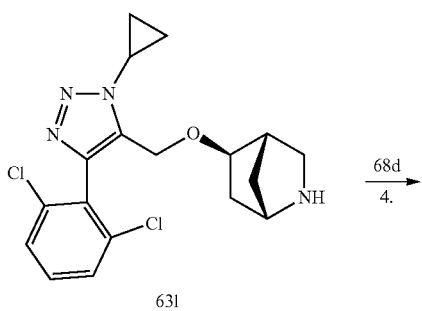
631

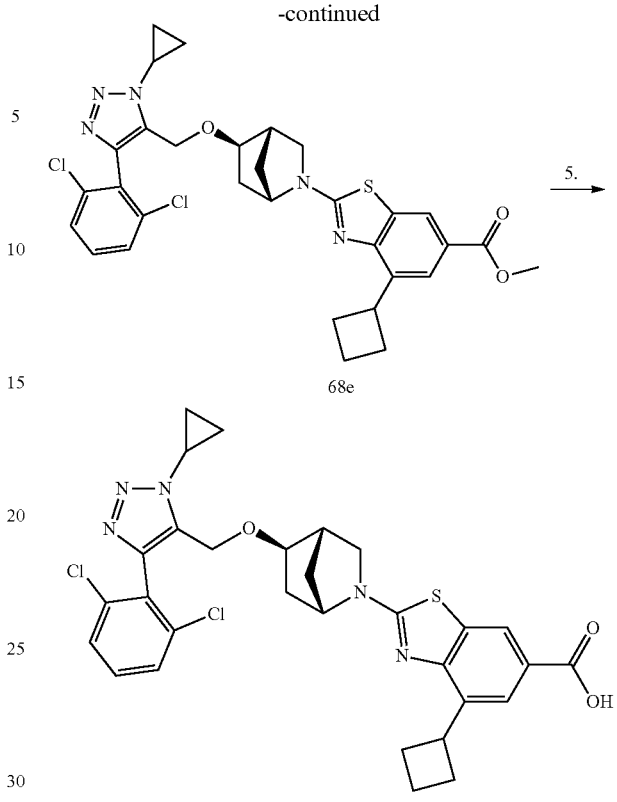
68e

I-68

Step 1. To a 250 mL round-bottom flask was added methyl 4-amino-3-bromobenzoate 68a (6 g, 26.08 mmol, 1.00 equiv.), Toluene (80 mL), cyclobutylboronic acid (5.4 g, 54.04 mmol, 2.00 equiv.), a solution of $Cs_2CO_3$ (13.67 g, 41.96 mmol, 1.60 equiv.) in water (21 mL), and Pd(dppf)$Cl_2$·DCM (2.14 g, 2.62 mmol, 0.10 equiv.). The resulting mixture was stirred at 90° C. for 2 days. After cooling to room temperature, the mixture was diluted with 750 mL of brine, and extracted with ethyl acetate (200 mL×2). The combined organic extracts were dried over anhydrous sodium sulfate and concentrated under vacuum. The crude product was purified by Flash-Prep-HPLC using the following conditions (IntelFlash-1): Column, silica gel; mobile phase, EA:PE increasing to EA:PE=100 within 30 min; Detector, UV 254 nm. Removal of solvents gave methyl 4-amino-3-cyclobutylbenzoate 68b (2.384 g, 45%) as a light yellow oil.

Step 2. To a 100 mL round-bottom flask was added methyl 4-amino-3-cyclobutylbenzoate 68b (1 g, 4.87 mmol, 1.00 equiv.), AcOH (10 mL), NaSCN (1.6 g), and a solution of $Br_2$ (780 mg, 4.88 mmol, 1.00 equiv.) in AcOH (10 mL). The resulting mixture was stirred at 10-25° C. overnight, then diluted with 200 mL of $H_2O$, and the pH value of the solution was adjusted to 8-9 using sodium carbonate. The solids were collected by filtration, dried, to afford methyl 2-amino-4-cyclobutyl-1,3-benzothiazole-6-carboxylate 68c (0.7g, 55%) as a light yellow solid.

Step 3. To a 250 mL round-bottom flask was added methyl 2-amino-4-cyclobutyl-1,3-benzothiazole-6-carboxylate 68c (1 g, 3.81 mmol, 1.00 equiv.), MeCN (20 mL), and $CuBr_2$ (1.28 g). t-BuONO (0.89 g) was added dropwise at 15-25° C. with stirring. The resulting mixture was stirred at 30° C. overnight and then concentrated under vacuum. The residue was purified by silica gel column chromatography eluting with ethyl acetate/petroleum ether (1:10-1:5-1:3) to afford methyl 2-bromo-4-cyclobutyl-1,3-benzothiazole-6-carboxylate 68d (0.79g, 64%) as a yellow solid.

Step 4. To a 100 mL round-bottom flask was added (1S,4S,5R)-5-[[1-cyclopropyl-4-(2,6-dichlorophenyl)-1H-1,2,3-triazol-5-yl]methoxy]-2-azabicyclo[2.2.1]heptane 63l (30 mg, 0.08 mmol, 1.00 equiv.), DMA (4 mL), methyl 2-bromo-4-cyclobutyl-1,3-benzothiazole-6-carboxylate 68d (30 mg, 0.09 mmol, 1.16 equiv.), and $Cs_2CO_3$ (80 mg, 0.25 mmol, 3.10 equiv.). The resulting solution was stirred at 60° C. overnight. After cooling to room temperature, the mixture was diluted with $H_2O$ (100 mL), and extracted with ethyl acetate (30 mL×3). The combined organic extracts were washed with brine, dried and concentrated to afford methyl 4-cyclobutyl-2-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]-1,3-benzothiazole-6-carboxylate 68e (41 mg, 83%) as a light brown oil.

Step 5. To a 100 mL round-bottom flask was added methyl 4-cyclobutyl-2-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]-1,3-benzothiazole-6-carboxylate 68e (41 mg, 0.07 mmol, 1.00 equiv.), ethanol (5 mL), water (1 mL), and LiOH (16 mg, 0.67 mmol, 10.18 equiv.). The resulting mixture was stirred at 60° C. for 2 h. After cooling to room temperature, the mixture was treated with a 1M hydrogen chloride aqueous solution to adjust the pH value to 7. The mixture was then concentrated under vacuum. The crude product was purified by Prep-HPLC using the following conditions Column, XBridge Shield RP18 OBD Column 5 um, 19*150 mm; mobile phase, Water (0.05% TFA) and ACN (58.0% ACN up to 76.0% in 8 min); Detector, UV 254 nm. After purification 4-cyclobutyl-2-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]-1,3-benzothiazole-6-carboxylic acid I-68 (33 mg, 82%) was obtained as a white solid. $^1$H NMR (400 MHz, $CD_3OD$): δ 8.20 (d, J=1.7 Hz, 1H), 7.97 (dd, J=1.8, 0.9 Hz, 1H), 7.56 (dd, J=7.6, 1.7 Hz, 1H), 7.55-7.40 (m, 2H), 4.72 (s, 2H), 4.44 (s, 1H), 4.09 (p, J=8.7 Hz, 1H), 3.89 (tt, J=7.4, 3.8 Hz, 1H), 3.78-3.71 (m, 1H), 3.56 (dd, J=10.1, 4.0 Hz, 1H), 3.09 (d, J=10.1 Hz, 1H), 2.71 (d, J=3.6 Hz, 1H), 2.45 (dtd, J=10.9, 5.4, 2.9 Hz, 2H), 2.36-2.19 (m, 2H), 2.19-2.01 (m, 2H), 2.01-1.90 (m, 1H), 1.86-1.72 (m, 2H), 1.55 (dt, J=13.9, 2.7 Hz, 1H), 1.50-1.36 (m, 2H), 1.36-1.24 (m, 2H). MS (ES, m/z): [M+1]=610.2.

Example 61: 4-cyclopentyl-2-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]-1,3-benzothiazole-6-carboxylic acid (I-69)

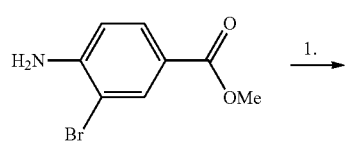

68a

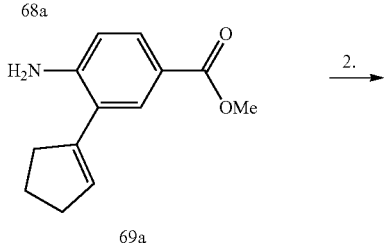

69a

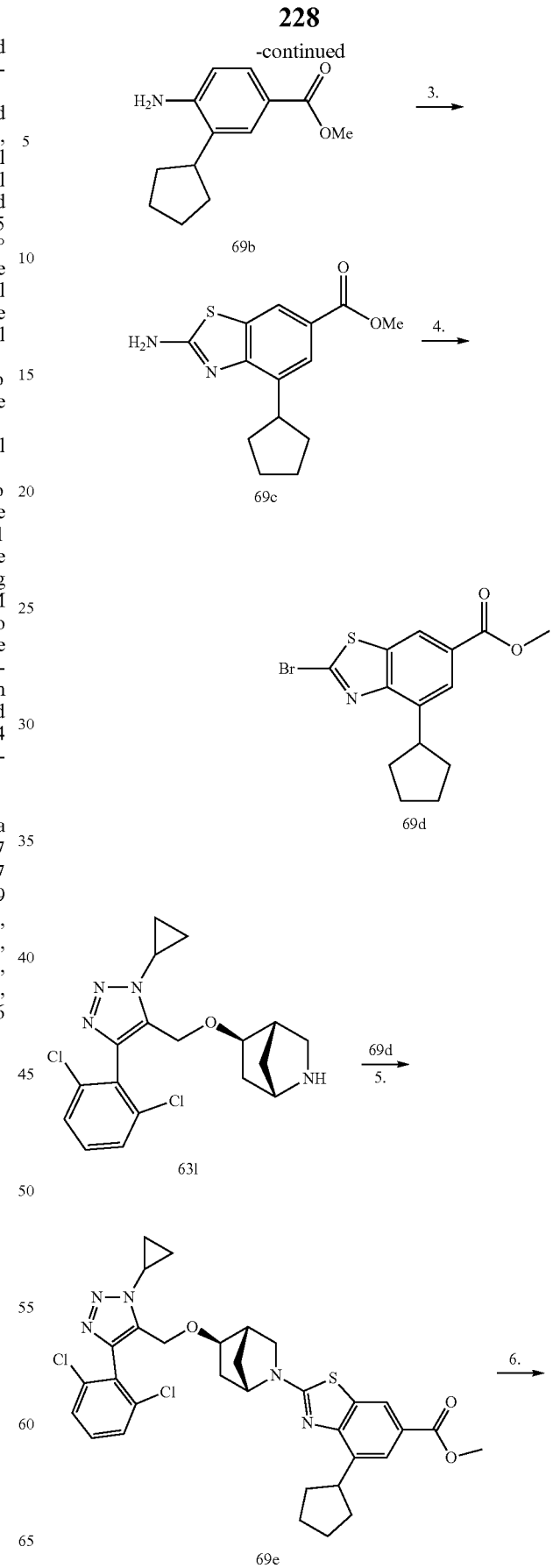

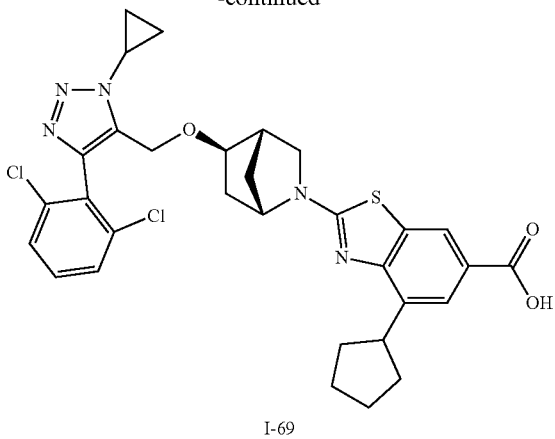

I-69

Step 1. To a 250 mL round-bottom flask purged with and maintained under an inert atmosphere of nitrogen was added methyl 4-amino-3-bromobenzoate 68a (2.2 g, 9.56 mmol, 1.00 equiv.), toluene (50 mL), water (10 mL), (cyclopent-1-en-1-yl)boronic acid (3.36 g, 30.02 mmol, 3.00 equiv), $K_3PO_4$ (6.36 g, 29.96 mmol, 3.00 equiv.), Pd(OAc)$_2$ (224 mg, 1.00 mmol, 0.10 equiv.), and P(Cy)$_3$ (0.280 g, 0.10 equiv.). The resulting mixture was heated at 110° C. for 16 h. The reaction was quenched by the addition of water/ice upon cooling to room temperature. The aqueous mixture was extracted with ethyl acetate (150 mL×3), and the combined organic extracts were washed with brine (300 mL), dried over anhydrous sodium sulfate, and concentrated. The residue was purified by silica gel column chromatography eluting with ethyl acetate/petroleum ether (1:10) to give methyl 4-amino-3-(cyclopent-1-en-1-yl)benzoate 69a (1.45 g, 70%) as a yellow solid.

Step 2. To a 100 mL round-bottom flask was added methyl 4-amino-3-(cyclopent-1-en-1-yl)benzoate 69a (1.56 g, 7.18 mmol, 1.00 equiv.) and methanol (30 mL). Palladium on carbon (2 g, 10 wt %) was added. Hydrogen gas was introduced via a balloon. The reaction mixture was stirred at room temperature for 16 h under a hydrogen atmosphere. Solids were filtered out, the filtrate was concentrated under vacuum to give methyl 4-amino-3-cyclopentylbenzoate 69b (1.6 g, Q) as a white solid.

Step 3. To a 250 mL round-bottom flask was added methyl 4-amino-3-cyclopentylbenzoate 69b (1.6 g, 7.30 mmol, 1.00 equiv.), NaSCN (25 mL), and AcOH (2.4 g, 39.97 mmol, 4.00 equiv.). A solution of Br$_2$ (2.3 g, 14.39 mmol, 2.00 equiv.) in AcOH (25 mL) was added dropwise with stirring at 0° C. The resulting mixture was stirred at 30° C. for 16 h, then quenched by the addition of 200 mL of water. The pH value of the solution was adjusted to 10 using sodium hydroxide pellets. The solids were collected by filtration, further dried in an oven under reduced pressure to give methyl 2-amino-4-cyclopentyl-1,3-benzothiazole-6-carboxylate 69c (2.5 g, crude) as a yellow solid.

Step 4. To a 250 mL round-bottom flask was added methyl 2-amino-4-cyclopentyl-1,3-benzothiazole-6-carboxylate 69c (2.15 g, 7.78 mmol, 1.00 equiv.), MeCN (100 mL), CuBr$_2$ (2.58 g, 1.50 equiv.), and t-BuONO (2.3 g, 2.26 equiv.). The resulting mixture was stirred at 30° C. for 16 h and concentrated. The residue was purified by silica gel column chromatography eluting with ethyl acetate/petroleum ether (1:10) to give methyl 2-bromo-4-cyclopentyl-1,3-benzothiazole-6-carboxylate 69d (1.6 g, 60%) as a white solid.

Step 5. To a 100 mL round-bottom flask was added (1S,4S,5R)-5-[[1-cyclopropyl-4-(2,6-dichlorophenyl)-1H-1,2,3-triazol-5-yl]methoxy]-2-azabicyclo[2.2.1]heptane 631 (40 mg, 0.11 mmol, 1.00 equiv.), DMA (5 mL), methyl 2-bromo-4-cyclopentyl-1,3-benzothiazole-6-carboxylate 69d (40 mg, 0.12 mmol, 1.11 equiv.), and Cs$_2$CO$_3$ (105 mg, 0.32 mmol, 3.06 equiv.). The resulting mixture was heated at 60° C. overnight. After cooling to room temperature, the mixture was diluted with H$_2$O (100 mL), and extracted with ethyl acetate (50 mL×3). The combined organic extracts were washed with brine, dried over anhydrous sodium sulfate, and concentrated under vacuum to give methyl 4-cyclopentyl-2-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]-1,3-benzothiazole-6-carboxylate 69e (60 mg, 89%) as a light brown crude oil.

Step 6. To a 100 mL round-bottom flask was added methyl 4-cyclopentyl-2-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]-1,3-benzothiazole-6-carboxylate 69e (60 mg, 0.09 mmol, 1.00 equiv.), ethanol (5 mL), water (1 mL), and LiOH (22.5 mg, 0.94 mmol, 10.00 equiv.). The resulting mixture was heated at 60° C. for 2 h. After cooling to room temperature, the mixture was treated with a 1M HCl aqueous solution to adjust the pH value to 7. The mixture was concentrated under vacuum. The crude product was purified by Prep-HPLC using the following conditions Column, XBridge Shield RP18 OBD Column 5 um, 19*150 mm; mobile phase, Water (0.05% TFA) and ACN (62.0% ACN up to 78.0% in 8 min); Detector, UV 254 nm. After purification 4-cyclopentyl-2-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]-1,3-benzothiazole-6-carboxylic acid I-69 (15 mg, 26%) was obtained as a white solid. $^1$H NMR (400 MHz, CD$_3$OD): δ 8.19 (t, J=1.2 Hz, 1H), 7.92 (d, J=1.5 Hz, 1H), 7.56 (dd, J=7.6, 1.7 Hz, 1H), 7.55-7.40 (m, 2H), 4.72 (s, 2H), 4.43 (s, 1H), 3.89 (tt, J=7.4, 3.9 Hz, 1H), 3.74 (d, J=6.3 Hz, 1H), 3.66 (q, J=8.6 Hz, 1H), 3.59-3.50 (m, 1H), 3.09 (d, J=10.0 Hz, 1H), 2.71 (s, 1H), 2.13 (d, J=9.7 Hz, 2H), 2.05 (dd, J=13.3, 6.7 Hz, 1H), 1.92 (d, J=6.0 Hz, 2H), 1.79 (dt, J=13.5, 9.0 Hz, 6H), 1.55 (d, J=13.6 Hz, 1H), 1.46-1.38 (m, 2H), 1.30 (dqt, J=7.0, 5.6, 3.8 Hz, 3H). MS (ES, m/z): [M+1]=624.2.

Example 62: 4-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]benzoic acid (I-70)

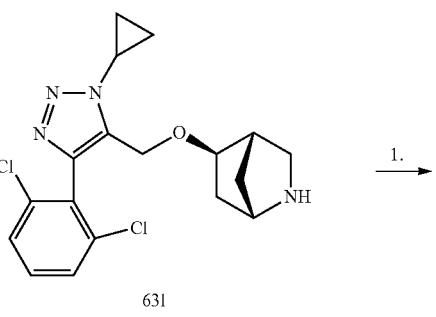

631

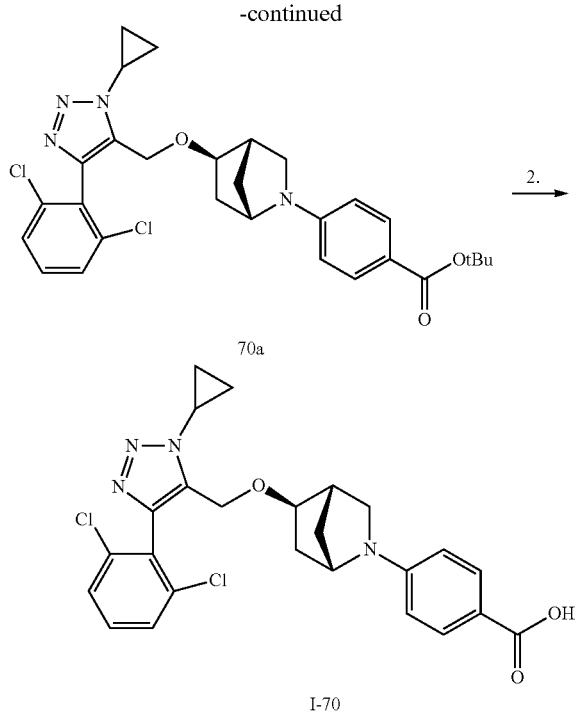

Step 1. To a 100 mL round-bottom flask purged and maintained under an inert atmosphere of nitrogen was added (1S,4S,5R)-5-[[1-cyclopropyl-4-(2,6-dichlorophenyl)-1H-1,2,3-triazol-5-yl]methoxy]-2-azabicyclo[2.2.1]heptane 621 (45 mg, 0.12 mmol, 1.00 equiv.), toluene (20 mL), tert-butyl 4-bromobenzoate (45.7 mg, 0.18 mmol, 1.50 equiv), BINAP (15 mg, 0.02 mmol, 0.20 equiv.), $Cs_2CO_3$ (116 mg, 0.36 mmol, 3.00 equiv.), and $Pd_2(dba)_3$ (11 mg, 0.01 mmol, 0.10 equiv.). The resulting mixture was heated for at 110° C. for 2 days. After cooling to room temperature, solids were filtered out, and the filtrate was concentrated under vacuum. The residue was purified by silica gel column chromatography eluting with ethyl acetate/petroleum ether (1:10 to 1:5, and to 1:3). Removal of solvents afforded tert-butyl 4-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]benzoate 70a (40 mg, 61%) as a light brown oil.

Step 2. To a 100 mL round-bottom flask was added tert-butyl 4-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]benzoate 70a (40 mg, 0.07 mmol, 1.00 equiv.), dichloromethane (1 mL), and trifluoroacetic acid (1 mL). The resulting mixture was stirred at room temperature for 2 h. The mixture was diluted with 100 mL of $H_2O$, extracted with dichloromethane (30 mL×3), and the combined organic extracts were washed with brine, dried over anhydrous sodium sulfate, concentrated under vacuum. The crude product was purified by Prep-HPLC using the following conditions Column, XBridge C18 OBD Prep Column, 19 mm×250 mm; mobile phase, Water (0.05% TFA) and ACN (50.0% ACN up to 68.0% in 8 min); Detector, uv 254 nm. After purification 4-[(1S,4S,5R)-5-[[1-cyclopropyl-4-(2,6-dichlorophenyl)-1H-1,2,3-triazol-5-yl]methoxy]-2-azabicyclo[2.2.1]heptan-2-yl]benzoic acid I-70 (18 mg, 50%) was obtained as a white solid. $^1$H NMR (300 MHz, $CDCl_3$): δ 7.94 (d, J=8.3 Hz, 2H), 7.55-7.42 (m, 1H), 7.42-7.32 (m, 2H), 6.48 (d, J=8.6 Hz, 2H), 4.67-4.51 (m, 2H), 4.19 (s, 1H), 3.78 (tt, J=7.5, 3.8 Hz, 1H), 3.55 (d, J=6.2 Hz, 1H), 3.42 (dd, J=9.7, 3.9 Hz, 1H), 2.64 (d, J=9.4 Hz, 1H), 2.56 (d, J=3.5 Hz, 1H), 1.91 (dd, J=13.2, 6.8 Hz, 1H), 1.75 (q, J=10.1 Hz, 2H), 1.52 (td, J=13.5, 13.1, 5.8 Hz, 3H), 1.26 (d, J=7.4 Hz, 2H). MS (ES, m/z): [M+1]=499.2.

Example 63: FXR Ligand Binding and Activation Assays

The affinity of FXR ligands for the ligand binding domain of FXR was determined using a commercially available human FXR ligand binding assay (LanthaScreen, Thermofisher Cat #PV4833). The purified ligand binding domain of human FXR tagged with GST (glutathiones-S-transferase) is incubated with a terbium labelled anti-GLT antibody and a fluorescein-labelled SRC2-2 peptide (LKEKH-KILHRLLQDSSSPV (SEQ ID NO.: 1)). Binding of FXR ligands to the FXR ligand binding domain promotes binding of the fluorescein-labelled SRC2-2 peptide. This causes a FRET signal between the terbium-labelled anti-GST antibody and the fluorescein-labelled SRC peptide which are both bound to the FXR ligand binding domain.

Test compounds are dissolved in DMSO and a 3-fold serial dilution series is generated, then further diluted into assay buffer. The compounds are mixed with 5 nM GST-tagged FXR ligand binding domain, 5 nM Tb-labelled anti-GST antibody and 500 nM fluorescein-labelled SRC2-2 peptide in a pH7.4 buffer. The reaction is incubated at room temperature for 1 hour, then the FRET signal is measured as the ratio of the 520 nm/495 nm emission following excitation at 340 nm. The change in FRET signal is plotted against the test article concentration and fit to a 3-parameter logistical equation. The concentration required to produce 50% activation is expressed as $pEC_{50}$ ($-\log EC_{50}$), and the extent of activation is expressed relative to GW4064 as % activation. The data for the compounds of the invention in the ligand binding assay are shown in Table 5.

Cell-Based Assay of FXR Activation.

FXR activation was measured using a cell line and procedure obtained from Life Technologies (Cat #K1691). FXR-UAS-bla HEK 293T cells contain a human Farnesoid X receptor ligand-binding domain/Gal4 DNA binding domain chimera stably integrated into the CellSensor® UAS-bla HEK 293T cell line. The CellSensor® UAS-bla HEK 293T contains a beta-lactamase reporter gene under control of a UAS response element stably integrated into HEK 293T cells. Activation of FXR by bound ligands results in transcriptional activation of the beta-lactamase reporter gene, which is detected via assay of beta-lactamase activity.

Cells are harvested and diluted into assay medium containing phenol red-free DMEM supplemented with 2% Charcoal-stripped FBS, pyruvate, non-essential amino acids. Cells are then transferred to a 384 well assay plate. Test compounds are dissolved in DMSO and a 3-fold serial dilution series is generated, then further diluted into assay medium. Compounds in assay medium are added to cells in the 384 well plate and allowed to incubate 16 h at 37 C in the presence of 5% $CO_2$.

Following incubation, FXR activity is detected via measurement of beta-lactamase that is produced under its transcriptional control. A FRET-based beta-lactamase (CCF4) is loaded into cells as its acetomethoxy ester. Intracellular esterases liberate free CCF4, a cephalosporin core linking 7-hydroxycoumarin to fluorescein. In the presence of beta-lactamase activity produced in the presence of FXR agonists, cleavage of CCF4 spatially separates the two dyes and disrupts FRET, so that exciting the coumarin at 409 nm now produces a blue fluorescence signal at 447 nm. The change in FRET signal is plotted against the test compound concentration and fit to a 3-parameter logistical equation. The concentration required to produce 50% activation is expressed as $pEC_{50}$ ($-\log EC_{50}$), and the extent of activation is expressed relative to GW4064 as % activation. The data for the compounds of the invention in the cell-based assay are shown in Table 5.

TABLE 5

| Cmpd No. | Ligand Binding $pEC_{50}$ | Ligand Binding % Efficacy | Cellular $pEC_{50}$ | Cellular % Efficacy |
|---|---|---|---|---|
| I-1 | 8.2 | 121 | 8.8 | 110 |
| I-2 | 8.3 | 133 | 8.7 | 104 |
| I-3 | 7.4 | 156 | | |
| I-4 | 7 | 132 | | |
| I-5 | 6.6 | 119 | | |
| I-6 | 5.6 | 101 | | |
| I-7 | 7.6 | 134 | | |
| I-8 | 8.1 | 164 | | |
| I-9 | 7.4 | 164 | | |
| I-10 | 6.8 | 164 | 7.5 | 118 |
| I-11 | 7.4 | 152 | | |
| I-12 | 7.4 | 176 | | |
| I-13 | 6.8 | 142 | | |
| I-14 | 6.4 | 48 | | |
| I-15 | 6 | 44 | | |
| I-16 | 6 | 52 | | |
| I-17 | 5.6 | 15 | | |
| I-18 | 5.6 | 47 | | |
| I-19 | 5.6 | 30 | | |
| I-20 | 8.5 | 147 | 9.1 | 102 |
| I-21 | 8.8 | 174 | | |
| I-22 | 8.4 | 166 | | |
| I-23 | 8.4 | 164 | 8.6 | 111 |
| I-24 | 8.5 | 164 | 8.6 | 107 |
| I-25 | 7.6 | 130 | | |
| I-26 | 8 | 169 | | |
| I-27 | 8.3 | 185 | | |
| I-28 | 6.4 | 56 | | |
| I-29 | 6.7 | 59 | | |
| I-30 | 7.8 | 151 | 8.8 | 106 |
| I-31 | 8.8 | 116 | 9.7 | 110 |
| I-32 | 8.6 | 128 | 9 | 101 |
| I-33 | 7.4 | 132 | 8.4 | 99 |
| I-34 | 7 | 144 | 8 | 98 |
| I-35 | 6.2 | 152 | | |
| I-36 | 6.8 | 134 | | |
| I-37 | 7.4 | 176 | | |
| I-38 | 6.8 | 185 | | |
| I-39 | 5.6 | 136 | | |
| I-40 | 7.5 | 156 | | |
| I-41 | 6.5 | 96 | 6.1 | 117 |
| I-42 | 6.6 | 102 | 6.4 | 110 |
| I-43 | >6.5 | | >7.5 | |
| I-44 | >6.2 | 96 | >7.5 | |
| I-45 | 6.4 | 57 | 6 | 92 |
| I-46 | 7 | 170 | >7.5 | |
| I-47 | 6.6 | 62 | 6.4 | 94 |
| I-48 | 7.4 | 88 | 7.7 | 101 |
| I-49 | 7 | 82 | >7.2 | 105 |
| I-50 | 7 | 78 | 7 | 100 |
| I-51 | 6.6 | 96 | 6.8 | 100 |
| I-52 | 8.2 | 140 | 8.4 | 106 |
| I-53 | 8.2 | 170 | 8.4 | 92 |
| I-54 | 7.7 | 152 | 7.9 | 100 |
| I-55 | 7.2 | 147 | 7.8 | 91 |
| I-56 | 8.7 | 180 | 8 | 104 |
| I-57 | 8.7 | 146 | 9.1 | 104 |
| I-58 | 8.7 | 145 | 9 | 102 |
| I-59 | 8.8 | 137 | 8.6 | 100 |
| I-60 | 9 | 138 | 8.8 | 104 |
| I-61 | 8.4 | 158 | 7.6 | 107 |
| I-62 | 8.4 | 158 | 7.6 | 106 |
| I-63 | 7.9 | 180 | 7.9 | 103 |
| I-64 | 8.3 | 172 | 8 | 113 |
| I-65 | 7.6 | 136 | 8 | 108 |
| I-66 | 7.8 | 140 | 7.8 | 110 |
| I-67 | 7.7 | 148 | 8 | 111 |
| I-68 | 8.4 | 178 | 8.8 | 106 |
| I-69 | 8.2 | 168 | 8.6 | 111 |
| I-70 | 7.2 | 155 | 7.4 | 106 |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound of the Formula (IIb), (IIc) or (IId):

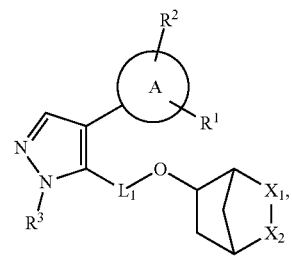

(IIb)

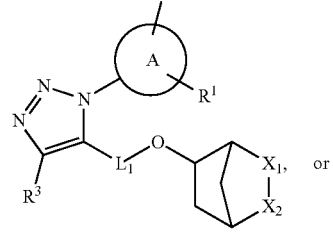

(IIc)

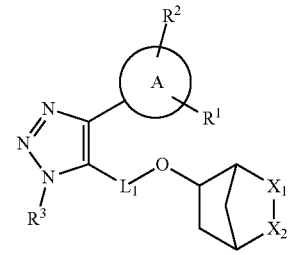

(IId)

or a salt thereof,
wherein:
one of $X_1$ or $X_2$ is $NR_x$ or $N^+(O^-)R_x$ and the other is $CHR_y$ or $C(O)$;
$R_x$ is

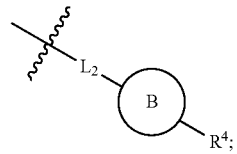

R$_y$ is H, alkyl, cycloalkyl or cycloalkylalkyl wherein said alkyl, cycloalkyl and cycloalkylalkyl are optionally substituted with halogen or alkoxy;

L$_1$ is —(CH$_2$)$_m$(C=O)— or —(CH$_2$)$_p$—;

L$_2$ is a bond or —S(O)$_2$—;

A is cycloalkyl, aryl, heterocycloalkyl or heteroaryl, wherein the cycloalkyl, aryl, heterocycloalkyl, or heteroaryl is optionally substituted with one or more R$^7$;

B is aryl or heteroaryl, wherein the aryl or heteroaryl is optionally substituted with one or more R$^5$;

R$^1$ and R$^2$ are each independently H, alkyl, alkoxy, haloalkyl, haloalkoxy, halogen, cycloalkyl, or CN, wherein the cycloalkyl is optionally substituted with one or more R$^9$;

or when A is cycloalkyl or heterocycloalkyl, R$^1$ and R$^2$ together when attached to the same carbon atom form a spirocycloalkyl ring optionally substituted with one or more R$^8$; or when A is cycloalkyl or heterocycloalkyl, R$^1$ and R$^2$ together when attached to the same atom form a spiroheterocycloalkyl ring optionally substituted with one or more R$^8$; or R$^1$ and R$^2$ when on adjacent atoms together with the atoms to which they are attached form a cycloalkyl ring optionally substituted with one or more R$^8$; or R$^1$ and R$^2$ when on adjacent atoms together with the atoms to which they are attached form a heterocycloalkyl ring optionally substituted with one or more R$^8$; or R$^1$ and R$^2$ when on adjacent atoms together with the atoms to which they are attached form an aryl ring optionally substituted with one or more R$^8$; or R$^1$ and R$^2$ when on adjacent atoms together with the atoms to which they are attached form a heteroaryl ring optionally substituted with one or more R$^8$; or when A is cycloalkyl or heterocycloalkyl, R$^1$ and R$^2$ when on non-adjacent atoms, together with the atoms to which they are attached form a cycloalkyl ring optionally substituted with one or more R$^8$; or when cycloalkyl or heterocycloalkyl, R$^1$ and R$^2$ when on non-adjacent atoms, together with the atoms to which they are attached form a heterocycloalkyl ring optionally substituted with one or more R$^8$; cycloalkyl ring optionally substituted with one or more R$^8$; or when cycloalkyl or heterocycloalkyl, R$^1$ and R$^2$ together with the atoms to which they are attached form a heterocycloalkyl ring optionally substituted with one or more R$^8$;

R$^3$ is alkyl, alkoxy, haloalkyl, haloalkoxy, hydroxyalkyl, or cycloalkyl optionally substituted with one or more substituents each independently selected from the group consisting of halogen, alkyl, alkoxy, haloalkyl, haloalkoxy, and —OH;

R$^4$ is COOR$^{6a}$, —(CH$_2$)$_n$—COOR$^{6a}$, CONR$^{6b}$OH, CONR$^{6b}$R$^{6c}$, CONH(CH$_2$)$_n$COOR$^{6a}$, CONH(CH$_2$)$_n$R$^{6a}$, —(CH$_2$)$_n$CONH(CH$_2$)$_n$R$^{6a}$, CONR$^{6b}$SO$_2$R$^{6d}$, CONR$^{6b}$SO$_2$(CH$_2$)$_n$R$^{6d}$, —(CH$_2$)$_n$—CONR$^{6b}$SO$_2$R$^{6d}$, CONR$^{6b}$SO$_2$(CH$_2$)$_n$N(CO)R$^{6d}$ CONH(CH$_2$)$_n$SO$_2$R$^{6e}$, COR$^{6f}$, (CH$_2$)$_n$PO(OR$^{6g}$)$_2$, CONR$^{6b}$(CH$_2$)$_n$PO(OR$^{6g}$)$_2$, CONR$^{6b}$SO$_2$(CH$_2$)$_n$N$^+$(R$^{6f}$)$_3$, COO(CH$_2$)$_n$PO(OR$^{6g}$)$_2$, SO$_2$NR$^{6b}$(CH$_2$)$_n$COOR$^{6a}$, SO$_2$R$^{6e}$, CN, —(CH$_2$)$_n$—NR$^{6b}$C(O)R$^{6c}$, —(CH$_2$)$_n$—N(OH)—C(O)R$^{6c}$, oxo, alkyl, cycloalkyl, —(CH$_2$)$_n$-cycloalkyl, heterocycloalkyl, —(CH$_2$)$_n$-heterocycloalkyl, heteroaryl or —(CH$_2$)$_n$-heteroaryl; wherein said alkyl, cycloalkyl, —(CH$_2$)$_n$-cycloalkyl, heterocycloalkyl, —(CH$_2$)$_n$-heterocycloalkyl, heteroaryl and —(CH$_2$)$_n$-heteroaryl are optionally substituted with COOR$^{6a}$, —(CH$_2$)$_n$— COOR$^{6a}$, CONR$^{6b}$OH, CONR$^{6b}$R$^{6c}$, CONH(CH$_2$)$_n$ COOR$^{6a}$, CONH(CH$_2$)$_n$R$^{6a}$, —(CH$_2$)$_n$CONH(CH$_2$)$_n$R$^{6a}$, CONR$^{6b}$SO$_2$R$^{6d}$, CONR$^{6b}$SO$_2$(CH$_2$)$_n$R$^{6d}$, —(CH$_2$)$_n$—CONR$^{6b}$SO$_2$R$^{6d}$, CONR$^{6b}$SO$_2$(CH$_2$)$_n$N(CO)R$^{6d}$ CONH(CH$_2$)$_n$SO$_2$R$^{6e}$, COR$^{6f}$, (CH$_2$)$_n$PO(OR$^{6g}$)$_2$, COO(CH$_2$)$_n$PO(OR$^{6g}$)$_2$, SO$_2$NR$^{6b}$(CH$_2$)$_n$COOR$^{6a}$, SO$_2$R$^{6e}$, CN, —(CH$_2$)$_n$—NR$^{6b}$C(O)R$^{6c}$, or —(CH$_2$)$_n$—N(OH)—C(O)R$^{6c}$;

each R$^5$ is independently at each occurrence halogen, alkyl, haloalkyl, alkoxy, haloalkoxy, CN, cycloalkyl, spiroheterocycloalkyl, —O-cycloalkyl, —O-heterocycloalkyl, aryl, heterocycloalkyl, or heteroaryl wherein the cycloalkyl, aryl, heterocycloalkyl or heteroaryl are optionally substituted with one or more substituents each independently selected from the group consisting of halogen, alkyl, haloalkyl, alkoxy, and haloalkoxy;

R$^{6a}$ is H, alkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, NR$^{6b}$R$^{6c}$, SO$_2$NR$^{6b}$R$^{6c}$, and —OH;

R$^{6b}$ and R$^{6c}$ are each independently H, alkyl, haloalkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

R$^{6d}$ is alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, COOH, alkyl, haloalkyl, alkoxy, haloalkoxy, alkoxyalkoxy, —O—CO-alkyl, —O—COcycloalkyl, —O—CO-alkyl-COOH, NR$^{6b}$R$^{6c}$, NR$^{6f}$CO-alkyl, NR$^{6f}$CO-alkoxy, cycloalkyl, heterocycloalkyl and —OH;

R$^{6e}$ is —OH, alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

R$^{6f}$ is alkyl or haloalkyl;

R$^{6g}$ is H or alkyl optionally substituted with —O—CO-alkyl;

each R$^7$ is independently at each occurrence OH, alkyl, alkoxy, haloalkyl, haloalkoxy, halogen, or CN;

each R$^8$ is independently at each occurrence alkyl, alkoxy, haloalkyl, haloalkoxy, halogen, or —OH;

each R$^9$ is independently at each occurrence alkyl, alkoxy, haloalkyl, haloalkoxy, halogen, or —OH;

m is 0, 1, or 2;

n is 1, 2, 3, 4, 5, 6, 7, 8, 9, 10, 11, or 12; and p is 1 or 2.

2. The compound of claim 1, having one of the Formulae (IIb1), (IIc1) or (IId1):

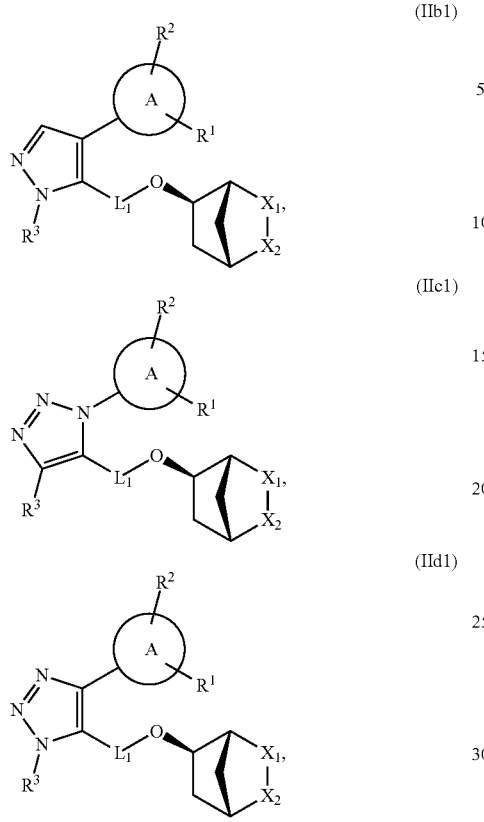

(IIb1)

(IIc1)

(IId1)

or a pharmaceutically acceptable salt thereof.

3. The compound of claim 1, wherein A is ($C_6$-$C_{10}$) aryl optionally substituted with one or more $R^7$, or a pharmaceutically acceptable salt thereof.

4. The compound of claim 1, wherein A is ($C_3$-$C_8$) cycloalkyl, or a pharmaceutically acceptable salt thereof.

5. The compound of claim 1, wherein A is phenyl optionally substituted with one or more $R^7$, or a pharmaceutically acceptable salt thereof.

6. The compound of claim 1, wherein A is cyclohexyl, or a pharmaceutically acceptable salt thereof.

7. The compound of claim 1, wherein $R^1$ and $R^2$ are each independently H, halogen, or ($C_1$-$C_6$) haloalkyl, or a pharmaceutically acceptable salt thereof.

8. The compound of claim 1, wherein B is ($C_6$-$C_{10}$) aryl optionally substituted with ($C_1$-$C_6$) alkyl, halogen, ($C_1$-$C_6$) alkoxy, ($C_1$-$C_6$) haloalkoxy or CN, or a pharmaceutically acceptable salt thereof.

9. The compound of claim 1, wherein B is unsubstituted heteroaryl comprising one or two 5- or 6-member rings and 1-4 heteroatoms selected from the group consisting of N, O and S, or a pharmaceutically acceptable salt, hydrate, solvate, prodrug, stereoisomer, or tautomer thereof.

10. The compound of claim 1, wherein B is heteroaryl comprising one or two 5- or 6-member rings and 1-4 heteroatoms selected from the group consisting of N, O and S, substituted with halogen, ($C_1$-$C_6$) alkyl, ($C_1$-$C_6$) alkoxy, or ($C_1$-$C_6$) haloalkoxy, or a pharmaceutically acceptable salt thereof.

11. The compound of claim 1, wherein $R^3$ is ($C_3$-$C_8$) cycloalkyl, or a pharmaceutically acceptable salt thereof.

12. The compound of claim 1, wherein $R^3$ is ($C_3$-$C_8$) cycloalkyl, substituted with halogen or a pharmaceutically acceptable salt thereof.

13. The compound of claim 1, having one of the Formulae (IIIb), (IIIc) or (IIId):

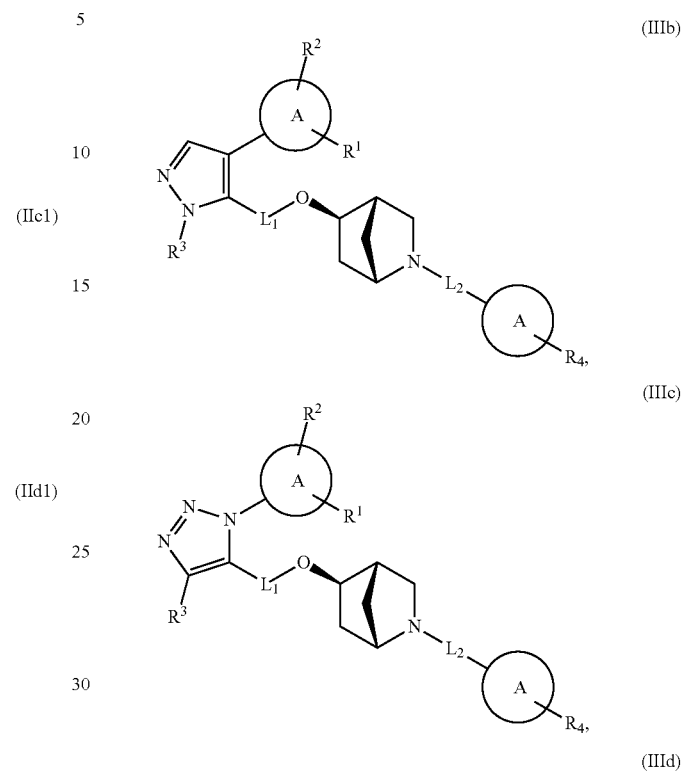

(IIIb)

(IIIc)

(IIId)

or a pharmaceutically acceptable salt thereof.

14. The compound of claim 1, having one of the (VIIb), (VIIc) or (VIId):

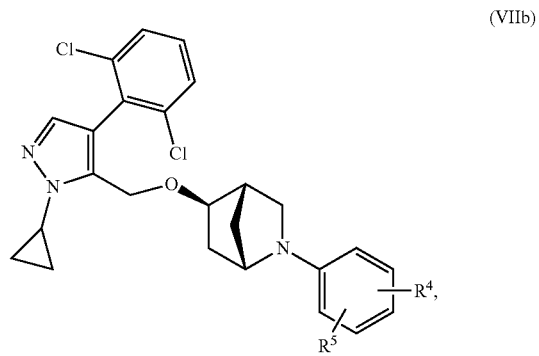

(VIIb)

(VIIc)

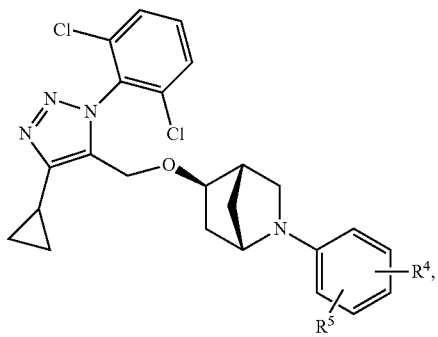

(VIId)

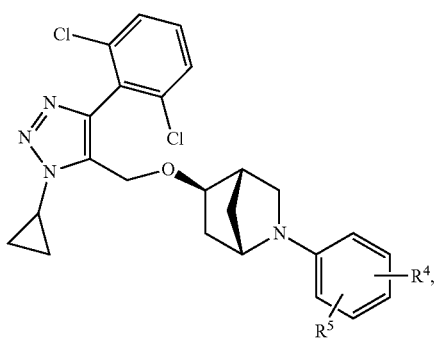

or a pharmaceutically acceptable salt thereof.

15. A compound having one of the Formulae (VIIIa), (VIIIb), (VIIIc) or (VIIId):

(VIIIa)

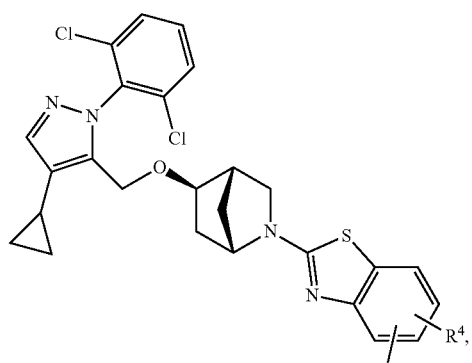

(VIIIb)

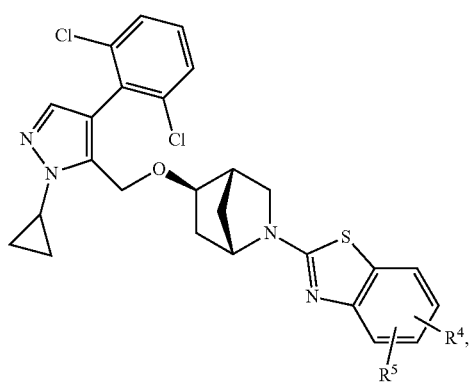

(VIIIc)

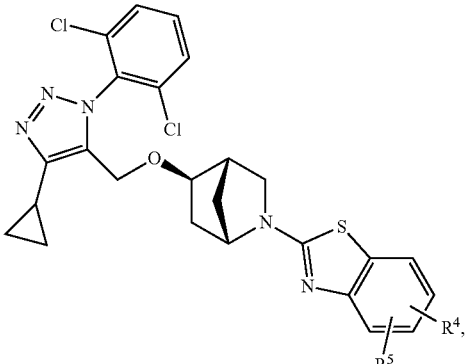

(VIIId)

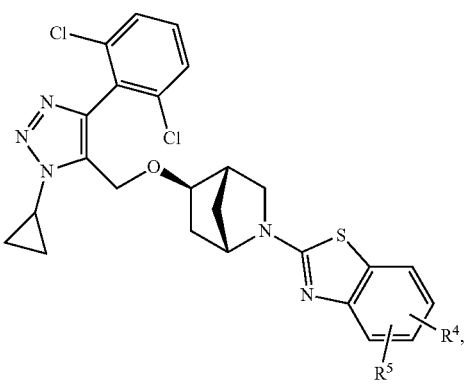

or a pharmaceutically acceptable salt thereof, wherein:

$R^4$ is $COOR^{6a}$, $-(CH_2)_n-COOR^{6a}$, $CONR^{6b}OH$, $CONR^{6b}R^{6c}$, $CONH(CH_2)_nCOOR^{6a}$, $CONH(CH_2)_nR^{6a}$, $-(CH_2)_nCONH(CH_2)_nR^{6a}$, $CONR^{6b}SO_2R^{6d}$, $CONR^{6b}SO_2(CH_2)_nR^{6d}$, $-(CH_2)_n-CONR^{6b}SO_2R^{6d}$, $CONR^{6b}SO_2(CH_2)_nN(CO)R^{6d}$ $CONH(CH_2)_nSO_2R^{6e}$, $COR^{6f}$, $(CH_2)_nPO(OR^{6g})_2$, $CONR^{6b}(CH_2)_nPO(OR^{6g})_2$, $CONR^{6b}SO_2(CH_2)_nN^+(R^{6f})_3$, $COO(CH_2)_nPO(OR^{6g})_2$, $SO_2NR^{6b}(CH_2)_nCOOR^{6a}$, $SO_2R^{6e}$, CN, $-(CH_2)_n-NR^{6b}C(O)R^{6c}$, $-(CH_2)_n-N(OH)-C(O)R^{6c}$, oxo, alkyl, cycloalkyl, $-(CH_2)_n$-cycloalkyl, heterocycloalkyl, $-(CH_2)_n$-heterocycloalkyl, heteroaryl or $-(CH_2)_n$-heteroaryl; wherein said alkyl, cycloalkyl, $-(CH_2)_n$-cycloalkyl, heterocycloalkyl, $-(CH_2)_n$-heterocycloalkyl, heteroaryl and $-(CH_2)_n$-heteroaryl are optionally substituted with $COOR^{6a}$, $-(CH_2)_n-COOR^{6a}$, $CONR^{6b}OH$, $CONR^{6b}R^{6c}$, $CONH(CH_2)_nCOOR^{6a}$, $CONH(CH_2)_nR^{6a}$, $-(CH_2)_nCONH(CH_2)_nR^{6a}$, $CONR^{6b}SO_2R^{6d}$, $CONR^{6b}SO_2(CH_2)_nR^{6d}$, $-(CH_2)_n-CONR^{6b}SO_2R^{6d}$, $CONR^{6b}SO_2(CH_2)_nN(CO)R^{6d}$ $CONH(CH_2)_nSO_2R^{6e}$, $COR^{6f}$, $(CH_2)_nPO(OR^{6g})_2$, $COO(CH_2)_nPO(OR^{6g})_2$, $SO_2NR^{6b}(CH_2)_nCOOR^{6a}$, $SO_2R^{6e}$, CN, $-(CH_2)_n-NR^{6b}C(O)R^{6c}$, or $-(CH_2)_n-N(OH)-C(O)R^{6c}$;

each $R^5$ is independently at each occurrence halogen, alkyl, haloalkyl, alkoxy, haloalkoxy, CN, cycloalkyl, spiroheterocycloalkyl, —O-cycloalkyl, —O-heterocycloalkyl, aryl, heterocycloalkyl, or heteroaryl wherein the cycloalkyl, aryl, heterocycloalkyl or heteroaryl are optionally substituted with one or more substituents each independently selected from the group consisting of halogen, alkyl, haloalkyl, alkoxy, and haloalkoxy;

$R^{6a}$ is H, alkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, $NR^{6b}R^{6c}$, $SO_2NR^{6b}R^{6c}$, and —OH;

$R^{6b}$ and $R^{6c}$ are each independently H, alkyl, haloalkyl, cycloalkyl, aryl, heterocycloalkyl, or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

$R^{6d}$ is alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, COOH, alkyl, haloalkyl, alkoxy, haloalkoxy, alkoxyalkyl, —O—CO-alkyl, —O—COcycloalkyl, —O—CO-alkyl-COOH, $NR^{6b}R^{6c}$, $NR^{6f}$CO-alkyl, $NR^{6f}$CO-alkoxy, cycloalkyl, heterocycloalkyl and —OH;

$R^{6e}$ is —OH, alkyl, haloalkyl, cycloalkyl, aryl, heterocycloalkyl or heteroaryl; wherein the alkyl, cycloalkyl, aryl, heterocycloalkyl, or heteroaryl is optionally substituted with one or more substituents each independently selected from the group consisting of halogen, alkyl, haloalkyl, alkoxy, haloalkoxy, and —OH;

$R^{6f}$ is alkyl or haloalkyl; and $R^{6g}$ is H or alkyl optionally substituted with —O—CO-alkyl.

16. A compound selected from the group consisting of:

4-[(1S,4S,5R)-5-{[4-cyclopropyl-1-(2,6-dichlorophenyl)-1H-pyrazol-5-yl]methoxy}-2-azabicyclo[2.2.1]heptan-2-yl]benzoic acid (I-1);

4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-2-fluorobenzoic acid (I-2);

4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-2,6-difluorobenzoic acid (I-3);

6-[(1S,4S,5R)-5-{[4-cyclopropyl-1-(2,6-dichlorophenyl)-1H-pyrazol-5-yl]methoxy}-2-azabicyclo[2.2.1]heptan-2-yl]pyridine-3-carboxylic acid (I-4);

5-[(1S,4S,5R)-5-{[4-cyclopropyl-1-(2,6-dichlorophenyl)-1H-pyrazol-5-yl]methoxy}-2-azabicyclo[2.2.1]heptan-2-yl]pyridine-2-carboxylic acid (I-5);

5-[(1S,4S,5R)-5-{[4-cyclopropyl-1-(2,6-dichlorophenyl)-1H-pyrazol-5-yl]methoxy}-2-azabicyclo[2.2.1]heptan-2-yl]pyrimidine-2-carboxylic acid (I-6);

4-[(1S,4S,5R)-5-{[4-cyclopropyl-1-(2,6-dimethylphenyl)-1H-pyrazol-5-yl]m ethoxy}-2-azabicyclo[2.2.1]heptan-2-yl]-2-fluorobenzoic acid (I-7);

4-[(1S,4S,5R)-5-{[1-(2-chloro-6-methylphenyl)-4-cyclopropyl-1H-pyrazol-5-yl]methoxy}-2-azabicyclo[2.2.1]heptan-2-yl]-2-fluorobenzoic acid (I-8);

4-[(1S,4S,5R)-5-{[1-(2-chloro-6-fluorophenyl)-4-cyclopropyl-1H-pyrazol-5-yl]methoxy}-2-azabicyclo[2.2.1]heptan-2-yl]-2-fluorobenzoic acid (I-9);

4-[(1S,4S,5R)-5-{[4-cyclopropyl-1-(2,6-difluorophenyl)-1H-pyrazol-5-yl]methoxy}-2-azabicyclo[2.2.1]heptan-2-yl]-2-fluorobenzoic acid (I-10);

4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]benzoic acid (I-11);

4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-2-fluorobenzoic acid (I-12);

4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-3-fluorobenzoic acid (I-13);

4-[(1S,3R,4S,5R)-5-{[4-cyclopropyl-1-(2,6-dichlorophenyl)-1H-pyrazol-5-yl]methoxy}-3-methyl-2-azabicyclo[2.2.1]heptan-2-yl]benzoic acid (I-14);

4-[(1S,3R,4S,5R)-5-{[4-cyclopropyl-1-(2,6-dichlorophenyl)-1H-pyrazol-5-yl]methoxy}-3-methyl-2-azabicyclo[2.2.1]heptan-2-yl]-2-fluorobenzoic acid (I-15);

4-[(1S,3R,4S,5R)-5-{[4-cyclopropyl-1-(2,6-dichlorophenyl)-1H-pyrazol-5-yl]methoxy}-3-ethyl-2-azabicyclo[2.2.1]heptan-2-yl]benzoic acid (I-16);

4-[(1R,3S,4R,5S)-5-{[4-cyclopropyl-1-(2,6-dichlorophenyl)-1H-pyrazol-5-yl]methoxy}-3-ethyl-2-azabicyclo[2.2.1]heptan-2-yl]benzoic acid (I-17);

4-[(1S,3R,4S,5R)-5-{[4-cyclopropyl-1-(2,6-dichlorophenyl)-1H-pyrazol-5-yl]methoxy}-3-ethyl-2-azabicyclo[2.2.1]heptan-2-yl]-2-fluorobenzoic acid (I-18);

4-[(1R,3S,4R,5S)-5-{[4-cyclopropyl-1-(2,6-dichlorophenyl)-1H-pyrazol-5-yl]methoxy}-3-ethyl-2-azabicyclo[2.2.1]heptan-2-yl]-2-fluorobenzoic acid (I-19);

4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-N-(oxane-4-sulfonyl)benzamide (I-20);

4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-N-[(2,2-dimethyloxan-4-yl)sulfonyl]benzamide (I-21);

4-((1S,4S,5R)-5-((4-cyclopropyl-1-(2,6-dichlorophenyl)-1H-pyrazol-5-yl)methoxy)-2-azabicyclo[2.2.1]heptan-2-yl)-N-(cyclopropylsulfonyl)benzamide (I-22);

4-((1S,4S,5R)-5-((4-cyclopropyl-1-(2,6-dichlorophenyl)-1H-pyrazol-5-yl)methoxy)-2-azabicyclo[2.2.1]heptan-2-yl)-N-((tetrahydrofuran-3-yl)sulfonyl)benzamide (I-23);

4-((1S,4S,5R)-5-((4-cyclopropyl-1-(2,6-dichlorophenyl)-1H-pyrazol-5-yl)methoxy)-2-azabicyclo[2.2.1]heptan-2-yl)-N-(((tetrahydrofuran-3-yl)methyl)sulfonyl)benzamide (I-24);

5-((1S,4S,5R)-5-((4-cyclopropyl-1-(2,6-dichlorophenyl)-1H-pyrazol-5-yl)methoxy)-2-azabicyclo[2.2.1]heptan-2-yl)-N-((tetrahydro-2H-pyran-4-yl)sulfonyl)picolinamide (I-25);

4-((1S,4R,5R)-5-((4-cyclopropyl-1-(2,6-dichlorophenyl)-1H-pyrazol-5-yl)methoxy)-3-oxo-2-azabicyclo[2.2.1]heptan-2-yl)-N-((tetrahydro-2H-pyran-4-yl)sulfonyl)benzamide (I-26);

4-((1S,4R,5R)-5-((4-cyclopropyl-1-(2,6-dichlorophenyl)-1H-pyrazol-5-yl)methoxy)-3-oxo-2-azabicyclo[2.2.1]heptan-2-yl)-2-fluoro-N-((tetrahydro-2H-pyran-4-yl)sulfonyl)benzamide (I-27);

4-((1S,3R,4S,5R)-5-((4-cyclopropyl-1-(2,6-dichlorophenyl)-1H-pyrazol-5-yl)methoxy)-3-methyl-2-azabicyclo[2.2.1]heptan-2-yl)-2-fluoro-N-((tetrahydro-2H-pyran-4-yl)sulfonyl)benzamide (I-28);

N-(cyclopropanesulfonyl)-4-[(1S,3R,4S,5R)-5-{[4-cyclopropyl-1-(2,6-dichlorophenyl)-1H-pyrazol-5-yl]methoxy}-3-methyl-2-azabicyclo[2.2.1]heptan-2-yl]-2-fluorobenzamide (I-29);

2-[(1S,4S,5R)-5-{[4-cyclopropyl-1-(2,6-dichlorophenyl)-1H-pyrazol-5-yl]methoxy}-2-azabicyclo[2.2.1]heptan-2-yl]-4-fluoro-1,3-benzothiazole-6-carboxylic acid (I-30);

4-cyclopropoxy-2-[(1S,4S,5R)-5-{[4-cyclopropyl-1-(2,6-dichlorophenyl)-1H-pyrazol-5-yl]methoxy}-2-azabicyclo[2.2.1]heptan-2-yl]-1,3-benzothiazole-6-carboxylic acid (I-31);

2-[(1S,4S,5R)-5-{[4-cyclopropyl-1-(2,6-dichlorophenyl)-1H-pyrazol-5-yl]methoxy}-2-azabicyclo[2.2.1]heptan-2-yl]-4-(oxan-4-yl)-1,3-benzothiazole-6-carboxylic acid (I-32);

3-{4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-3-fluorophenyl}propanoic acid (I-33);

3-{4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-2-fluorophenyl}propanoic acid (I-34);

3-{4-[(1S,4S,5R)-5-{[4-cyclopropyl-1-(2,6-difluorophenyl)-1H-pyrazol-5-yl]methoxy}-2-azabicyclo[2.2.1]heptan-2-yl]-3-fluorophenyl}propanoic acid (I-35);

3-{4-[(1S,4S,5R)-5-{[4-cyclopropyl-1-(2,6-dimethylphenyl)-1H-pyrazol-5-yl]methoxy}-2-azabicyclo[2.2.1]heptan-2-yl]-3-fluorophenyl}propanoic acid (I-36);

3-{4-[(1S,4S,5R)-5-{[1-(2-chloro-6-methylphenyl)-4-cyclopropyl-1H-pyrazol-5-yl]methoxy}-2-azabicyclo[2.2.1]heptan-2-yl]-3-fluorophenyl}propanoic acid (I-37);

3-{4-[(1S,4S,5R)-5-{[1-(2-chloro-6-fluorophenyl)-4-cyclopropyl-1H-pyrazol-5-yl]methoxy}-2-azabicyclo[2.2.1]heptan-2-yl]-3-fluorophenyl}propanoic acid (I-38);

3-{4-[(1S,4R,5R)-5-{[4-cyclopropyl-1-(2,6-dichlorophenyl)-1H-pyrazol-5-yl]methoxy}-3-oxo-2-azabicyclo[2.2.1]heptan-2-yl]-3-fluorophenyl}propanoic acid (I-39);

3-{4-[(1S,4S,5R)-5-{[4-cyclopropyl-1-(2,6-dichlorophenyl)-1H-pyrazol-5-yl]methoxy}-2-azabicyclo[2.2.1]heptan-2-yl]-3-fluorophenyl}cyclobutane-1-carboxylic acid (I-40);

4-[(1S,4S,5R)-5-{[1-cyclopropyl-4-(2,6-dichlorophenyl)-1H-pyrazol-5-yl]methoxy}-2-azabicyclo[2.2.1]heptan-2-yl]benzoic acid (I-41);

4-[(1S,4S,5R)-5-{[1-cyclopropyl-4-(2,6-dichlorophenyl)-1H-pyrazol-5-yl]methoxy}-2-azabicyclo[2.2.1]heptan-2-yl]-2-fluorobenzoic acid (I-42);

3-{4-[(1S,4S,5R)-5-{[1-cyclopropyl-4-(2,6-dichlorophenyl)-1H-pyrazol-5-yl]methoxy}-2-azabicyclo[2.2.1]heptan-2-yl]phenyl}propanoic acid (I-43);

3-{4-[(1S,4S,5R)-5-{[1-cyclopropyl-4-(2,6-dichlorophenyl)-1H-pyrazol-5-yl]methoxy}-2-azabicyclo[2.2.1]heptan-2-yl]-3-fluorophenyl}propanoic acid (I-44);

4-[(1S,4S,5R)-5-{[1-cyclopropyl-4-(2,6-dichlorophenyl)-1H-pyrazol-5-yl]methoxy}-2-azabicyclo[2.2.1]heptan-2-yl]-2-fluoro-N-(2-methanesulfonylethyl)benzamide (I-45);

4-[(1S,4S,5R)-5-{[1-cyclopropyl-4-(2,6-dichlorophenyl)-1H-pyrazol-5-yl]methoxy}-2-azabicyclo[2.2.1]heptan-2-yl]-N-(oxane-4-sulfonyl)benzamide (I-46);

2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-fluoro-1,3-benzothiazole-6-carboxylic acid (I-47);

4-cyclopropoxy-2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-1,3-benzothiazole-6-carboxylic acid (I-48);

2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-(oxan-4-yl)-1,3-benzothiazole-6-carboxylic acid (I-49);

2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-[(3S)-oxolan-3-yl]-1,3-benzothiazole-6-carboxylic acid (I-50);

2-[(1S,4S,5R)-5-{[1-cyclopropyl-4-(2,6-dichlorophenyl)-1H-pyrazol-5-yl]methoxy}-2-azabicyclo[2.2.1]heptan-2-yl]-4-[(3R)-oxolan-3-yl]-1,3-benzothiazole-6-carboxylic acid (I-51);

4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]benzoic acid (I-52);

4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-2-fluorobenzoic acid (I-53);

3-{4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-3-fluorophenyl}propanoic acid (I-54);

3-{4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-2-fluorophenyl}propanoic acid (I-55);

4-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-N-(oxane-4-sulfonyl)benzamide (I-56);

4-cyclopropoxy-2-((1S,4S,5R)-5-((4-cyclopropyl-1-(2,6-dichlorophenyl)-1H-1,2,3-triazol-5-yl)methoxy)-2-azabicyclo[2.2.1]heptan-2-yl)benzo[d]thiazole-6-carboxylic acid (I-57);

2-((1S,4S,5R)-5-((4-cyclopropyl-1-(2,6-dichlorophenyl)-1H-1,2,3-triazol-5-yl)methoxy)-2-azabicyclo[2.2.1]heptan-2-yl)-4-((R)-tetrahydrofuran-3-yl)benzo[d]thiazole-6-carboxylic acid (I-58);

2-((1S,4S,5R)-5-((4-cyclopropyl-1-(2,6-dichlorophenyl)-1H-1,2,3-triazol-5-yl)methoxy)-2-azabicyclo[2.2.1]heptan-2-yl)-4-((S)-tetrahydrofuran-3-yl)benzo[d]thiazole-6-carboxylic acid (I-59);

2-((1S,4S,5R)-5-((4-cyclopropyl-1-(2,6-dichlorophenyl)-1H-1,2,3-triazol-5-yl)methoxy)-2-azabicyclo[2.2.1]heptan-2-yl)-4-(tetrahydro-2H-pyran-4-yl)benzo[d]thiazole-6-carboxylic acid (I-60);

2-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-4-[(3S)-oxolan-3-yloxy]-1,3-benzothiazole-6-carboxylic acid (I-61);

2-[(1S,4S,5R)-5-{[4-cyclopropyl-1-(2,6-dichlorophenyl)-1H-1,2,3-triazol-5-yl]methoxy}-2-azabicyclo[2.2.1]heptan-2-yl]-4-[(3R)-oxolan-3-yloxy]-1,3-benzothiazole-6-carboxylic acid (I-62);

2-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]-4-(trifluoromethoxy)-1,3-benzothiazole-6-carboxylic acid (I-63);

4-cyclopropoxy-2-((1S,4S,5R)-5-((1-cyclopropyl-4-(2,6-dichlorophenyl)-1H-1,2,3-triazol-5-yl)methoxy)-2-azabicyclo[2.2.1]heptan-2-yl)benzo[d]thiazole-6-carboxylic acid (I-64);

2-((1S,4S,5R)-5-((1-cyclopropyl-4-(2,6-dichlorophenyl)-1H-1,2,3-triazol-5-yl)methoxy)-2-azabicyclo[2.2.1]heptan-2-yl)-4-((R)-tetrahydrofuran-3-yl)benzo[d]thiazole-6-carboxylic acid (I-65);

2-((1S,4S,5R)-5-((1-cyclopropyl-4-(2,6-dichlorophenyl)-1H-1,2,3-triazol-5-yl)methoxy)-2-azabicyclo[2.2.1]heptan-2-yl)-4-((S)-tetrahydrofuran-3-yl)benzo[d]thiazole-6-carboxylic acid (I-66);

2-((1S,4S,5R)-5-((1-cyclopropyl-4-(2,6-dichlorophenyl)-1H-1,2,3-triazol-5-yl)methoxy)-2-azabicyclo[2.2.1]heptan-2-yl)-4-(tetrahydro-2H-pyran-4-yl)benzo[d]thiazole-6-carboxylic acid (I-67);

4-cyclobutyl-2-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]-1,3-benzothiazole-6-carboxylic acid (I-68)

4-cyclopentyl-2-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]-1,3-benzothiazole-6-carboxylic acid (I-69); and 4-[(1S,4S,5R)-5-{[1-cyclopropyl-4-(2,6-dichlorophenyl)-1H-1,2,3-triazol-5-yl]methoxy}-2-azabicyclo[2.2.1]heptan-2-yl]benzoic acid (I-70), or a pharmaceutically acceptable salt thereof.

17. A pharmaceutical composition comprising, a compound of claim 1 or a pharmaceutically acceptable salt thereof, and a pharmaceutically acceptable carrier.

18. A pharmaceutical composition comprising, a compound of claim 15 or a pharmaceutically acceptable salt thereof, and a pharmaceutically acceptable carrier.

19. A pharmaceutical composition comprising, a compound of claim 16 or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO.         : 11,753,410 B2
APPLICATION NO.    : 16/647385
DATED              : September 12, 2023
INVENTOR(S)        : Jianhua Chao Page 1 of 3

It is certified that error appears in the above-identified patent and that said Letters Patent is hereby corrected as shown below:

In the Claims

Column 235, Line 55, Claim 1, please delete "(CO)R$^{6d}$ CONH" and insert --(CO)R$^{6d}$, CONH--;

Column 236, Line 3, Claim 1, please delete "(CO)R$^{6d}$ CONH" and insert --(CO)R$^{6d}$, CONH--;

Column 236, Line 40, Claim 1, please delete "-O-COcycloalkyl" and insert -- -O-CO-cycloalkyl--;

Column 238, Lines 5-47, Claim 13, please delete

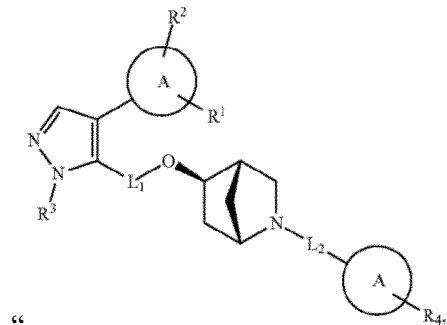

"

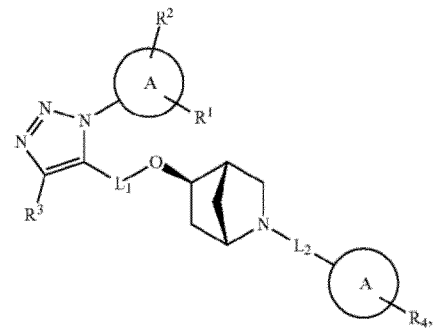

Signed and Sealed this
Seventeenth Day of September, 2024

Katherine Kelly Vidal
*Director of the United States Patent and Trademark Office*

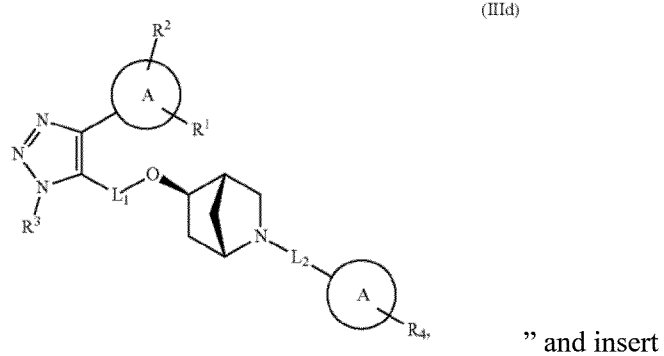
(IIId)
" and insert
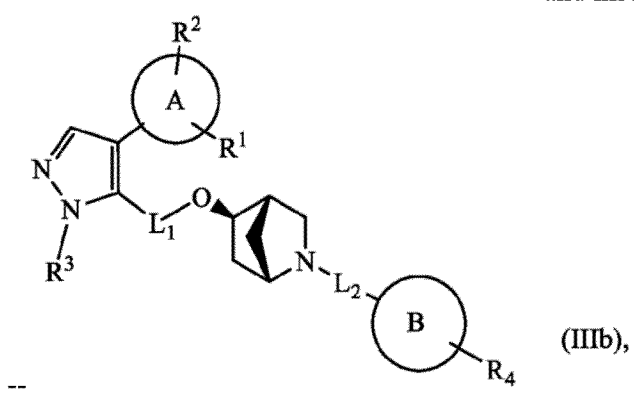
(IIIb),
--
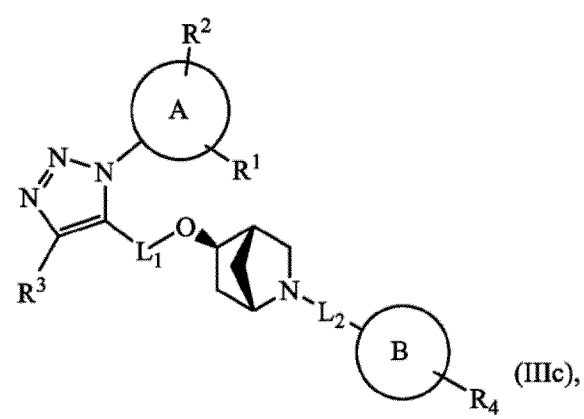
(IIIc),
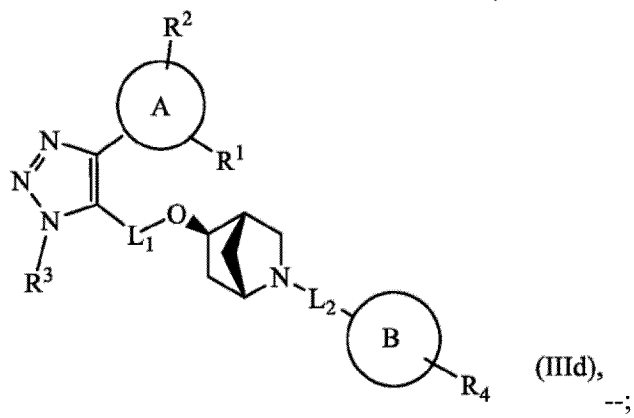
(IIId),
--;
Column 239, Line 32, Claim 15, please delete "VILLa" and insert --VIIIa--;

CERTIFICATE OF CORRECTION (continued)
U.S. Pat. No. 11,753,410 B2

Column 239, Line 33, Claim 15, please delete "VILLc" and insert --VIIIc--;

Column 240, Line 39, Claim 15, please delete "(CO)$R^{6d}$ CONH" and insert --(CO)$R^{6d}$, CONH--;

Column 240, Line 54, Claim 15, please delete "(CO)$R^{6d}$ CONH" and insert --(CO)$R^{6d}$, CONH--; and Column 241, Line 51, Claim 16, please delete "m ethoxy" and insert --methoxy-- therefor.